US009732167B2

(12) United States Patent
Okada et al.

(10) Patent No.: US 9,732,167 B2
(45) Date of Patent: Aug. 15, 2017

(54) OXYGEN-ABSORBING RESIN COMPOSITION AND OXYGEN-ABSORBING MULTILAYER BODY USING SAME, AND MOLDED ARTICLE AND MEDICAL CONTAINER USING THESE

(71) Applicant: MITSUBISHI GAS CHEMICAL COMPANY, INC., Tokyo (JP)

(72) Inventors: Satoshi Okada, Kanagawa (JP); Toshiya Takagi, Tokyo (JP); Takashi Kashiba, Kanagawa (JP); Shinpei Iwamoto, Kanagawa (JP); Shinichi Ikeda, Kanagawa (JP); Fumihiro Ito, Kanagawa (JP); Shun Ogawa, Kanagawa (JP); Shota Arakawa, Kanagawa (JP); Kenichiro Usuda, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 323 days.

(21) Appl. No.: 14/376,563

(22) PCT Filed: Feb. 8, 2013

(86) PCT No.: PCT/JP2013/053121
§ 371 (c)(1),
(2) Date: Aug. 4, 2014

(87) PCT Pub. No.: WO2013/118882
PCT Pub. Date: Aug. 15, 2013

(65) Prior Publication Data
US 2014/0373485 A1 Dec. 25, 2014

(30) Foreign Application Priority Data

| Feb. 8, 2012 | (JP) | 2012-025177 |
| Jul. 30, 2012 | (JP) | 2012-168304 |
| Jan. 18, 2013 | (JP) | 2013-007769 |
| Jan. 22, 2013 | (JP) | 2013-009176 |
| Jan. 23, 2013 | (JP) | 2013-010498 |
| Jan. 25, 2013 | (JP) | 2013-012444 |
| Jan. 29, 2013 | (JP) | 2013-014493 |
| Jan. 29, 2013 | (JP) | 2013-014562 |
| Jan. 30, 2013 | (JP) | 2013-015002 |
| Jan. 31, 2013 | (JP) | 2013-016602 |
| Jan. 31, 2013 | (JP) | 2013-017248 |
| Jan. 31, 2013 | (JP) | 2013-017330 |
| Jan. 31, 2013 | (JP) | 2013-017424 |
| Feb. 1, 2013 | (JP) | 2013-018142 |
| Feb. 1, 2013 | (JP) | 2013-018203 |
| Feb. 1, 2013 | (JP) | 2013-018216 |
| Feb. 1, 2013 | (JP) | 2013-018243 |
| Feb. 1, 2013 | (JP) | 2013-018696 |
| Feb. 4, 2013 | (JP) | 2013-019543 |
| Feb. 5, 2013 | (JP) | 2013-020299 |

(51) Int. Cl.
| C08F 8/06 | (2006.01) |
| B65D 81/24 | (2006.01) |
| B32B 27/10 | (2006.01) |
| B32B 27/34 | (2006.01) |
| B32B 27/32 | (2006.01) |
| B65D 1/02 | (2006.01) |
| C08F 8/14 | (2006.01) |
| A61J 1/14 | (2006.01) |
| B65D 81/26 | (2006.01) |

(Continued)

(52) U.S. Cl.
CPC ...... *C08F 8/06* (2013.01); *A61J 1/14* (2013.01); *A61J 1/16* (2013.01); *A61M 5/3129* (2013.01); *B32B 27/08* (2013.01); *B32B 27/10* (2013.01); *B32B 27/18* (2013.01); *B32B 27/32* (2013.01); *B32B 27/325* (2013.01);
(Continued)

(58) Field of Classification Search
CPC ... C08F 8/06; C08F 8/14; B65D 81/24; B65D 1/0215; B65D 1/40; B65D 5/42; B65D 81/267; B65D 81/26; B32B 27/10; B32B 27/36; B32B 27/34; B32B 27/327; B32B 27/325; B32B 27/18; B32B 27/08;
(Continued)

(56) References Cited

U.S. PATENT DOCUMENTS

| 4,966,699 A | 10/1990 | Sasaki et al. |
| 5,021,515 A | 6/1991 | Cochran et al. |
(Continued)

FOREIGN PATENT DOCUMENTS

| CN | 1301280 | 6/2001 |
| CN | 1430627 | 7/2003 |
(Continued)

OTHER PUBLICATIONS

Tanaka et al. Tetrahedron 66 (2010) 1563-1569.*
(Continued)

*Primary Examiner* — Peter F Godenschwager
*Assistant Examiner* — Andrew J Oyer
(74) *Attorney, Agent, or Firm* — Greenblum & Bernstein, P.L.C.

(57) ABSTRACT

Provided is a novel oxygen-absorbing resin composition having excellent oxygen-absorbing performance and suppressing odor generation after absorption of oxygen even if a material responsive to a metal detector is not used. Further provided is an oxygen-absorbing resin composition having excellent oxygen-absorbing performance in a wide range of humidity conditions from low humidity to high humidity. Such an oxygen-absorbing resin composition contains a copolymerized polyolefin compound and a transition metal catalyst, in which the copolymerized polyolefin compound contains at least one constituent unit having a tetralin ring.

24 Claims, No Drawings

(51) Int. Cl.
*A61J 1/16* (2006.01)
*A61M 5/31* (2006.01)
*B65B 25/00* (2006.01)
*B32B 27/08* (2006.01)
*B32B 27/18* (2006.01)
*B32B 27/36* (2006.01)

(52) U.S. Cl.
CPC ............ *B32B 27/327* (2013.01); *B32B 27/34* (2013.01); *B32B 27/36* (2013.01); *B65B 25/00* (2013.01); *B65D 1/0215* (2013.01); *B65D 81/24* (2013.01); *B65D 81/26* (2013.01); *B65D 81/267* (2013.01); *C08F 8/14* (2013.01); *A61J 1/1468* (2015.05); *A61M 2005/3117* (2013.01); *B32B 2250/00* (2013.01); *B32B 2250/02* (2013.01); *B32B 2250/05* (2013.01); *B32B 2250/24* (2013.01); *B32B 2250/242* (2013.01); *B32B 2307/726* (2013.01); *B32B 2307/7242* (2013.01); *B32B 2307/7244* (2013.01); *B32B 2307/7265* (2013.01); *B32B 2307/74* (2013.01); *B32B 2439/70* (2013.01); *B32B 2439/80* (2013.01); *B32B 2553/00* (2013.01); *C08F 2800/20* (2013.01); *C08F 2810/50* (2013.01); *Y10T 428/31935* (2015.04)

(58) Field of Classification Search
CPC .... B32B 27/32; A61J 1/16; A61J 1/14; B65B 25/00; A61M 5/3129
See application file for complete search history.

(56) References Cited

U.S. PATENT DOCUMENTS

| | | |
|---|---|---|
| 5,211,875 A | 5/1993 | Speer et al. |
| 5,346,644 A | 9/1994 | Speer et al. |
| 5,350,622 A | 9/1994 | Speer et al. |
| 5,529,833 A | 6/1996 | Speer et al. |
| 5,700,554 A | 12/1997 | Speer et al. |
| 6,063,503 A | 5/2000 | Hatakeyama et al. |
| 6,254,803 B1 | 7/2001 | Matthews et al. |
| 6,254,804 B1 | 7/2001 | Matthews et al. |
| 7,056,565 B1* | 6/2006 | Cai .................... B32B 27/18 428/36.7 |
| 7,097,890 B1 | 8/2006 | Ching et al. |
| 2002/0022144 A1 | 2/2002 | Yang |
| 2002/0102424 A1 | 8/2002 | Yang et al. |
| 2003/0235708 A1 | 12/2003 | Yang et al. |
| 2004/0267194 A1 | 12/2004 | Sano et al. |
| 2009/0297979 A1 | 12/2009 | Hatakeyama et al. |

FOREIGN PATENT DOCUMENTS

| | | |
|---|---|---|
| EP | 0244458 | 11/1987 |
| JP | 51-136845 | 11/1976 |
| JP | 1-259870 | 10/1989 |
| JP | 2-500846 | 3/1990 |
| JP | 5-115776 | 5/1993 |
| JP | 8-127641 | 5/1996 |
| JP | 1997110790 A * | 4/1997 |
| JP | 9-234832 | 9/1997 |
| JP | 2001-252560 | 9/2001 |
| JP | 2003-521552 | 7/2003 |
| JP | 2004-229750 | 8/2004 |
| JP | 2004-323058 | 11/2004 |
| JP | 2007-140289 | 6/2007 |
| JP | 2007-164145 | 6/2007 |
| JP | 2009-108153 | 5/2009 |
| JP | 2010-013627 | 1/2010 |
| JP | 2011-132502 | 7/2011 |
| JP | 2011-136761 | 7/2011 |
| JP | 2011-168674 | 9/2011 |
| WO | 87-02389 | 4/1987 |
| WO | 9948963 A | 9/1999 |

OTHER PUBLICATIONS

English Translation of JP1997110790A.*
International Preliminary Report on Patentability issued in PCT/JP2013/053121 on Aug. 12, 2014.
Search report from International Bureau of WIPO, mail date is Mar. 12, 2013.

* cited by examiner

OXYGEN-ABSORBING RESIN COMPOSITION AND OXYGEN-ABSORBING MULTILAYER BODY USING SAME, AND MOLDED ARTICLE AND MEDICAL CONTAINER USING THESE

TECHNICAL FIELD

The present invention relates to an oxygen-absorbing resin composition, particularly to an oxygen-absorbing resin composition containing at least a copolymerized polyolefin compound having a tetralin ring and a transition metal catalyst. The present invention also relates to e.g., an oxygen-absorbing multilayer body, an oxygen-absorbing multilayer container, an oxygen-absorbing paper container, a tubular container, an oxygen-absorbing PTP packaging body and an oxygen-absorbing multilayer bottle excellent in oxygen barrier performance and oxygen-absorbing performance in a wide range of humidity conditions from low humidity to high humidity. The present invention further relates to a medical container and a molded article containing an oxygen-absorbing multilayer body having oxygen barrier performance and oxygen-absorbing function, more specifically, to an oxygen-absorbing sealed container etc., using an oxygen-absorbing multilayer body as the cover material for a gas barrier molded container, and a store method using them.

BACKGROUND ART

In order to prevent oxygen oxidation and store various types of articles, represented by foods, beverages, medicinal products, and cosmetics, which easily deteriorate or degrade under the effect of oxygen for a long time, oxygen absorbents are used for removing oxygen within packaging bodies storing these articles.

As the oxygen absorbent, an oxygen absorbent containing an iron powder as a reactive main component is generally used in view of oxygen-absorbing ability, handling and safety. However, the iron-based oxygen absorbent is responsive to a metal detector and thus it is difficult to use a metal detector in inspecting foreign matter. Furthermore, packaging bodies containing an iron-based oxygen absorbent have a risk of ignition, and thus, they cannot be heated by a microwave oven. Moreover, the oxidation reaction of an iron powder requires water, and thus, an oxygen-absorbing effect is exerted only on an article to be packaged rich in moisture content.

Packaging containers are developed by making the container of a multilayer material having an oxygen-absorbing layer formed of an oxygen-absorbing resin composition containing a thermoplastic resin and an iron-based oxygen absorbent, thereby improving a gas barrier property of the container and providing an oxygen-absorbing function to the container itself (see, Patent Literature 1). Specifically, the multilayer material is an oxygen-absorbing multilayer film, which is obtained by providing an oxygen-absorbing layer formed of a thermoplastic resin having an iron-based oxygen absorbent dispersed therein between layers of a gas barrier multilayer film having a conventional structure (in which a heat sealing layer and a gas a barrier layer are laminated), which has a function of absorbing oxygen within the container in addition to a function of preventing oxygen transmission from outside, and which is manufactured using a conventional manufacturing method known in the art, such as extrusion lamination, coextrusion lamination and dry lamination. However, such an oxygen-absorbing multilayer film has the same problems: a metal detector for inspecting foreign matters cannot be used since it responds to the metal detector for inspecting foreign matters in foods etc.; heating cannot be made by a microwave oven; and the effect is only exerted on an article to be packaged rich in moisture content. In addition, the multilayer film has a problem of opacity, leading to insufficient visibility of content.

In addition to these problems, in molding an oxygen-absorbing multilayer sheet using an iron powder, since the sheet itself is heavy due to the presence of the iron powder, imperfect molding occurs during article molding. Examples of problems include neck-in and thickness deviation during sheet molding and draw-down during thermoforming. In addition, an uneven surface may be resulted in molding.

In the aforementioned circumstances, it has been desired to develop an oxygen absorbent containing an organic substance as a reactive main component. As the oxygen absorbent containing an organic substance as a reactive main component, an oxygen absorbent containing ascorbic acid as a main component is known (see, Patent Literature 2).

In the meantime, an oxygen-absorbing resin composition composed of a resin and a transition metal catalyst is known. For example, a resin composition composed of a polyamide as an oxidizable organic component (in particular, a xylylene group-containing polyamide) and a transition metal catalyst, is known (see, Patent Literatures 3 and 4). In Patent Literatures 3 and 4, articles obtained by molding such a resin composition, such as an oxygen absorbent, a packaging material and a multilayer laminated film for packaging are further exemplified.

As an oxygen-absorbing resin composition requiring no moisture content for absorbing oxygen, an oxygen-absorbing resin composition composed of a resin having a carbon-carbon unsaturated bond and a transition metal catalyst, is known (see, Patent Literature 5).

As a composition for trapping oxygen, a composition composed of a polymer containing a substituted cyclohexene functional group or a low molecular-weight substance bound with the cyclohexene functional group and a transition metal is known (see, Patent Literature 6).

A tubular container is used for storing a wide variety of articles including foods, medicinal products, cosmetics, hygiene products such as toothpastes and chemical products such as adhesives. There are many structures of materials for forming the containers, shapes of the containers and manufacturing methods thereof known in the art. As these tubular containers, containers using an aluminum-foil as a gas barrier layer, which is laminated with other layer(s), have long been used to prevent deterioration of contents, particularly deterioration by oxygen. The aluminum foil is excellent as a material that can completely block transmission of a gas such as oxygen and has been used as a container, particularly for medicinal products etc.

However, in a tubular container using an aluminum-foil laminate, it is extremely difficult to separate a laminated resin from aluminum foil and collect them separately for recycling after use. In discarding it by incineration, aluminum foil produces an ash-like residue. Disposal of waste becomes difficult due to the ash-like residue. As a means for solving such a problem, many proposals have been made, in forming a tubular container, to replace aluminum foil with a thermoplastic resin excellent in gas barrier property, such as an ethylene-vinyl alcohol copolymer and a polyamide (hereinafter, sometimes referred to as "nylon MXD6") obtained from metaxylylenediamine and adipic acid, or with a resin film, which is formed by vapor deposition of an inorganic oxide such as aluminum oxide and silicon oxide, and such containers have been put into practical use.

In the meantime, in the cases of containers filled with drug solutions such as medicinal products, an oxygen absorbent is used for removing oxygen within the packaging bodies containing these containers in order to prevent oxygen oxidation of the drug solutions, which easily deteriorate and degrade upon the effect of oxygen, in the containers and store them for a long time.

The container filled with a drug solution is packed in an outer package formed of a synthetic resin film in order to prevent contamination of the container until actually put in use and the container is handled while being packed in the outer package. Since the container is made of an oxygen transmissible resin in view of sanitation etc., the outer package needs to have a gas barrier property in order to prevent deterioration of the content fluid due to oxygen. However, oxygen is more or less present in the outer package even if package is sealed, and oxygen transmits with the passage of time even if the gas-barrier outer package is used. Thus, it is necessary to prevent deterioration of the content fluid caused by such oxygen. Then, up to now, a container filled with a drug solution is not only stored at a low oxygen concentration, but also placed in an outer package together with an oxygen absorbent. Since residual oxygen in the outer package as well as oxygen transmitted from outside are absorbed by the oxygen absorbent, the amount of oxygen within the outer package can be maintained at a low level to prevent the deterioration of the content fluid in an infusion container.

As anti-inflammatory agents for joint pain, muscular pain, etc., patches containing various types of medicinal ingredients are hermetically packaged and stored by use of a film having a barrier property.

When patches containing medicinal ingredients are stored, in order to prevent deterioration of the medicinal ingredients by oxygen, it is necessary for the film to be used in hermetic packaging to have a gas barrier property. However, since oxygen remains within the packaging body after hermetical closing and a small amount of oxygen transmits even if the packaging body has a gas barrier property, such oxygen must be removed in order to suppress deterioration of medicinal ingredients. Up to present, patches have been hermetically packed together with an oxygen absorbent or in a packaging bag having an oxygen-absorbing function.

In the meantime, in the field of packaging medicinal products and foods, etc., containers and packaging bodies such as PTP packaging body (press-through package, also called a blister package) are widely used for packaging medicinal agents such as tablets and capsules, particulate foods, etc. The PTP packaging body refers to a packaging body using a plastic sheet of, e.g., a polyvinyl chloride resin and a polypropylene resin as a bottom material and having a pocket portion for containing an article to be packaged, which is formed by applying air-pressure forming, vacuum molding, etc. After an article to be packaged is contained in the pocket portion, the pocket portion is sealed by laminating a foil or a film made of a material that can be easily torn or easily opened by hand, such as aluminum foil serving as a cover material. In the PTP packaging body, if a transparent plastic sheet is used as a bottom material, an article to be packaged contained in the pocket portion can be directly observed by the naked eye before opening it. In opening the packaging body, the cover material is broken by pressing a perverse from the pocket portion side by a finger. In this way, an article to be packaged can easily be taken out.

As a method for storing fruit pulps such as mandarin orange, chestnut, cherry, peach, apple and pineapple, a technique for storing them in a metal can like canned food is known. As a method for storing alcohol beverages such as Japanese sake, wine and shochu and liquid-state tea or paste-state tea, a technique for storing them in metal cans and glass bottles is known. Recently, fruit juices and/or vegetable juices obtained by processing various types of fruits and/or vegetables have been developed. If these fruit juices and/or vegetable juices are exposed to oxygen, their components such as flavor components, sugars and vitamins are oxidatively decomposed and cause degradation, with the result that the juices change in color tone and lose taste and flavor. Then, a technique for storing fruit juices and/or vegetable juices in metal cans and glass bottles is conceived, in the same manner as in alcohol beverages. However, metal cans and glass bottles have a problem of non-combustible waste treatment and are required to reduce weight. In addition, metal cans have a problem in that metal components leak out into a content. Because of this, metal cans and glass bottles have been replaced with plastic containers such as a gas barrier bag and a gas barrier tray.

In dry products such as coffees, teas, peanuts, lavers, fish clause powders, seasonings and dried vegetables, whose taste and flavor and color tone determine commodity values, it is important to keep taste and flavor and color tone in maintaining commodity value and product life for a long time. Degradation of dry products and reduction of characteristic taste and flavor of dry products during distribution and storage period of products are mainly caused by oxygen present in their packaging containers.

In addition, as medical packaging containers for packaging and storing a drug solution in a hermetically closed condition, glass ampoules, vials, prefilled syringes, etc. have been conventionally used. However, these glass containers have problems: sodium ion etc. elute off from the container to a liquid content stored therein; and micro substances called flakes generate; when a light-blocking glass container colored with a metal is used, the content is contaminated with the coloring metal; and the container is easily broken by drop impact. In addition to these problems, since glass containers have a relatively large specific gravity, medical packaging containers become heavy. For these reasons, development of alternate materials has been desired. To be more specific, materials lighter than glass, such as a polyester, a polycarbonate, a polypropylene and a cycloolefin polymer, have been investigated as glass alternatives.

For example, a medical container formed of a polyester resin material is proposed (see, Patent Literature 7).

In the meantime, a multilayer container having a gas barrier layer as an intermediate layer in order to provide a gas barrier property to a container made of plastic, has been investigated. Specifically, a prefilled syringe improved in oxygen barrier property by constituting the innermost layer and the outermost layer formed of a polyolefin resin and an intermediate layer formed of a resin composition excellent in oxygen barrier property is proposed (see, Patent Literature 8). Other than this, multilayer containers obtained by laminating a gas barrier layer formed of e.g., a polyamide, which is obtained from metaxylylenediamine and adipic acid, an ethylene-vinyl alcohol copolymer, a polyacrylonitrile, a poly (vinylidene chloride), an aluminum foil, a carbon coat or a vapor-deposited inorganic oxide, on a resin layer, have been investigated.

In recent years, it has been proposed that a small amount of transition metal compound is added to nylon MXD6 and mixed to provide an oxygen-absorbing function and the resultant material is used as an oxygen barrier material constituting containers and packaging materials (see, Patent Literature 9).

Examples of the medical containers include ampoules, vials and syringes. Other than these, examples of the medical containers include an artificial kidney hemodialyzer (dialyzer). As a housing of a dialyzer, a polystyrene and a polycarbonate are used as a transparent (easy to see the content) plastic. Of them, a polycarbonate having satisfactory impact resistance is more favorably used in order to avoid breakage by impact of dropping or other causes (see Patent Literature 10).

CITATION LIST

Patent Literatures

Patent Literature 1: Japanese Patent Application Laid-Open No. 9-234832
Patent Literature 2: Japanese Patent Application Laid-Open No. 51-136845
Patent Literature 3: Japanese Patent Application Laid-Open No. 2001-252560
Patent Literature 4: Japanese Patent Application Laid-Open No. 2009-108153
Patent Literature 5: Japanese Patent Application Laid-Open No. 5-115776
Patent Literature 6: National Publication of International Patent Application No. 2003-521552
Patent Literature 7: Japanese Patent Application Laid-Open No. 8-127641
Patent Literature 8: Japanese Patent Application Laid-Open No. 2004-229750
Patent Literature 9: Japanese Patent Application Laid-Open No. 2-500846
Patent Literature 10: Japanese Patent Application Laid-Open No. 1-259870

SUMMARY OF INVENTION

Technical Problem

However, the oxygen absorbent of Patent Literature 2 has problems in that the oxygen-absorbing performance is primarily low; an effect is exerted only on an article to be packaged rich in moisture content; and the cost is relatively high.

The resin composition of Patent Literature 3 has the following problem. Since an oxygen-absorbing function is exerted by oxidizing a xylylene group-containing polyamide resin in the presence of a transition metal catalyst being included in the composition, the polymer chain of the resin is cut by oxidation degradation after absorption of oxygen, with the result that the strength of the packaging container itself decreases. In addition, the oxygen-absorbing performance of the resin composition described therein is still insufficient and the oxygen-absorbing effect is exerted only on an article to be packaged rich in moisture content. In Patent Literature 4, a method of improving interlayer peeling is described; however, the effect is limited. In addition to this problem, the oxygen-absorbing performance of the resin composition described therein is still insufficient and the effect is exerted only on an article to be packaged rich in moisture content.

The oxygen-absorbing resin composition of Patent Literature 5 has the same problem as mentioned above, that is, the polymer chain of the resin is cut by oxidation to produce low molecular-weight organic compounds serving as odor-producing components, with the result that odor is produced after absorption of oxygen.

In the composition of Patent Literature 6, a special material containing a cyclohexene functional group must be used. This material still has a problem in relatively easily producing odor.

In the meantime, in the conventional gas barrier multilayer container and medical multilayer container mentioned above, the basic performance including oxygen barrier property, water vapor barrier property, drug solution adsorptivity, durability, etc. is not sufficient. Because of this, in view of storage stability of a content such as a drug solution and a food, improvement is required.

In particular, when foods, drug solutions, etc. are stored in conventional gas barrier multilayer containers, as a matter of fact, it is difficult and economically extremely unfavorable to completely remove oxygen in a packaging container no matter how gas displacement operation is performed. In other words, it is difficult to completely eliminate oxygen such as oxygen dissolved in a liquid content, oxygen contained in air bubbles generated and introduced in mixing contents, and oxygen dissolved in water when water is added. It is possible to remove oxygen as much as possible by highly strictly controlling conditions for selecting and preparing raw materials and manufacturing conditions; however, such an operation ignores an economic aspect and thus unrealistic. In addition, since the oxygen barrier property of the gas barrier multilayer containers as mentioned above is not sufficient, a small amount of oxygen entering through the wall of containers from the outside cannot be completely eliminated.

A medical container formed of a polyester resin, for example, disclosed in Patent Literature 7, has relatively excellent oxygen barrier property; however, the oxygen barrier property is insufficient to completely block oxygen. Such a medical container is inferior also in water vapor barrier property, compared to a container formed of a polyolefin resin. In addition, the polyester resin has no oxygen-absorbing performance. Because of this, when oxygen enters a container from the outside or when oxygen remains in the head space above the content (drug solution) in a container, degradation of the drug solution within the container cannot be prevented. The medical container has such a problem.

Furthermore, the prefilled syringe of Patent Literature 8 has relatively excellent oxygen barrier property and water vapor barrier property; however, the oxygen barrier property is insufficient to completely block oxygen. In addition, the oxygen barrier resin composition used in an intermediate layer does not have oxygen-absorbing performance. Therefore, when oxygen enters the container from the outside or when oxygen remains in the head space above the content in the container, degradation of the drug solution within the container cannot be prevented. The prefilled syringe has such a problem.

The resin composition of Patent Literature 9 has the same problem as in Patent Literatures 3 and 4. The strength of a resin decreases due to oxidation degradation after oxidation absorption and the strength of a packaging container itself decreases. In addition, the resin composition has problems in that oxygen-absorbing performance is still insufficient and an effect is exerted only on an article to be packaged rich in moisture content.

The housing of the dialyzer described in Patent Literature 10 has excellent transparency and impact resistance; however, polycarbonate is insufficient in oxygen barrier property and water vapor barrier property for applying it to a container for containing and storing a drug solution and has a problem in view of long-term storage stability of a content.

When an oxygen absorbent packed in a small bag is placed as it is in the aforementioned outer package, there is a risk of taking the oxygen absorbent mistakenly. In contrast, fixing the oxygen absorbent to the outer package in order for the absorbent not to be easily taken out from the outer package is unfavorable since manufacturing steps become very complicated and productivity becomes low.

In addition, placing such an oxygen absorbent packed in a small bag as it is creates a problem of a foreign matter and sanitation. In contrast, fixing the oxygen absorbent to a packaging bag so as not to be easily taken out from the packaging bag creates a problem of very complication of manufacturing steps, lowering productivity.

In placing an article to be packaged in a container or a packaging body such as a PTP packaging body and then sealed, if this step is carried out in air, air is taken into the container or packaging body and contained. Naturally, a certain amount of oxygen is accordingly taken into the container or packaging body. Consequently, the oxygen contaminant more or less affects the article to be packaged. The degree of influence of oxygen varies depending upon the chemical properties of the article to be packaged; however, the medicinal ingredients of medicinal agents and the taste and flavor and color tone of foods might gradually degrade after hermetical closing. The longer the storage period or the distribution period after hermetical closing, the larger the effect is given by oxygen. As a result, the quality of the article to be packaged may degrade. For the reason, even if the amount of oxygen is small, the presence of oxygen is not negligible.

When fruit pulps, alcohol beverages, liquid-state teas or paste-state teas, fruit juices and/or vegetable juices and dry products are stored in conventional gas barrier containers such as gas barrier bags, if fruit pulps, alcohol beverages, liquid-state teas or paste-state teas, fruit juices and/or vegetable juices and dry product are packed in packaging containers in air, as a matter of course, contamination of air cannot be eliminated. Contamination of air is prevented by use of an inert gas, mostly by nitrogen gas. Nevertheless, contamination of air cannot be completely prevented by this method. In addition, if such a method is employed in an actual production process, the number of steps increases, reducing production efficiency. In other words, no matter how completely the container is purged with a gas, a small amount of oxygen remains in the container. Due to such a small amount of oxygen or a trace amount of oxygen dissolved in syrups packed together with fruit pulps, alcohol beverages, liquid-state teas or paste-state teas, fruit juices and/or vegetable juices, taste-and-flavor degradation and brown discoloration of fruit pulps, alcohol beverages, liquid-state teas or paste-state teas, fruit juices and/or vegetable juices and dry products inevitably occur.

The present invention was made in consideration of the problems mentioned above. An object of the invention is to provide a novel oxygen-absorbing resin composition having excellent oxygen-absorbing performance and suppressing odor generation after absorption of oxygen even if a material responsive to a metal detector is not used.

Another object of the present invention is to provide a novel oxygen-absorbing multilayer body and an oxygen-absorbing multilayer container containing the multilayer body; an oxygen-absorbing multilayer container; an oxygen-absorbing sealed container using the oxygen-absorbing multilayer body as a cover material for a gas barrier molded container; an oxygen-absorbing paper container; a tubular container; an oxygen-absorbing PTP packaging body using the oxygen-absorbing multilayer body as a bottom material for an oxygen-absorbing PTP packaging body; and an oxygen-absorbing multilayer bottle, which have excellent oxygen-absorbing performance and suppressing odor generation after absorption of oxygen even if a material responsive to a metal detector is not used.

Another object of the present invention is to provide an oxygen-absorbing resin composition, an oxygen-absorbing multilayer body and an oxygen-absorbing multilayer container containing the multilayer body; an oxygen-absorbing multilayer container; an oxygen-absorbing sealed container using the oxygen-absorbing multilayer body as a cover material for a gas barrier molded container; an oxygen-absorbing paper container; a tubular container; an oxygen-absorbing PTP packaging body using the oxygen-absorbing multilayer body as a bottom material for the oxygen-absorbing PTP packaging body; and an oxygen-absorbing multilayer bottle, which have excellent oxygen-absorbing performance in a wide range of humidity conditions from low humidity to high humidity.

Another object of the present invention is to provide a novel oxygen-absorbing medical multilayer molded container and an oxygen-absorbing prefilled syringe significantly suppressing production of low molecular weight compounds after absorption of oxygen, which have excellent oxygen-absorbing performance, preferably having also excellent water vapor barrier performance, maintaining strength even in long-term storage, eluting an extremely small amount of impurities and having a low drug solution adsorptive property. Another object of the present invention is to provide an oxygen-absorbing medical multilayer molded container and an oxygen-absorbing prefilled syringe, which have excellent oxygen-absorbing performance in a wide range of humidity conditions from low humidity to high humidity.

Another object of the present invention is to provide a method for storing a biopharmaceutical for a long term while suppressing deterioration, efficacy reduction of the biopharmaceutical and preventing contamination of impurities. Another object of the present invention is to provide a method for storing a container filled with a drug solution while suppressing degradation of drug-solution components and a patch containing a medicinal ingredient for a long term.

Another object of the present invention is to provide a method for storing fruit pulps, liquid-state teas or paste-state teas, fruit juices and/or vegetable juices and dry products for a long term without degrading taste and flavor of fruit pulps, alcohol beverages, liquid-state teas or paste-state teas, fruit juices and/or vegetable juices and dry products while maintaining color tone of them and a method for storing alcohols for a long term.

Solution to Problem

The present inventors conducted intensive studies on an oxygen-absorbing resin composition, etc. As a result, they found that the aforementioned problems are solved by using a copolymerized polyolefin compound having a predetermined tetralin ring and a transition metal catalyst, and accomplished the present invention.

More specifically, the present invention provides the following <1-1> to <1-23>.

<1-1> An oxygen-absorbing resin composition comprising a copolymerized polyolefin compound and a transition metal catalyst, wherein the copolymerized polyolefin compound contains at least one constituent unit (a) selected from the group consisting of the constituent units represented by the following general formula (1):

[Formula 1]

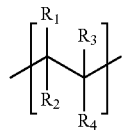

(1)

where $R_1$, $R_2$, $R_3$ and $R_4$ each independently represent a hydrogen atom or a first monovalent substituent which is at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; and at least one constituent unit (b) having a tetralin ring, selected from the group consisting of the constituent units represented by the following general formulas (2) and (3):

[Formula 2]

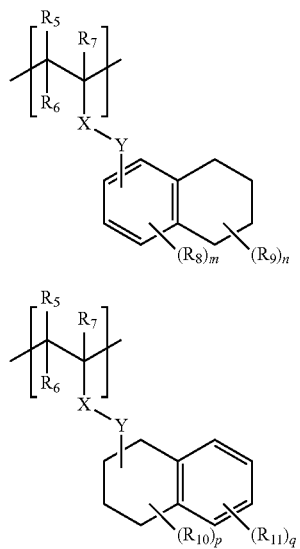

(2)

(3)

where $R_5$, $R_6$ and $R_7$ each independently represent a hydrogen atom or a second monovalent substituent, $R_8$, $R_9$, $R_{10}$ and $R_{11}$ each independently represent a third monovalent substituent; the second monovalent substituent and the third monovalent substituent each independently represent at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; if a plurality of elements are present as $R_8$, $R_9$, $R_{10}$ or $R_{11}$, the plural elements of each of $R_8$, $R_9$, $R_{10}$ and $R_{11}$ may mutually the same or different; m represents an integer of 0 to 3, n 0 to 7, p 0 to 6 and q 0 to 4, respectively; at least one hydrogen atom is bound to a benzyl position of the tetralin ring; X represents a bivalent group selected from the group consisting of —(C=O)O—, —(C=O)NH—, —O(C=O)—, —NH(C=O)— and —(CHR)s- where s represents an integer of 0 to 12; Y represents —(CHR)t- where t represents an integer of 0 to 12; and R represents a monovalent chemical species selected from the group consisting of a hydrogen atom, a methyl group and an ethyl group.

<1-2> The oxygen-absorbing resin composition according to the above <1-1>, wherein the transition metal catalyst comprises at least one transition metal selected from the group consisting of manganese, iron, cobalt, nickel and copper.

<1-3> The oxygen-absorbing resin composition according to the above <1-1> or <1-2>, wherein the transition metal catalyst is contained in an amount of 0.001 to 10 parts by mass in terms of a transition metal based on 100 parts by mass of the copolymerized polyolefin compound.

<1-4> The oxygen-absorbing resin composition according to any one of the above <1-1> to <1-3>, wherein a ratio of a content of the constituent unit (a) to a content of the constituent unit (b) contained in the copolymerized polyolefin compound is 1/99 to 99/1 by molar ratio.

<1-5> The oxygen-absorbing resin composition according to any one of the above <1-1> to <1-4>, wherein the constituent unit (a) is at least one constituent unit selected from the group consisting of the constituent units represented by the following formulas (4) and (5):

[Formula 3]

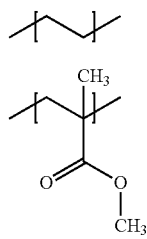

(4)

(5)

and the constituent unit (b) is at least one constituent unit selected from the group consisting of the constituent units represented by the following formulas (6) and (7):

[Formula 4]

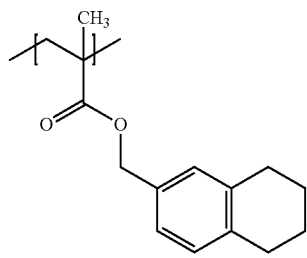

(6)

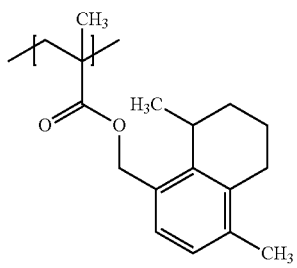

(7)

<1-6> An oxygen-absorbing multilayer body comprising at least three layers comprising a sealant layer containing a thermoplastic resin, an oxygen-absorbing layer comprising the oxygen-absorbing resin composition according to any one of the above <1-1> to <1-5> and a gas barrier layer containing a gas barrier substance, laminated in this order.

<1-7> An oxygen-absorbing multilayer container comprising the oxygen-absorbing multilayer body according to the above <1-6>.

<1-8> An oxygen-absorbing multilayer container obtained by thermoforming of an oxygen-absorbing multilayer body comprising at least three layers comprising an oxygen transmission layer containing a thermoplastic resin, an oxygen-absorbing layer comprising the oxygen-absorbing resin composition according to any one of the above <1-1> to <1-5> and a gas barrier layer containing a gas barrier substance, laminated in this order, such that the oxygen transmission layer faces inside.

<1-9> An oxygen-absorbing sealed container, comprising a cover material containing the oxygen-absorbing multilayer body according to the above <1-6> and a gas barrier molded container comprising at least three layers comprising an inner layer containing a thermoplastic resin, a gas barrier layer containing a gas barrier substance and an outer layer containing a thermoplastic resin, laminated in this order, in which the sealant layer of the cover material and the inner layer of the gas barrier molded container are bonded.

<1-10> An oxygen-absorbing paper container obtained by forming a carton from an oxygen-absorbing multilayer body comprising at least four layers comprising an isolation layer containing a thermoplastic resin, an oxygen-absorbing layer comprising the oxygen-absorbing resin composition according to any one of the above <1-1> to <1-5>, a gas barrier layer containing a gas barrier substance and a paper substrate layer, laminated in this order.

<1-11> A tubular container comprising an oxygen-absorbing multilayer body comprising at least three layers comprising an inner layer containing a thermoplastic resin, an oxygen-absorbing layer comprising the oxygen-absorbing resin composition according to any one of the above <1-1> to <1-5> and a gas barrier layer containing a gas barrier substance, laminated in this order.

<1-12> An oxygen-absorbing medical multilayer molded container comprising at least three layers comprising a first resin layer at least containing a polyester, an oxygen-absorbing layer comprising the oxygen-absorbing resin composition according to any one of the above <1-1> to <1-5> and a second resin layer at least containing a polyester, laminated in this order.

<1-13> An oxygen-absorbing prefilled syringe made capable of storing a medicinal agent in a sealed condition in advance and releasing the sealed condition to eject the medical agent at the time of use, wherein the prefilled syringe comprises a multilayered structure having at least three layers comprising a first resin layer containing at least a polyester, an oxygen-absorbing layer comprising the oxygen-absorbing resin composition according to any one of the above <1-1> to <1-5>, and a second resin layer containing at least a polyester, laminated in this order.

<1-14> A method for storing a biopharmaceutical, comprising storing the biopharmaceutical in the oxygen-absorbing medical multilayer molded container according to the above <1-12> or in the oxygen-absorbing prefilled syringe according to the above <1-13>.

<1-15> A method for storing a container filled with a drug solution, comprising storing the container filled with a drug solution in an oxygen-absorbing container using the oxygen-absorbing multilayer body according to the above <1-6> in whole or in part.

<1-16> A method for storing a patch containing a medicinal ingredient, comprising storing the patch containing a medicinal ingredient in an oxygen-absorbing container using the oxygen-absorbing multilayer body according to the above <1-6> in whole or in part.

<1-17> An oxygen-absorbing PTP packaging body, which comprises an oxygen-absorbing bottom material formed by molding the oxygen-absorbing multilayer body according to the above <1-6> and a gas barrier cover material comprising at least two layers including an inner layer containing a thermoplastic resin and a gas barrier layer containing a gas barrier substance, laminated in this order, in which the sealant layer of the oxygen-absorbing bottom material and the inner layer of the gas barrier cover material are bonded.

<1-18> An oxygen-absorbing multilayer bottle having at least three layers comprising an oxygen transmission layer containing a thermoplastic resin, an oxygen-absorbing layer comprising the oxygen-absorbing resin composition according to any one of the above <1-1> to <1-5> and a gas barrier layer containing a gas barrier substance, laminated in this order from inside.

<1-19> A method for storing fruit pulps, comprising storing the fruit pulps in an oxygen-absorbing container using the oxygen-absorbing multilayer body according to the above <1-6> in whole or in part.

<1-20> A method for storing an alcohol beverage, comprising storing the alcohol beverage in an oxygen-absorbing container using the oxygen-absorbing multilayer body according to the above <1-6> in whole or in part.

<1-21> A method for storing liquid-state tea or paste-state tea, comprising storing the liquid-state tea or paste-state tea in an oxygen-absorbing container using the oxygen-absorbing multilayer body according to the above <1-6> in whole or in part.

<1-22> A method for storing fruit juice and/or vegetable juice, comprising storing the fruit juice and/or vegetable juice in an oxygen-absorbing container using the oxygen-absorbing multilayer body according to the above <1-6> in whole or in part.

<1-23> A method for storing a dry product, comprising storing the dry product in an oxygen-absorbing container using the oxygen-absorbing multilayer body according to the above <1-6> in whole or in part.

Furthermore, the present inventors conducted intensive studies on an oxygen-absorbing resin composition. As a result, they found that the aforementioned problems are solved by using a copolymerized polyolefin compound having a predetermined tetralin ring and a transition metal catalyst, and accomplished the present invention.

More specifically, the present invention provides the following <2-1> to <2-4>.

<2-1> An oxygen-absorbing resin composition containing a copolymerized polyolefin compound and a transition metal catalyst, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<2-2> The oxygen-absorbing resin composition according to the above <2-1>, in which the transition metal catalyst contains at least one transition metal selected from the group consisting of manganese, iron, cobalt, nickel and copper.

<2-3> The oxygen-absorbing resin composition according to the above <2-1> or <2-2>, in which the transition metal catalyst is contained in an amount of 0.001 to 10 parts by mass in terms of a transition metal based on 100 parts by mass of the copolymerized polyolefin compound.

<2-4> The oxygen-absorbing resin composition according to any one of the above <2-1> to <2-3>, in which a ratio of the content of the constituent unit (a) to the content of the constituent unit (b) contained in the copolymerized polyolefin compound is 1/99 to 99/1 by molar ratio.

<2-5> The oxygen-absorbing resin composition according to any one of the above <2-1> to <2-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the following formulas (6) and (7).

The present inventors conducted intensive studies on an oxygen-absorbing multilayer body. As a result, they found that the aforementioned problems are solved by using a copolymerized polyolefin compound having a predetermined tetralin ring and a transition metal catalyst, and accomplished the present invention.

More specifically, the present invention provides the following <3-1> to <3-6>.

<3-1> An oxygen-absorbing multilayer body comprising at least three layers comprising a sealant layer containing a thermoplastic resin, an oxygen-absorbing layer comprising an oxygen-absorbing resin composition containing a copolymerized polyolefin compound and a transition metal catalyst, and a gas barrier layer containing a gas barrier substance, laminated in this order, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<3-2> The oxygen-absorbing multilayer body according to the above <3-1>, in which the transition metal catalyst contains at least one transition metal selected from the group consisting of manganese, iron, cobalt, nickel and copper.

<3-3> The oxygen-absorbing multilayer body according to the above <3-1> or <3-2>, in which the transition metal catalyst is contained in an amount of 0.001 to 10 parts by mass in terms of a transition metal based on 100 parts by mass of the copolymerized polyolefin compound.

<3-4> The oxygen-absorbing multilayer body according to any one of the above <3-1> to <3-3>, in which a ratio of the content of the constituent unit (a) to the content of the constituent unit (b) contained in the copolymerized polyolefin compound is 1/99 to 99/1 by molar ratio.

<3-5> The oxygen-absorbing multilayer body according to any one of the above <3-1> to <3-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

<3-6> An oxygen-absorbing multilayer container having the oxygen-absorbing multilayer body according to any one of the above <3-1> to <3-5>.

The present inventors further conducted intensive studies on an oxygen-absorbing multilayer container. As a result, they found that the aforementioned problems are solved by using a copolymerized polyolefin compound having a predetermined tetralin ring and a transition metal catalyst in at least one layer of a multilayer container, and accomplished the present invention.

More specifically, the present invention provides the following <4-1> to <4-5>.

<4-1> An oxygen-absorbing multilayer container obtained by thermoforming an oxygen-absorbing multilayer body, which comprises at least three layers comprising an oxygen transmission layer containing a thermoplastic resin, an oxygen-absorbing layer comprising an oxygen-absorbing resin composition containing a copolymerized polyolefin compound and a transition metal catalyst, and a gas barrier layer containing a gas barrier substance, laminated in this order, such that the oxygen transmission layer faces inside, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<4-2> The oxygen-absorbing multilayer container according to the above <4-1>, in which the transition metal catalyst contains at least one transition metal selected from the group consisting of manganese, iron, cobalt, nickel and copper.

<4-3> The oxygen-absorbing multilayer container according to the above <4-1> or <4-2>, in which the transition metal catalyst is contained in an amount of 0.001 to 10 parts by mass in terms of a transition metal based on 100 parts by mass of the copolymerized polyolefin compound.

<4-4> The oxygen-absorbing multilayer container according to any one of the above <4-1> to <4-3>, in which a ratio of the content of the constituent unit (a) to the content of the constituent unit (b) contained in the copolymerized polyolefin compound is 1/99 to 99/1 by molar ratio.

<4-5> The oxygen-absorbing multilayer container according to any one of the above <4-1> to <4-4>, in which the constituent unit (a) is at least one constituent unit selected from the group consisting of the constituent units represented by the above formulas (4) and (5).

The present inventors conducted intensive studies on an oxygen-absorbing sealed container. As a result, they found that the aforementioned problems are solved by using a copolymerized polyolefin compound having a predetermined tetralin ring and a transition metal catalyst, and accomplished the present invention.

More specifically, the present invention provides the following <5-1> to <5-5>.

<5-1> An oxygen-absorbing sealed container, which has a cover material containing an oxygen-absorbing multilayer body comprising at least three layers comprising a sealant layer containing a thermoplastic resin, an oxygen-absorbing layer comprising an oxygen-absorbing resin composition containing a copolymerized polyolefin compound and a transition metal catalyst, and a gas barrier layer containing a gas barrier substance, laminated in this order; and a gas barrier molded container comprising at least three layers comprising an inner layer containing a thermoplastic resin, a gas barrier layer containing a gas barrier substance and an outer layer containing a thermoplastic resin, laminated in this order, in which the sealant layer of the cover material and the inner layer of the gas barrier molded container are bonded, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<5-2> The oxygen-absorbing sealed container according to the above <5-1>, in which the transition metal catalyst contains at least one transition metal selected from the group consisting of manganese, iron, cobalt, nickel and copper.

<5-3> The oxygen-absorbing sealed container according to the above <5-1> or <5-2>, in which the transition metal catalyst is contained in an amount of 0.001 to 10 parts by mass in terms of a transition metal based on 100 parts by mass of the copolymerized polyolefin compound.

<5-4> The oxygen-absorbing sealed container according to any one of the above <5-1> to <5-3>, in which a ratio of the content of the constituent unit (a) to the content of the constituent unit (b) contained in the copolymerized polyolefin compound is 1/99 to 99/1 by molar ratio.

<5-5> The oxygen-absorbing sealed container according to any one of the above <5-1> to <5-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

The present inventors further conducted intensive studies on an oxygen-absorbing paper container. As a result, they found that the aforementioned problems are solved by using an oxygen-absorbing resin composition containing a copolymerized polyolefin compound having a predetermined tetralin ring and a transition metal catalyst in at least one layer of a multilayer body constituting a paper container, and accomplished the present invention.

More specifically, the present invention provides the following <6-1> to <6-5>.

<6-1> An oxygen-absorbing paper container obtained by forming a carton of an oxygen-absorbing multilayer body comprising at least four layers comprising an isolation layer containing a thermoplastic resin, an oxygen-absorbing layer comprising an oxygen-absorbing resin composition containing a copolymerized polyolefin compound and a transition metal catalyst, a gas barrier layer containing a gas barrier substance and a paper substrate layer, laminated in this order, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<6-2> The oxygen-absorbing paper container according to the above <6-1>, in which the transition metal catalyst contains at least one transition metal selected from the group consisting of manganese, iron, cobalt, nickel and copper.

<6-3> The oxygen-absorbing paper container according to the above <6-1> or <6-2>, in which the transition metal catalyst is contained in an amount of 0.001 to 10 parts by mass in terms of a transition metal based on 100 parts by mass of the copolymerized polyolefin compound.

<6-4> The oxygen-absorbing paper container according to any one of the above <6-1> to <6-3>, in which a ratio of the content of the constituent unit (a) to the content of the constituent unit (b) contained in the copolymerized polyolefin compound is 1/99 to 99/1 by molar ratio.

<6-5> The oxygen-absorbing paper container according to any one of the above <6-1> to <6-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

The present inventors further conducted intensive studies on a tubular container. As a result, they found that the aforementioned problems are solved by using an oxygen-absorbing resin composition containing a copolymerized polyolefin compound having a predetermined tetralin ring and a transition metal catalyst in at least one layer of a multilayer body constituting a tubular container, and accomplished the present invention.

More specifically, the present invention provides the following <7-1> to <7-5>.

<7-1> A tubular container having an oxygen-absorbing multilayer body comprising at least three layers comprising an inner layer containing a thermoplastic resin, an oxygen-absorbing layer comprising an oxygen-absorbing resin composition containing a copolymerized polyolefin compound and a transition metal catalyst, and a gas barrier layer containing a gas barrier substance, laminated in this order, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<7-2> The tubular container according to the above <7-1>, in which the transition metal catalyst contains at least one transition metal selected from the group consisting of manganese, iron, cobalt, nickel and copper.

<7-3> The tubular container according to the above <7-1> or <7-2>, in which the transition metal catalyst is contained in an amount of 0.001 to 10 parts by mass in terms of a transition metal based on 100 parts by mass of the copolymerized polyolefin compound.

<7-4> The tubular container according to any one of the above <7-1> to <7-3>, in which a ratio of the content of the constituent unit (a) to the content of the constituent unit (b) contained in the copolymerized polyolefin compound is 1/99 to 99/1 by molar ratio.

<7-5> The tubular container according to any one of the above <7-1> to <7-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

The present inventors conducted intensive studies on an oxygen-absorbing medical multilayer molded container. As a result, they found that the aforementioned problems are solved by laminating an oxygen-absorbing layer using a copolymerized polyolefin compound having a predetermined tetralin ring and a transition metal catalyst and a resin layer using a polyester, and accomplished the present invention.

More specifically, the present invention provides the following <8-1> to <8-10>.

<8-1> An oxygen-absorbing medical multilayer molded container comprising at least three layers comprising a first resin layer at least containing a polyester, an oxygen-absorbing layer comprising an oxygen-absorbing resin composition containing a copolymerized polyolefin compound and a transition metal catalyst and a second resin layer at least containing a polyester, laminated in this order, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<8-2> The oxygen-absorbing medical multilayer molded container according to the above <8-1>, in which the transition metal catalyst contains at least one transition metal selected from the group consisting of manganese, iron, cobalt, nickel and copper.

<8-3> The oxygen-absorbing medical multilayer molded container according to the above <8-1> or <8-2>, in which the transition metal catalyst is contained in an amount of 0.001 to 10 parts by mass in terms of a transition metal based on 100 parts by mass of the copolymerized polyolefin compound.

<8-4> The oxygen-absorbing medical multilayer molded container according to any one of the above <8-1> to <8-3>, in which a ratio of the content of the constituent unit (a) to the content of the constituent unit (b) contained in the copolymerized polyolefin compound is 1/99 to 99/1 by molar ratio.

<8-5> The oxygen-absorbing medical multilayer molded container according to any one of the above <8-1> to <8-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

<8-6> The oxygen-absorbing medical multilayer molded container according to any one of the above <8-1> to <8-5>, in which the polyester contains a dicarboxylic acid unit, 70 mole % or more of which is derived from at least one dicarboxylic acid selected from the group consisting of terephthalic acid, isophthalic acid, 1,3-naphthalenedicarboxylic acid, 1,4-naphthalenedicarboxylic acid, 1,5-naphthalenedicarboxylic acid, 2,6-naphthalenedicarboxylic acid and 2,7-naphthalenedicarboxylic acid.

<8-7> The oxygen-absorbing medical multilayer molded container according to any one of the above <8-1> to <8-5>, in which the polyester contains a dicarboxylic acid unit, 70 mole % or more of which is derived from terephthalic acid.

<8-8> The oxygen-absorbing medical multilayer molded container according to any one of the above <8-1> to <8-5>, in which the polyester contains a dicarboxylic acid unit, 90 mole % or more of which is derived from terephthalic acid.

<8-9> The oxygen-absorbing medical multilayer molded container according to any one of the above <8-1> to <8-5>, in which the polyester contains a dicarboxylic acid unit, 70 mole % or more of which is derived from 2,6-naphthalenedicarboxylic acid.

<8-10> The oxygen-absorbing medical multilayer molded container according to any one of the above <8-1> to <8-5>, in which the polyester contains a dicarboxylic acid unit, 90 mole % or more of which has a 2,6-naphthalenedicarboxylic acid skeleton.

The present inventors conducted intensive studies on an oxygen-absorbing prefilled syringe. As a result, they found that the aforementioned problems are solved by laminating an oxygen-absorbing layer using a copolymerized polyolefin compound having a predetermined tetralin ring and a transition metal catalyst, and a resin layer using a polyester, and accomplished the present invention.

More specifically, the present invention provides the following <9-1> to <9-10>.

<9-1> An oxygen-absorbing prefilled syringe made capable of storing a medicinal agent in a sealed condition in advance and releasing the sealed condition to eject the medical agent at the time of use, in which the prefilled syringe comprises a multilayered structure having at least three layers comprising a first resin layer at least containing a polyester, an oxygen-absorbing layer comprising an oxygen-absorbing resin composition containing a copolymerized polyolefin compound and a transition metal catalyst and a second resin layer at least containing a polyester, laminated in this order, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<9-2> The oxygen-absorbing prefilled syringe according to the above <9-1>, in which the transition metal catalyst contains at least one transition metal selected from the group consisting of manganese, iron, cobalt, nickel and copper.

<9-3> The oxygen-absorbing prefilled syringe according to the above <9-1> or <9-2>, in which the transition metal catalyst is contained in an amount of 0.001 to 10 parts by mass in terms of a transition metal based on 100 parts by mass of the copolymerized polyolefin compound.

<9-4> The oxygen-absorbing prefilled syringe according to any one of the above <9-1> to <9-3>, in which a ratio of the content of the constituent unit (a) to the content of the constituent unit (b) contained in the copolymerized polyolefin compound is 1/99 to 99/1 by molar ratio.

<9-5> The oxygen-absorbing prefilled syringe according to any one of the above <9-1> to <9-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

<9-6> The oxygen-absorbing prefilled syringe according to any one of the above <9-1> to <9-5>, in which the polyester contains a dicarboxylic acid unit, 70 mole % or more of which is derived from at least one dicarboxylic acid selected from the group consisting of terephthalic acid, isophthalic acid, 1,3-naphthalenedicarboxylic acid, 1,4- naphthalenedicarboxylic acid, 1,5-naphthalenedicarboxylic acid, 2,6-naphthalenedicarboxylic acid and 2,7-naphthalenedicarboxylic acid.

<9-7> The oxygen-absorbing prefilled syringe according to any one of the above <9-1> to <9-5>, in which the polyester contains a dicarboxylic acid unit, 70 mole % or more of which is derived from terephthalic acid.

<9-8> The oxygen-absorbing prefilled syringe according to any one of the above <9-1> to <9-5>, in which the polyester contains a dicarboxylic acid unit, 90 mole % or more of which is derived from terephthalic acid.

<9-9> The oxygen-absorbing prefilled syringe according to any one of the above <9-1> to <9-5>, in which the polyester contains a dicarboxylic acid unit, 70 mole % or more of which is derived from 2,6-naphthalenedicarboxylic acid.

<9-10> The oxygen-absorbing prefilled syringe according to any one of the above <9-1> to <9-5>, in which the polyester contains a dicarboxylic acid unit, 90 mole % or more of which has a 2,6-naphthalenedicarboxylic acid skeleton.

The present inventors conducted intensive studies on a method for storing a biopharmaceutical. As a result, they found that the aforementioned problems are solved by laminating an oxygen-absorbing layer using a copolymerized polyolefin compound having a predetermined tetralin ring and a transition metal catalyst, and a resin layer using a polyester, and accomplished the present invention.

More specifically, the present invention provides the following <10-1> to <10-10>.

<10-1> A method for storing a biopharmaceutical in an oxygen-absorbing medical multilayer molded container comprising at least three layers comprising a first resin layer at least containing a polyester, an oxygen-absorbing layer comprising an oxygen-absorbing resin composition containing a copolymerized polyolefin compound and a transition metal catalyst, and a second resin layer at least containing a polyester, laminated in this order, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<10-2> The method for storing a biopharmaceutical according to the above <10-1>, in which the transition metal catalyst contains at least one transition metal selected from the group consisting of manganese, iron, cobalt, nickel and copper.

<10-3> The method for storing a biopharmaceutical according to the above <10-1> or <10-2>, in which the transition metal catalyst is contained in an amount of 0.001 to 10 parts by mass in terms of a transition metal based on 100 parts by mass of the copolymerized polyolefin compound.

<10-4> The method for storing a biopharmaceutical according to any one of the above <10-1> to <10-3>, in which a ratio of the content of the constituent unit (a) to the content of the constituent unit (b) contained in the copolymerized polyolefin compound is 1/99 to 99/1 by molar ratio.

<10-5> The method for storing a biopharmaceutical according to any one of the above <10-1> to <10-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

<10-6> The method for storing a biopharmaceutical according to any one of the above <10-1> to <10-5>, in which the polyester contains a dicarboxylic acid unit, 70 mole % or more of which is derived from at least one dicarboxylic acid selected from the group consisting of terephthalic acid, isophthalic acid, 1,3-naphthalenedicarboxylic acid, 1,4-naphthalenedicarboxylic acid, 1,5-naphthalenedicarboxylic acid, 2,6-naphthalenedicarboxylic acid and 2,7-naphthalenedicarboxylic acid.

<10-7> The method for storing a biopharmaceutical according to any one of the above <10-1> to <10-5>, in which the polyester contains a dicarboxylic acid unit, 70 mole % or more of which is derived from terephthalic acid.

<10-8> The method for storing a biopharmaceutical according to any one of the above <10-1> to <10-5>, in which the polyester contains a dicarboxylic acid unit, 90 mole % or more of which is derived from terephthalic acid.

<10-9> The method for storing a biopharmaceutical according to any one of the above <10-1> to <10-5>, in which the polyester contains a dicarboxylic acid unit, 70 mole % or more of which is derived from 2,6-naphthalenedicarboxylic acid.

<10-10> The method for storing a biopharmaceutical according to any one of the above <10-1> to <10-5>, in which the polyester contains a dicarboxylic acid unit, 90 mole % or more of which has a 2,6-naphthalenedicarboxylic acid skeleton.

The present inventors further conducted intensive studies on a method for storing a container filled with a drug solution. As a result, they found that the aforementioned problems are solved by storing a container filled with a drug solution in a container using an oxygen-absorbing resin composition composed of a copolymerized polyolefin compound having a predetermined tetralin ring and a transition metal catalyst as one of the layers constituting the container, and accomplished the present invention.

More specifically, the present invention provides the following <11-1> to <11-5>

<11-1> A method for storing a container filled with a drug solution in an oxygen-absorbing container using an oxygen-absorbing multilayer body comprising at least three layers comprising a sealant layer containing a thermoplastic resin, an oxygen-absorbing layer comprising an oxygen-absorbing resin composition containing a copolymerized polyolefin compound and a transition metal catalyst, and a gas barrier layer containing a gas barrier substance, laminated in this order, in whole or in part, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<11-2> The method for storing a container filled with a drug solution according to the above <11-1>, in which the transition metal catalyst contains at least one transition metal selected from the group consisting of manganese, iron, cobalt, nickel and copper.

<11-3> The method for storing a container filled with a drug solution according to the above <11-1> or <11-2>, in which the transition metal catalyst is contained in an amount of 0.001 to 10 parts by mass in terms of a transition metal based on 100 parts by mass of the copolymerized polyolefin compound.

<11-4> The method for storing a container filled with a drug solution according to any one of the above <11-1> to <11-3>, in which a ratio of the content of the constituent unit (a) to the content of the constituent unit (b) contained in the copolymerized polyolefin compound is 1/99 to 99/1 by molar ratio.

<11-5> The method for storing a container filled with a drug solution according to any one of the above <11-1> to <11-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

The present inventors conducted intensive studies on a method for storing a patch containing a medicinal ingredient. As a result, they found that the aforementioned problems are solved by storing a patch containing a medicinal ingredient in a container using an oxygen-absorbing resin composition containing a copolymerized polyolefin compound having a predetermined tetralin ring and a transition metal catalyst, and accomplished the present invention.

More specifically, the present invention provides the following <12-1> to <12-5>.

<12-1> A method for storing a patch containing a medicinal ingredient, in an oxygen-absorbing container using an oxygen-absorbing multilayer body comprising at least three layers comprising a sealant layer containing a thermoplastic resin, an oxygen-absorbing layer comprising an oxygen-absorbing resin composition containing a copolymerized polyolefin compound and a transition metal catalyst, and a gas barrier layer containing a gas barrier substance, laminated in this order, in whole or in part, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<12-2> The method for storing a patch containing a medicinal ingredient according to the above <12-1>, in which the transition metal catalyst contains at least one transition metal selected from the group consisting of manganese, iron, cobalt, nickel and copper.

<12-3> The method for storing a patch containing a medicinal ingredient according to the above <12-1> or <12-2>, in which the transition metal catalyst is contained in an amount of 0.001 to 10 parts by mass in terms of a transition metal based on 100 parts by mass of the copolymerized polyolefin compound.

<12-4> The method for storing a patch containing a medicinal ingredient according to any one of the above <12-1> to <12-3>, in which a ratio of the content of the constituent unit (a) to the content of the constituent unit (b) contained in the copolymerized polyolefin compound is 1/99 to 99/1 by molar ratio.

<12-5> The method for storing a patch containing a medicinal ingredient according to any one of the above <12-1> to <12-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

The present inventors conducted intensive studies on an oxygen-absorbing PTP packaging body. As a result, they found that the aforementioned problems are solved by using an oxygen-absorbing resin composition containing a copolymerized polyolefin compound having a predetermined tetralin ring and a transition metal catalyst, and accomplished the present invention.

More specifically, the present invention provides the following <13-1> to <13-5>.

<13-1> An oxygen-absorbing PTP packaging body comprising an oxygen-absorbing bottom material formed of an oxygen-absorbing multilayer body comprising at least three layers comprising a sealant layer containing a thermoplastic resin, an oxygen-absorbing layer comprising an oxygen-absorbing resin composition containing a copolymerized polyolefin compound and a transition metal catalyst and a gas barrier layer containing a gas barrier substance, laminated in this order; and a gas barrier cover material comprising at least two layer comprising an inner layer containing a thermoplastic resin and a gas barrier layer containing a gas barrier substance, laminated in this order, in which the sealant layer of the oxygen-absorbing bottom material and the inner layer of the gas barrier cover material are bonded, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<13-2> The oxygen-absorbing PTP packaging body according to the above <13-1>, in which the transition metal catalyst contains at least one transition metal selected from the group consisting of manganese, iron, cobalt, nickel and copper.

<13-3> The oxygen-absorbing PTP packaging body according to the above <13-1> or <13-2>, in which the transition metal catalyst is contained in an amount of 0.001 to 10 parts by mass in terms of a transition metal based on 100 parts by mass of the copolymerized polyolefin compound.

<13-4> The oxygen-absorbing PTP packaging body according to any one of the above <13-1> to <13-3>, in which a ratio of the content of the constituent unit (a) to the content of the constituent unit (b) contained in the copolymerized polyolefin compound is 1/99 to 99/1 by molar ratio.

<13-5> The oxygen-absorbing PTP packaging body according to any one of the above <13-1> to <13-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

The present inventors further conducted intensive studies on an oxygen-absorbing multilayer bottle. As a result, they found that the aforementioned problems are solved by using a copolymerized polyolefin compound having a predetermined tetralin ring and a transition metal catalyst in at least one layer of a multilayer bottle, and accomplished the present invention.

More specifically, the present invention provides the following <14-1> to <14-6>.

<14-1> An oxygen-absorbing multilayer bottle having at least three layers comprising an oxygen transmission layer containing a thermoplastic resin, an oxygen-absorbing layer comprising an oxygen-absorbing resin composition containing a copolymerized polyolefin compound and a transition metal catalyst and a gas barrier layer containing a gas barrier substance, laminated in this order from inside, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<14-2> The oxygen-absorbing multilayer bottle according to the above <14-1>, in which the transition metal catalyst contains at least one transition metal selected from the group consisting of manganese, iron, cobalt, nickel and copper.

<14-3> The oxygen-absorbing multilayer bottle according to the above <14-1> or <14-2>, in which the transition metal catalyst is contained in an amount of 0.001 to 10 parts by mass in terms of a transition metal based on 100 parts by mass of the copolymerized polyolefin compound.

<14-4> The oxygen-absorbing multilayer bottle according to any one of the above <14-1> to <14-3>, in which a ratio of the content of the constituent unit (a) to the content of the constituent unit (b) contained in the copolymerized polyolefin compound is 1/99 to 99/1 by molar ratio.

<14-5> The oxygen-absorbing multilayer bottle according to any one of the above <14-1> to <14-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

<14-6> The oxygen-absorbing multilayer bottle according to any one of the above <14-1> to <14-5>, in which the oxygen-absorbing multilayer bottle is obtained by coextrusion blow molding.

The present inventors conducted intensive studies on a method for storing fruit pulps. As a result, they found that the aforementioned problems are solved by storing fruit pulps in a container using an oxygen-absorbing resin composition containing a copolymerized polyolefin compound having a predetermined tetralin ring and a transition metal catalyst, as one of the layers constituting the container, and accomplished the present invention.

More specifically, the present invention provides the following <15-1> to <15-5>.

<15-1> A method for storing fruit pulps in an oxygen-absorbing container using an oxygen-absorbing multilayer body comprising at least three layers comprising a sealant layer containing a thermoplastic resin, an oxygen-absorbing layer comprising an oxygen-absorbing resin composition containing a copolymerized polyolefin compound and a transition metal catalyst and a gas barrier layer containing a gas barrier substance, laminated in this order, in whole or in part, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<15-2> The method for storing fruit pulps according to the above <15-1>, in which the transition metal catalyst contains at least one transition metal selected from the group consisting of manganese, iron, cobalt, nickel and copper.

<15-3> The method for storing fruit pulps according to the above <15-1> or <15-2>, in which the transition metal catalyst is contained in an amount of 0.001 to 10 parts by mass in terms of a transition metal based on 100 parts by mass of the copolymerized polyolefin compound.

<15-4> The method for storing fruit pulps according to any one of the above <15-1> to <15-3>, in which a ratio of the content of the constituent unit (a) to the content of the constituent unit (b) contained in the copolymerized polyolefin compound is 1/99 to 99/1 by molar ratio.

<15-5> The method for storing fruit pulps according to any one of the above <15-1> to <15-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

The present inventors conducted studies on a method for storing an alcohol beverage. As a result, they found that the aforementioned problems are solved by storing the alcohol beverage in a container using an oxygen-absorbing resin composition containing a copolymerized polyolefin compound having a predetermined tetralin ring and a transition metal catalyst as one of the layers constituting the container, and accomplished the present invention.

More specifically, the present invention provides the following <16-1> to <16-5>.

<16-1> A method for storing an alcohol beverage in an oxygen-absorbing container using an oxygen-absorbing multilayer body comprising at least three layers comprising a sealant layer containing a thermoplastic resin, an oxygen-absorbing layer comprising an oxygen-absorbing resin composition containing a copolymerized polyolefin compound and a transition metal catalyst and a gas barrier layer containing a gas barrier substance, laminated in this order, in whole or in part, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<16-2> The method for storing an alcohol beverage according to the above <16-1>, in which the transition metal catalyst contains at least one transition metal selected from the group consisting of manganese, iron, cobalt, nickel and copper.

<16-3> The method for storing an alcohol beverage according to the above <16-1> or <16-2>, in which the transition metal catalyst is contained in an amount of 0.001 to 10 parts by mass in terms of a transition metal based on 100 parts by mass of the copolymerized polyolefin compound.

<16-4> The method for storing an alcohol beverage according to any one of the above <16-1> to <16-3>, in which a ratio of the content of the constituent unit (a) to the content of the constituent unit (b) contained in the copolymerized polyolefin compound is 1/99 to 99/1 by molar ratio.

<16-5> The method for storing an alcohol beverage according to any one of the above <16-1> to <16-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

The present inventors conducted studies on a method for storing a liquid-state tea or a paste-state tea. As a result, they found that the aforementioned problems are solved by storing the liquid-state tea or the paste-state tea in a container using an oxygen-absorbing resin composition containing a copolymerized polyolefin compound having a predetermined tetralin ring and a transition metal catalyst as one of the layers constituting the container, and accomplished the present invention.

More specifically, the present invention provides the following <17-1> to <17-5>.

<17-1> A method for storing liquid-state tea or paste-state tea in an oxygen-absorbing container using an oxygen-absorbing multilayer body comprising at least three layers comprising a sealant layer containing a thermoplastic resin, an oxygen-absorbing layer comprising an oxygen-absorbing resin composition containing a copolymerized polyolefin compound and a transition metal catalyst and a gas barrier layer containing a gas barrier substance, laminated in this order, in whole or in part, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<17-2> The method for storing liquid-state tea or paste-state tea according to the above <17-1>, in which the transition metal catalyst contains at least one transition metal selected from the group consisting of manganese, iron, cobalt, nickel and copper.

<17-3> The method for storing liquid-state tea or paste-state tea according to the above <17-1> or <17-2>, in which the transition metal catalyst is contained in an amount of 0.001 to 10 parts by mass in terms of a transition metal based on 100 parts by mass of the copolymerized polyolefin compound.

<17-4> The method for storing liquid-state tea or paste-state tea according to any one of the above <17-1> to <17-3>, in which a ratio of the content of the constituent unit (a) to the content of the constituent unit (b) contained in the copolymerized polyolefin compound is 1/99 to 99/1 by molar ratio.

<17-5> The method for storing liquid-state tea or paste-state tea according to any one of the above <17-1> to <17-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

The present inventors further conducted studies on a method for storing a fruit juice and/or a vegetable juice. As a result, they found that the aforementioned problems are solved by storing the fruit juice and/or a vegetable juice in a container using an oxygen-absorbing resin composition containing a copolymerized polyolefin compound having a predetermined tetralin ring and a transition metal catalyst as one of the layers constituting the container, and accomplished the present invention.

More specifically, the present invention provides the following <18-1> to <18-5>.

<18-1> A method for storing fruit juice and/or vegetable juice in an oxygen-absorbing container using an oxygen-absorbing multilayer body comprising at least three layers comprising a sealant layer containing a thermoplastic resin, an oxygen-absorbing layer comprising an oxygen-absorbing resin composition containing a copolymerized polyolefin compound and a transition metal catalyst and a gas barrier layer containing a gas barrier substance, laminated in this order, in whole or in part, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<18-2> The method for storing fruit juice and/or vegetable juice according to the above <18-1>, in which the transition metal catalyst contains at least one transition metal selected from the group consisting of manganese, iron, cobalt, nickel and copper.

<18-3> The method for storing fruit juice and/or vegetable juice according to the above <18-1> or <18-2>, in which the transition metal catalyst is contained in an amount of 0.001 to 10 parts by mass in terms of a transition metal based on 100 parts by mass of the copolymerized polyolefin compound.

<18-4> The method for storing fruit juice and/or vegetable juice according to any one of the above <18-1> to <18-3>, in which a ratio of the content of the constituent unit (a) to the content of the constituent unit (b) contained in the copolymerized polyolefin compound is 1/99 to 99/1 by molar ratio.

<18-5> The method for storing fruit juice and/or vegetable juice according to any one of the above <18-1> to <18-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

The present inventors conducted intensive studies on a method for storing dry products. As a result, they found that the aforementioned problems are solved by storing dry products in a container using an oxygen-absorbing resin composition containing a copolymerized polyolefin compound having a predetermined tetralin ring and a transition metal catalyst as one of the layers constituting the container, and accomplished the present invention.

More specifically, the present invention provides the following <19-1> to <19-5>.

<19-1> A method for storing a dry product in an oxygen-absorbing container using an oxygen-absorbing multilayer body comprising at least three layers comprising a sealant layer containing a thermoplastic resin, an oxygen-absorbing layer comprising an oxygen-absorbing resin composition containing a copolymerized polyolefin compound and a transition metal catalyst and a gas barrier layer containing a gas barrier substance, laminated in this order, in whole or in part, in which the copolymerized polyolefin compound contains at least one constituent unit (a) selected from the group consisting of the constituent units represented by the above general formula (1) and at least one constituent unit (b) having a tetralin ring, selected from the group consisting of the constituent units represented by the above general formulas (2) and (3).

<19-2> The method for storing dry products according to the above <19-1>, in which the transition metal catalyst contains at least one transition metal selected from the group consisting of manganese, iron, cobalt, nickel and copper.

<19-3> The method for storing dry products according to the above <19-1> or <19-2>, in which the transition metal catalyst is contained in an amount of 0.001 to 10 parts by mass in terms of a transition metal based on 100 parts by mass of the copolymerized polyolefin compound.

<19-4> The method for storing dry products according to any one of the above <19-1> to <19-3>, in which a ratio of the content of the constituent unit (a) to the content of the constituent unit (b) contained in the copolymerized polyolefin compound is 1/99 to 99/1 by molar ratio.

<19-5> The method for storing dry products according to any one of the above <19-1> to <19-4>, in which the constituent unit (a) is at least one constituent unit selected from the group consisting of the constituent units represented by the above formulas (4) and (5), and the constituent unit (b) is at least one constituent unit selected from the group consisting of the constituent units represented by the above formulas (6) and (7).

Advantageous Effects of Invention

According to some aspects of the present invention, it is possible to provide an oxygen-absorbing resin composition and an oxygen-absorbing multilayer body; an oxygen-absorbing multilayer container containing the multilayer body; an oxygen-absorbing multilayer container; an oxygen-absorbing sealed container using an oxygen-absorbing multilayer body as a cover material for a gas barrier molded container; an oxygen-absorbing paper container; a tubular container; an oxygen-absorbing PTP packaging body using the oxygen-absorbing multilayer body as a bottom material; oxygen-absorbing multilayer bottle; and a method for storing a container filled with a drug solution and a patch containing a medicinal ingredient by using the oxygen-absorbing multilayer body, which have excellent oxygen-absorbing performance in a wide range of humidity conditions from low humidity to high humidity. The oxygen-absorbing resin composition etc., since they can absorb oxygen regardless of the presence or absence of the moisture content of an article to be packaged and produce no odor after absorption of oxygen, can be applied to a wide variety of uses including foods, cooking foods, beverages, medicinal products and health foods, no matter what products they are. Furthermore, it is also possible to provide an oxygen-absorbing resin composition etc. not responsive to a metal detector. According to a preferable aspect of the present invention, since a reduction in strength of a copolymerized polyolefin compound by oxidation is extremely low even after absorption of oxygen, and the strength of the oxygen-absorbing layer is maintained even for long-term use, it is possible to realize an oxygen-absorbing multilayer body and an oxygen-absorbing multilayer container containing the multilayer body, an oxygen-absorbing multilayer container, an oxygen-absorbing sealed container using the oxygen-absorbing multilayer body as a cover material for a gas barrier molded container, an oxygen-absorbing paper container, a tubular container and an oxygen-absorbing multilayer bottle, which rarely have interlayer peeling. In addition, since the oxygen-absorbing multilayer body has satisfactory visibility of a content, a container filled with a drug solution and a patch containing a medicinal ingredient can be suitably stored and suitably used as a bottom material for an oxygen-absorbing PTP packaging body.

Furthermore, according to the present invention, it is possible to provide an oxygen-absorbing medical multilayer molded container, such as a vial and a prefilled syringe, having excellent oxygen-absorbing performance in a wide range of humidity conditions from low humidity to high humidity and satisfactory oxygen barrier property and, in a preferable aspect, further excellent water vapor barrier property. Such an oxygen-absorbing medical multilayer molded container can absorb oxygen regardless of the presence or absence of the moisture content of an article to be packaged. Since a reduction in strength of the copolymerized polyolefin compound having a tetralin ring by oxidation is extremely low even after absorption of oxygen, and the strength of the oxygen-absorbing layer is maintained even for long-term use, it is possible to realize an oxygen-absorbing medical multilayer molded container and an oxygen-absorbing PTP packaging body rarely having interlayer peeling and thus an article to be packaged can be suitably stored. In addition, since production of low-molecular weight organic compounds is significantly suppressed after absorption of oxygen, it is possible to realize an oxygen-absorbing medical multilayer molded container in which contamination of the content with low-molecular weight organic compound is extremely low. Because of this, the oxygen-absorbing medical multilayer molded container of the present invention is particularly useful in storing medicinal products, biopharmaceuticals, medical supplies, etc. requiring storage under a low oxygen concentration.

According to the present invention, since a biopharmaceutical can be stored under low oxygen concentration, deterioration and efficacy reduction of a biopharmaceutical can be suppressed. According to the present invention, since the medical multilayer container used in the present invention suppresses generation of low-molecular weight organic compounds after absorption of oxygen, it is possible to prevent contamination of a content with impurities. According to the present invention, in the medical multilayer container to be used in the present invention, since degradation of a copolymerized polyolefin compound having a tetralin ring by oxidation is extremely low even after absorption of oxygen and the strength of the container is maintained even in long-term use, a biopharmaceutical can be stored for a long-term.

According to the present invention, it is possible to provide a method for storing fruit pulps, alcohol beverages, liquid-state teas or paste-state teas, fruit juices and/or vegetable juices and dry products without degrading taste and flavor of fruit pulps, alcohol beverages, liquid-state teas or paste-state teas, fruit juices and/or vegetable juices and dry products and generating odor while maintaining color tone of them. Furthermore, even after long-term storage, the containers storing them maintain their strength.

DESCRIPTION OF EMBODIMENTS

Now, embodiments of the present invention will be described below. Note that the following embodiments are examples for explaining the present invention and the present invention is not limited to the embodiments alone.
(First Embodiment)
[Oxygen-absorbing Resin Composition]
The oxygen-absorbing resin composition of the embodiment at least contains a copolymerized polyolefin compound (hereinafter, simply referred to as "tetralin ring-containing copolymerized polyolefin compound") containing a constituent unit (a), which is at least one ethylene or substituted ethylene constituent unit selected from the group consisting of the constituent units represented by the above general formula (1) and a constituent unit (b), which is at least one substituted ethylene constituent unit having a tetralin ring selected from the group consisting of the constituent units represented by the above general formula (2) or (3); and a transition metal catalyst.

<Tetralin Ring-containing Copolymerized Polyolefin Compound>

The tetralin ring-containing copolymerized polyolefin compound of the embodiment contains a constituent unit (a), which is at least one ethylene or substituted ethylene constituent unit selected from the group consisting of the constituent units represented by the above general formula (1) and a constituent unit (b), which is at least one substituted ethylene constituent unit having a tetralin ring selected from the group consisting of the constituent units represented by the above general formulas (2) and (3).

The constituent unit (a) represented by the above general formula (1) is preferably at least one selected from the group consisting of the constituent units represented by the above formulas (4) and (5), and the constituent unit (b) represented by the above general formula (2) is preferably at least one selected from the group consisting of the constituent units represented by the above formulas (6) and (7). The phrase "containing a constituent unit" herein means that one or more constituent units are contained in a compound. Such a constituent unit is preferably contained as a repeat unit in a tetralin ring-containing copolymerized polyolefin compound. The tetralin ring-containing copolymerized polyolefin compound may be either a random copolymer of the constituent unit (a) and the constituent unit (b) or a block copolymer of the constituent unit (a) and constituent unit (b). Alternatively, the type of copolymerization of the constituent units may be, for example, either one of alternative copolymerization and graft copolymerization.

The tetralin ring-containing copolymerized polyolefin compound may contain constituent unit(s) other than the constituent unit (a) and the constituent unit (b) and may be either one of a random copolymer of the constituent unit (a), the constituent unit (b) and other constituent unit(s) and a block copolymer of the above constituent unit (a), the constituent unit (b) and other constituent unit(s). Alternatively, the type of copolymerization of these constituent units may be, for example, either one of alternative copolymerization and graft copolymerization.

In the constituent units represented by the above general formulas (1) to (3), examples of the monovalent substituent (first monovalent substituent, second monovalent substituent, and third monovalent substituent) represented by $R_1$, $R_2$, $R_3$, $R_4$, $R_5$, $R_6$, $R_7$, $R_8$, $R_9$, $R_{10}$ and $R_{11}$ (hereinafter referred to as "$R_1$ to $R_{11}$") include, but not particularly limited to, a halogen atom (for example, a chlorine atom, a bromine atom, an iodine atom), an alkyl group (a linear, branched or cyclic alkyl group having preferably 1 to 15 carbon atoms and more preferably 1 to 6 carbon atoms, such as a methyl group, an ethyl group, a n-propyl group, an isopropyl group, a t-butyl group, a n-octyl group, a 2-ethylhexyl group, a cyclopropyl group, and a cyclopentyl group), an alkenyl group (a linear, branched or cyclic alkenyl group having preferably 2 to 10 carbon atoms and more preferably 2 to 6 carbon atoms, such as a vinyl group and an allyl group), an alkynyl group (an alkynyl group having preferably 2 to 10 carbon atoms and more preferably 2 to 6 carbon atoms, such as an ethynyl group and a propargyl group), an aryl group (an aryl group having preferably 6 to 16 carbon atoms and more preferably 6 to 10 carbon atoms, such as a phenyl group and a naphthyl group), a heterocyclic group (a monovalent group obtained by removing a single hydrogen atom from a 5-member or 6-member aromatic or non-aromatic heterocyclic compound having preferably 1 to 12 carbon atoms and more preferable 2 to 6 carbon atoms, such as a 1-pyrazolyl group, a 1-imidazolyl group and a 2-furyl group), a cyano group, a hydroxy group, a carboxyl group, an ester group, an amido group, a nitro group, an alkoxy group (linear, branched or cyclic alkoxy group having preferably 1 to 10 carbon atoms and more preferably 1 to 6 carbon atoms, such as a methoxy group and an ethoxy group), an aryloxy group (an aryloxy group having preferably 6 to 12 carbon atoms and more preferably 6 to 8 carbon atoms, such as a phenoxy group), an acyl group (including a formyl group. An alkyl carbonyl group having preferably 2 to 10 carbon atoms and more preferably 2 to 6 carbon atoms, and an arylcarbonyl group having preferably 7 to 12 carbon atoms and more preferably 7 to 9 carbon atoms, such as an acetyl group, a pivaloyl group and a benzoyl group), an amino group (an alkylamino group having preferably 1 to 10 carbon atoms and more preferably 1 to 6 carbon atoms, an anilino group having preferably 6 to 12 carbon atoms and more preferably 6 to 8 carbon atoms, a heterocyclic amino group having preferably 1 to 12 carbon atoms and more preferably 2 to 6 carbon atoms, such as an amino group, a methylamino group and an anilino group), a mercapto group, an alkylthio group (an alkylthio group having preferably 1 to 10 carbon atoms and more preferably 1 to 6 carbon atoms, such as a methylthio group and an ethylthio group), an arylthio group (an arylthio group having preferably 6 to 12 carbon atoms and more preferably 6 to 8 carbon atoms, such as a phenylthio group), a heterocyclic thio group (a heterocyclic thio group having preferably 2 to 10 carbon atoms and more preferably 1 to 6 carbon atoms, such as a 2-benzothiazolylthio group), an imido group (an imido group having preferably 2 to 10 carbon atoms and more preferably 4 to 8 carbon atoms, such as a N-succinimido group and a N-phthalimido group).

Note that when the above monovalent substituents $R_1$ to $R_{11}$ have a hydrogen atom, the hydrogen atom may be further substituted with a substituent T (herein, substituent T is the same as defined in the above monovalent substituents $R_1$ to $R_{11}$). Specific examples thereof include, but not particularly limited to, an alkyl group substituted with a hydroxy group (for example, a hydroxyethyl group), an alkyl group substituted with an alkoxy group (for example, a methoxyethyl group), an alkyl group substituted with an aryl group (for example, a benzyl group), an alkyl group substituted with a primary or secondary amino group (for example, an aminoethyl group), an aryl group substituted with an alkyl group (for example, a p-tolyl group) and an aryloxy group substituted with an alkyl group (for example, a 2-methylphenoxy group). Note that when the monovalent substituents $R_1$ to $R_{11}$ have a monovalent substituent T, the number of carbon atoms of the substituent T is not included in the number of carbon atoms mentioned above. For example, a benzyl group is regarded as an alkyl group having a single carbon atom substituted with a phenyl group and not regarded as an alkyl group having 7 carbon atoms substituted with a phenyl group. Furthermore, when the above monovalent substituents $R_1$ to $R_{11}$ have a substituent T, the substituent T may be plural.

In the constituent unit represented by the above general formula (2) or (3), X represents a bivalent group selected from the group consisting of —(C=O)O—, —(C=O)NH—, —O(C=O)—, —NH(C=O)— and —(CHR)s— where s represents an integer of 0 to 12; Y represents —(CHR)t— where t represents an integer of 0 to 12; and R represents a monovalent chemical species selected from the group consisting of a hydrogen atom (—H), a methyl group (—CH$_3$) and an ethyl group (—C$_2$H$_5$).

The tetralin ring-containing copolymerized polyolefin compound of the embodiment can be obtained by copolymerizing a vinyl compound (I) having a tetralin ring and another type of vinyl compound (II).

Examples of the vinyl compound (I) having a tetralin ring and to be used in the embodiment include a vinyl compound selected from the group consisting of the compounds represented by the following general formulas (8) and (9). The vinyl compounds (I) having a tetralin ring can be used alone or in combination with two or more.

[Formula 5]

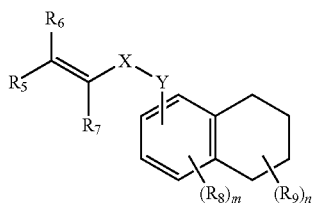
(8)

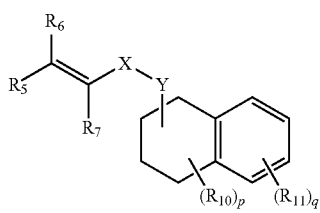
(9)

where, $R_5$ to $R_7$ each independently represent a hydrogen atom or a second monovalent substituent; $R_8$ to $R_{11}$ each independently represent a third monovalent substituent; the second monovalent substituent and the third monovalent substituent each independently represent at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a mercapto group, an alkylthio group, an arylthio group, a heterocyclic thio group and an imido group, which may further have a substituent; if a plurality of elements are present as $R_8$, $R_9$, $R_{10}$ or $R_{11}$, the plural elements of each of $R_8$, $R_9$, $R_{10}$ and $R_{11}$ may mutually the same or different; m represents an integer of 0 to 3; n represents an integer of 0 to 7, p represents an integer of 0 to 6, and q represents an integer of 0 to 4; at least one hydrogen atom is bound to a benzyl position of the tetralin ring; X represents a bivalent group selected from the group consisting of —(C=O)O—, —(C=O)NH—, —O(C=O)—, —NH(C=O)— and —(CHR)s- where s represents an integer of 0 to 12; Y represents —(CHR)t- where t represents an integer of 0 to 12; and R represents a monovalent chemical species selected from the group consisting of —H, —CH$_3$ and —C$_2$H$_5$.

Examples of the vinyl compound (II) to be used in the embodiment include a vinyl compound selected from the group consisting of the compounds represented by the following general formula (10). The vinyl compounds (II) can be used alone or in combination with two or more.

[Formula 6]

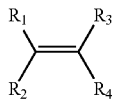
(10)

where $R_1$ to $R_4$ each independently represent a hydrogen atom or a first monovalent substituent, which is at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a mercapto group, an alkylthio group, an arylthio group, a heterocyclic thio group and an imido group which may further have a substituent.

Examples of the vinyl compound represented by the above general formula (10) include ethylenes or α-olefins having 2 to 20 carbon atoms such as ethylene, propylene, 1-butene, 1-pentene, 1-hexene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 1-octene, 1-decene, 1-dodecene, 1-tetradecene, 1-hexadecene, 1-octadecene and 1-eicosene; cycloolefins such as cyclobutene, cyclopentene, cyclohexene, 3,4-dimethylcyclopentene, 3-methylcyclohexene, 2-(2-methylbutyl)-1-cyclohexene and cyclooctene; non-conjugated dienes such as 1,4-hexadiene, 4-methyl-1,4-hexadiene, 5-methyl-1,4-hexadiene and 1,7-octadiene; conjugated dienes such as butadiene, isoprene, 2,3-dimethylbutadiene, pentadiene and hexadiene; styrenes such as styrene, α-methylstyrene, 2-methylstyrene, 4-methylstyrene, 4-propylstyrene, 4-tert-butylstyrene, 4-cyclohexylstyrene, 4-dodecylstyrene, 2-ethyl-4-benzylstyrene and 2,4,6-trimethylstyrene;

methyl (meth)acrylate, ethyl (meth)acrylate, n-propyl (meth)acrylate, i-propyl (meth)acrylate, n-butyl (meth)acrylate, i-butyl (meth)acrylate, sec-butyl (meth)acrylate, t-butyl (meth)acrylate, n-amyl (meth)acrylate, i-amyl (meth)acrylate, (meth)acryl acid, crotonic acid, cinnamic acid, maleic acid, fumaric acid, itaconic acid, monomethyl maleate, monoethyl maleate, hydroxymethyl (meth)acrylate, 2-hydroxyethyl (meth)acrylate, 2-hydroxypropyl (meth)acrylate, 3-hydroxypropyl (meth)acrylate, 2-dimethylaminoethyl (meth)acrylate, 2-diethylaminoethyl (meth)acrylate, 2-dimethylaminopropyl (meth)acrylate, (meth)acrylonitrile, α-chloroacrylonitrile, ethacrylonitrile, 2-cyanoethyl (meth)acrylate, 2-cyanopropyl (meth)acrylate, (meth)acrylamide, α-chloro(meth)acrylamide, ethacrylamide, N-methyl (meth)acrylamide, N-vinyl-ε-caprolactum, N-vinylpyrrolidone, 2-nitroethyl (meth)acrylate and 3-nitropropyl (meth)acrylate. These can be used alone or in combination with two or more. Note that the (meth)acrylate refers to an acrylate and the methacrylate corresponding to the acrylate, and (meth) acrylic acid refers to acrylic acid and methacrylic acid corresponding to the acrylic acid.

The tetralin ring-containing copolymerized polyolefin compound of the embodiment can be obtained by reacting a copolymerized polyolefin compound, which contains the above constituent unit (a) and a substituted ethylene constituent unit (c) containing a substituent having at least one naphthalene ring selected from the group consisting of the constituent units represented by the following general formula (11), and hydrogen.

[Formula 7]

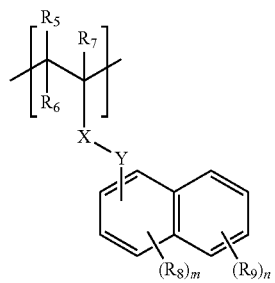

(11)

where, $R_5$ to $R_7$ each independently represent a hydrogen atom or a second monovalent substituent; $R_8$ and $R_9$ each independently represent a third monovalent substituent; the second monovalent substituent and the third monovalent substituent each independently represent at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a mercapto group, an alkylthio group, an arylthio group, a heterocyclic thio group and an imido group, which may further have a substituent; if a plurality of elements are present as $R_8$ or $R_9$, the plural elements of each of $R_8$ and $R_9$ may mutually the same or different; m represents an integer of 0 to 3; n 0 to 4, respectively; X represents a bivalent group selected from the group consisting of —(C=O)O—, —(C=O)NH—, —O(C=O)—, —NH(C=O)— and —(CHR)s- where s represents an integer of 0 to 12; Y represents —(CHR)t- where t represents an integer of 0 to 12; and R represents a monovalent chemical species selected from the group consisting of —H, —$CH_3$ and —$C_2H_5$.

Examples of a further different method for manufacturing a tetralin ring-containing copolymerized polyolefin compound of the embodiment include a method of reacting a polyolefin (III) having a reactive functional group at the side chain and a compound (IV) having a tetralin ring.

Examples of the polyolefin (III) having a reactive functional group at the side chain include unsaturated carboxylic acid polymers such as poly(meth)acrylic acid; unsaturated carboxylic acid ester polymers such as poly(methyl (meth) acrylate); poly(vinyl acetate) derivatives such as polyvinyl alcohol and poly(vinyl acetate); ethylene-unsaturated carboxylic acid copolymers; ethylene-unsaturated carboxylic acid ester copolymers; ethylene-vinyl alcohol copolymers; and maleic anhydride modified polyolefins such as maleic anhydride modified polyethylene and maleic anhydride modified polypropylene. These can be used alone or in combination with two or more.

As the above compound (IV) having a tetralin ring, a compound having a functional group, which easily binds to the polyolefin (III) having a reactive functional group at the side chain, is preferable. Examples thereof include alcohol compounds, amine compounds, carboxylic acid compounds, acid anhydride compounds and epoxide compounds having a tetralin ring. These can be used alone or in combination with two or more.

Particularly, the method for manufacturing the tetralin ring-containing copolymerized polyolefin compound preferably includes adding an alcohol compound having a tetralin ring serving as a compound (IV) having a tetralin ring as mentioned above and a transesterification catalyst to a solution obtained by dissolving a polyolefin having an ester group at the side chain serving as the polyolefin (III) having a reactive functional group at the side chain in an organic solvent to perform a transesterification reaction.

The transesterification reaction can be carried out in accordance with a method known in the art. The reaction temperature and reaction time are not particularly limited as long as they fall within the range where a transesterification reaction can be carried out. The reaction temperature is preferably 50 to 300° C. and the reaction time is preferably 10 minutes to 24 hours. The organic solvent to be used in the transesterification reaction is not particularly limited as long as it is an organic solvent that can dissolve a polymer. Examples of such an organic solvent include benzene, toluene, xylene and decalin.

As another method for the transesterification reaction, for example, a method of melt-kneading a polyolefin having an ester group at the side chain serving as the polyolefin (III) having a reactive functional group at the side chain, an alcohol compound having a tetralin ring serving as the compound (IV) having a tetralin ring and a transesterification catalyst by e.g., a single screw extruder, a double screw extruder or a kneader.

As the transesterification catalyst to be used in the transesterification reaction, a substance known in the art can be used. Examples thereof include sodium-tert-butoxide, sodium propoxide, sodium ethoxide, sodium hydroxide, tetraisopropyl titanate, tetrabutyl titanate, titanium oxide, titanium chloride, zirconium chloride, hafnium chloride, tin chloride, and metallocene complex catalysts such as titanium, zirconium and tin. These can be used alone or in combination of two types.

The molar ratio ((a)/(b)) of a ratio of the content of the constituent unit (a) to the content of the constituent unit (b) contained in the tetralin ring-containing copolymerized polyolefin compound of the embodiment is preferably 1/99 to 99/1, more preferably 1/19 to 19/1, and particularly preferably 1/9 to 9/1.

The melt mass flow rate (hereinafter, described as "MFR") of the tetralin ring-containing copolymerized polyolefin compound of the embodiment is not particularly limited, preferably 0.1 to 500 g/10 minutes at 190° C., and more preferably 0.2 to 100 g/10 minutes, in view of moldability. Note that, in the specification, unless otherwise specified, MFR refers to a value measured by an apparatus according to JIS K7210, at a predetermined temperature under application of a load of 2160 g and represented by a unit of "g/10 minutes" together with the measurement temperature.

Preferable examples of the constituent unit (a) include, but not limited to, the constituent units represented by the above formula (4) or (5).

Preferable examples of the constituent unit (b) include, but not limited to, the constituent units represented by the above formula (6) or (7) and the constituent units represented by the following formula (12) or (13).

[Formula 8]

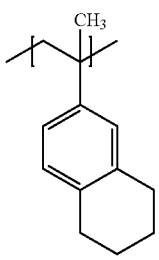

(12)

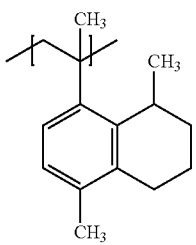

(13)

The molecular weight of the above tetralin ring-containing copolymerized polyolefin compounds, which can be appropriately specified in consideration of desired performance, handling property, etc., is not particularly limited. Generally, the weight average molecular weight (Mw) is preferably $1.0 \times 10^3$ to $8.0 \times 10^5$ and more preferably $5.0 \times 10^3$ to $5.0 \times 10^5$. Similarly, the number average molecular weight (Mn) thereof is preferably $1.0 \times 10^3$ to $1.0 \times 10^6$ and more preferably $5.0 \times 10^3$ to $1.0 \times 10^5$. Note that the molecular weights used herein each refer to a polystyrene equivalent value. Note that the above tetralin ring-containing copolymerized polyolefin compounds can be used alone or in combination with two or more.

The above tetralin ring-containing copolymerized polyolefin compounds all have hydrogen at the benzyl position of the tetralin ring. Since the hydrogen at the benzyl position is removed by using a tetralin ring-containing polyester compound in combination with a transition metal catalyst as described in detail below, more excellent oxygen absorptivity is exhibited.

The oxygen-absorbing resin composition of the embodiment is significantly suppressed in odor generation after absorption of oxygen. The reason is not elucidated; however, for example, the following oxidation reaction mechanism is presumable. In the tetralin ring-containing copolymerized polyolefin compound as mentioned above, first hydrogen at the benzyl position of the tetralin ring is removed to produce a radical. The radical then reacts with oxygen to oxidize carbon at the benzyl position. In this manner, a hydroxy group or a ketone group is considered to be produced. Because of this, it is presumed that, in the oxygen-absorbing resin composition of the embodiment, a molecular chain of a main oxygen-absorbing component is not cut by an oxidation reaction as is in the prior art and the structure of a tetralin ring-containing copolymerized polyolefin compound is maintained, with the result that a low molecular weight organic compound serving as a cause of odor is rarely produced after absorption of oxygen.

<Transition Metal Catalyst>

As the transition metal catalyst to be used in the oxygen-absorbing resin composition of the embodiment, any catalyst known in the art can be appropriately selected and used as long as it can serve as a catalyst for the oxidation reaction of a tetralin ring-containing copolymerized polyolefin compound as mentioned above. The transition metal catalyst is not particularly limited.

Specific examples of such a transition metal catalyst include organic acid salts, halides, phosphates, phosphites, hypophosphites, nitrates, sulfates, oxides and hydroxides of transition metals. Examples of the transition metal to be contained in the transition metal catalyst include, but not limited to, titanium, vanadium, chromium, manganese, iron, cobalt, nickel, copper, zinc, ruthenium and rhodium. Of them, manganese, iron, cobalt, nickel and copper are preferable. Examples of the organic acids include, but not limited to, acetic acid, propionic acid, octanoic acid, lauric acid, stearic acid, acetylacetone, dimethyldithiocarbamic acid, palmitic acid, 2-ethylhexanoic acid, neodecanoic acid, linoleic acid, tall acid, oleic acid, capric acid and naphthenic acid. As the transition metal catalyst, a combination of a transition metal as mentioned above and an organic acid is preferable. The transition metal is more preferably manganese, iron, cobalt, nickel or copper, and further preferably, manganese, iron or cobalt. The organic acid is more preferably acetic acid, stearic acid, 2-ethylhexanoic acid, oleic acid or naphthenic acid, and further preferably, acetic acid and stearic acid. A combination of any one of these transition metals and any one of these organic acids is particularly preferable. Note that transition metal catalysts can be used alone or in combination with two or more.

In the oxygen-absorbing resin composition of the embodiment, the content rate of a tetralin ring-containing copolymerized polyolefin compound and a transition metal catalyst, which can be appropriately specified depending upon the types of tetralin ring-containing copolymerized polyolefin compound and transition metal catalyst to be used and the desired performances thereof, is not particularly limited.

In view of amount of oxygen absorbed by the oxygen-absorbing resin composition, the content of the transition metal catalyst based on the tetralin ring-containing copolymerized polyolefin compound (100 parts by mass) in terms of transition metal is preferably 0.001 to 10 parts by mass, more preferably 0.002 to 2 parts by mass, further preferably 0.005 to 1 parts by mass, still further preferably 0.008 to 0.5 parts by mass, and particularly preferably 0.01 to 0.2 parts by mass.

A tetralin ring-containing copolymerized polyolefin compound and a transition metal catalyst can be mixed in accordance with a method known in the art. If these are kneaded by use of an extruder, an oxygen-absorbing resin composition having higher dispersibility can be obtained.

<Additives>

The oxygen-absorbing resin composition of the embodiment herein may contain additives known in the art other than the aforementioned components, as long as the effect of the embodiment is not excessively damaged. Examples of such optional additives include, but not particularly limited to, additives such as a drying agent, a pigment such as titanium oxide, a dye, an antioxidant, a slipping agent, an antistatic agent and a stabilizer; fillers such as calcium carbonate, clay, mica and silica; and a deodorant.

The oxygen-absorbing resin composition of the embodiment may further contain a radical generator and a photo initiator, if necessary, in order to facilitate an oxygen absorption reaction. Specific examples of the radical generator include various types of N-hydroxy imide compounds. Specific examples thereof include, but not particularly limited to, N-hydroxysuccinimide, N-hydroxymaleimide, N,N'-dihydroxycyclohexanetetracarboxydiimide, N-hydroxyphthalimide, N-hydroxytetrachlorophthalimide, N-hydroxytetrabromophthalimide, N-hydroxyhexahydrophthalimide, 3-sulfonyl-N-hydroxyphthalimide, 3-methoxycarbonyl-N-hydroxyphthalimide, 3-methyl-N-hydroxyphthalimide, 3-hydroxy-N-hydroxyphthalimide, 4-nitro-N-hydroxyphthalimide, 4-chloro-N-hydroxyphthalimide, 4-methoxy-N-hydroxyphthalimide, 4-dimethylamino-N-hydroxyphthalimide, 4-carboxy-N-hydroxyhexahydrophthalimide, 4-methyl-N-hydroxyhexahydrophthalimide, N-hydroxyhetimide, N-hydroxyhimimide, N-hydroxytrimellitimide and N,N-dihydroxypyromellitdiimide. Specific examples of the photo initiator include, but not particularly limited to, benzophenone and a derivative thereof, a thiazine dye, a metal porphyrin derivative and an anthraquinone derivative. Note that these radical generators and photo initiators can be used alone or in combination with two or more.

The oxygen-absorbing resin composition of the embodiment, as necessary, may further contain a thermoplastic resin other than the above tetralin ring-containing copolymerized polyolefin compound as long as the object of the embodiment is not inhibited. Moldability and handling property can be improved by use of the other thermoplastic resin in combination.

As the other thermoplastic resin, a thermoplastic resin known in the art can be appropriately used. Examples thereof include, but not limited to, polyethylenes such as a low-density polyethylene, a medium-density polyethylene, a high-density polyethylene, a linear and low-density polyethylene, a linear and extremely low-density polyethylene and a polyethylene obtained in the presence of a metallocene catalyst; polypropylenes such as a propylene homopolymer, a propylene-ethylene block copolymer and a propylene-ethylene random copolymer; polyolefins such as poly-1-butene, poly-4-methyl-1-pentene, or random or block copolymers of α-olefins such as ethylene, propylene, 1-butene and 4-methyl-1-pentene; acid modified polyolefins such as maleic anhydride grafted polyethylene and maleic anhydride grafted polypropylene; ethylene-vinyl compound copolymers such as an ethylene-vinyl acetate copolymer, an ethylene-vinyl chloride copolymer, an ethylene-(meth)acrylic acid copolymer and ion crosslinked compounds thereof (ionomers) and ethylene-methyl methacrylate copolymer; styrene resins such as a polystyrene, an acrylonitrile-styrene copolymer and an α-methylstyrene-styrene copolymer; polyvinyl compounds such as methyl polyacrylate and methyl polymethacrylate; polyamides such as nylon 6, nylon 66, nylon 610, nylon 12 and polymetaxylylene adipamide (MXD6); polyesters such as poly(ethylene terephthalate) (PET), poly(butylene terephthalate) (PBT), poly(trimethylene terephthalate) (PTT), poly(ethylene naphthalate) (PEN), glycol-modified poly(ethylene terephthalate) (PETG), poly(ethylene succinate) (PES), poly(butylene succinate) (PBS), poly(lactic acid), poly(glycol acid), polycaprolactone and poly(hydroxy alkanoate); polycarbonate; polyethers such as polyethylene oxide; cyclic polyolefin such as a cycloolefin polymer and a cycloolefin copolymer using a cyclic olefin and mixtures of these. These thermoplastic resins can be used alone or in combination with two or more.

The tetralin ring-containing copolymerized polyolefin compounds and transition metal catalysts, various types of additives and thermoplastic resins to be contained, as necessary, may be added by a method known in the art. Furthermore, an oxygen-absorbing resin composition having further higher dispersibility can be obtained by kneading these by an extruder.

<Usage>

To the oxygen-absorbing resin composition of the embodiment, a known granulation method or a known molding method such as an extrusion molding can be applied. The composition is molded into, for example, powdery, granular, pellet, film or sheet-forms or other small-piece forms. The oxygen-absorbing resin molded article thus obtained can be used directly as an oxygen absorbent. Alternatively, if the obtained oxygen-absorbing resin molded article is packed in an air-permeable packaging material, the molded article can also be used as an oxygen absorbent packaging body. Furthermore, if the oxygen-absorbing resin composition of the embodiment is molded into film-form or sheet-form, the molded article can also be used in the form of a label, a card, a packing, etc. Note that a molded article having a thickness of 0.1 to 500 μm is specified as a film, whereas a molded article having a thickness exceeding 500 μm is specified as a sheet.

It is preferable that a pellet-form oxygen-absorbing resin molded article herein is further ground into powdery grains when used in order to increase the contact area with oxygen to thereby effectively deliver oxygen-absorbing performance.

Note that as the air-permeable packaging material, which is not particularly limited, a known packaging material having air permeability can be applied. In view of sufficiently exerting the oxygen absorption effect, an air-permeable packaging material having high air permeability is preferred. Specific examples of the air-permeable packaging material include, but not particularly limited to, highly air-permeable packaging materials used in various usages, including paper sheets such as Japanese paper, machine-made paper and rayon paper; non-woven clothes using various types of fibers obtained from pulp, cellulose and a synthetic resin; a plastic film or a porous plastic film; or a microporous film obtained by adding calcium carbonate etc., followed by drawing it; and a laminate obtained by stacking two types or more selected from these. As the plastic film, laminate films, each formed by laminating and attaching a film of e.g., a polyethylene terephthalate, a polyamide, a polypropylene or a polycarbonate film and a film serving as a sealing film and formed of a polyethylene, an ionomer, a polybutadiene, an ethylene acrylate copolymer, an ethylene methacrylate copolymer or an ethylene vinyl acetate copolymer, can be used.

The oxygen-absorbing resin composition of the embodiment molded can be not only used as a packaging material or a packaging container in the form of a single-layer form but also used in combination with another substrate in the form of a laminate. Typical example of such a laminate is a laminate obtained by stacking at least one layer formed of the oxygen-absorbing resin composition of the embodiment and at least one layer selected from other resin layers, paper substrate layers or metal foil layers. This laminate can be used as an oxygen-absorbing multi-layer packaging material or an oxygen-absorbing multi-layer packaging container. Note that generally, the oxygen-absorbing resin composition (layer) of the embodiment molded into a film form or a sheet form is preferably provided to an interior side rather than the outer surface of a container etc. so as not to be exposed at the outer surface of the container etc. In view of avoiding direct contact with the content of a container, the oxygen-absorbing resin composition (layer) of the embodiment molded into a film form or a sheet form is preferably provided outer than the inner surface of the container etc. Likewise, in using the oxygen-absorbing resin composition (layer) of the embodiment in a multilayer body, it is preferable that the composition is molded into a film form or a sheet form and arranged as at least one intermediate layer.

Examples of one preferable aspect of the laminate mentioned above include an oxygen-absorbing multilayer body including at least three layers, i.e., a sealant layer containing a thermoplastic resin, an oxygen-absorbing layer containing the oxygen-absorbing resin composition of the embodiment and a gas barrier layer containing a gas barrier substance, in this order. The phrase "including at least three layers . . . in this order" means that the sealant layer, oxygen-absorbing layer and gas barrier layer are arranged in this order; and is a concept including not only an aspect where a sealant layer, an oxygen-absorbing layer and a gas barrier layer are directly stacked (hereinafter, referred to as a "sealant layer/oxygen-absorbing layer/gas barrier layer") but also an aspect where one or more other layers such as a resin layer, a metal foil layer or an adhesive layer are interposed between a sealant layer and an oxygen-absorbing layer or between an oxygen-absorbing layer and a gas barrier layer (hereinafter, referred to as an "intermediate layer") (for example, "sealant layer/resin layer/oxygen-absorbing layer/adhesion layer/gas barrier layer", and "sealant layer/resin layer/adhesion layer/oxygen-absorbing layer/adhesion layer/resin layer/adhesion layer/gas barrier layer/adhesion layer/support") (the same applied hereinafter without an exception).

Examples of another preferable aspect of the laminate mentioned above include an oxygen-absorbing multilayer body including at least three layers, i.e., a sealant layer having a polyolefin resin, an oxygen-absorbing layer containing the oxygen-absorbing resin composition of the embodiment and a gas barrier layer containing a gas barrier substance in this order.

As the thermoplastic resin and polyolefin resin used in the sealant layer, thermoplastic resins and polyolefin resins similar to the other thermoplastic resins and polyolefin resins described in the oxygen-absorbing resin composition of the embodiment can be used. It is preferable that the thermoplastic resin and polyolefin resin to be used in the sealant layer are appropriately selected in consideration of compatibility with other layers (oxygen-absorbing layer, gas barrier layer, resin layer, adhesive layer, support, etc.) in adjacent to the sealant layer.

As the gas barrier substance to be used as a gas barrier layer, a gas barrier thermoplastic resin, a gas barrier thermosetting resin, silica, alumina, aluminum, etc., (as vapor deposition films) and a metal (as aluminum in the form of foil) can be used. Examples of the gas barrier thermoplastic resin include an ethylene-vinyl alcohol copolymer, MXD6 and poly(vinylidene chloride). As the gas barrier thermosetting resin, a gas barrier epoxy resin, for example, "MAX-IVE" manufactured by Mitsubishi Gas Chemical Company, Inc., can be mentioned.

As a method for manufacturing an oxygen-absorbing multilayer body as mentioned above, which is not particularly limited, known methods such as a coextrusion method, a laminating method and a coating method can be applied depending upon e.g., the properties of the material, purpose of processing and processing step. For example, a film or a sheet can be formed by a manufacturing method of extruding a molten resin composition from an extruder provided with e.g., a T die and a circular die or by a method of applying an adhesive to an oxygen-absorbing film or a sheet and adhering it to another film or sheet. Also, if molten resins are simultaneously injected or sequentially injected through multi-layered multiple dies into an injection mold by use of an injector, a multilayer container or a preform for manufacturing a container having a predetermined shape can be formed.

The preform is heated to a drawing temperature and stretched in the axial direction and simultaneously stretched in the circumferential direction in accordance with stretch blow-molding by hydrostatic pressure to obtain a bottle.

For example, a film-form oxygen-absorbing multilayer body can be further processed into a bag-form or a cover material. For example, a sheet-form oxygen-absorbing multilayer body is thermoformed into an oxygen-absorbing multilayer container of a predetermined shape such as a tray, a cup, a bottle and a tube by a molding method such as vacuum molding, air-pressure forming and plug assist molding. The bag-form container, if it is filled with stuff such as food and an open hole is provided, can be preferably used as a pouch for microwave cooking provided with a hole for easily releasing water vapor during microwave cooking.

In using the oxygen-absorbing resin composition of the embodiment and various types of moldings such as laminates using the composition, initiation of an oxygen absorption reaction can be facilitated and an oxygen-absorbing rate can be increased by irradiation of an energy beam. Examples of the usable energy beam include visible ray, UV ray, X-ray, electron ray and γ ray. The amount of irradiation energy can be appropriately selected depending upon the type of energy line to be used.

The oxygen-absorbing resin composition of the embodiment and various types of moldings such as laminates (e.g., containers) using the composition do not require a moisture content for absorbing oxygen. In other words, oxygen can be absorbed regardless of the presence or absence of the moisture content of an article to be packaged. Thus, the composition and moldings can be used in a wide variety of uses no matter which type of article to be packaged is contained. In particular, no odor is produced after absorption of oxygen, the composition and moldings can be particularly preferably used in e.g., foods, cooking foods, beverages, health foods and medicinal products. More specifically, since the oxygen-absorbing resin composition of the embodiment and various types of moldings such as laminates using the composition are excellent in oxygen-absorbing performance in a wide range of humidity conditions from low humidity to high humidity (relative humidity 0% to 100%) and excellent in taste and flavor retention property of a content, they are suitable for packaging various articles. In addition, unlike a conventional oxygen-absorbing resin composition using iron powder, the oxygen-absorbing resin composition of the embodiment can be suitably used for storing an article to be packaged (for example, alcohol beverages and carbonate beverages) which cannot be stored because of the presence of iron.

Specific examples of the article to be packaged include, but not particularly limited to, beverages such as cow milk, juice, coffee, tea and alcohol beverage; liquid seasonings such as source, soy sauce, noodle broth and dressing; cooking foods such as soup, stew and curry; paste foods such as jam and mayonnaise; seafood products such as tuna and fish and shellfish; processed milk products or processed egg products such as cheese, butter and egg; processed livestock products such as meat, salami sausage, sausage and ham; vegetables such as carrot, potato, asparagus and shiitake mushroom; fruits; egg; noodles; rices such as rice and polished rice; cereals such as beans; processed rice foods or processed cereal foods such as steamed rice, festive red rice, rice cake and rice gruel; confectionaries such as adzuki-bean jelly, pudding, cake and steamed bean-jam buns; dry foods (food having a low water activity) such as powdered seasoning, powdered coffee, coffee bean, tea, powdered milk for infants, cooking food for infants, powdered dietary food, nursing care cooking food, dry vegetable, Japanese cracker and rice cracker; chemical products such as an adhesive, a gluing agent, an agrichemical and a pesticide; medicinal products; health foods such as a vitamin supplement; pet foods; sundry articles such as a cosmetic, a shampoo, a conditioner and a detergent; and other various articles. Particularly, the oxygen-absorbing resin composition of the embodiment is suitable for packaging materials for an article to be packaged easily degrading in the presence of oxygen. Examples of such an article to be packaged include beverages such as beer, wine, Japanese sake, shochu, fruit juice beverage, fruit juice, vegetable juice, carbonate soft drink and tea; foods such as fruit, nut, vegetable, meat products, infant food, coffee, jam, mayonnaise, ketchup, edible oil, dressing, source, food boiled in soy sauce and milk products; and others such as medicinal products and cosmetics. Note that the term "water activity" refers to a scale showing the content of free water in an article and represented by a numeral from 0 to 1. The article containing no water is represented by 0 and pure water is represented by 1. More specifically, the water activity Aw of an article is defined as follows:

$Aw=P/P_0=RH/100$ where P represents a water vapor pressure of a space where an article is sealed and the state of the space reaches equivalent, $P_0$ represents the water vapor pressure of pure water and RH (%) represents the relative humidity of the space.

Note that before and after filling (packaging) of an article to be packaged, the container and the article to be packaged can be sterilized by a method suitable for the article to be packaged. Examples of the sterilization method include heat treatments such as a hot water treatment at 100° C. or less, a hot water treatment under pressure at 100° C. or more and a heat treatment performed at an ultrahigh temperature of 130° C. or more; sterilization treatments with an electromagnetic wave such as UV rays, microwave and gamma ray; gas treatments with ethylene oxide etc.; and sterilization treatments with a chemical agent such as hydrogen peroxide and hypochlorite.

More specific embodiment using the oxygen-absorbing resin composition of the first embodiment will be described in detail below.

(Second Embodiment)

Now, the second embodiment of the present invention will be described below. Note that repetition of explanation with respect to the same content as in the first embodiment is avoided herein.

[Oxygen-absorbing Multilayer Body]

The oxygen-absorbing multilayer body of the embodiment includes at least three layers, i.e., a sealant layer (layer C) containing a thermoplastic resin, an oxygen-absorbing layer (layer A) formed of an oxygen-absorbing resin composition of the first embodiment, and a gas barrier layer (layer D) containing a gas barrier substance, these of which are laminated in this order. The oxygen-absorbing multilayer body of the embodiment may have a layer other than these three layers in any position, if necessary.

By using the oxygen-absorbing multilayer body of the embodiment in part or in whole of a packaging container for sealing such that layer C faces inside, oxygen within the container can be absorbed (even if the amount of oxygen transmitting or coming into the container from the outside through the wall of the container is small, transmitting or incoming oxygen is also absorbed) to prevent deterioration etc. of the content (article to be packaged) stored therein by oxygen.

[Sealant Layer (Layer C)]

The sealant layer (layer C) of the oxygen-absorbing multilayer body of the embodiment contains a thermoplastic resin. Layer C has, in addition to a role as a sealant, a role in transmitting oxygen in the container up to an oxygen-absorbing layer; at the same time, isolating the content (article to be packaged) from the oxygen-absorbing layer (layer A) (inhibiting physical contact between layer A and the article to be packaged). The oxygen transmission rate of layer C measured in the case of a film having a thickness of 20 μm at 23° C. under the conditions of a relative humidity of 60% is preferably 300 mL/(m²·day·atm) or more, more preferably 400 mL/(m²·day·atm) or more and further preferably 500 mL/(m²·day·atm) or more. If the oxygen transmission rate satisfies the aforementioned preferable values or more, the oxygen-absorbing rate of layer A can be more enhanced, compared to the case where the oxygen transmission rate does not satisfy the above values.

Examples of the thermoplastic resin to be used in layer C of the oxygen-absorbing multilayer body of the embodiment include polyethylenes such as a high-density polyethylene, a medium-density polyethylene, a low-density polyethylene, linear and low-density polyethylene, a linear and extremely low-density polyethylene and a polyethylene obtained in the presence of a metallocene catalyst; polystyrenes; polymethylpentenes; polypropylenes such as a propylene homo polymer, a propylene-ethylene block copolymer and a propylene-ethylene random copolymer; polyesters having a heat sealing property such as PET, A-PET, PETG and PBT; and amorphous nylon. These can be used alone or in a combination. To these thermoplastic resins, if necessary, an ethylene-vinyl acetate copolymer, an ethylene-methyl acrylate copolymer, an ethylene-ethyl acrylate copolymer, an ethylene-acrylate copolymer, an ethylene-methacrylate copolymer, an ethylene-methyl methacrylate copolymer and a thermoplastic elastomer may be added. The thermoplastic resin to be preferably used in layer C of the oxygen-absorbing multilayer body of the embodiment has an MFR at 200° C. of 1 to 35 g/10 minutes or an MFR at 240° C. of 2 to 45 g/10 minutes, in consideration of moldability and processability of a multilayer body.

Furthermore, layer C of the oxygen-absorbing multilayer body of the embodiment may contain additives known in the art other than a thermoplastic resin as mentioned above. Examples of such optional components include, but not particularly limited to, additives such as a drying agent, a pigment such as titanium oxide, a dye, an antioxidant, a slipping agent, an antistatic agent, a plasticizer, a stabilizer and a lubricant; fillers such as calcium carbonate, clay, mica and silica; and a deodorant. Particularly, in view of recycling and reprocessing offcuts generated during manufacturing, it is preferable to add an antioxidant to layer C.

The content rate of the thermoplastic resin in layer C, which can be appropriately specified, is not particularly limited; however the content rate is preferably 70 to 100 mass % based on the total amount of layer C, more preferably 80 to 100 mass % and further preferably 90 to 100 mass %. The thermoplastic resin to be used in layer C of the embodiment preferably contains a thermoplastic resin other than a tetralin ring-containing copolymerized polyolefin compound, in an amount of 50 to 100 mass % based on the total amount of thermoplastic resins contained in the layer C, more preferably 70 to 100 mass % and further preferably 90 to 100 mass %.

[Oxygen-absorbing Layer (Layer A)]

The oxygen-absorbing layer (layer A) of the oxygen-absorbing multilayer body of the embodiment comprises an oxygen-absorbing resin composition containing a copolymerized polyolefin compound containing a constituent unit (a), which is at least one ethylene or substituted ethylene constituent unit selected from the group consisting of the constituent units represented by the above general formula (1) and a constituent unit (b), which is at least one substituted ethylene constituent unit having a tetralin ring selected from the group consisting of the constituent units represented by the above general formula (2) or (3), and a transition metal catalyst. The oxygen-absorbing resin composition used herein is the same as described in the first embodiment.

The content rate of the tetralin ring-containing copolymerized polyolefin compound in layer A, which is not particularly limited, is preferably 50 mass % or more based on the total amount of layer A, more preferably 70 mass % or more and further preferably 90 mass % or more. If the content rate of a tetralin ring-containing copolymerized polyolefin compound is the preferable value or more, the oxygen-absorbing performance can be more enhanced, compared to the case where the content rate does not satisfy the above value.

In the oxygen-absorbing multilayer body of the embodiment, the thickness of the oxygen-absorbing layer (layer A), which can be appropriately specified depending upon use and desired performance, is not particularly limited. The thickness is preferably 5 to 200 μm and more preferably 10 to 100 μm. If the thickness falls within the preferable range mentioned above, the performance of layer A to absorb oxygen can be more enhanced; at the same time, the processability and economic aspect can be maintained at high levels, compared to the case where the thickness does not fall the above range. The thickness of the sealant layer (layer C), which can be also appropriately specified depending upon use and desired performance, is not particularly limited. The thickness is preferably 5 to 200 μm and more preferably 10 to 80 μm. If thickness falls within the preferable range mentioned above, the oxygen-absorbing rate of layer A can be more enhanced; at the same time, the processability and economic aspect can be maintained at high levels, compared to the case where the thickness does not fall within the above range. In consideration of processability of the resultant oxygen-absorbing multilayer body, the thickness ratio of layer C and layer A is preferably 1:0.5 to 1:3 and more preferably 1:1.5 to 1:2.5.

[Gas Barrier Layer (Layer D)]

The gas barrier layer (layer D) of the oxygen-absorbing multilayer body of the embodiment contains a gas barrier substance. The oxygen transmission rate of layer D measured in the case of a film having a thickness of 20 μm at 23° C. under the conditions of a relative humidity of 60% is preferably 100 mL/(m$^2$·day·atm) or less, more preferably 80 mL/(m$^2$·day·atm) or less and further preferably 50 mL/(m$^2$·day·atm) or less.

As the gas barrier substance to be used in layer D of the oxygen-absorbing multilayer body of the embodiment, a gas barrier thermoplastic resin, a gas barrier thermosetting resin, a silica, alumina, aluminum, etc. (used in the form of a vapor deposition film) and a metal such as aluminum (used in the form of foil) can be used. Examples of the gas barrier thermoplastic resin include an ethylene-vinyl alcohol copolymer, MXD6 and a poly(vinylidene chloride). Examples of the gas barrier thermosetting resin include gas barrier epoxy resin such as "MAXIVE" manufactured by Mitsubishi Gas Chemical Company, Inc.

When a thermoplastic resin is used as a gas barrier substance, the thickness of the gas barrier layer (layer D) is preferably 5 to 200 μm and more preferably 10 to 100 μm. When a thermosetting resin such as an amine-epoxy hardening agent is used as a gas barrier substance or in a gas barrier adhesive layer, the thickness of layer D is preferably 0.1 to 100 μm and more preferably 0.5 to 20 μm. If the thickness falls within the preferable range mentioned above, the gas barrier property tends to be more enhanced; at the same time, the processability and economic aspect can be maintained at high levels, compared to the case where the thickness does not fall within the aforementioned range.

[Optional Layer]

Note that the oxygen-absorbing multilayer body of the embodiment may have one or more other layers such as a resin layer, a metal foil layer or an adhesive layer between layer C and layer A, between layer A and layer D or as an outer layer of layer C or as an outer layer of layer D. For example, to prevent breakage of layer D and formation of a pin hole, a protecting layer formed of a thermoplastic resin can be provided inside or outside layer D. Examples of the resin to be used in the protecting layer include polyethylenes such as a high-density polyethylene; polypropylenes such as a propylene homo polymer, a propylene-ethylene random copolymer and a propylene-ethylene block copolymer; polyamides such as nylon 6 and nylon 6,6; polyesters such as PET; and combinations of these.

In consideration of processability, the oxygen-absorbing multilayer body of the embodiment preferably has an intermediate layer formed of a polyolefin resin interposed between layer D and layer A. The thickness of the intermediate layer is preferably substantially the same as the thickness of layer C in view of processability. Note that herein, in consideration of variation by processing, if a thickness ratio of the layers falls within ±10%, the thicknesses of the layers are regarded as being substantially same.

Alternatively, a paper base material is laminated as an outer layer of layer D and the oxygen-absorbing multilayer body of the embodiment can be used as an oxygen-absorbing paper base material or as an oxygen-absorbing paper container. In view of maintaining processability in manufacturing a paper container by laminating with a paper base material at a high level, the total thickness of the layers present inside layer D is preferably 100 μm or less and more preferably 80 μm or less.

The oxygen-absorbing multilayer body of the embodiment can be manufactured by using a known method such as a coextrusion method, a laminating method and a coating method, which varies depending upon e.g., the properties of the material, processing purpose and processing step. The manufacturing method is not particularly limited. For example, a general method for laminating packaging materials such as a wet lamination process, a dry lamination process, a dry lamination process in the absence of a solvent, an extrusion lamination process, a T die coextrusion molding method, a coextrusion lamination process and an inflation process can be applied. For example, for molding a film or a sheet, a method of extruding a molten resin composition from an extruder provided with a T die, a circular die, etc., and a method of applying an adhesive to an oxygen-absorbing film or sheet separately formed and attaching it to another film or sheet are known. If necessary, for example, a pretreatment such as a corona treatment and an ozone treatment can be applied to a film etc. Furthermore, a known anchor coating agent, an adhesive, etc. can also be used. Examples of the anchor coating agent include isocyanate (urethane), polyethylene imine, polybutadiene and organic titanium. Examples of the adhesive include polyurethane, polyacrylate, polyester, epoxy, poly(vinyl acetate), cellulose and other adhesives for lamination.

[Oxygen-absorbing Multilayer Container]

The oxygen-absorbing multilayer container of the embodiment has an oxygen-absorbing multilayer body as mentioned above in the packaging container in whole or in part. The oxygen-absorbing multilayer container of the embodiment can absorb oxygen within the container (even if the amount of oxygen transmitting or coming into the container from the outside through the wall of the container is small, transmitting or incoming oxygen is also absorbed) to prevent deterioration etc. of the content (article to be packaged) stored therein by oxygen.

The shape of the oxygen-absorbing multilayer container of the embodiment is not particularly limited and can be appropriately specified depending upon the article to be contained and stored. For example, a film-form or sheet-form oxygen-absorbing multilayer body as mentioned above can be formed into a bag such as a three-side sealed flat bag, a standing pouch, a gusset packaging bag, a pillow packaging bag, a multi-chamber pouch, which contains a main chamber and a sub chamber having an easy-to-peel wall between the main chamber and the sub chamber, and a shrink film package; and can be also formed into a container having an arbitrary shape by thermoforming.

More specifically, if a film-form or sheet-form oxygen-absorbing multilayer body as mentioned above is subjected to a molding such as vacuum molding, air-pressure forming and plug assist molding, oxygen-absorbing multilayer containers having a predetermined shape such as a tray, a cup, a bottle, a tube and PTP (press-through package) can be manufactured. Also, if molten resins are simultaneously injected or sequentially injected through multi-layered multiple dies into an injection mold by use of an injector, a multilayer container having a predetermined shape can be formed at a time.

Note that when a container having a flange portion is manufactured by thermoforming, a special process for imparting an easy-peeling function may be applied to the flange portion. If an oxygen-absorbing multilayer body as mentioned above is used as a material for a cover of a container, top seal, etc., oxygen-absorbing function can be imparted to these containers.

In using the oxygen-absorbing multilayer body of the embodiment and the oxygen-absorbing multilayer container containing the multilayer body, initiation of an oxygen absorption reaction can be facilitated and an oxygen-absorbing rate can be increased by irradiation of an energy ray. Examples of the usable energy ray include visible ray, UV ray, X-ray, electron ray and γ ray. The amount of irradiation energy can be appropriately selected depending upon the type of energy ray to be used.

The oxygen-absorbing multilayer body of the embodiment and the oxygen-absorbing multilayer container containing the multilayer body do not require water in absorbing oxygen. In other words, since they can absorb oxygen regardless of the presence or absence of the moisture content of an article to be packaged, they can be used in a wide variety of uses no matter which type of article to be packaged is used. In particular, no odor is produced after absorption of oxygen. Thus, they can be particularly preferably used, for example, in foods, cooking foods, beverages, health foods and medicinal products. In other words, since the oxygen-absorbing multilayer body of the embodiment and the oxygen-absorbing multilayer container containing the multilayer body are excellent in oxygen-absorbing performance in a wide range of humidity conditions from low humidity to high humidity (relative humidity 0% to 100%) and excellent in taste and flavor retention property of a content, they are suitable for packaging various articles. In addition, unlike conventional oxygen-absorbing resin compositions using an iron powder, the oxygen-absorbing resin composition of the embodiment can be suitably used for storing articles to be packaged (for example, alcohol beverage and carbonate beverage) which cannot be stored because of the presence of iron.

Specific examples of the article to be packaged are the same as those described in the first embodiment. The containers and articles to be packaged can be sterilized by a method suitable for the articles before and after packing (packaging) the articles. Any sterilization method may be applied as long as it is the same as described in the first embodiment.

[Drug Solution and Container Filled with Drug Solution]

The oxygen-absorbing multilayer container of the embodiment is preferably used also for storing a container filled with a drug solution (hereinafter, simply referred also to as "drug-solution containing container"). In the embodiment, the drug solution to be contained in drug solution containing container is not particularly limited and any conventional drug solution known in the art may be used. Examples thereof include protein medicinal products such as glucose, amino acids, vitamins, dobutamine, morphine hydrochloride, insulin, epinephrine and elcatonin; electrolytes such as injection solutions of biopharmaceuticals including nucleic acid medicinal products, and sorbitol-added lactated Ringer's solutions and maltose-added lactated Ringer's solutions; and eye drops containing various medicinal ingredients such as vitamins, amino acids, dipotassium glycyrrhizinate, epsilon-aminocaproic acid, naphazoline hydrochloride and tetrahydrozoline hydrochloride.

The drug solution containing container is not particularly limited and conventional containers known in the art may be used. Examples thereof include, infusion bags (inner bags), eye drop containers, prefilled syringes, ampoules and vials. The materials for containers are not particularly limited and conventional materials known in the art may be used. Examples thereof include thermoplastic resins including polyethylenes such as a high-density polyethylene, a medium-density polyethylene, a low-density polyethylene, a linear and low-density polyethylene, a linear extremely low-density polyethylene and a polyethylene obtained in the presence of a metallocene catalyst; polystyrenes; polymethylpentenes; polypropylenes such as a propylene homopolymer, a propylene-ethylene block copolymer and a propylene-ethylene random copolymer; polyesters having heat sealing property such as PET, A-PET, PETG and PBT; and amorphous nylon. These can be used alone or in combination. To these thermoplastic resins, as necessary, an ethylene-vinyl acetate copolymer, an ethylene-methyl acrylate copolymer, an ethylene-ethyl acrylate copolymer, an ethylene-acrylic acid copolymer, an ethylene-methacrylic acid copolymer, an ethylene-methyl methacrylate copolymer and a thermoplastic elastomer may be added. Of them, in view of visibility, moldability and heat-sterilization resistance, polypropylenes are preferably used.

[Medicinal Ingredient and Patch]

The oxygen-absorbing multilayer container of the embodiment can be preferably used for storing a patch containing a medicinal ingredient. The medicinal ingredient contained in the patch of the embodiment is not particularly limited and those known in the art may be used. Examples thereof include indomethacin or derivatives thereof, ketoprofen, methyl salicylate, glycol salicylate or derivatives thereof, dl-camphor, I-menthol, nonanoic acid vanillylamide, a capsicum extract, ascorbic acid or ascorbic acid derivatives, retinoid, vitamin E, powdered phellodendron bark, bark of *Myrica rubra*, peppermint oil, a nicotinic acid ester, and resorcin.

The patch itself is primarily formed of a sheet-form support and a medicinal composition, more specifically, a sheet-form support at least one surface of which a medicinal composition is applied. The sheet-form support to be used in the patch of the embodiment is not particularly limited and any support can be used as long as it is usually used in patches. Examples of such a sheet-form support include non-woven cloth, a polyurethane film, a nylon film and a polypropylene film. A laminate obtained by stacking some of these may be used. A medicinal composition can be held on a support in accordance with a method routinely performed in patches, for example, by putting a medicinal composition on a sheet-form support or impregnating the sheet-form support with a medicinal composition.

In general, to a patch before use, a detachable film is provided so as to cover the entire surface of a medicinal composition applied on the patch. When used, the film is removed and then the patch is applied to an affected area. Also in the patch of the embodiment, it is desirable to provide a detachable film for convenience sake of storage etc. As the film covering the medicinal composition applied on the patch, a film usually used in patches can be used. Examples of such a film include a polyethylene film, a polypropylene film and a polyethylene terephthalate film.

[Fruit Pulps]

The oxygen-absorbing multilayer container of the embodiment can be also preferably used for storing fruit pulps. The fruit pulps of the embodiment are not particularly limited and any conventional fruit pulps known in the art can be used. Examples thereof include cherry, mandarin orange, grapefruit, apple, strawberry, pineapple, peach, chestnut, grape, pear, kiwi fruit, watermelon, banana and mixtures of these. Mixtures of fruit pulps with syrup and other food materials may be included.

[Alcohol Beverage]

The oxygen-absorbing multilayer container of the embodiment can be also preferably used for storing alcohol beverages. The alcohol beverages of the embodiment are not particularly limited as long as they contain ethyl alcohol and the concentration of alcohol is not particularly limited. Specific examples thereof include, but not particularly limited to, low alcohol beverages such as cocktails; distilled alcoholic beverages (whiskey, rum, cachaca, vodka, gin, tequila, brandy, raki, arrack, ouzo, white sake, shochu, Okinawan millet brandy); brewages (wine, beer, fruit wine, Chinese rice wine, Japanese sake); mixed liquors (liqueur, sweet sake), and beverages containing these.

[Liquid-state Tea or Paste-state Tea]

The oxygen-absorbing multilayer container of the embodiment can be also preferably used for storing liquid-state tea or paste-state tea. The liquid-state tea of the embodiment refers to a liquid-state tea beverage obtained by extracting tea as it is or ground tea powder with hot water and refers to concentrated tea liquid obtained by treating such a tea beverage by a known method such as vacuum concentration. The paste-state tea refers to tea obtained by blending powdered tea obtained by grinding tea with a fat and oil and/or water. Herein, examples of tea serving as a raw material include non-fermented tea (green tea), half fermented tea and fermented tea. Examples of the non-fermented tea include green teas such as high-quality green tea, powdered green tea, green tea of medium quality, green tea of ordinary quality, sweet tea and curled leaf tea, and roasted teas obtained by roasting green teas. Examples of the half-fermented tea include oolong tea and Pouchong tea. Examples of the fermented tea include red tea.

The fat and oil that may be contained in paste-state tea, which can be appropriately selected from known fats and oils and put in use, is not particularly limited. In view of a liquid state at normal temperature and easiness in blending with powdered tea, for example, vegetable oils such as cotton seed oil, sesame oil, olive oil, camellia oil, palm oil, corn oil, bean oil, rapeseed oil, sunflower oil and coconut oil; and oil mixtures containing two or more oils selected from these are preferred. In view of not damaging color, taste and flavor, and scent of tea, fat and oil having no taste, no odor and no color is preferable. To obtain paste-state tea, an emulsifier may be appropriately added. If an emulsifier is added, water soluble paste-state tea can be easily obtained, which can be used, for example, in processed foods such as a soft cream. Furthermore, depending upon the use, a seasoning such as a sweetener may be appropriately added in advance. Moreover, a nutrient such as ascorbic acid may be appropriately added.

These liquid-state tea beverage (including concentrated tea) and paste-state tea may be treated with heat. The temperature and time of the heat treatment, which can be specified in accordance with a conventional method, are not particularly limited. For example, conditions where a coliform group cannot survive and conditions where other general viable bacteria cannot survive, are particularly mentioned.

[Fruit Juice and/or Vegetable Juice]

The oxygen-absorbing multilayer container of the embodiment can be also preferably used for storing fruit juice and/or vegetable juice. The fruit juice and/or vegetable juice of the embodiment refers to a liquid obtained by grinding or squeezing fruits and/or vegetables used as a raw material and may contain solid substances derived from the raw materials. The fruits and/or vegetables used as raw materials are not particularly limited. Examples of raw-material fruit and/or vegetables include fruit vegetables such as orange, mandarin orange, apple, peach, pear, grape, blueberry, grapefruit, pineapple, *Citrus depressa*, guava, acerola, prune, papaya, mango, melon, kiwi fruit, candleberry, banana, citron, citrus lemon, tomato, eggplant, pumpkin, green pepper, bitter gourd, sponge gourd, wax gourd, okra, green soybean, snow peas, green bean, fava bean, red pepper, corn and cucumber; root vegetables such as carrot, burdock, onion, bamboo shoot, lotus root, radish, Japanese radish, potato, sweet potato, taro, rakkyo, garlic and ginger; and leaf vegetables such as molokheiya, asparagus, celery, kale, qing-geng-cai, spinach, Chinese cabbage, cabbage, lettuce, napa, broccoli, cauliflower, honewort, parsley, leek, crown daisy and Chinese leek. Fruit juice and/or vegetable juice obtained by applying a heat treatment such as boiling, baking, warming and steaming and a non-heat treatment such as sufficient wash with water, immersion in water and treatment with a chemical agent before and after squeezing can be used as a raw material. Furthermore, fruit juice and/or vegetable juice, from which a predetermined component(s) is removed, for example, by passing the fruit juice and/or vegetable juice through a predetermined resin, can be used as a raw material. Moreover, these fruit juices and/or vegetable juices may be used alone or a mixture of two types or more.

As the flavor components of fruit juice and/or vegetable juice, for example, terpenes such as d-limonene, γ-terpinene, myrcene, α-pinene, β-pinene, citronellol and linalool and aldehydes such as n-octylaldehyde and n-decylaldehyde are contained in citrus fruit juices; esters such as amyl butyrate and amyl acetate and aldehydes such as hexanal and trans-2-hexanal are contained in apple juices; esters such as methyl anthranilate and ethyl crotonate and terpenes such as linalool and geraniol are contained in grape juices; and terpenes such as α-pinene, myrcene and d-limonene and aldehydes such as hexanal and heptanal are contained in vegetable juices using tomato as a raw material. When these flavor components are oxidatively decomposed with oxygen, taste and flavor and color tone degrade.

The fruit juices and/or vegetable juices may contain additives including sugars and sweeteners such as sugar, glucose, fructose, fructose glucose liquid sugar syrup, glucose fructose liquid sugar syrup, high-fructose liquid sugar syrup, oligosaccharide, trehalose, xylitol, sucralose, stevia extract, sorbitol, sweetroot extract and *Momordica grosvenori* extract; thickening stabilizers such as pectin, gelatin, collagen, agar, carrageenan, sodium alginate, soybean polysaccharide, gum Arabic, guar gum, xanthan gum, Tamarindus seed gum and gellan gum; acidulants such as citric acid, malic acid, tartaric acid, lactic acid and gluconic acid; antioxidants such as L-ascorbic acid, sodium L-ascorbate; pH moderators such as sodium hydrogen carbonate; emulsifiers such as glycerin fatty acid ester and sucrose fatty acid ester; nutritional enhancements such as dietary fiber, calcium salt, magnesium salt, niacin and pantothenic acid; spice such as turmeric; and flavoring.

[Dry Product]

The oxygen-absorbing multilayer container of the embodiment can be also preferably used for storing dry products. In the embodiment, the dry products to be packaged are foods in a dry state. The dry state herein should not be understood in a narrow sense. Not only general dried foods but also semi-dried foods are directed. Examples of the dried foods and semi-dried foods are as follows.

(1) Sea food processed products: dried adductors, sardine paper, dried cuttlefish, dried cuttlefish processed products, fish Denbu and dried fish sprinkle (2) Food delicacies: beef jerky, nut mixtures and toasted layer (3) Nut foods: peanuts, almonds, almond flakes, cashew nuts and chick peas (4) Snack foods: potato chips, shoestrings and popcorns (5) Serial foods: Corn flakes and Muesli (6) Favorite foods: powdered instant coffees, powdered instant teas, coffee beans, red tea (leaves), green tea (leaves) and Woo-long tea (leaves)

(7) Dried noodles/pastas: dried noodles, dried thin noodles, macaroni, spaghetti, instant ramen, rice vermicelli, bean-starch vermicelli, hardtack, powdered instant potage soup and crouton (8) White crops/grain flour: polished milled rice, "glue made of glutinous rice", "pancake pre-mix" and wheat germ (9) Dried vegetables: dried shiitake, dried flowering fern, freeze-dried leek, dried cut radish, dried laver, dried seaweed, dried brown alga and roast sesame powder

(10) Confectionaries: "baumkuchen", "sponge cake", "pancake filled with bean jam", "biscuit", "cracker", "cookie", "fried dough cake", "millet-cake", "Rakugan (hard candy)", Japanese cake called "Suama", Japanese cake called "Nerikiri", "sweetened bean-jelly", Japanese cakes called "Monaka", "Gokabou" and "morokosi"

(11) Rice confectionaries: Rice crackers called "Kaki-no-tane", "Souka-senbei", "Kawara-senbei", "Okaki" and "Abura-age-okaki"

(12) Milk products: Parmesan cheese powder, powdered skim milk and modified milk powder

(13) Seasonings: powder seasoning made of e.g., fish clause powder and monosodium glutamate, dried fish shavings, baked and dried fish, dried small sardines, kombu powder, powder pepper and grain pepper.

(Third Embodiment)

The third embodiment of the present invention will be described below. Note that repetition of explanation with respect to the same contents as in the first and second embodiments is avoided herein.

[Oxygen-absorbing Multilayer Body]

The oxygen-absorbing multilayer body of the embodiment includes at least three layers including an oxygen transmission layer containing a thermoplastic resin (layer H), an oxygen-absorbing layer (layer A) comprising the oxygen-absorbing resin composition according to the first embodiment, and a gas barrier layer containing a gas barrier substance (layer D), these of which are laminated in this order. The oxygen-absorbing multilayer body of the embodiment may have a layer other than these three layers at any position, as necessary.

By using the oxygen-absorbing multilayer body of the embodiment in part or in whole of a packaging container for hermetical closing such that layer H faces inside, oxygen within the container can be absorbed (even if the amount of oxygen transmitting or coming into the container from the outside through the wall of the container is small, transmitting or incoming oxygen is also absorbed) to prevent e.g., deterioration of the content (article to be packaged) stored therein by oxygen.

[Oxygen Transmission Layer (Layer H)]

The oxygen transmission layer (layer H) of the oxygen-absorbing multilayer body of the embodiment contains a thermoplastic resin. Layer H plays a role in transmitting oxygen in a container up to the oxygen-absorbing layer; at the same time, isolating the oxygen-absorbing layer (layer A) and a content (an article to be packaged) (inhibiting physical contact between layer A and the article to be packaged). Furthermore, layer H can also serve as a sealant in sealing the multilayer container when the oxygen-absorbing multilayer container of the embodiment is heat-sealed with a top film (cover material) having a gas barrier property. Herein, the oxygen transmission rate of layer H measured in the case of a film having a thickness of 20 μm under the conditions of 23° C. and a relative humidity of 60% is preferably 300 mL/(m²·day·atm) or more, more preferably 400 mL/(m²·day·atm) or more and further preferably 500 mL/(m²·day·atm) or more. If the oxygen transmission rate satisfies the aforementioned preferable value or more, the oxygen-absorbing rate of layer A can be more enhanced, compared to the case where the oxygen transmission rate does not satisfy the above value.

Examples of the thermoplastic resin to be used in layer H of the oxygen-absorbing multilayer body of the embodiment include polyethylenes such as a high-density polyethylene, a medium-density polyethylene, a low-density polyethylene, a linear and low-density polyethylene, a linear and extremely low-density polyethylene and a polyethylene obtained in the presence of a metallocene catalyst; polystyrenes; polymethylpentenes; polypropylenes such as a propylene homo polymer, a propylene-ethylene block copolymer and a propylene-ethylene random copolymer; polyesters having heat sealing property such as PET, A-PET, PETG and PBT; and amorphous nylon. These can be used alone or in combination. To these thermoplastic resins, as necessary, an ethylene-vinyl acetate copolymer, an ethylene-methyl acrylate copolymer, an ethylene-ethyl acrylate copolymer, an ethylene-acrylic acid copolymer, an ethylene-methacrylic acid copolymer, an ethylene-methyl methacrylate copolymer and a thermoplastic elastomer may be added.

Layer H of the oxygen-absorbing multilayer body of the embodiment may contain various types of additives known in the art other than a thermoplastic resin as mentioned above. Examples of such optional components include, but not particularly limited to, additives such as a drying agent, a pigment such as titanium oxide, a dye, an antioxidant, a slipping agent, an antistatic agent, a plasticizer, a stabilizer and a lubricant; fillers such as calcium carbonate, clay, mica and silica; and a deodorant. Particularly, in view of recycling and reprocessing offcuts generated during manufacturing, it is preferable to add an antioxidant to layer H.

The content rate of the thermoplastic resin in layer H, which can be appropriately specified, is not particularly limited; however the content rate is preferably 70 to 100 mass % based on the total amount of layer H, more preferably 80 to 100 mass % and further preferably 90 to 100 mass %. Thermoplastic resin to be used in layer H of the embodiment preferably contains a thermoplastic resin other than a tetralin ring-containing copolymerized polyolefin compound in an amount of 50 to 100 mass % based on the total amount of layer H, more preferably 70 to 100 mass % and further preferably 90 to 100 mass %.

[Oxygen-absorbing Layer (Layer A)]

The oxygen-absorbing layer (layer A) of the oxygen-absorbing multilayer body of the embodiment comprises an oxygen-absorbing resin composition containing a copolymerized polyolefin compound, which contains a constituent unit (a), which is at least one ethylene or substituted ethylene constituent unit selected from the group consisting of the constituent units represented by the above general formula (1) and a constituent unit (b), which is at least one substituted ethylene constituent unit having a tetralin ring selected from the group consisting of the constituent units represented by the above general formula (2) or (3), and a transition metal catalyst. The oxygen-absorbing resin composition used herein is the same as described in the first embodiment. Furthermore, the oxygen-absorbing layer (layer A) is the same as that described in the second embodiment except the matters specifically described below.

In the oxygen-absorbing multilayer body of the embodiment the thickness of the oxygen-absorbing layer (layer A), which can be appropriately specified depending upon use and desired performance, is not particularly limited. The thickness is preferably 5 to 800 µm, more preferably 10 to 600 µm and particularly preferably 20 to 500 µm. If the thickness falls within the preferable range as mentioned above, the performance of layer A to absorb oxygen can be more enhanced; at the same time, the processability and economic aspect can be maintained at high levels, compared to the case where the thickness does not fall the preferable range. The thickness of the oxygen transmission layer (layer H), which can be also appropriately specified depending upon use and desired performance, is not particularly limited. The thickness is preferably 1 to 1000 µm, more preferably 5 to 800 µm and particularly preferably 10 to 700 µm. If thickness falls within a preferable range as mentioned above, the oxygen-absorbing rate of layer A can be more enhanced; at the same time, the processability and economic aspect can be maintained at high levels, compared to the case where the thickness does not fall within the preferable range.

[Gas Barrier Layer (Layer D)]

The gas barrier layer (layer D) of the oxygen-absorbing multilayer body of the embodiment contains a gas barrier substance. The gas barrier layer (layer D) and the gas barrier substance are the same as those described in the second embodiment except the matters specifically described below.

When a thermoplastic resin is used as a gas barrier substance, the thickness of the gas barrier layer (layer D) is preferably 5 to 500 µm and more preferably 10 to 300 µm. Furthermore, when a thermosetting resin such as an amine-epoxy hardening agent is used as the gas barrier substance or a gas barrier adhesive layer, the thickness of layer D is preferably 0.1 to 100 µm and more preferably 0.5 to 20 µm. If the thickness falls within a preferable range as mentioned above, the gas barrier property tends to be more enhanced; at the same time, the processability and economic aspect can be maintained at high levels, compared to the case where the thickness does not fall within the preferable range.

[Optional Layer]

Note that the oxygen-absorbing multilayer body of the embodiment may have one or more other layers such as a resin layer, a metal foil layer or an adhesive layer between layer H and layer A, between layer A and layer D or as an outer layer of layer H or as an outer layer of layer D. For example, to prevent breakage of layer D and formation of a pin hole, a protecting layer comprising a thermoplastic resin can be provided inside or outside layer D. Examples of the resin to be used in the protecting layer include polyethylenes such as a high-density polyethylene; polypropylenes such as a propylene homo polymer, a propylene-ethylene random copolymer and a propylene-ethylene block copolymer; polyamides such as nylon 6 and nylon 6,6; polyesters such as PET; and combinations of these.

In the oxygen-absorbing multilayer body of the embodiment, if practical interlayer adhesive strength between adjacent two layers cannot be obtained, it is preferable to provide an adhesion layer between the two layers. The adhesion layer preferably contains a thermoplastic resin having adhesiveness. Examples of the thermoplastic resin having adhesiveness include acid-modified polyolefin resins obtained by modifying a polyolefin resin such as a polyethylene or a polypropylene with an unsaturated carboxylic acid such as acrylic acid, methacrylic acid, maleic acid, maleic anhydride, fumaric acid and itaconic acid.

In consideration of processability, the oxygen-absorbing multilayer body of the embodiment preferably has an intermediate layer comprising a polyolefin resin between layer D and layer A. It is preferable that the thickness of the intermediate layer is substantially the same as the thickness of layer H in view of processability. Note that in consideration of variation by processing herein, if the difference in the thickness of the layers falls within ±10%, the thicknesses of the layers are regarded as substantially the same.

The method for manufacturing the oxygen-absorbing multilayer body of the embodiment is the same as that described in the second embodiment.

[Oxygen-absorbing Multilayer Container]

The oxygen-absorbing multilayer container of the embodiment contains an oxygen-absorbing multilayer body as mentioned above in whole or in part thereof. The oxygen-absorbing multilayer container of the embodiment can absorb oxygen within the container (even if the amount of oxygen transmitting or coming into the container from the outside through the wall of the container is small, transmitting or incoming oxygen is also absorbed) to prevent e.g., deterioration of the content (article to be packaged) stored therein by oxygen.

The constitution of the oxygen-absorbing multilayer container of the embodiment, which is not particularly limited, can be appropriately set depending upon the article to be contained and stored. For example, the aforementioned oxygen-absorbing multilayer body is thermoformed to obtain a packaging container main body. This is bonded with a top film (cover material) having a gas barrier layer containing a gas barrier substance to prepare a sealed container. As the gas barrier substance to be used in the gas barrier layer of the top film (cover material), the gas barrier substances used in layer D of the aforementioned oxygen-absorbing multilayer body can be used. The oxygen transmission rate of the top film (cover material) measured in the case of a film having a thickness of 20 μm under the conditions of 23° C. and a relative humidity of 60% is preferably 100 mL/($m^2$·day·atm) or less, more preferably 80 mL/($m^2$·day·atm) or less and further preferably 50 mL/($m^2$·day·atm) or less. Note that if the top film (cover material) is manufactured as a multilayer body and the thermoplastic resin to be used in layer H of the aforementioned oxygen-absorbing multilayer body is used as an inner layer, layer H and the top film (cover material) inner layer can be sealed by heat-sealing.

The oxygen-absorbing multilayer body of the embodiment can be thermoformed into a container of a predetermined shape by a method of softening it by heating, followed by squeezing by use of vacuum, air-pressure or a combination of vacuum and air-pressure. More specifically, the aforementioned film-form or sheet-form oxygen-absorbing multilayer body with the oxygen transmission layer faced inside is subjected to molding such as vacuum molding, air-pressure forming, press-molding or free-blow molding to thermoform the body into an oxygen-absorbing multilayer container having a predetermined shape such as a tray, a cup, a bottle, a tube and PTP (press-through package).

Note that when a container having a flange portion is manufactured by thermoforming, a special process for providing an easy-peeling function may be applied to the flange portion. If an oxygen-absorbing multilayer body as mentioned above is used as a member for a main body of a container, oxygen-absorbing function can be provided to the container.

In using the oxygen-absorbing multilayer container of the embodiment, initiation of an oxygen absorption reaction can be facilitated and an oxygen-absorbing rate can be increased by irradiation of an energy ray. Examples of the usable energy ray include visible ray, UV ray, X-ray, electron ray and γ ray. The amount of irradiation energy can be appropriately selected depending upon the type of energy line to be used.

The oxygen-absorbing multilayer container of the embodiment does not require a moisture content for absorbing oxygen. In other words, oxygen can be absorbed regardless of the presence or absence of the moisture content of an article to be packaged. Thus, the oxygen-absorbing multilayer container of the embodiment can be used in a wide variety of uses no matter which type of article to be packaged is used. In particular, no odor is produced after absorption of oxygen. Thus, the multilayer container can be particularly preferably used in e.g., foods, cooking foods, beverages, health foods and medicinal products. More specifically, since the oxygen-absorbing multilayer container of the embodiment is excellent in oxygen-absorbing performance in a wide range of humidity conditions from low humidity to high humidity (relative humidity 0% to 100%) and excellent in taste and flavor retention property of a content, it is suitable for packaging various articles. In addition, unlike conventional oxygen-absorbing multilayer containers using iron powder, the oxygen-absorbing multilayer container of the embodiment can be suitably used for storing an article to be packaged (for example, alcohol beverages and carbonate beverages) which cannot be stored because of the presence of iron.

Specific examples of the article to be packaged are the same as those described in the first embodiment. The containers and articles can be sterilized by a method suitable for the articles before and after packing (packaging) the articles. Any sterilization method may be applied as long as it is the same as described in the first embodiment.

(Fourth Embodiment)

Now, the fourth embodiment of the present invention will be described below. Note that repetition of explanation with respect to the same content as in the first to third embodiments is avoided herein.

The oxygen-absorbing sealed container of the embodiment has a cover material containing an oxygen-absorbing multilayer body, and a gas barrier molded container including at least three layers including an inner layer containing a thermoplastic resin, a gas barrier layer containing a gas barrier substance and an outer layer containing a thermoplastic resin, laminated in this order, in which the sealant layer (layer C) of the cover material and the inner layer of the gas barrier molded container are bonded.

[Oxygen-absorbing Multilayer Body]

The oxygen-absorbing multilayer body of the embodiment includes at least three layers, i.e., a sealant layer (layer C) containing a thermoplastic resin, an oxygen-absorbing layer (layer A) formed of an oxygen-absorbing resin composition of the first embodiment, and a gas barrier layer (layer D) containing a gas barrier substance, these of which are laminated in this order. The oxygen-absorbing multilayer body of the embodiment may have a layer other than these three layers in any position, if necessary.

By using the oxygen-absorbing multilayer body of the embodiment for the cover material of the sealed container such that layer C faces inside, oxygen within the sealed container can be absorbed (even if the amount of oxygen transmitting or coming into the sealed container from the outside through the cover material is small, transmitting or incoming oxygen is also absorbed) to prevent deterioration etc. of the content (article to be packaged) stored therein by oxygen.

[Sealant Layer (Layer C)]

The sealant layer (layer C) of the oxygen-absorbing multilayer body of the embodiment contains a thermoplastic resin. The sealant layer (layer C) of the oxygen-absorbing multilayer body of the embodiment and the thermoplastic resin are the same as described in the third embodiment.

[Oxygen-absorbing Layer (Layer A)]

The oxygen-absorbing layer (A) of the oxygen-absorbing multilayer body of the embodiment comprises an oxygen-absorbing resin composition containing the copolymerized polyolefin compound which contains a constituent unit (a), which is at least one ethylene or substituted ethylene constituent unit selected from the group consisting of the constituent units represented by the above general formula (1) and a constituent unit (b), which is at least one substituted ethylene constituent unit having a tetralin ring, selected from the group consisting of the constituent units represented by the above general formula (2) or (3) and a transition metal catalyst. The oxygen-absorbing resin composition used herein is the same as that described in the first embodiment. Furthermore, the oxygen-absorbing layer (layer A) is the same as that described in the second embodiment.

[Gas Barrier Layer (Layer D)]

The gas barrier layer (layer D) of the oxygen-absorbing multilayer body of the embodiment contains a gas barrier substance. The gas barrier layer (layer D) and gas barrier substance are the same as described in the second embodiment.

[Optional Layer]

The oxygen-absorbing multilayer body of the embodiment may have one or more other layers such as a resin layer, a metal foil layer or an adhesive layer between layer C and layer A, between layer A and layer D or as an outer layer of layer C or as an outer layer of layer D. For example, to prevent breakage of layer D and formation of a pin hole, a protecting layer formed of a thermoplastic resin can be provided inside or outside layer D. Examples of the resin to be used in the protecting layer include polyethylenes such as a high-density polyethylene; polypropylenes such as a propylene homo polymer, a propylene-ethylene random copolymer and a propylene-ethylene block copolymer; polyamides such as nylon 6 and nylon 6,6; polyesters such as PET; and combinations of these. Alternatively, a paper base material is laminated as an outer layer of layer D and the resultant laminate can be used as an oxygen-absorbing paper base material.

The method for manufacturing an oxygen-absorbing multilayer body of the embodiment is the same as that described in the third embodiment.

[Gas Barrier Molded Container]

The gas barrier molded container of the embodiment includes at least three layers including an inner layer containing a thermoplastic resin, a gas barrier layer containing a gas barrier substance and an outer layer containing a thermoplastic resin, laminated in this order, and can reduce the amount of oxygen transmitting or coming into the oxygen-absorbing sealed container from the outside through the wall of the gas barrier molded container. Furthermore, a gas barrier molded article of the embodiment may have a layer other than these three layers at any position, as necessary.

The thermoplastic resin to be used in the inner layer or outer layer of the gas barrier molded container of the embodiment is not particularly limited. Examples thereof include polyethylenes such as a high-density polyethylene, a medium-density polyethylene, a low-density polyethylene, a linear and low-density polyethylene, a linear and extremely low-density polyethylene and a polyethylene obtained in the presence of a metallocene catalyst; polystyrenes; polymethylpentenes; polypropylenes such as a propylene homopolymer, a propylene-ethylene block copolymer and a propylene-ethylene random copolymer; polyesters having a heat sealing property such as PET, A-PET, PETG and PBT; and amorphous nylon. These can be used alone or in combination. To these thermoplastic resins, as necessary, e.g., an ethylene-vinyl acetate copolymer, an ethylene-methyl acrylate copolymer, an ethylene-ethyl acrylate copolymer, an ethylene-acrylic acid copolymer, an ethylene-methacrylic acid copolymer, an ethylene-methyl methacrylate copolymer and a thermoplastic elastomer may be added.

The inner layer or outer layer of the gas barrier molded container of the embodiment may contain various types of additives known in the art other than a thermoplastic resin as mentioned above. Examples of such optional components include, but not particularly limited to, additives such as a drying agent, a pigment such as titanium oxide, a dye, an antioxidant, a slipping agent, an antistatic agent, a plasticizer, a stabilizer and a lubricant; fillers such as calcium carbonate, clay, mica and silica; and a deodorant. Particularly, in view of recycling and reprocessing offcuts generated during manufacturing, it is preferable to add an antioxidant.

The content rate of the thermoplastic resin in the inner layer or outer layer, which can be appropriately specified, is not particularly limited; however the content rate is preferably 70 to 100 mass % based on the total amount of layer C, more preferably 80 to 100 mass % and further preferably 90 to 100 mass %.

Thermoplastic resin to be used in the inner layer of the gas barrier molded container of the embodiment is preferably the same type of thermoplastic resin used in layer C of the above oxygen-absorbing multilayer body in view of ensuring heat sealing strength of a sealed container.

The gas barrier layer of the gas barrier molded container of the embodiment contains a gas barrier substance. The oxygen transmission rate of the gas barrier layer measured in the case of a film having a thickness of 20 μm under the conditions of 23° C. and a relative humidity of 60% is preferably 100 mL/(m$^2$·day·atm) or less, more preferably 80 mL/(m$^2$·day·atm) or less and further preferably 50 mL/(m$^2$·day·atm) or less.

As the gas barrier substance to be used in the gas barrier layer of the gas barrier molded container of the embodiment, a gas barrier thermoplastic resin, a gas barrier thermosetting resin, silica, alumina, aluminum, etc. (as vapor deposition films) and a metal (such as aluminum, in the form of foil) can be used. Examples of the gas barrier thermoplastic resin include an ethylene-vinyl alcohol copolymer, MXD6 and a poly(vinylidene chloride). Of them, MXD6 is preferable when an article to be packaged in the gas barrier molded container is sterilized by heating at a temperature of 80° C. or more. Examples of the gas barrier thermosetting resin include gas barrier epoxy resins such as "MAXIVE", manufactured by Mitsubishi Gas Chemical Company, Inc.

When a thermoplastic resin is used as a gas barrier substance, the thickness of the gas barrier layer is preferably 5 to 200 μm and more preferably 10 to 100 μm. When a thermosetting resin such as an amine-epoxy hardening agent is used as a gas barrier substance or in a gas barrier adhesive layer, the thickness of the gas barrier layer is preferably 0.1 to 100 μm and more preferably 0.5 to 20 μm. If the thickness falls within a preferable range as mentioned above, the gas barrier property tends to be more enhanced; at the same time, the processability and economic aspect can be maintained at high levels, compared to the case where the thickness does not fall within the preferable range.

[Oxygen-absorbing Sealed Container]

The oxygen-absorbing sealed container of the embodiment has a cover material containing an oxygen-absorbing multilayer body as mentioned above and a gas barrier molded container and is formed by bonding the sealant layer of the cover material and the inner layer of the gas barrier molded container. The oxygen-absorbing sealed container of the embodiment can absorb oxygen within the container (even if the amount of oxygen coming into the container from the outside is small, incoming oxygen is also absorbed) to prevent e.g., deterioration of the content (article to be packaged) stored therein by oxygen.

How to bond the sealant layer of the cover material and the inner layer of the gas barrier molded container is not particularly limited. For example, heat sealing and adhesion by an adhesive can be mentioned. These bonding methods can be used alone or in combination with two or more. Of these, heat sealing is preferable. Bonding conditions may be appropriately determined in consideration of e.g., the qualities of materials, shapes and dimensions of the sealant layer and the inner layer.

In using the oxygen-absorbing sealed container of the embodiment, initiation of an oxygen absorption reaction can be facilitated and an oxygen-absorbing rate can be increased by irradiation of an energy ray. Examples of the usable energy ray include visible ray, UV ray, X-ray, electron ray and γ ray. The amount of irradiation energy can be appropriately selected depending upon the type of energy line to be used.

The oxygen-absorbing sealed container of the embodiment does not require a moisture content for absorbing oxygen. In other words, oxygen can be absorbed regardless of the presence or absence of the moisture content of an article to be packaged. Thus, the oxygen-absorbing sealed container of the embodiment can be used in a wide variety of uses no matter which type of article to be packaged is used. In particular, no odor is produced after absorption of oxygen. Thus, the sealed container can be particularly preferably used in e.g., foods, cooking foods, beverages, health foods and medicinal products. More specifically, since the oxygen-absorbing sealed container of the embodiment is excellent in oxygen-absorbing performance in a wide range of humidity conditions from low humidity to high humidity (relative humidity 0% to 100%) and excellent in taste and flavor retention property of a content, it is suitable for packaging various articles. In addition, unlike conventional oxygen-absorbing resin composition using iron powder, the oxygen-absorbing resin composition of the embodiment can be suitably used for storing an article to be packaged (for example, alcohol beverages and carbonate beverages) which cannot be stored because of the presence of iron.

Specific examples of the article to be packaged are the same as those described in the first embodiment. The containers and articles can be sterilized by a method suitable for the articles before and after packing (packaging) the articles. Any sterilization method may be applied as long as it is the same as described in the first embodiment.

The shape and dimensions of the oxygen-absorbing sealed container having the cover material and the of the embodiment are not particularly limited as long as the cover material and the gas barrier molded container have the shape and dimensions suitable for the aforementioned uses and for storing an article to be packaged, and may be the conventional shape and dimensions known in the art. Furthermore, the manufacturing method for the container is not particularly limited. For example, a film-form or a sheet-form oxygen-absorbing multilayer body may be used as a cover material. On the other hand, a film-form or a sheet-form laminate, which constituted of an inner layer containing a thermoplastic resin, a gas barrier layer containing a gas barrier substance and an outer layer containing a thermoplastic resin, is subjected to molding such as vacuum molding, air-pressure forming and plug assist molding, while applying heat as necessary, to manufacture a gas barrier molded container having a predetermined shape such as a cup, a bottle and a tube. If thermoforming is applied, a container of any shape can be manufactured. Alternatively, if molten resins are simultaneously injected or sequentially injected through multi-layered multiple dies into an injection mold by use of an injector, a multilayer container having a predetermined shape can be formed at a time. Subsequently, the obtained cover material and gas barrier molded container are bonded by the aforementioned bonding method to obtain the oxygen-absorbing sealed container of the embodiment.

(Fifth Embodiment)

The fifth embodiment of the present invention will be described below. Note that repetition of explanation with respect to the same content as in the first to fourth embodiments is avoided herein.

[Oxygen-absorbing Paper Container and Oxygen-absorbing Multilayer Body]

The oxygen-absorbing paper container of the embodiment is a paper container obtained by forming an oxygen-absorbing multilayer body into a carton. To describe more specifically, the oxygen-absorbing multilayer body constituting a paper container comprises at least four layers, i.e., an isolation layer (layer F) containing a thermoplastic resin, an oxygen-absorbing layer (layer A) formed of the oxygen-absorbing multilayer body of the embodiment, a gas barrier layer (layer D) containing a gas barrier substance and a paper substrate layer (layer E), these of which are laminated in this order. The oxygen-absorbing multilayer body of the embodiment may have, if necessary, a layer other than these four layers at any position.

By use of the oxygen-absorbing multilayer body in part or in whole of an packaging container for sealing such that layer F faces inside, the oxygen-absorbing paper container of the embodiment can absorb oxygen within the container (even if the amount of oxygen transmitting or coming into the container from the outside through the wall of the container is small, transmitting or incoming oxygen is also absorbed) to prevent deterioration etc. of the content (article to be packaged) stored therein by oxygen.

[Isolation Layer Containing a Thermoplastic Resin (Layer F)]

In the embodiment, the isolation layer (layer F) of the oxygen-absorbing multilayer body contains a thermoplastic resin. Layer F has a role in transmitting oxygen in the container up to an oxygen-absorbing layer (layer A); at the same time, isolating the content (article to be packaged) from the oxygen-absorbing layer (layer A) (inhibiting physical contact between layer A and an article to be packaged). Furthermore, when the container is formed by molding the oxygen-absorbing multilayer body into a carton, layer F can serve as a sealant for sealing the paper container by fusing with another part of layer F by application of heat.

As a thermoplastic resin having the thermal adhesiveness which can be used in layer F, thermoplastic resins such as polyolefin resins capable of melting by heat and mutually adhere are exemplified. Specific examples thereof include acid modified polyolefin resins obtained by modifying a polyolefin resin such as a low-density polyethylene, a medium-density polyethylene, a high-density polyethylene, straight (linear) low-density polyethylene, an ethylene-α-olefin copolymer obtained by polymerization in the presence of a metallocene catalyst, polypropylene, an ethylene-vinyl acetate copolymer, an ionomer resin, an ethylene-acrylic acid copolymer, an ethylene-ethyl acrylate copolymer, an ethylene-methacrylate copolymer, an ethylene-propylene copolymer, a methylpentene polymer, a polybutene polymer, a poly(vinyl acetate) resin, a poly(meth)acrylate resin, a poly(vinyl chloride) resin, a polyethylene or a polypropylene with an unsaturated carboxylic acid such as acrylic acid, methacrylic acid, maleic acid, maleic anhydride, fumaric acid or itaconic acid. These can be used alone or in combination with two or more. Of them, in view of molding processability, sanitation, odor, etc., a low-density polyethylene, a medium-density polyethylene, a high-density polyethylene, a straight (linear) low-density polyethylene and an ethylene-α-olefin copolymer obtained by polymerization in the presence of a metallocene catalyst are preferable.

The content rate of the thermoplastic resin in layer F, which can be appropriately specified, is not particularly limited. The content rate is preferably 70 to 100 mass % based on the total amount of layer F, more preferably 80 to 100 mass % and further preferably 90 to 100 mass %. The thermoplastic resin to be used in layer F of the embodiment preferably contains a thermoplastic resin other than a tetralin ring-containing copolymerized polyolefin compound in an amount of 50 to 100 mass % based on the total amount of layer F, more preferably 70 to 100 mass % and further preferably 90 to 100 mass %.

Layer F may contain additives known in the art other than the thermoplastic resins as mentioned above. Examples of such optional components include, but not particularly limited to, additives such as a drying agent, a pigment such as titanium oxide, a dye, an antioxidant, a slipping agent, an antistatic agent, plasticizer, a stabilizer and a lubricant; fillers such as calcium carbonate, clay, mica and silica; and a deodorant. Particularly, in view of recycling and reprocessing offcuts generated during manufacturing, it is preferable to add an antioxidant to layer F.

Furthermore, in the oxygen-absorbing multilayer body of the embodiment, the thickness of the isolation layer (layer F), which can be appropriately specified depending upon the use and desired performance, is not particularly limited. The thickness is preferably 5 to 50 μm and more preferably 10 to 40 μm. If the thickness falls within the preferable range mentioned above, the rate of absorbing oxygen by the oxygen-absorbing layer can be more enhanced; at the same time, the processability and economic aspect can be maintained at high levels, compared to the case where the thickness does not fall the above range.

[Oxygen-absorbing Layer (Layer A)]

The oxygen-absorbing layer (layer A) of the oxygen-absorbing multilayer body of the embodiment comprises an oxygen-absorbing resin composition containing the tetralin ring-containing copolymerized polyolefin compound which contains a constituent unit (a), which is at least one ethylene or substituted ethylene constituent unit selected from the group consisting of the constituent units represented by the above general formula (1) and a constituent unit (b), which is at least one substituted ethylene constituent unit having a tetralin ring, selected from the group consisting of the constituent units represented by the above general formula (2) or (3) and a transition metal catalyst. The oxygen-absorbing resin composition used herein is the same as that described in the first embodiment. Furthermore, the oxygen-absorbing layer (layer A) is the same as that described in the second embodiment except the matters specifically described below.

In the oxygen-absorbing multilayer body of the embodiment, the thickness of the oxygen-absorbing layer (layer A), which can be appropriately specified depending upon use and desired performance, is not particularly limited. The thickness is preferably 5 to 50 μm and more preferably 10 to 40 μm. If the thickness falls within the preferable range mentioned above, the performance of the oxygen-absorbing layer to absorb oxygen can be more enhanced; at the same time, the processability and economic aspect can be maintained at high levels, compared to the case where the thickness does not fall the above range.

[Gas Barrier Layer (Layer D)]

The gas barrier layer (layer D) of the oxygen-absorbing multilayer body of the embodiment contains a gas barrier substance. The gas barrier layer (layer D) and the gas barrier substance thereof are the same as described in the second embodiment.

[Paper Substrate Layer (Layer E)]

In the embodiment, the paper substrate layer (layer E), since it serves as a base material constituting a container, is preferably excellent in shaping property, flex resistance, rigidity, elasticity, strength, etc. As the paper base material constituting layer E, various types of paper base materials such as bleached or unbleached paper base material excellent in sizing property, snow-white roll, craft paper, cardboard, processed paper and others can be used. The basis weight of layer E, which can be appropriately specified, is not particularly limited. The basis weight preferably falls within the range of about 80 to 600 g/m$^2$ and more preferably within the range of 100 to 450 g/m$^2$. Note that, in the embodiment, on the paper substrate layer, for example, letters, figures, pictures, symbols and other desired pictures may be optionally printed by a conventional printing system.

[Optional Layer]

Note that the oxygen-absorbing multilayer body of the embodiment may have one or more other layers such as a resin layer, a metal foil layer or an adhesive layer between layer F and layer A, between layer A and layer D, between layer D and layer E or as an outer layer of layer F or as an outer layer of layer E. For example, to prevent breakage of layer D and formation of a pin hole, a protecting layer formed of a thermoplastic resin can be provided inside or outside layer D. Examples of the resin to be used in the protecting layer include polyethylenes such as a high-density polyethylene; polypropylenes such as a propylene homo polymer, a propylene-ethylene random copolymer and a propylene-ethylene block copolymer; polyamides such as nylon 6 and nylon 6,6; polyesters such as PET; and combinations of these.

As the outer layer of the paper substrate (layer E), if necessary, an outer layer formed of a thermoplastic resin may be provided. When such a thermoplastic resin outer layer is provided, if the same thermoplastic resin as used in the aforementioned isolation layer (layer F) is used, layer F and the thermoplastic resin outer layer can be heat-sealed airtight.

In consideration of processability, an intermediate layer formed of a polyolefin resin can be interposed between layer A and layer D. It is preferable that the thickness of the intermediate layer is substantially the same as the thickness of layer F, in view of processability. Note that herein, in consideration of variation by processing, if a thickness ratio of the layers falls within ±10%, the thicknesses of the layers are regarded as being substantially same.

The method for manufacturing the oxygen-absorbing multilayer body of the embodiment is the same as described in the second embodiment.

[Oxygen-absorbing Paper Container]

The oxygen-absorbing paper container of the embodiment employs the aforementioned oxygen-absorbing multilayer body in part or in whole of the structure. Note that a paper container fully formed of an oxygen-absorbing multilayer body refers to a paper container formed only of the oxygen-absorbing multilayer body. A paper container partly formed of an oxygen-absorbing multilayer body refers to a paper container, which has a part formed of the oxygen-absorbing multilayer body and the other part formed of another material. Examples of the latter container include a paper container having a part formed of a transparent material (for example, a material formed of the oxygen-absorbing multilayer body layer without using a paper base material) so as to see an article (article to be packaged) contained in the container from the outside.

Usage of the oxygen-absorbing paper container of the embodiment and the shape thereof are not particularly limited and can be appropriately specified depending upon the article to be contained and stored. Examples of the shape of the oxygen-absorbing paper container of the embodiment various shapes such as a gable-top type, a brick type and a flat top.

In using the oxygen-absorbing paper container of the embodiment initiation of an oxygen absorption reaction can be facilitated and an oxygen-absorbing rate can be increased by irradiation of an energy ray. Examples of the usable energy ray include visible ray, UV ray, X-ray, electron ray and γ ray. The amount of irradiation energy can be appropriately selected depending upon the type of energy line to be used.

The oxygen-absorbing paper container of the embodiment does not require a moisture content for absorbing oxygen. In other words, oxygen can be absorbed regardless of the presence or absence of the moisture content of an article to be packaged. Thus, the container can be used in a wide variety of uses no matter which type of article to be packaged is contained. In particular, no odor is produced after absorption of oxygen. Thus, the container can be particularly preferably used in e.g., foods, cooking foods, beverages, health foods and medicinal products. More specifically, since the oxygen-absorbing paper container of the embodiment is excellent in oxygen-absorbing performance in a wide range of humidity conditions from low humidity to high humidity (relative humidity 0% to 100%) and excellent in taste and flavor retention property of a content, the container is suitable for packaging various articles. In addition, unlike a conventional oxygen-absorbing resin composition using an iron powder, the oxygen-absorbing resin composition of the embodiment can be suitably used for storing an article to be packaged (for example, alcohol beverages and carbonate beverages) which cannot be stored because of the presence of iron.

Specific examples of the article to be packaged include, but not particularly limited to, beverages such as cow milk, juice, coffee, tea and alcohol beverage; liquid seasonings such as source, soy sauce, noodle broth and dressing; chemical products such as an adhesive, a gluing agent, an agrichemical and a pesticide; medicinal products; sundry articles such as cosmetic, shampoo, conditioner and detergent; and other various articles. Particularly, the oxygen-absorbing paper container of the embodiment is suitable for packaging an article to be packaged easily degrading in the presence of oxygen. Examples of such an article to be packaged include beverages such as beer, wine, Japanese sake, shochu, fruit juice beverage, fruit juice, vegetable juice, carbonate soft drink, coffee, tea, mayonnaise, ketchup, edible oil, dressing and source.

Note that, the containers and articles to be packaged can be sterilized by a method suitable for the articles before and after packing (packaging) the articles. Any sterilization method may be applied as long as it is the same as described in the first embodiment.

(Sixth Embodiment)

Now, the sixth embodiment of the present invention will be described below. Note that repetition of explanation with respect to the same content as in the first to fifth embodiments is avoided herein.

[Tubular Container]

The tubular container of the embodiment has an oxygen-absorbing multilayer body (in the embodiment, hereinafter, simply referred to as the "multilayer body") including at least three layers including an inner layer (layer G) containing a thermoplastic resin, an oxygen-absorbing layer (layer A) formed of the oxygen-absorbing resin composition of the first embodiment and a gas barrier layer (layer D) containing a gas barrier substance, laminated in this order. Furthermore, the multilayer body provided in the tubular container of the embodiment may have a layer other than these three layers at any position, as necessary.

The tubular container of the embodiment can absorb oxygen within the container (even if the amount of oxygen transmitting or coming into the tubular container from the outside is small, transmitting or incoming oxygen is also absorbed) to prevent e.g., deterioration of the content (article to be packaged) stored therein by oxygen.

[Inner Layer (Layer G)]

The inner layer (layer G) of the multilayer body to be provided in the tubular container of the embodiment contains a thermoplastic resin. Layer G plays a role in transmitting oxygen within the container to the oxygen-absorbing layer; at the same time, isolating the oxygen-absorbing layer (layer A) and a content (an article to be packaged) (inhibiting physical contact between layer A and the article to be packaged). Furthermore, layer G may have a bonding area with the mouth part to be provided in the tubular container. Herein, the oxygen transmission rate of layer G measured in the case of a film having a thickness of 20 μm under the conditions of 23° C. and a relative humidity of 60% is preferably 300 mL/(m$^2$·day·atm) or more, more preferably 400 mL/(m$^2$·day·atm) or more and further preferably 500 mL/(m$^2$·day·atm) or more. If the oxygen transmission rate satisfies the aforementioned preferable value or more, the oxygen-absorbing rate of layer A can be more enhanced, compared to the case where the oxygen transmission rate does not satisfy the above value.

Examples of the thermoplastic resin to be used in layer G of the multilayer body to be provided in the tubular container of the embodiment include polyethylenes such as a high-density polyethylene, a medium-density polyethylene, a low-density polyethylene, a linear and low-density polyethylene, a linear and extremely low-density polyethylene and a polyethylene obtained in the presence of a metallocene catalyst; polystyrenes; polymethylpentenes; polypropylenes such as a propylene homo polymer, a propylene-ethylene block copolymer and a propylene-ethylene random copolymer. These can be used alone or in combination. To these thermoplastic resins, as necessary, an ethylene-vinyl acetate copolymer, an ethylene-methyl acrylate copolymer, an ethylene-ethyl acrylate copolymer, an ethylene-acrylic acid copolymer, an ethylene-methacrylic acid copolymer, an ethylene-methyl methacrylate copolymer and a thermoplastic elastomer may be added. As the thermoplastic resin to be used in layer G of the multilayer body to be provided in the tubular container of the embodiment, a thermo plastic resin having an MFR at 200° C. of 1 to 35 g/10 minutes or an MFR at 240° C. of 2 to 45 g/10 minutes is preferably used in consideration of moldability and processability of the tubular container.

Layer G of the multilayer body provided in the tubular container of the embodiment may contain additives known in the art other than a thermoplastic resin as mentioned above. Examples of such optional components include, but not particularly limited to, additives such as a drying agent, pigments such as titanium oxide, a dye, an antioxidant, a slipping agent, an antistatic agent, a plasticizer, a stabilizer and a lubricant; fillers such as calcium carbonate, clay, mica and silica; and a deodorant. Particularly, in view of recycling and reprocessing offcuts generated during manufacturing, it is preferable to add an antioxidant to layer G.

The content rate of the thermoplastic resin in layer G, which can be appropriately specified, is not particularly limited; however the content rate is preferably 70 to 100 mass % based on the total amount of layer G, more preferably 80 to 100 mass % and further preferably 90 to 100 mass %. Thermoplastic resin to be used in layer G of the embodiment preferably contains a thermoplastic resin other than a tetralin ring-containing copolymerized polyolefin compound, in an amount of 50 to 100 mass % based on the total amount of thermoplastic resins, more preferably 70 to 100 mass % and further preferably 90 to 100 mass %.

[Oxygen-absorbing Layer (Layer A)]

The oxygen-absorbing layer (A) of the multilayer body to be provided in the tubular container of the embodiment is formed of an oxygen-absorbing resin composition containing a copolymerized polyolefin compound containing a constituent unit (a), which is at least one ethylene or substituted ethylene constituent unit selected from the group consisting of the constituent units represented by the above general formula (1) and a constituent unit (b), which is at least one substituted ethylene constituent unit having a tetralin ring selected from the group consisting of the constituent units represented by the above general formula (2) or (3), and a transition metal catalyst. The oxygen-absorbing resin composition to be used herein is the same as that described in the first embodiment. Furthermore, the oxygen-absorbing layer (layer A) is the same as that described in the second embodiment except the matters specifically described below.

In the multilayer body provided in the tubular container of the embodiment, the thickness of the oxygen-absorbing layer (layer A), which can be appropriately specified depending upon use and desired performance, is not particularly limited. The thickness is preferably 5 to 200 μm and more preferably 10 to 150 μm. If the thickness falls within a preferable range as mentioned above, the performance of layer A to absorb oxygen can be more enhanced; at the same time, the processability and economic aspect can be maintained at high levels, compared to the case where the thickness does not fall within the above preferable range. The thickness of the inner layer (layer G), which can be also appropriately specified depending upon use and desired performance, is not particularly limited; however, the thickness is preferably 5 to 200 μm and more preferably 10 to 150 μm. If thickness falls within a preferable range as mentioned above, the oxygen-absorbing rate of layer A can be more enhanced; at the same time, the processability and economic aspect can be maintained at high levels, compared to the case where the thickness does not fall within the preferable range. In consideration of processability of the resultant oxygen-absorbing multilayer body, the thickness ratio of layer G and layer A (layer G:layer A) is preferably 1:0.5 to 1:3 and more preferably 1:1 to 1:2.5.

[Gas Barrier Layer (Layer D)]

The gas barrier layer (layer D) of the multilayer body to be provided in the tubular container of the embodiment contains a gas barrier substance. The gas barrier layer (layer D) and the gas barrier substance are the same as those described in the second embodiment except the matters specifically described below.

As the gas barrier substance to be used in the layer D of the multilayer body to be provided in the tubular container of the embodiment, a gas barrier thermoplastic resin, a gas barrier thermosetting resin, silica, alumina, aluminum, etc. (as vapor deposition films) and a metal (such as aluminum, in the form of foil) can be used. Examples of the gas barrier thermoplastic resin include an ethylene-vinyl alcohol copolymer, MXD6 and a poly(vinylidene chloride). Examples of the gas barrier thermosetting resin include gas barrier epoxy resins such as "MAXIVE", manufactured by Mitsubishi Gas Chemical Company, Inc. Note that the multilayer body to be provided in the tubular container of the embodiment can satisfactorily prevent deterioration of a content caused by oxygen, particularly due to the presence of the oxygen-absorbing layer (layer A), even though aluminum foil is not used in layer D. However, use of aluminum foil serving as layer D is not impeded.

[Optional Layer]

Note that the multilayer body to be provided in the tubular container of the embodiment may have one or more other layers such as a resin layer, a metal foil layer or an adhesive layer between layer G and layer A, layer A and layer D, or as the outer layer of layer G or as the outer layer of layer D. For example, to prevent breakage of layer D and formation of a pin hole, a protecting layer formed of a thermoplastic resin can be provided inside or outside layer D. Examples of the resin to be used in the protecting layer include polyethylenes such as a high-density polyethylene; polypropylenes such as a propylene homo polymer, a propylene-ethylene random copolymer and a propylene-ethylene block copolymer; polyamides such as nylon 6 and nylon 6,6; polyesters such as PET; and combinations of these.

In consideration of processability, the multilayer body to be provided in the tubular container of the embodiment preferably has an intermediate layer formed of a polyolefin resin between layer D and layer A. It is preferable that the thickness of the intermediate layer is substantially the same as the thickness of layer G in view of processability. Note that in consideration of variation by processing herein, if a thickness ratio of the layers falls within ±10%, the thicknesses of the layers are regarded as substantially same.

In the multilayer body, a paper base material is laminated as an outer layer of layer D and the resultant tubular container of the embodiment can be used as an oxygen-absorbing paper base material or as an oxygen-absorbing paper container. In view of maintaining processability in manufacturing a paper container by laminating with a paper base material at a high level, the total thickness of the layers present inside layer D is preferably 100 μm or less and more preferably 80 μm or less.

The tubular container of the embodiment is not particularly limited as long as it has a multilayer body obtained by forming a laminate film of the aforementioned layer G, layer A and layer D into a tubular form, and may have the same structure, shape and dimensions as those of a conventional tubular container. For example, the tubular container of the embodiment may further has a mouth part having an opening for ejecting an article to be packaged (content) and may have a cap for hermetically closing the tubular container. Furthermore, a method for manufacturing the tubular container of the embodiment is not particularly limited. The tubular container of the embodiment may be manufactured by a method known in the art, for example, the tubular container of the embodiment may be manufactured as follows.

First, at least layer G, layer A and layer D as mentioned above are laminated to manufacture a laminate film and both edge portions of the film are mutually sealed to obtain a tubular form. Thereafter, the tubular form is cut into pieces having a desired size, which are molded to obtain molded articles. A mouth part having an opening (ejection part) is bonded to an end of each of the molded articles to manufacture the tubular container of the embodiment. Alternatively, the tubular container of the embodiment can be manufactured by bonding a mouth part having an opening (ejection part) with a parison having a multilayered structure molded by coextrusion, in the same manner as in the art.

The aforementioned laminate film can be manufactured by using a known method such as a coextrusion method, a lamination method and a coating method, depending upon e.g., the properties of materials, processing purpose and processing step. The manufacturing method is not particularly limited. For example, a general method of laminating packaging materials such as a wet lamination process, a dry lamination process, a dry lamination process in the absence of a solvent, an extrusion lamination process, a T-die coextrusion molding method, a coextrusion lamination process and an inflation process can be applied. For example, for molding a film or a sheet, a method of extruding a molten resin composition from an extruder provided with a T die, a circular die, etc., and a method of applying an adhesive to an oxygen-absorbing film or sheet separately formed and attaching it to another film or sheet, are known. If necessary, for example, a pretreatment such as a corona treatment and an ozone treatment can be applied to a film etc. Also, e.g., a known anchor coating agent and an adhesive can be used. Examples of the anchor coating agent to be used include isocyanate (urethane), polyethylene imine, polybutadiene and organic titanium. Examples of the adhesive include polyurethane, polyacrylate, polyester, epoxy, poly(vinyl acetate), cellulose and other adhesives for lamination.

In using the tubular container of the embodiment, initiation of an oxygen absorption reaction can be facilitated and an oxygen-absorbing rate can be increased by irradiation of an energy ray. Examples of the usable energy ray include visible ray, UV ray, X-ray, electron ray and γ ray. The amount of irradiation energy can be appropriately selected depending upon the type of energy line to be used.

The tubular container of the embodiment does not require a moisture content for absorbing oxygen. In other words, oxygen can be absorbed regardless of the presence or absence of the moisture content of an article to be packaged. Thus, the tubular container can be used in a wide variety of uses no matter which type of article to be packaged is contained. In particular, no odor is produced after absorption of oxygen. Thus, the tubular container can be particularly preferably used in e.g., foods, cooking foods, beverages, health foods, cosmetics and medicinal products. More specifically, since the tubular container of the embodiment is excellent in oxygen-absorbing performance in a wide range of humidity conditions from low humidity to high humidity (relative humidity 0% to 100%) and excellent in taste and flavor retention property of a content, it is suitable for packaging various articles.

Specific examples of the article to be packaged include, but not particularly limited to, seasonings such as mayonnaise, miso, mustard, grated spices including wasabi, zinger and garlic; paste foods such as jam, dairy cream, butter, margarine and chocolate paste; cosmetics and medicated cosmetics such as toothpastes, hair dyes, coloring agents and soaps; medicinal products; chemicals; and other various articles. Particularly, the tubular container is suitable as a packaging material for an article to be packaged easily causing degradation in the presence of oxygen, such as seasonings, medicinal products and cosmetics.

Note that the containers and articles to be packaged can be sterilized by a method suitable for the articles before and after packing (packaging) the articles. Any sterilization method may be applied as long as it is the same as described in the first embodiment.

(Seventh Embodiment)

Now, the seventh embodiment of the present invention will be described below. Note that repetition of explanation with respect to the same content as in the first to sixth embodiments is avoided herein.

[Oxygen-absorbing Medical Multilayer Molded Container]

The oxygen-absorbing medical multilayer molded container of the embodiment includes at least three layers, i.e., a first resin layer (layer B) at least containing polyester, an oxygen-absorbing layer (layer A) formed of an oxygen-absorbing resin composition of the first embodiment, a second resin layer (layer B) at least containing polyester, laminated in this order.

The oxygen-absorbing medical multilayer molded container of the embodiment can absorb oxygen within the container (even if the amount of oxygen transmitting or coming into the container from the outside through the wall of the container is small, transmitting or incoming oxygen is also absorbed) to prevent deterioration etc. of the content (article to be packaged) stored therein by oxygen.

The layer constitution of the oxygen-absorbing medical multilayer molded container of the embodiment is not particularly limited. More specifically, the numbers and types of oxygen-absorbing layers (layer A) and resin layers (layer B) are not particularly limited as long as these layers are arranged in the order of B/A/B. For example, a five-layer (B1/B2/A/B2/B1) structure, which is constituted of one layer A and two layers B1 and two layers B2, may be acceptable. Furthermore, the oxygen-absorbing medical multilayer molded container of the embodiment, may have an optional layer, if necessary, such as an adhesion layer (layer AD). For example, seven-layer (B1/B2/AD/A/AD/B2/B1) structure is acceptable.

[Oxygen-absorbing Layer (Layer A)]

In the oxygen-absorbing medical multilayer molded container of the embodiment, the oxygen-absorbing layer (A) comprises an oxygen-absorbing resin composition containing a copolymerized polyolefin compound which contains a constituent unit (a), which is at least one ethylene or substituted ethylene constituent unit selected from the group consisting of the constituent units represented by the above general formula (1) and a constituent unit (b), which is at least one substituted ethylene constituent unit having a tetralin ring, selected from the group consisting of the constituent units represented by the above general formula (2) or (3) and a transition metal catalyst. The oxygen-absorbing resin composition used here is the same as that described in the first embodiment. Furthermore, the oxygen-absorbing layer (layer A) is the same as that described in the second embodiment except the following matters particularly described.

In the oxygen-absorbing medical multilayer molded container of the embodiment, the thickness of the oxygen-absorbing layer (layer A), which can be appropriately specified depending upon use and desired performance, is not particularly limited. In view of having high oxygen-absorbing performance and ensuring physical properties required for a medical multilayer molded container, the thickness is preferably 1 to 1000 μm, more preferably 50 to 900 μm and further preferably 100 to 800 μm.

[Resin Layer (Layer B) Containing Polyester]

In the oxygen-absorbing medical multilayer molded container of the embodiment, the resin layer (layer B) is a layer containing polyester. The content rate of polyester in layer B, which can be appropriately specified, is not particularly limited. The content rate is preferably 70 to 100 mass % based on the total amount of layer B, more preferably 80 to 100 mass % and further preferably 90 to 100 mass %. Drug solution storage stability can be improved and the low adsorptivity of a drug solution can be enhanced by setting the content rate of polyester to 70 mass % or more.

The oxygen-absorbing medical multilayer molded container of the embodiment may have a plurality of layers B such as the layers B1 and B2. The constitution of the plural layers B may be the same or different. The thickness of layer B, which can be appropriately determined depending upon the use, is not particularly limited. In view of ensuring physical properties required for a medical multilayer molded container, the thickness is preferably 50 to 10000 μm, more preferably 100 to 7000 μm and further preferably 300 to 5000 μm.

<Polyester>

As specific examples of the polyester used in layer B of the embodiment, those formed of one or two or more compounds selected from polyvalent carboxylic acids containing a dicarboxylic acid and ester-forming derivatives of these and one or two or more compounds selected from polyhydric alcohols including a glycol; those formed of hydroxy carboxylic acids and ester-forming derivative of these; or those formed of cyclic esters are mentioned.

Specific examples of the dicarboxylic acid include saturated aliphatic dicarboxylic acids such as oxalic acid, malonic acid, succinic acid, glutaric acid, adipic acid, pimelic acid, suberic acid, azelaic acid, sebacic acid, decanedicarboxylic acid, dodecanedicarboxylic acid, tetradecanedicarboxylic acid, hexadecanedicarboxylic acid, 3-cyclobutanedicarboxylic acid, 1,3-cyclopentanedicarboxylic acid, 1,2-cyclohexanedicarboxylic acid, 1,3-cyclohexanedicarboxylic acid, 1,4-cyclohexanedicarboxylic acid, 2,5-norbornanedicarboxylic acid and dimer acid or ester-forming derivatives of these; unsaturated aliphatic dicarboxylic acids such as fumaric acid, maleic acid and itaconic acid or ester-forming derivatives of these; naphthalenedicarboxylic acids such as orthophthalic acid, isophthalic acid, terephthalic acid, 1,3-naphthalenedicarboxylic acid, 1,4-naphthalenedicarboxylic acid, 1,5-naphthalenedicarboxylic acid, 2,6-naphthalenedicarboxylic acid and 2,7-naphthalenedicarboxylic acid; aromatic dicarboxylic acids such as 4,4'-biphenyldicarboxylic acid, 4,4'-biphenylsulfonedicarboxylic acid, 4,4'-biphenyletherdicarboxylic acid, 1,2-bis(phenoxy)ethane-p,p'-dicarboxylic acid and anthracenedicarboxylic acid or ester-forming derivatives of these; and metal sulfonate group-containing aromatic dicarboxylic acids such as 5-sodium sulfo-isophthalic acid, 2-sodium sulfo-terephthalic acid, 5-lithium sulfo-isophthalic acid, 2-lithium sulfo-terephthalic acid, 5-potassium sulfo-isophthalic acid and 2-potassium sulfo-terephthalic acid or lower alkyl ester derivatives of these.

Of the aforementioned dicarboxylic acids, particularly, terephthalic acid, isophthalic acid and naphthalene dicarboxylic acid are preferably used in view of the physical properties etc. of the polyesters to be obtained. Note that, if necessary, other dicarboxylic acids may be copolymerized.

Specific examples of the polyvalent carboxylic acids other than these dicarboxylic acids include ethane tricarboxylic acid, propane tricarboxylic acid, butane tetracarboxylic acid, pyromellitic acid, trimellitic acid, trimesic acid, 3,4,3',4'-biphenyltetracarboxylic acid and ester-forming derivatives of these.

Specific examples of the glycol include aliphatic glycols such as ethylene glycol, 1,2-propylene glycol, 1,3-propylene glycol, diethylene glycol, triethylene glycol, 1,2-butylene glycol, 1,3-butylene glycol, 2,3-butylene glycol, 1,4-butylene glycol, 1,5-pentanediol, neopentyl glycol, 1,6-hexanediol, 1,2-cyclohexanediol, 1,3-cyclohexanediol, 1,4-cyclohexanediol, 1,2-cyclohexane dimethanol, 1,3-cyclohexane dimethanol, 1,4-cyclohexane dimethanol, 1,4-cyclohexane diethanol, 1,10-dacamethylene glycol, 1,12-dodecane diol, polyethylene glycol, poly(trimethylene glycol) and poly(tetramethylene glycol); and aromatic glycols such as hydroquinone, 4,4'-dihydroxy bisphenol, 1,4-bis(β-hydroxyethoxy)benzene, 1,4-bis(β-hydroxyethoxyphenyl)sulfone, bis(p-hydroxyphenyl)ether, bis(p-hydroxyphenyl)sulfone, bis(p-hydroxyphenyl)methane, 1,2-bis(p-hydroxyphenyl)ethane, bisphenol A, bisphenol C, 2,5-naphthalene diol and glycols formed by adding an ethylene oxide to these glycols.

Of the glycols mentioned above, particularly, ethylene glycol, 1,3-propylene glycol, 1,4-butylene glycol, and 1,4-cyclohexane dimethanol are preferably used as a main component.

Specific examples of the polyhydric alcohols other than these glycols include trimethylol methane, trimethylol ethane, trimethylol propane, pentaerythritol, glycerol and hexane triol.

Specific examples of the hydroxy carboxylic acid include, lactic acid, citric acid, malic acid, tartaric acid, hydroxyacetic acid, 3-hydroxybutyrate, p-hydroxybenzoate, p-(2-hydroxyethoxy)benzoate, 4-hydroxycyclohexanecarboxylic acid and ester-forming derivatives of these.

Specific examples of the cyclic esters include ε-caprolactone, β-propiolactone, β-methyl-β-propiolactone, δ-valerolactone, glycolide and lactide.

Specific examples of the ester-forming derivatives of a polyvalent carboxylic acid and a hydroxy carboxylic acid include alkyl esters, acid chlorides and acid anhydrides of these.

Of the aforementioned ones, a polyester containing terephthalic acid or an ester-forming derivative thereof or a naphthalene dicarboxylic acid or an ester-forming derivative thereof as a main acid component and an alkylene glycol as a main glycol component is preferable.

Note that the polyester containing terephthalic acid or an ester-forming derivative thereof as a main acid component is a polyester preferably containing the terephthalic acids or an ester-forming derivatives thereof in total in an amount of 70 mole % or more based on the total amount (mole) of the acid components, more preferably in an amount of 80 mole % or more and further preferably in an amount of 90 mole % or more. Similarly, the polyester containing naphthalene dicarboxylic acids or ester-forming derivatives thereof as a main acid component is a polyester preferably containing naphthalene dicarboxylic acids or ester-forming derivatives thereof in total in an amount of 70 mole % or more, more preferably in an amount of 80 mole % or more and further preferably in an amount of 90 mole % or more.

Of the aforementioned naphthalene dicarboxylic acids or ester-forming derivatives of these, dicarboxylic acids exemplified above such as 1,3-naphthalene dicarboxylic acid, 1,4-naphthalene dicarboxylic acid, 1,5-naphthalene dicarboxylic acid, 2,6-naphthalene dicarboxylic acid and 2,7-naphthalene dicarboxylic acid or ester-forming derivatives of these are preferable.

Another preferable example of the polyester to be used in layer B of the oxygen-absorbing multilayer body of the embodiment is poly(glycolic acid), which is obtained through polycondensation of a glycolic acid and methyl glycolate or ring-opening polycondensation of glycolide. Note that the poly(glycolic acid) may be copolymerized with another component such as lactide.

In particular, as the polyester to be used in layer B of the embodiment, a polyester containing terephthalic acid or an ester-forming derivative thereof or a naphthalene dicarboxylic acid or an ester-forming derivative thereof as a main acid component and containing an alkylene glycol as a main glycol component, is preferable. Furthermore, alkylene glycol is preferably contained in an amount of 70 mole % or more and more preferably 90 mole % or more, in view of physical properties etc. Of the aforementioned dicarboxylic acids, particularly, use of terephthalic acid, isophthalic acid, 1,3-naphthalene dicarboxylic acid, 1,4-naphthalene dicarboxylic acid, 1,5-naphthalene dicarboxylic acid, 2,6-naphthalene dicarboxylic acid or 2,7-naphthalene dicarboxylic acid is preferable in view of physical properties etc. of the resultant polyester. Such polyester is preferably contained in an amount of 70 mole % or more. Of these dicarboxylic acids, particularly terephthalic acid and/or 2,6-naphthalene dicarboxylic acid are preferable. Furthermore, terephthalic acid and/or 2,6-naphthalene dicarboxylic acid are preferably contained in an amount of 70 mole % or more in view of physical properties etc., and more preferably in an amount of 90 mole % or more. If necessary, another dicarboxylic acid may be copolymerized. Furthermore, use of at least one copolymer component selected from the group consisting of isophthalic acid, diethylene glycol, neo-pentyl glycol, 1,4-cyclohexane dimethanol, 1,2-propanediol, 1,3-propanediol and 2-methyl-1,3-propanediol is preferable in view of obtaining transparency and moldability at the same time, particularly at least one selected from the group consisting of isophthalic acid, diethylene glycol, neopentyl glycol and 1,4-cyclohexanedimethanol is more preferable.

The oxygen-absorbing medical multilayer molded container of the embodiment may have an optional layer, which varies depending upon desired performance etc., other than the aforementioned oxygen-absorbing layer (layer A) and resin layer (layer B) containing polyester. Examples of such an optional layer include an adhesion layer.

For example, in view of more enhancing interlayer adhesion strength between adjacent two layers, an adhesion layer (layer AD) is preferably provided between the two layers. The adhesion layer preferably contains a thermoplastic resin having adhesiveness. Examples of the thermoplastic resin having adhesiveness include acid modified polyolefin resins obtained by modifying a polyolefin resin such as a polyethylene or a polypropylene with an unsaturated carboxylic acid such as acrylic acid, methacrylic acid, maleic acid, maleic anhydride, fumaric acid and itaconic acid; and polyester thermoplastic elastomers containing a polyester block copolymer as a main component. Note that the thickness of the adhesion layer is not particularly limited; however, in view of ensuring molding processability while exerting practical adhesion strength, the thickness of the adhesion layer is preferably 2 to 100 µm, more preferably 5 to 90 µm and further preferably 10 to 80 µm.

As a method for manufacturing the oxygen-absorbing medical multilayer molded container of the embodiment, a known method varying depending upon the properties of materials, a desired shape, etc. can be applied, but is not particularly limited. For example, a multilayer molded container can be manufactured by applying various types of injection molding methods.

The thickness of the oxygen-absorbing medical multilayer molded container of the embodiment is not particularly limited. In view of enhancing oxygen-absorbing performance and ensuring physical properties required for a medical multilayer molded container, the thickness is preferably 3 to 5000 µm, more preferably 5 to 4500 µm and further preferably 10 to 4000 µm.

A multilayer molded article can be obtained by a method other than the injection molding method, for example, a compression molding method. To the resultant multilayer molded article, secondary processing is applied to mold the article into a container having a desired shape. For example, in a polyester melt, an oxygen-absorbing resin composition is provided and a molten lump is supplied to a positive die and simultaneously compressed by a negative die and then compression molded product is cooled and solidified. In this manner, a multilayer molded article can be obtained. As the secondary processing, for example, extrusion molding, compression molding (sheet molding, blow-molding), etc. are applicable.

Usage of the oxygen-absorbing medical multilayer molded container of the embodiment is not particularly limited. The container can be used for various uses and in various forms. Examples of preferable usage thereof include, but not particularly limited to, vials, ampules, prefilled syringes and vacuum blood collection tubes. Now, preferable usage will be described in detail, below.

[Vial]

The oxygen-absorbing medical multilayer molded container of the embodiment can be used as a vial. Generally, a vial is constituted of a bottle, a rubber tap and a cap. The bottle is filled with a drug solution, stoppered by the rubber tap and further capped to hermetically close the bottle. The oxygen-absorbing medical multilayer molded container of the embodiment can be used as the bottle portion of the vial.

As a method for molding the oxygen-absorbing medical multilayer molded container of the embodiment into a bottle portion of a vial, for example, injection blow-molding and extrusion blow-molding are preferable. As a specific example thereof, an injection blow-molding method will be described below. For example, using a molding machine having two or more injectors and an injection mold, a material for constituting layer A and a material for constituting layer B are separately injected from respective injection cylinders through a mold hot runner into the cavity of the injection mold to manufacture a multilayer injection-molded article constituted of three layers (B/A/B) having a shape in accordance with a cavity shape of the injection mold. Furthermore, first, a material for constituting layer B is injected from the injection cylinder, and then, a material for constituting layer A is injected from another injection cylinder simultaneously with a resin for constituting layer B, subsequently, the resin for constituting layer B is injected in a necessary amount to fill the cavity to manufacture a multilayer injection-molded article constituted of three layers (B/A/B). Furthermore, first, a material for constituting layer B is injected, then a material for constituting layer A is solely injected, and finally the material for constituting layer B is injected in a necessary amount to fill the mold cavity to manufacture a multilayer injection-molded article constituted of five layers (B/A/B/A/B). Moreover, first, a material for constituting layer B1 is injected from an injection cylinder and then a material for constituting layer B2 is injected from another injection cylinder simultaneously with a resin for constituting layer B1, subsequently a resin for constituting layer A is injected simultaneously with resins for constituting layer B1 and layer B2 and thereafter the resin for constituting layer B1 is injected in a necessary amount to fill the cavity to manufacture a multilayer injection-molded article constituted of five layers (B1/B2/A/B2/B1). In the injection blow-molding, the multilayer injection-molded article obtained by the above method is heated to some extent. While keeping this state, the article is fit in a final-shape mold (blow mold) and air is fed to swollen the article, with the result that the article comes into contact with the mold. Then, the article was cooled and solidified to mold a bottle.

[Ampule]

The oxygen-absorbing medical multilayer molded container of the embodiment can be used as an ampule. Generally, an ampule is constituted of a small container having a narrow neck. The container is filled with a drug solution and the tip of the neck portion is welded to hermetically close the container. The oxygen-absorbing medical multilayer molded container of the embodiment can be used as the ampule (small container). As a method for molding the oxygen-absorbing medical multilayer molded container of the embodiment into an ampule, for example, injection blow-molding and extrusion blow-molding are preferred.

[Prefilled Syringe]

The oxygen-absorbing medical multilayer molded container of the embodiment can be used as a prefilled syringe. Generally, a prefilled syringe is at least constituted of a barrel to be filled with drug solution, a joint portion for joining an injection needle at an end of the barrel and a plunger for pushing the drug solution at the time of use. This is a syringe constituted in such a manner that a drug solution is stored in advance in a sealed condition in the barrel and the tip portion of the barrel is opened and an injection needle is fit to the barrel at the time of use. Owing to its convenience, prefilled syringe is widely used. The oxygen-absorbing medical multilayer molded container of the embodiment can be used as the barrel.

As a method for molding the oxygen-absorbing medical multilayer molded container of the embodiment into a barrel of the prefilled syringe, for example, an injection molding method is preferred. To describe more specifically, first, a resin for constituting layer B is injected into the cavity of an injection mold in a predetermined amount. Then, a resin for constituting layer A is injected in a predetermined amount and the resin for constituting layer B is again injected in a predetermined amount to manufacture a multilayer injection-molded article serving as a barrel. The oxygen-absorbing layer (layer A) is preferably formed up to the vicinity of a nozzle tip surface.

The barrier property of the barrel is further ensured by the formation of the oxygen-absorbing layer (layer A) up to the vicinity of the nozzle tip surface. Furthermore, the oxygen-absorbing layer (layer A) is preferably formed up to the position at which a gasket to be inserted into the barrel. The barrier property of a barrel is further ensured by the formation of the oxygen-absorbing layer (layer A) up to the position at which a gasket to be inserted in the barrel. Note that the barrel and the joint portion can be integrally molded or they are separately molded and then joined. After the barrel is filled with a drug solution, the tip portion of the joint portion must be sealed. As the sealing method, which is not particularly limited, a known method can be employed. For example, the resin of the joint tip portion is heated, melted and clipped by a pincher etc. to fuse.

The thickness of the barrel container of the prefilled syringe, which can be appropriately specified depending upon the purpose of use and size, is not particularly limited. Generally, in view of long-term storage stability of a drug solution, moldability and operability of the syringe, the thickness is preferably about 0.5 to 20 mm and more preferably about 0.5 to 5 mm. The thickness may be uniform or nonuniform. As the shape of the barrel, a cylindrical shape having a male luer-taper nozzle, to which a syringe can connect liquid-tight, at the top, and having a shoulder portion from a nozzle base to the cylinder wall; and having a flange for finger at the open end, is preferably employed. For the purpose of long-term storage stability, another gas barrier film and light blocking film may be further formed on the barrel surface. These optional films and a method for forming them are described, for example, in Japanese Patent Application Laid-Open No. 2004-323058.

[Vacuum Blood Collection Tube]

The oxygen-absorbing medical multilayer molded container of the embodiment can be used as a vacuum blood collection tube. Generally, a vacuum blood collection tube is constituted of a tubular body and a tap. The oxygen-absorbing medical multilayer molded container of the embodiment can be used as the tubular body.

As a method for molding the oxygen-absorbing medical multilayer molded container of the embodiment into a tubular body of a vacuum blood collection tube, for example, an injection molding method is preferred. To describe more specifically, first, a resin for constituting layer B is injected into the cavity of an injection mold in a predetermined amount and then a resin for constituting layer A is injected in a predetermined amount, and then, the resin for constituting layer B is injected again in a predetermined amount to manufacture a multilayer injection-molded article serving as the tubular body.

[Article to be Packaged]

Examples of the article to be packaged (content) that is to be packed in the oxygen-absorbing medical multilayer molded container of the embodiment include, but not particularly limited to, arbitrary natural substances and compounds including vitamins such as vitamin A, vitamin B2, vitamin B12, vitamin C, vitamin D, vitamin E and vitamin K; alkaloids such as atropine; hormones such as adrenaline and insulin; sugars such as glucose and maltose; antibiotics such as ceftriaxone, cephalosporin and cyclosporine; and benzodiazepine medicinal agents such as oxazolam, flunitrazepam, clotiazepam and clobazam. When these natural substances and compounds each are packed in the oxygen-absorbing medical multilayer molded container of the embodiment, the amount of natural substances and compounds adsorbed is small and deterioration of these by oxidation can be suppressed. In addition, evaporation of a solvent (for example moisture content) can be suppressed.

[Biopharmaceutical]

The oxygen-absorbing medical multilayer molded container of the embodiment can be preferably used as a storage container for biopharmaceutical. In view of the effect of the embodiment, as a biopharmaceutical that can be preferably used include protein preparations and nucleic acid pharmaceutical preparations. Specific examples thereof include, but not particularly limited to, monoclonal antibodies, vaccines, interferon, insulin, growth hormone, erythropoietin, colony stimulating factor, TPA, interleukin, blood coagulation factor VIII, blood coagulation factor IX, sodium diuresis hormone, somatomedin, glucagon, serum albumin, calcitonin, growth hormone-releasing factor, digestive enzymes, anti-inflammatory enzymes, antibiotics, antisense nucleic acids, antigene nucleic acids, decoy nucleic acids, aptamers, siRNA and microRNA. When these biopharmaceuticals each are packed in a medical multilayer container, the amount of these biopharmaceuticals adsorbed is small and deterioration of these medicines by oxidation and reduction of drug efficacy can be suppressed. In addition, evaporation of a solvent (for example moisture content) can be suppressed.

Note that, before and after packing of these articles to be packaged, sterilization treatment can be applied to medical multilayer containers and the articles by a method suitable for the articles. Examples of a sterilization method include a hot water treatment performed at 100° C. or less, a hot water treatment under application of pressure performed at 100° C. or more, thermal sterilization performed at a temperature as high as 121° C. or more, sterilization by electromagnetic wave such as UV ray, microwave and gamma ray, a treatment with a gas such as ethylene oxide and sterilization with a chemical agent such as hydrogen peroxide and hypochlorite.

(Eighth Embodiment)

Now, the eighth embodiment of the present invention will be described below. Note that repetition of explanation with respect to the same content as in the first to seventh embodiments is avoided herein.

The oxygen-absorbing PTP packaging body of the embodiment has an oxygen-absorbing bottom material formed of an oxygen-absorbing multilayer body, a gas barrier cover material including at least two layers including an inner layer containing a thermoplastic resin and a gas barrier layer containing a bas barrier substance, laminated in this order, in which the sealant layer (layer C) of the oxygen-absorbing bottom material and the inner layer of the gas barrier cover material are bonded

[Oxygen-absorbing Multilayer Body]

The oxygen-absorbing multilayer body of the embodiment includes at least three layers including a sealant layer (layer C) containing a thermoplastic resin, an oxygen-absorbing layer (layer A) formed of the oxygen-absorbing resin composition according to the first embodiment and a gas barrier layer (layer D) containing a gas barrier substance, these of which are laminated in this order. Furthermore, the oxygen-absorbing multilayer body of the embodiment may have a layer other than these three layers at any position, as necessary.

By using the oxygen-absorbing multilayer body of the embodiment in an oxygen-absorbing PTP packaging body such that layer C faces inside, oxygen within the container can be absorbed (even if the amount of oxygen transmitting or coming into the container from the outside through the wall of the container is small, transmitting or incoming oxygen is also absorbed) to prevent e.g., deterioration of the content (article to be packaged) stored therein by oxygen.

[Sealant Layer (Layer C)]

The sealant layer (layer C) of the oxygen-absorbing multilayer body of the embodiment contains a thermoplastic resin. The sealant layer (layer C) of the oxygen-absorbing multilayer body of the embodiment and a thermoplastic resin thereof are the same as those described in the second embodiment.

[Oxygen-absorbing Layer (Layer A)]

The oxygen-absorbing layer (layer A) of the oxygen-absorbing multilayer body of the embodiment is formed of an oxygen-absorbing resin composition containing the copolymerized polyolefin compound, which contains a constituent unit (a), which is at least one ethylene or substituted ethylene constituent unit selected from the group consisting of the constituent units represented by the above general formula (1) and a constituent unit (b), which is at least one substituted ethylene constituent unit having a tetralin ring selected from the group consisting of the constituent units represented by the above general formula (2) or (3), and a transition metal catalyst. The oxygen-absorbing resin composition used herein is the same as described in the first embodiment. Furthermore, the oxygen-absorbing layer (layer A) is the same as that described in the second embodiment.

[Gas Barrier Layer (Layer D)]

The gas barrier layer (layer D) of the oxygen-absorbing multilayer body of the embodiment contains a gas barrier substance. The gas barrier layer (layer D) and the gas barrier substance are the same as those described in the second embodiment except the matters specifically described below.

As the gas barrier substance to be used in layer D of the oxygen-absorbing multilayer body of the embodiment, a gas barrier thermoplastic resin, a gas barrier thermosetting resin, silica, alumina, aluminum, etc. (as vapor deposition films) and a metal (such as aluminum, in the form of foil) can be used. Examples of the gas barrier thermoplastic resin having visibility of an article to be packaged include an ethylene-vinyl alcohol copolymer, MXD6, and a poly(vinylidene chloride). Examples of the gas barrier thermosetting resin include gas barrier epoxy resins such as "MAXIVE", manufactured by Mitsubishi Gas Chemical Company, Inc.

[Optional Layer]

Note that the oxygen-absorbing multilayer body of the embodiment may have one or more other layers such as a resin layer, a metal foil layer or an adhesive layer between layer C and layer A, layer A and layer D, or as the outer layer of layer C or as the outer layer of layer D. The optional layer is the same as that described in the second embodiment.

The method for manufacturing the oxygen-absorbing multilayer body of the embodiment is the same as that described in the second embodiment.

[Oxygen-absorbing Bottom Material]

The oxygen-absorbing bottom material of the embodiment is formed by molding the aforementioned oxygen-absorbing multilayer body. The oxygen-absorbing bottom material of the embodiment is not particularly limited in shape and can be formed into a container having any shape by thermoforming depending upon the article to be contained and stored.

More specifically, a film-form or sheet-form oxygen-absorbing multilayer body as mentioned above is subjected to molding such as vacuum molding, air-pressure forming and plug assist molding to manufacture an oxygen-absorbing bottom material having a space where an article to be packaged such as tablets, is to be contained.

Note that, in manufacturing an oxygen-absorbing bottom material having a flange portion, a special process for imparting an easy-peeling function may be applied to the flange portion. Furthermore, if the above oxygen-absorbing multilayer body is used as a material for a cover of a container, a top seal, etc., an oxygen-absorbing function can be provided to these containers.

[Gas Barrier Cover Material]

The gas barrier cover material of the embodiment includes at least two layers including an inner layer containing a thermoplastic resin and a gas barrier layer containing a bas barrier substance, laminated in this order, and can reduce the amount of oxygen transmitting or coming into the oxygen-absorbing PTP packaging body from the outside of the gas barrier cover material through the cover material. Furthermore, the gas barrier molded article of the embodiment may have a layer other than these two layers at any position, as necessary. Particularly, if the oxygen-absorbing layer (layer A) of the aforementioned embodiment is provided between these two layers, an oxygen-absorbing function can be provided to the cover material.

The thermoplastic resin to be used in the inner layer of the gas barrier cover material of the embodiment is not particularly limited. Specific examples thereof include those described as thermoplastic resins that are preferably used as the sealant layer (layer C) of the aforementioned oxygen-absorbing multilayer body.

The inner layer of the gas barrier cover material of the embodiment may contain various types of additives known in the art other than a thermoplastic resin as mentioned above. Specific examples thereof include those described as the additives that are preferably used in the sealant layer (layer C) of the aforementioned oxygen-absorbing multilayer body.

The content rate of the thermoplastic resin in the inner layer, which can be appropriately specified, is not particularly limited; however the content rate is preferably 70 to 100 mass % based on the total amount of the inner layer, more preferably 80 to 100 mass % and further preferably 90 to 100 mass %. The thickness of the inner layer, which can be appropriately set depending upon use and desired performance, is not particularly limited, however, the thickness is preferably 1 to 50 μm and more preferably 5 to 20 μm.

Thermoplastic resin to be used in the inner layer of the gas barrier cover material of the embodiment is preferably the same type of thermoplastic resin used in layer C of the above oxygen-absorbing multilayer body in view of ensuring heat sealing strength of an oxygen-absorbing PTP packaging body.

The gas barrier layer of the gas barrier cover material of the embodiment contains a gas barrier substance. The oxygen transmission rate of the gas barrier layer measured in the case of a film having a thickness of 20 μm under the conditions of 23° C. and a relative humidity of 60% is preferably 100 mL/(m$^2$·day·atm) or less, more preferably 80 mL/(m$^2$·day·atm) or less and further preferably 50 mL/(m$^2$·day·atm) or less.

Specific examples of the gas barrier substance to be used in the gas barrier layer of the gas barrier cover material of the embodiment include those described as the gas barrier substances that are preferably used in the gas barrier layer (layer D) of the aforementioned oxygen-absorbing multilayer body. Particularly, in the oxygen-absorbing PTP packaging body, aluminum foil is particularly preferably used since the stored article to be packaged is taken out by squeezing. The thickness of the gas barrier layer of the gas barrier cover material is preferably 1 to 100 μm and more preferably 5 to 20 μm.

[Oxygen-absorbing PTP Packaging Body]

The oxygen-absorbing PTP packaging body of the embodiment has an oxygen-absorbing bottom material formed of the aforementioned oxygen-absorbing multilayer body and a gas barrier cover material, in which the sealant layer of the oxygen-absorbing bottom material and the inner layer of the gas barrier cover material are bonded. The oxygen-absorbing PTP packaging body of the embodiment can absorb oxygen within the container (even if the amount of oxygen coming into the container from the outside is small, incoming oxygen is also absorbed) to prevent e.g., deterioration of the content (article to be packaged) stored therein by oxygen. Note that a PTP (press-through package) packaging body is identical with a blister package called in foreign countries.

In using the oxygen-absorbing multilayer body of the embodiment and oxygen-absorbing PTP packaging body containing the multilayer body, initiation of an oxygen absorption reaction can be facilitated and an oxygen-absorbing rate can be increased by irradiation of an energy ray. Examples of the usable energy ray include visible ray, UV ray, X-ray, electron ray and γ ray. The amount of irradiation energy can be appropriately selected depending upon the type of energy line to be used.

The containers and articles to be packaged can be sterilized by a method suitable for the articles before and after containing (packaging) the articles. Any sterilization method may be applied as long as it is the same as described in the first embodiment.

[Article to be Packaged]

The article to be packaged to be contained in the oxygen-absorbing PTP packaging body of the embodiment is not particularly limited, for example, tablets are mentioned. More specifically, for example, health foods such as vitamin C and vitamin E; and medicinal products such as swallowable tablets and orally-disintegrating tablets (OD tablets) can be contained.

(Ninth Embodiment)

The ninth embodiment of the present invention will be described below. Note that repetition of explanation with respect to the same contents as in the first to eighth embodiments is avoided herein.

[Oxygen-absorbing Multilayer Bottle]

The oxygen-absorbing multilayer bottle of the embodiment includes at least three layers including an oxygen transmission layer (layer H) containing a thermoplastic resin, an oxygen-absorbing layer (layer A) formed of the oxygen-absorbing resin composition according to the first embodiment and a gas barrier layer (layer D) containing a gas barrier substance, these of which are laminated in this order from inside. Furthermore, the oxygen-absorbing multilayer bottle of the embodiment may have a layer other than these three layers at any position, as necessary.

By using the oxygen-absorbing multilayer bottle of the embodiment in part or in whole of a packaging container for hermetic closing such that layer H faces inside, oxygen within the container can be absorbed (even if the amount of oxygen transmitting or coming into the container from the outside through the wall of the container is small, transmitting or incoming oxygen is also absorbed) to prevent e.g., deterioration of the content (article to be packaged) stored therein by oxygen.

[Oxygen Transmission Layer (Layer H)]

The oxygen transmission layer (layer H) of the oxygen-absorbing multilayer bottle of the embodiment contains a thermoplastic resin. Layer H plays a role in transmitting oxygen within a container up to the oxygen-absorbing layer; at the same time, isolating the oxygen-absorbing layer (layer A) and a content (an article to be packaged) (inhibiting physical contact between layer A and the article). Furthermore, layer H also serves as a sealant in sealing the multilayer bottle when the oxygen-absorbing multilayer bottle of the embodiment is heat-sealed with a top film (cover material) having a gas barrier property. The layer H of the oxygen-absorbing multilayer bottle of the embodiment is the same as oxygen transmission layer (layer H) of the oxygen-absorbing multilayer body in the third embodiment.

[Oxygen-absorbing Layer (Layer A)]

The oxygen-absorbing layer (layer A) of the oxygen-absorbing multilayer bottle of the embodiment is formed of an oxygen-absorbing resin composition containing the copolymerized polyolefin compound, which contains a constituent unit (a), which is at least one ethylene or substituted ethylene constituent unit selected from the group consisting of the constituent units represented by the above general formula (1) and a constituent unit (b), which is at least one substituted ethylene constituent unit having a tetralin ring selected from the group consisting of the constituent units represented by the above general formula (2) or (3); and a transition metal catalyst. The oxygen-absorbing resin composition used herein is the same as described in the first embodiment. Furthermore, the oxygen-absorbing layer (layer A) is the same as the oxygen-absorbing layer (layer A) of the oxygen-absorbing multilayer body described in the third embodiment.

[Gas Barrier Layer (Layer D)]

The gas barrier layer (layer D) of the oxygen-absorbing multilayer bottle of the embodiment contains a gas barrier substance. The gas barrier layer (layer D) is the same as the gas barrier layer (layer D) of the oxygen-absorbing multilayer body described in the third embodiment.

[Optional Layer]

Note that the oxygen-absorbing multilayer bottle of the embodiment may have one or more other layers such as a resin layer, a metal foil layer or an adhesive layer between layer H and layer A, layer A and layer D, or as the outer layer of layer H or as the outer layer of layer D. The optional layer is the same as the optional layer of the oxygen-absorbing multilayer body described in the third embodiment.

The oxygen-absorbing multilayer bottle of the embodiment can be manufactured by using a known method such as a coextrusion method, a lamination method and a coating method depending upon e.g., the properties of the materials, processing purpose and processing step. The manufacturing method is not particularly limited. For example, a general method of laminating packaging materials such as a wet lamination process, a dry lamination process, a dry lamination process in the absence of a solvent, an extrusion lamination process, a T die coextrusion molding method, a coextrusion lamination process, a coextrusion blow molding method and an inflation process can be applied. Of them, a general method for molding a bottle such as a coextrusion blow molding method is preferably used. Furthermore, for example, for molding a film or a sheet, a method of extruding a molten resin composition from an extruder provided with a T die, a circular die, etc., and a method of applying an adhesive to an oxygen-absorbing film or sheet separately formed and attaching it to another film or sheet are known. If necessary, for example, a pretreatment such as a corona treatment and an ozone treatment can be applied to a film etc. Furthermore, a known anchor coating agent, an adhesive, etc. can also be used. Examples of the anchor coating agent to be used include isocyanate (urethane), polyethylene imine, polybutadiene and organic titanium. Examples of the adhesive include polyurethane, polyacrylate, polyester, epoxy, poly(vinyl acetate), cellulose and other adhesives for lamination.

The constitution of the oxygen-absorbing multilayer bottle of the embodiment, which is not particularly limited, can be appropriately set depending upon the article to be contained and stored. For example, the aforementioned oxygen-absorbing multilayer body is thermoformed to obtain a packaging container (bottle) main body comprising the aforementioned layers formed by coextrusion blow molding. This is bonded with a top film (cover material) having a gas barrier layer containing a gas barrier substance to manufacture a sealed container. As the gas barrier substance to be used in gas barrier layer of the top film (cover material), the gas barrier substances used in layer D of the aforementioned oxygen-absorbing multilayer bottle can be used. The oxygen transmission rate of the top film (cover material) measured in the case of a film having a thickness of 20 μm under the conditions of 23° C. and a relative humidity of 60% is preferably 100 mL/(m$^2$·day·atm) or less, more preferably 80 mL/(m$^2$·day·atm) or less and further preferably 50 mL/(m$^2$·day·atm) or less. Note that if the top film (cover material) is manufactured as a multilayer body and a thermoplastic resin to be used in layer H of the aforementioned oxygen-absorbing multilayer bottle is used as an inner layer, layer H and the inner layer of the top film (cover material) can be sealed by heat-sealing.

Note that when a container having a flange portion is manufactured by thermoforming, a special process for providing an easy-peeling function may be applied to the flange portion. If an oxygen-absorbing multilayer bottle as mentioned above is used as a member for a main body of a container, oxygen-absorbing function can be provided to the container.

In using the oxygen-absorbing multilayer bottle of the embodiment, initiation of an oxygen absorption reaction can be facilitated and an oxygen-absorbing rate can be increased by irradiation of an energy ray. Examples of the usable energy ray include visible ray, UV ray, X-ray, electron ray and γ ray. The amount of irradiation energy can be appropriately selected depending upon the type of energy line to be used.

The oxygen-absorbing multilayer bottle of the embodiment does not require a moisture content for absorbing oxygen. In other words, oxygen can be absorbed regardless of the presence or absence of the moisture content of an article to be packaged. Thus, the oxygen-absorbing multilayer bottle can be used in a wide variety of uses no matter which type of article is contained. In particular, no odor is produced after absorption of oxygen. Thus, the oxygen-absorbing multilayer bottle can be particularly preferably used in e.g., foods, cooking foods, beverages, health foods and medicinal products. More specifically, since the oxygen-absorbing multilayer bottle of the embodiment is excellent in oxygen-absorbing performance in a wide range of humidity conditions from low humidity to high humidity (relative humidity 0% to 100%) and excellent in taste and flavor retention property of a content, it is suitable for packaging various articles. In addition, unlike a conventional oxygen-absorbing multilayer bottle using an iron powder, the oxygen-absorbing multilayer bottle of the embodiment can be suitably used for storing an article to be packaged (for example, alcohol beverages and carbonate beverages) which cannot be stored because of the presence of iron.

Specific examples of the article to be packaged include, but not particularly limited to, medicinal products; health foods such as vitamins; sundry articles such as a cosmetic, a shampoo, a conditioner and a detergent; and other various articles.

Note that the containers and articles to be packaged can be sterilized by a method suitable for the articles before and after packing (packaging) the articles. Any sterilization method may be applied as long as it is the same as described in the first embodiment.

EXAMPLE 1

The present invention will be more specifically described by use of Examples and Comparative Examples, below; however, the present invention is not limited by these.

SYNTHESIS EXAMPLE 1

To a four-neck separable flask of 1000 mL (inner volume), 100 g of an ethylene-methyl methacrylate copolymer (product name: "Acryft WK402", manufactured by Sumitomo Chemical Co., Ltd.) having a methyl methacrylate content of 25 mass %; 6-hydroxylmethyl-1,2,3,4-tetrahydronaphthalene (81 g), decalin (160 g) and tetrabutyl titanate (0.2 g) serving as a transesterification catalyst, were supplied. The temperature of the reaction solution was raised to 210° C. while stirring under a nitrogen atmosphere and a reaction was performed for 3 hours while distilling away methanol. After distillation of methanol was terminated, the pressure of the reaction solution was gradually reduced to distill away unreacted 6-hydroxylmethyl-1,2,3,4-tetrahydronaphthalene and decalin. Thereafter, the pressure of the reaction solution was returned to normal pressure and the reaction solution was cooled to obtain a solid-state crude reaction product. Subsequently, to the obtained crude reaction product, toluene was added up to a concentration of 3 to 4 mass % and the mixture solution was heated to 80° C. to dissolve the crude reaction product. After the solution was cooled to about 40° C., methanol was added. Tetralin ring-containing copolymerized polyolefin compound A was reprecipitated and collected by filtration.

The weight average molecular weight and number average molecular weight of the obtained tetralin ring-containing copolymerized polyolefin compound A were determined by GPC (gel permeation chromatography). As a result, the polystyrene-equivalent weight average molecular weight was $9.5 \times 10^4$ and the number average molecular weight was $3.1 \times 10^4$. The melting point was determined by DSC. As a result, the melting point was 71° C.

SYNTHESIS EXAMPLE 2

Tetralin ring-containing copolymerized polyolefin compound B was synthesized in the same manner as in Synthesis Example 1 except that 1,5-dimethyl-8-hydroxylmethyl-1,2,3,4-tetrahydronaphthalene (95.0 g by mass) was used in place of 6-hydroxylmethyl-1,2,3,4-tetrahydronaphthalene of Synthesis Example 1. The polystyrene-equivalent weight average molecular weight of tetralin ring-containing copolymerized polyolefin compound B was $9.1 \times 10^4$, the number average molecule weight was $3.0 \times 10^4$ and the melting point was 71° C.

SYNTHESIS EXAMPLE 3

Tetralin ring-containing copolymerized polyolefin compound C was synthesized in the same manner as in Synthesis Example 1 except that an ethylene-methyl methacrylate copolymer (product name: "Acryft WD203-1", manufactured by Sumitomo Chemical Co., Ltd.) having a methyl methacrylate content of 5 mass % was used in place of the ethylene-methyl methacrylate copolymer having a methyl methacrylate content of 25 mass % of Synthesis Example 1 and the amount of 6-hydroxylmethyl-1,2,3,4-tetrahydronaphthalene was changed from 81 g to 16.2 g. The polystyrene-equivalent weight average molecular weight of tetralin ring-containing copolymerized polyolefin compound C was $9.6 \times 10^4$, the number average molecule weight was $3.0 \times 10^4$ and the melting point was 98° C.

SYNTHESIS EXAMPLE 4

Tetralin ring-containing copolymerized polyolefin compound D was synthesized in the same manner as in Synthesis Example 1 except that an ethylene-methyl methacrylate copolymer (Product name: "Acryft WD201-F", manufactured by Sumitomo Chemical Co., Ltd.) having a methyl methacrylate content of 10 mass % was used in place of the ethylene-methyl methacrylate copolymer having a methyl methacrylate content of 25 mass % of Synthesis Example 1 and the amount of 6-hydroxylmethyl-1,2,3,4-tetrahydronaphthalene was changed from 81 g to 32.4 g. The polystyrene-equivalent weight average molecular weight of tetralin ring-containing copolymerized polyolefin compound D was $9.3 \times 10^4$, the number average molecule weight was $3.1 \times 10^4$ and the melting point was 92° C.

EXAMPLE 1-1

With tetralin ring-containing copolymerized polyolefin compound A (100 parts by mass), cobalt (II) stearate (0.1 parts by mass in terms of cobalt) was dry-blended. The obtained mixture was formed into a film by use of a double-screw extruder having two screws of 20 mm in diameter at an extrusion temperature of 220° C., a screw rotation number of 60 rpm, a feed screw rotation number of 16 rpm and a haul-off speed of 1.0 m/min. In this manner, an oxygen-absorbing film (film-form oxygen absorbing resin composition) having a width of 130 mm and a thickness of 95 to 100 μm was manufactured. Next, two gas barrier bags formed of an aluminum foil laminate film were prepared. Two test pieces (100 mm in length×100 mm in width) of the obtained oxygen-absorbing film were put in the two gas barrier bags together with 500 cc of air. The relative humidity in one of the bags was adjusted to be 100%; whereas the relative humidity of the other bag was adjusted to be 30% and then the bags were separately sealed. The sealed bags thus obtained were stored at 23° C. for 3 days. The total amount of oxygen absorbed during this period was measured. The bags were opened and odor of the film was checked. Similarly, sealed bags were manufactured so as to have a relative humidity of 100% and stored at 40° C. and under a relative humidity of 100% for one month. The appearance of the film after the storage of one month was visually checked. These results are shown in Table 1.

EXAMPLE 1-2

An oxygen-absorbing film was manufactured in the same manner as in Example 1-1 except that cobalt (II) stearate (0.05 parts by mass in terms of cobalt) was dry-blended in place of cobalt (II) stearate (0.1 parts by mass in terms of cobalt). The amount of oxygen absorbed was measured; odor was checked; and appearance of the film was visually observed in the same manner as in Example 1-1. These results are shown in Table 1.

EXAMPLE 1-3

An oxygen-absorbing film was manufactured in the same manner as in Example 1-1 except that cobalt (II) stearate (0.01 parts by mass in terms of cobalt) was dry-blended in place of cobalt (II) stearate (0.1 parts by mass in terms of cobalt). The amount of oxygen absorbed was measured; odor was checked; and appearance of the film was visually observed in the same manner as in Example 1-1. These results are shown in Table 1.

EXAMPLE 1-4

An oxygen-absorbing film was manufactured in the same manner as in Example 1-1 except that cobalt (II) acetate was used in place of cobalt (II) stearate. The amount of oxygen absorbed was measured; odor was checked; and appearance of the film was visually observed in the same manner as in Example 1-1. These results are shown in Table 1.

EXAMPLE 1-5

An oxygen-absorbing film was manufactured in the same manner as in Example 1-1 except that manganese stearate (H) (0.1 parts by mass in terms of manganese) was dry-blended in place of cobalt (II) stearate (0.1 parts by mass in terms of cobalt). The amount of oxygen absorbed was measured; odor was checked; and appearance of the film was visually observed in the same manner as in Example 1-1. These results are shown in Table 1.

EXAMPLE 1-6

An oxygen-absorbing film was manufactured in the same manner as in Example 1-1 except that iron (III) stearate (0.1 parts by mass in terms of iron) was dry-blended in place of cobalt (H) stearate (0.1 parts by mass in terms of cobalt). The amount of oxygen absorbed was measured; odor was checked; and appearance of the film was visually observed in the same manner as in Example 1-1. These results are shown in Table 1.

EXAMPLE 1-7

An oxygen-absorbing film was manufactured in the same manner as in Example 1-1 except that tetralin ring-containing copolymerized polyolefin compound B was used in place of tetralin ring-containing copolymerized polyolefin compound A.

The amount of oxygen absorbed was measured; odor was checked; and appearance of the film was visually observed in the same manner as in Example 1-1. These results are shown in Table 1.

EXAMPLE 1-8

An oxygen-absorbing film was manufactured in the same manner as in Example 1-7 except that manganese (II) stearate (0.1 parts by mass in terms of manganese) was dry-blended in place of cobalt (II) stearate (0.1 parts by mass in terms of cobalt). The amount of oxygen absorbed was measured; odor was checked; and appearance of the film was visually observed in the same manner as in Example 1-7. These results are shown in Table 1.

EXAMPLE 1-9

An oxygen-absorbing film was manufactured in the same manner as in Example 1-7 except that iron (III) stearate (0.1 parts by mass in terms of iron) was dry-blended in place of cobalt (II) stearate (0.1 parts by mass in terms of cobalt). The amount of oxygen absorbed was measured; odor was checked; and appearance of the film was visually observed in the same manner as in Example 1-7. These results are shown in Table 1.

EXAMPLE 1-10

An oxygen-absorbing film was manufactured in the same manner as in Example 1-1 except that tetralin ring-containing copolymerized polyolefin compound C was used in place of tetralin ring-containing copolymerized polyolefin compound A. The amount of oxygen absorbed was measured; odor was checked; and appearance of the film was visually observed in the same manner as in Example 1-1. These results are shown in Table 1.

EXAMPLE 1-11

An oxygen-absorbing film was manufactured in the same manner as in Example 1-1 except that tetralin ring-containing copolymerized polyolefin compound D was used in place of tetralin ring-containing copolymerized polyolefin compound A. The amount of oxygen absorbed was measured; odor was checked; and appearance of the film was visually observed in the same manner as in Example 1-1. These results are shown in Table 1.

COMPARATIVE EXAMPLE 1-1

An oxygen-absorbing film was manufactured in the same manner as in Example 1-1 except that nylon MXD6 (product name: "MX nylon S6011", hereinafter sometimes referred to as "N-MXD6", manufactured by Mitsubishi Gas Chemical Company, Inc.) was used in place of tetralin ring-containing copolymerized polyolefin compound A. The amount of oxygen absorbed was measured; odor was checked; and appearance of the film was visually observed in the same manner as in Example 1-1. These results are shown in Table 1.

TABLE 1

| | | Transition metal catalyst | | Amount of oxygen absorbed[2] | | Odor[3] | | |
|---|---|---|---|---|---|---|---|---|
| | Resin used in oxygen absorbing resin composition | Type | Amount of transition metal[1] | Relative humidity 100% | Relative humidity 30% | Relative humidity 100% | Relative humidity 30% | Appearance[4] |
| Example 1-1 | Tetralin ring-containing copolymerized polyolefin compound A | Cobalt stearate | 0.1 | 28 cc | 21 cc | None | None | Shape was maintained |
| Example 1-2 | Tetralin ring-containing copolymerized polyolefin compound A | Cobalt stearate | 0.05 | 25 cc | 22 cc | None | None | Shape was maintained |
| Example 1-3 | Tetralin ring-containing copolymerized polyolefin compound A | Cobalt stearate | 0.01 | 12 cc | 10 cc | None | None | Shape was maintained |

TABLE 1-continued

| | Resin used in oxygen absorbing resin composition | Transition metal catalyst | | Amount of oxygen absorbed[2] | | Odor[3] | | Appearance[4] |
| | | Type | Amount of transition metal[1] | Relative humidity 100% | Relative humidity 30% | Relative humidity 100% | Relative humidity 30% | |
|---|---|---|---|---|---|---|---|---|
| Example 1-4 | Tetralin ring-containing copolymerized polyolefin compound A | Cobalt acetate | 0.1 | 20 cc | 20 cc | None | None | Shape was maintained |
| Example 1-5 | Tetralin ring-containing copolymerized polyolefin compound A | Manganese stearate | 0.1 | 23 cc | 28 cc | None | None | Shape was maintained |
| Example 1-6 | Tetralin ring-containing copolymerized polyolefin compound A | Iron stearate | 0.1 | 19 cc | 20 cc | None | None | Shape was maintained |
| Example 1-7 | Tetralin ring-containing copolymerized polyolefin compound B | Cobalt stearate | 0.1 | 28 cc | 28 cc | None | None | Shape was maintained |
| Example 1-8 | Tetralin ring-containing copolymerized polyolefin compound B | Manganese stearate | 0.1 | 24 cc | 25 cc | None | None | Shape was maintained |
| Example 1-9 | Tetralin ring-containing copolymerized polyolefin compound B | Iron stearate | 0.1 | 17 cc | 16 cc | None | None | Shape was maintained |
| Example 1-10 | Tetralin ring-containing copolymerized polyolefin compound C | Cobalt stearate | 0.1 | 13 cc | 14 cc | None | None | Shape was maintained |
| Example 1-11 | Tetralin ring-containing copolymerized polyolefin compound D | Cobalt stearate | 0.1 | 18 cc | 15 cc | None | None | Shape was maintained |
| Comparative Example 1-1 | N-MXD6 | Cobalt stearate | 0.1 | 1 cc | 0 cc | None | None | Collapsed |

[1] Parts by mass based on resin (100 parts by mass)
[2] Total amount of oxygen absorbed at 23° C. during three days from initiation of test
[3] Odor of film 3rd day after initiation of test
[4] Evaluated after one-month storage at 40° C. and a relative humidity of 100%

As is apparent from Examples 1-1 to 1-11, the oxygen-absorbing resin compositions of the present invention delivered satisfactory oxygen-absorbing performance under both high humidity and low humidity conditions; generated no odor; and the shapes of films were maintained after absorption of oxygen without collapse.

EXAMPLE 2-1

First, tetralin ring-containing copolymerized polyolefin compound A (100 parts by mass) and cobalt (II) stearate (0.05 parts by mass in terms of cobalt) were dry-blended. The obtained mixture was supplied to a double-screw extruder having two screws of 37 mm in diameter and kneaded at an extrusion temperature of 220° C. and a screw rotation number of 100 rpm to obtain oxygen-absorbing resin composition A.

Next, using a multilayer-film manufacturing apparatus equipped with two extruders, a feed block, a T die, a cooling roll, a corona discharge unit, a winder, etc., a linear and low-density polyethylene (product name: "NOVATEC LL UF641" manufactured by Japan Polyethylene Corporation, hereinafter referred to as "LLDPE1" in Examples 2-1 to 2-13 and Comparative Examples 2-1 to 2-3, MFR at 190° C. of 2.1 g/10 minutes (measured in accordance with JIS K7210), MFR at 240° C. of 4.4 g/10 minutes and MFR at 250° C. of 5.2 g/10 minutes) serving as a material for a sealant layer was extruded from a first extruder; and oxygen-absorbing resin composition A serving as a material for an oxygen-absorbing layer was extruded from a second extruder; and passed through the feed block to manufacture a two-layer film formed of two types of materials (thickness: oxygen-absorbing layer 20 μm/sealant layer 20 μm) having a width of 900 mm. Thereafter, the surface of the oxygen-absorbing layer was treated with corona discharge at a rate of 60 m/minute to manufacture a film roll. When the obtained film roll was observed, thickness deviation such as bumps was not seen. Furthermore, when the obtained film was observed, the appearance was satisfactory and a HAZE of the film was 8%.

Next, nylon 6 film (product name: "N1202", manufactured by Toyobo Co., Ltd.), an aluminum foil and a PET film (product name: "E5102", manufactured by Toyobo Co., Ltd.) were stacked in accordance with dry lamination with the application of a urethane dry-lamination adhesive (product name: "TM-319/CAT-19B", manufactured by Toyo-Morton, Ltd.) to the corona treated surface to obtain an oxygen-absorbing multilayer film formed of an oxygen-absorbing multilayer body, which was constituted of PET film (12 μm)/urethane dry-lamination adhesive (3 μm)/aluminum foil (9 μm)/urethane dry-lamination adhesive (3 μm)/nylon 6 film (15 μm)/urethane dry-lamination adhesive (3 μm)/oxygen-absorbing layer (20 μm)/LLDPE1 (20 μm). Note that the numeric character within parentheses refers to the thickness (unit: μm) of each layer. The same description is also employed in the following Examples unless otherwise specified.

Next, using the obtained oxygen-absorbing multilayer film, a three-side sealed bag of 10 cm×20 cm was manufactured such that the LLDPE1 side faced inside, filled with a powder seasoning, "instant bouillon" (150 g) having a water activity of 0.35, and then sealed. The sealed bag thus obtained was stored at 23° C. After storage for 7 days and one month, the oxygen concentration in the bag was measured. The taste and flavor of the powder seasoning after one month storage and odor of the opened bag were checked. Furthermore, the sealing strength of the bag before and after storage of one month was measured. These results are shown in Table 2. In measuring the sealing strength, the sealing strength of the short side portion of the three-side sealed bag was measured in accordance with JIS 20238 (the same shall apply hereinafter).

EXAMPLE 2-2

An oxygen-absorbing multilayer film was obtained in the same manner as in Example 2-1 except that cobalt (II) stearate (0.01 parts by mass in terms of cobalt) was dry-blended in place of cobalt (II) stearate (0.05 parts by mass in terms of cobalt). Thereafter, a three-side sealed bag was manufactured in the same manner as in Example 2-1. The oxygen concentration in the bag was measured; the taste and flavor of the powder seasoning and odor after the bag was opened were checked; and the sealing strength of the bag was measured in the same manner as in Example 2-1. These results are shown in Table 2.

EXAMPLE 2-3

An oxygen-absorbing multilayer film was obtained in the same manner as in Example 2-1 except that cobalt (II) stearate (0.1 parts by mass in terms of cobalt) was dry-blended in place of cobalt (II) stearate (0.05 parts by mass in terms of cobalt). Thereafter, a three-side sealed bag was manufactured in the same manner as in Example 2-1. The oxygen concentration in the bag was measured; the taste and flavor of the powder seasoning and odor after the bag was opened were checked; and the sealing strength of the bag was measured in the same manner as in Example 2-1. These results are shown in Table 2.

EXAMPLE 2-4

An oxygen-absorbing multilayer film was obtained in the same manner as in Example 2-1 except that cobalt (II) acetate was used in place of cobalt (II) stearate. Thereafter, a three-side sealed bag was manufactured in the same manner as in Example 2-1. The oxygen concentration in the bag was measured; the taste and flavor of the powder seasoning and odor after the bag was opened were checked; and the sealing strength of the bag was measured in the same manner as in Example 2-1. These results are shown in Table 2.

EXAMPLE 2-5

An oxygen-absorbing multilayer film was obtained in the same manner as in Example 2-1 except that manganese (II) stearate (0.05 parts by mass in terms of manganese) was dry-blended in place of cobalt (II) stearate (0.05 parts by mass in terms of cobalt). Thereafter, a three-side sealed bag was manufactured in the same manner as in Example 2-1. The oxygen concentration in the bag was measured; the taste and flavor of the powder seasoning and odor after the bag was opened were checked; and the sealing strength of the bag was measured in the same manner as in Example 2-1. These results are shown in Table 2.

EXAMPLE 2-6

An oxygen-absorbing multilayer film was obtained in the same manner as in Example 2-1 except that iron (III) stearate (0.05 parts by mass in terms of iron) was dry-blended in place of cobalt (II) stearate (0.05 parts by mass in terms of cobalt). Thereafter, a three-side sealed bag was manufactured in the same manner as in Example 2-1. The oxygen concentration in the bag was measured; the taste and flavor of the powder seasoning and odor after the bag was opened were checked; and the sealing strength of the bag was measured in the same manner as in Example 2-1. These results are shown in Table 2.

EXAMPLE 2-7

An oxygen-absorbing multilayer film was obtained in the same manner as in Example 2-1 except that tetralin ring-containing copolymerized polyolefin compound B was used in place of tetralin ring-containing copolymerized polyolefin compound A. Thereafter, a three-side sealed bag was manufactured in the same manner as in Example 2-1. The oxygen concentration in the bag was measured; the taste and flavor of the powder seasoning and odor after the bag was opened were checked; and the sealing strength of the bag was measured in the same manner as in Example 2-1. These results are shown in Table 2.

EXAMPLE 2-8

An oxygen-absorbing multilayer film was obtained in the same manner as in Example 2-7 except that manganese (II) stearate (0.05 parts by mass in terms of manganese) was dry-blended in place of cobalt (II) stearate (0.05 parts by mass in terms of cobalt). Thereafter, a three-side sealed bag was manufactured in the same manner as in Example 2-1. The oxygen concentration in the bag was measured; the taste and flavor of the powder seasoning and odor after the bag was opened were checked; and the sealing strength of the bag was measured in the same manner as in Example 2-1. These results are shown in Table 2.

EXAMPLE 2-9

An oxygen-absorbing multilayer film was obtained in the same manner as in Example 2-7 except that iron (III) stearate (0.05 parts by mass in terms of iron) was dry-blended in place of cobalt (II) stearate (0.05 parts by mass in terms of cobalt). Thereafter, a three-side sealed bag was manufactured in the same manner as in Example 2-1. The oxygen concentration in the bag was measured; the taste and flavor of the powder seasoning and odor after the bag was opened were checked; and the sealing strength of the bag was measured in the same manner as in Example 2-1. These results are shown in Table 2.

EXAMPLE 2-10

An oxygen-absorbing multilayer film was obtained in the same manner as in Example 2-1 except that tetralin ring-containing copolymerized polyolefin compound C was used in place of tetralin ring-containing copolymerized polyolefin compound A. Thereafter, a three-side sealed bag was manufactured in the same manner as in Example 2-1. The oxygen concentration in the bag was measured; the taste and flavor of the powder seasoning and odor after the bag was opened were checked; and the sealing strength of the bag was measured in the same manner as in Example 2-1. These results are shown in Table 2.

EXAMPLE 2-11

An oxygen-absorbing multilayer film was obtained in the same manner as in Example 2-1 except that tetralin ring-containing copolymerized polyolefin compound D was used in place of tetralin ring-containing copolymerized polyolefin compound A. Thereafter, a three-side sealed bag was manufactured in the same manner as in Example 2-1. The oxygen concentration in the bag was measured; the taste and flavor of the powder seasoning and odor after the bag was opened were checked; and the sealing strength of the bag was measured in the same manner as in Example 2-1. These results are shown in Table 2.

COMPARATIVE EXAMPLE 2-1

An iron powder having an average particle diameter of 20 μm and calcium chloride were mixed in a mass ratio of 100:1. The mixture and LLDPE1 were kneaded in a mass ratio of 30:70 to obtain an iron based oxygen-absorbing resin composition. We tried to manufacture a two-layer film formed of two types of materials by use of the iron based oxygen-absorbing resin composition in the same manner as in Example 2-1; however, a film having smooth surface that can be sufficiently subjected to further studies could not be obtained since convexoconcave portions were produced in the surface of the film due to the iron powder. Because of this, on the linear and low-density polyethylene film (product name: "Tohcello T. U. X HC", hereinafter referred to as "LLDPE2" in Comparative Examples 2-1 to 2-3, manufactured by Tohcello Inc.) having a thickness of 40 μm, a film of the iron based oxygen-absorbing resin composition of 20 μm in thickness serving as an oxygen-absorbing layer was stacked in accordance with extrusion lamination, and thereafter, the surface of the layer formed of the iron based oxygen-absorbing resin composition was treated with corona discharge at a rate of 60 m/minute to obtain a laminate film.

Next, on the corona treated surface of the laminate film, dry laminate was performed in the same manner as in Example 2-1 to manufacture an iron based oxygen-absorbing multilayer film, which was constituted of PET film (12 μm)/urethane dry-lamination adhesive (3 μm)/aluminum foil (9 μm)/urethane dry-lamination adhesive (3 μm)/nylon 6 film (15 μm)/urethane dry-lamination adhesive (3 μm)/oxygen-absorbing layer (20 μm)/LLDPE2 (40 μm).

Subsequently, a three-side sealed bag was manufactured by use of the obtained iron based oxygen-absorbing multilayer film in the same manner as in Example 2-1. The oxygen concentration in the bag was measured; the taste and flavor of the powder seasoning and odor after the bag was opened were checked; and the sealing strength of the bag was measured in the same manner as in Example 2-1. These results are shown in Table 2.

TABLE 2

| | Resin used in oxygen-absorbing resin composition | Transition metal catalyst Type | Amount of transition metal[1] | Oxygen concentration (vol %) After 7 days | After one month | Taste and flavor after one month | Odor in bag after one month | Sealing strength (kg/15 mm) Before storage | After one month |
|---|---|---|---|---|---|---|---|---|---|
| Example 2-1 | Tetralin ring-containing copolymerized polyolefin compound A | Cobalt stearate | 0.05 | 2.1 | 0.1 or less | Satisfactory | Satisfactory | 5.8 | 5.5 |
| Example 2-2 | Tetralin ring-containing copolymerized polyolefin compound A | Cobalt stearate | 0.01 | 6.2 | 0.3 | Almost satisfactory | Satisfactory | 5.9 | 5.8 |
| Example 2-3 | Tetralin ring-containing copolymerized polyolefin compound A | Cobalt stearate | 0.1 | 1.4 | 0.1 or less | Satisfactory | Satisfactory | 5.7 | 5.7 |
| Example 2-4 | Tetralin ring-containing copolymerized polyolefin compound A | Cobalt acetate | 0.05 | 2.5 | 0.1 or less | Satisfactory | Satisfactory | 5.5 | 5.7 |
| Example 2-5 | Tetralin ring-containing copolymerized polyolefin compound A | Manganese stearate | 0.05 | 1.8 | 0.1 or less | Satisfactory | Satisfactory | 5.8 | 5.6 |
| Example 2-6 | Tetralin ring-containing copolymerized polyolefin compound A | Iron stearate | 0.05 | 3.7 | 0.1 or less | Satisfactory | Satisfactory | 5.8 | 5.8 |
| Example 2-7 | Tetralin ring-containing copolymerized polyolefin compound B | Cobalt stearate | 0.05 | 1.7 | 0.1 or less | Satisfactory | Satisfactory | 5.9 | 5.7 |
| Example 2-8 | Tetralin ring-containing copolymerized polyolefin compound B | Manganese stearate | 0.05 | 1.5 | 0.1 or less | Satisfactory | Satisfactory | 5.4 | 5.3 |
| Example 2-9 | Tetralin ring-containing copolymerized polyolefin compound B | Iron stearate | 0.05 | 3.1 | 0.1 or less | Satisfactory | Satisfactory | 5.8 | 5.8 |
| Example 2-10 | Tetralin ring-containing copolymerized polyolefin compound C | Cobalt stearate | 0.05 | 6.2 | 0.8 | Almost satisfactory | Satisfactory | 5.8 | 5.8 |

TABLE 2-continued

| | Resin used in oxygen-absorbing resin composition | Transition metal catalyst Type | Amount of transition metal[1] | Oxygen concentration (vol %) After 7 days | Oxygen concentration (vol %) After one month | Taste and flavor after one month | Odor in bag after one month | Sealing strength (kg/15 mm) Before storage | Sealing strength (kg/15 mm) After one month |
|---|---|---|---|---|---|---|---|---|---|
| Example 2-11 | Tetralin ring-containing copolymerized polyolefin compound D | Cobalt stearate | 0.05 | 4.5 | 0.1 or less | Satisfactory | Satisfactory | 5.8 | 5.8 |
| Comparative Example 2-1 | LLPDE + iron powder | — | — | 20.8 | 20.6 | Reduced | Slight iron odor | 5.9 | 5.8 |

[1] Parts by mass based on resin (100 parts by mass)

As is apparent from the results of Examples 2-1 to 2-11, the oxygen-absorbing multilayer bodies of the present invention delivered satisfactory oxygen-absorbing performance under low humidity conditions; suppressed reduction of taste and flavor of a content; generated no odor after absorption of oxygen; and retained sealing strength before storage.

EXAMPLE 2-12

Using a multilayer-film manufacturing apparatus equipped with two extruders, a feed block, a T die, a cooling roll, a corona discharge unit, a winder, etc., LLDPE1 was extruded from a first extruder; and oxygen-absorbing resin composition A obtained in Example 2-1 was extruded from a second extruder to manufacture a three-layer film of two types of materials of 800 mm in width (thickness: 10 µm/20 µm/10 µm) having a core layer formed of oxygen-absorbing resin composition A and a skin layer formed of LLDPE1 present on both surfaces of the core layer. Thereafter, one of the surfaces of the film was treated with corona discharge at a rate of 60 m/minute. On the corona treated surface of the obtained film, the following layers were stacked in accordance with extrusion lamination using a low-density polyethylene (product name: "NOVATEC LD LC604", 20 µm, manufactured by Japan Polyethylene Corporation) to obtain an oxygen-absorbing multilayer paper base material, which was constituted of bleached craft paper (basis weight: 340 g/m²)/urethane dry-lamination adhesive (product name: "TM251/CAT-RT88", manufactured by Toyo-Morton, Ltd., 3 µm)/alumina vapor deposition PET film (product name: "GL-ARH-F", manufactured by Toppan Printing Co., Ltd., 12 µm)/urethane anchor coating agent ("EL-557A/B", manufactured by Toyo-Morton, Ltd., 0.5 µm)/low-density polyethylene (20 µm)/LLDPE1 (10 µm)/oxygen-absorbing resin composition A (20 µm)/LLDPE1 (10 µm).

The obtained oxygen-absorbing multilayer paper base material was molded into a 1-liter gable-top paper container. The moldability of the container was satisfactory. The paper container was filled with Japanese sake and then sealed. The sealed container thus obtained was stored at 23° C. for one month. After storage for one month, the oxygen concentration in the paper container was 0.1 vol % or less and the taste and flavor of the Japanese sake was satisfactorily maintained.

COMPARATIVE EXAMPLE 2-2

We tried to manufacture a gable-top paper container from the oxygen-absorbing multilayer paper base material, which was constituted of bleached craft paper (basis weight: 340 g/m²)/urethane dry-lamination adhesive (3 µm)/alumina vapor deposition PET film (12 µm)/urethane anchor coating agent (0.5 µm)/low-density polyethylene (20 µm)/oxygen-absorbing layer (20 µm)/LLDPE2 (40 µm), in the same manner as in Example 2-12 except that the laminate film obtained in Comparative Example 2-1 was used in place of the three-layer film formed of two types of materials; however, it was difficult to form corners of the paper container since the oxygen-absorbing multilayer paper base material was thick. Then, we tried to manufacture a paper container by lowering the speed of manufacturing a container. As a result, the paper container was finally obtained with a large number of defective products (that were eliminated). Using the obtained paper container, a storage test of Japanese sake was performed in the same manner as in Example 2-12. After one month, the container was opened. As a result, aldehyde odor generated and the taste and flavor significantly reduced.

EXAMPLE 2-13

An oxygen-absorbing resin composition B was prepared in the same manner as in Example 2-1 except that tetralin ring-containing copolymerized polyolefin compound C was used in place of tetralin ring-containing copolymerized polyolefin compound A. Then, a three-layer film formed of two types of materials (thickness: 10 µm/20 µm/10 µm) was manufactured in the same manner as in Example 2-12 except that oxygen-absorbing resin composition B was used in place of oxygen-absorbing resin composition A, and thereafter, one of the surfaces was treated with corona discharge at a rate of 60 m/minute. On the corona treated surface of the obtained film, a nylon 6 film (product name: "N1202", manufactured by Toyobo Co., Ltd.) and an alumina vapor deposition PET film (product name: "GL-ARH-F", manufactured by Toppan Printing Co., Ltd.) were stacked in accordance with dry lamination using a urethane dry-lamination adhesive (product name: "AD-817/CAT-RT86L-60", manufactured by Toyo-Morton, Ltd.) to obtain an oxygen-absorbing multilayer film formed of an oxygen-absorbing multilayer body, which was constituted of an alumina vapor deposition PET film (12 µm)/urethane dry-lamination adhesive (3 µm)/nylon 6 film (15 µm)/urethane dry-lamination adhesive (3 µm)/LLDPE1 (10 µm)/oxygen-absorbing resin composition B (20 µm)/LLDPE1 (10 µm). Subsequently, using the obtained oxygen absorbing multilayer film, a self-supporting bag (standing pouch of 11 cm in side×17 cm in length×3 cm in bottom gore) with an open top was manufactured by bonding two side-films and a single bottom-surface film by heat sealing such that the LLDPE1 layer side faced inside. Next, the self-supporting bag was filled with mandarin orange (80 g) and fruit syrup (80 g), sealed such that 5 cc of air was left in the head space, boiled at 90° C. for 30 minutes, and stored at 40° C. After storage of 2 weeks, oxygen concentration in the bag was measured. It was 0.1 vol % or less. The color tone of the mandarin orange was observed outside the bag, it was satisfactorily maintained.

COMPARATIVE EXAMPLE 2-3

An oxygen-absorbing multilayer film formed of an oxygen-absorbing multilayer body, which was constituted of alumina vapor deposition PET film (12 µm)/urethane dry-lamination adhesive (3 µm)/nylon 6 film (15 µm)/urethane dry-lamination adhesive (3 µm)/oxygen-absorbing layer (20 µm)/LLDPE2 (40 µm), was manufactured in the same manner as in Example 2-13 except that the laminate film obtained in the same manner as in Comparative Example 2-1 was used in place of the oxygen-absorbing multilayer film. A self-supporting bag was manufactured in the same manner as in Example 2-13 and subjected to storage test. As a result, the oxygen concentration in the bag was 0.1 vol % or less; however, the color tone of mandarin orange cannot be observed from outside the bag.

As is apparent from the results of Examples 2-12 and 2-13, the oxygen-absorbing multilayer bodies of the present invention delivered satisfactory oxygen-absorbing performance even under high humidity conditions, and the content within the bag can be seen from outside the bag.

EXAMPLE 3-1

First, oxygen-absorbing resin composition A was obtained in the same manner as in Example 2-1. Then, using a multilayer-film manufacturing apparatus equipped with first to fourth extruders, a feed block, a T die, a cooling roll, a corona discharge unit, a winder, etc., a linear and low-density polyethylene (product name: "NOVATEC LL UF641", hereinafter referred to as "LLDPE" in Examples 3-1 to 3-11 and Comparative Examples 3-1 to 3-3, manufactured by Japan Polyethylene Corporation) was extruded from the first extruder; the above oxygen-absorbing resin composition A serving as a material for the oxygen-absorbing layer was extruded from the second extruder; a polyethylene adhesive resin (product name: "MODIC M545", hereinafter referred to as "AD" in Examples 3-1 to 3-11 and Comparative Examples 3-1 to 3-3, manufactured by Mitsubishi Chemical Corporation) was extruded from the third extruder, and an ethylene-vinyl alcohol copolymer (product name: "EVAL L104B", hereinafter referred to as "EVOH" in Examples 3-1 to 3-11 and Comparative Examples 3-1 to 3-3, manufactured by Kuraray Co., Ltd) was extruded from the fourth extruder; and passed through the feed block to obtain a four-layer film formed of four types of materials having a width of 300 mm. The multilayer film was constituted of LLDPE (20 µm)/oxygen-absorbing layer (40 µm)/AD (10 µm)/EVOH (10 µm), laminated in this order from inside.

Subsequently, to the outer layer (EVOH surface) of the obtained multilayer film, a non-stretched polyethylene terephthalate sheet of 250 µm in thickness (product name: "Novaclear", hereinafter referred to as "PET" in Examples 3-1 to 3-11 and Comparative Examples 3-1 to 3-3, manufactured by Mitsubishi Chemical Corporation) was attached in accordance with dry lamination to manufacture an oxygen-absorbing multilayer body. Note that a two-component curable adhesive (product name: "LX-75A/KW-40", manufactured by DIC graphics Corporation) was used as the dry-lamination adhesive and the thickness was set at 3 µm. The obtained multilayer body was thermoformed into a cup-form oxygen-absorbing multilayer container (inner volume: 70 cc, aperture: 62 mm×bottom diameter: 52 mm×depth 28 mm) by a vacuum molding machine such that the inner layer (LLDPE) faced inside. The obtained oxygen-absorbing multilayer container had good appearance without thickness deviation.

The obtained oxygen-absorbing multilayer container was filled with a humidity conditioning agent (10 g) to adjust the relative humidity of the container at 100% or 30%. The container was sealed using an aluminum foil laminate film as a top film such that the initial oxygen concentration was controlled to 5 vol % with nitrogen purge. Thereafter, the container was stored at 23° C. and a relative humidity of 50%. The oxygen concentration in the container after one month was measured and odor of the container was checked by removing the top film.

EXAMPLE 3-2

An oxygen-absorbing multilayer body was obtained in the same manner as in Example 3-1 except that cobalt (II) stearate (0.01 parts by mass in terms of cobalt) was dry-blended in place of cobalt (II) stearate (0.05 parts by mass). Thereafter, an oxygen-absorbing multilayer container was manufactured in the same manner as in Example 3-1. The oxygen concentration in the container was measured and odor of the container was checked in the same manner as in Example 3-1. These results are shown in Table 3.

EXAMPLE 3-3

An oxygen-absorbing multilayer body was obtained in the same manner as in Example 3-1 except that cobalt (II) stearate (0.1 parts by mass in terms of cobalt) was dry-blended in place of cobalt (II) stearate (0.05 parts by mass). Thereafter, an oxygen-absorbing multilayer container was manufactured in the same manner as in Example 3-1. The oxygen concentration in the container was measured and odor of the container was checked in the same manner as in Example 3-1. These results are shown in Table 3.

EXAMPLE 3-4

An oxygen-absorbing multilayer body was obtained in the same manner as in Example 3-1 except that cobalt (II) acetate was used in place of cobalt (II) stearate. Thereafter, an oxygen-absorbing multilayer container was manufactured in the same manner as sin Example 3-1. The oxygen concentration in the container was measured and odor of the container was checked in the same manner as in Example 3-1. These results are shown in Table 3.

EXAMPLE 3-5

An oxygen-absorbing multilayer body was obtained in the same manner as in Example 3-1 except that manganese (II) stearate (0.05 parts by mass in terms of manganese) was dry-blended in place of cobalt (II) stearate (0.05 parts by mass in terms of cobalt). Thereafter, an oxygen-absorbing multilayer container was manufactured in the same manner as sin Example 3-1. The oxygen concentration in the container was measured and odor of the container was checked in the same manner as in Example 3-1. These results are shown in Table 3.

EXAMPLE 3-6

An oxygen-absorbing multilayer body was obtained in the same manner as in Example 3-1 except that iron (III) stearate (0.05 parts by mass in terms of iron) was dry-blended in place of cobalt (II) stearate (0.05 parts by mass in terms of cobalt). Thereafter, an oxygen-absorbing multilayer container was manufactured in the same manner as in Example 3-1. The oxygen concentration in the container was measured and odor of the container was checked in the same manner as in Example 3-1. These results are shown in Table 3.

EXAMPLE 3-7

An oxygen-absorbing multilayer body was obtained in the same manner as in Example 3-1 except that tetralin ring-containing copolymerized polyolefin compound B was used in place of tetralin ring-containing copolymerized polyolefin compound A. Thereafter, an oxygen-absorbing multilayer container was manufactured in the same as in Example 3-1. The oxygen concentration in the container was measured and odor of the container was checked in the same manner as in Example 3-1. These results are shown in Table 3.

EXAMPLE 3-8

An oxygen-absorbing multilayer body was obtained in the same manner as in Example 3-7 except that manganese (II) stearate (0.05 parts by mass in terms of manganese) was dry-blended in place of cobalt (II) stearate (0.05 parts by mass in terms of cobalt). Thereafter, an oxygen-absorbing multilayer container was manufactured in the same manner as in Example 3-1. The oxygen concentration in the container was measured and odor of the container was checked in the same manner as in Example 3-1. These results are shown in Table 3.

EXAMPLE 3-9

An oxygen-absorbing multilayer body was obtained in the same manner as in Example 3-7 except that iron (III) stearate (0.05 parts by mass in terms of iron) was dry-blended in place of cobalt (II) stearate (0.05 parts by mass in term of cobalt). Thereafter, an oxygen-absorbing multilayer container was manufactured in the same manner as in Example 3-1. The oxygen concentration in the container was measured and odor of the container was checked in the same manner as in Example 3-1. These results are shown in Table 3.

EXAMPLE 3-10

An oxygen-absorbing multilayer body was obtained in the same manner as in Example 3-1 except that tetralin ring-containing copolymerized polyolefin compound C was used in place of tetralin ring-containing copolymerized polyolefin compound A. Thereafter, an oxygen-absorbing multilayer container was manufactured in the same as in Example 3-1. The oxygen concentration in the container was measured and odor of the container was checked in the same manner as in Example 3-1. These results are shown in Table 3.

EXAMPLE 3-11

An oxygen-absorbing multilayer body was obtained in the same manner as in Example 3-1 except that tetralin ring-containing copolymerized polyolefin compound D was used in place of tetralin ring-containing copolymerized polyolefin compound A. Thereafter, an oxygen-absorbing multilayer container was manufactured in the same as in Example 3-1. The oxygen concentration in the container was measured and odor of the container was checked in the same manner as in Example 3-1. These results are shown in Table 3.

COMPARATIVE EXAMPLE 3-1

A multilayer body was obtained in the same manner as in Example 3-1 except that an ethylene-methyl methacrylate copolymer having a methyl methacrylate content of 25 mass % and used in Synthesis Example 1 was used in place of tetralin ring-containing copolymerized polyolefin compound A. Thereafter, a multilayer container was manufactured in the same manner as in Example 3-1. The oxygen concentration in the container was measured and odor of the container was checked in the same manner as in Example 3-1. These results are shown in Table 3.

COMPARATIVE EXAMPLE 3-2

Iron powder having an average particle diameter of 20 μm and calcium chloride were mixed in a mass ratio of 100:1. The mixture and LLDPE were kneaded in a mass ratio of 30:70 to obtain an iron-based oxygen-absorbing resin composition. Subsequently, an oxygen-absorbing multilayer body was obtained in the same manner as in Example 3-1 except that the iron based oxygen-absorbing resin composition was used in place of oxygen-absorbing resin composition A. We tried to manufacture a cup-form container by thermoforming the obtained oxygen-absorbing multilayer body; however, it was difficult to perform processing due to generation of draw down. Furthermore, appearance was not good because of convexoconcave portions due to the iron powder. With respect to the containers having just acceptable appearance, the oxygen concentration in the container was measured and odor of the container was checked in the same manner as in Example 3-1. These results are shown in Table 3.

COMPARATIVE EXAMPLE 3-3

An oxygen-absorbing resin composition L was prepared in the same manner as in Example 3-1 except that N-MXD6 (product name: "MX nylon S6011", manufactured by Mitsubishi Gas Chemical Company Inc.) was used in place of tetralin ring-containing copolymerized polyolefin compound A and the extrusion temperature was set at 270° C. Subsequently, using a multilayer-film manufacturing apparatus equipped with first to third extruders, a feed block, a T die, a cooling roll, a corona discharge unit, a winder, etc., a linear and low-density polyethylene was extruded from the first extruder; oxygen-absorbing resin composition L serving as a material for an oxygen-absorbing layer was extruded from the second extruder; and a polyethylene adhesive resin was extruded from the third extruder; and passed through the feed block to obtain a five-layer film formed of three types of materials having a width of 300 mm. The multilayer film was constituted of LLDPE (20 μm)/AD (10 μm)/oxygen-absorbing layer (40 μm)/AD (10 μm)/LLDPE (20 μm) in the order from inside. Subsequently, an oxygen-absorbing multilayer body was obtained and then, an oxygen-absorbing multilayer container was manufactured in the same manner as in Example 3-1. The oxygen concentration in the container was measured and odor of the container was checked in the same manner as in Example 3-1. These results are shown in Table 3.

discharge unit, a winder, etc., the above oxygen-absorbing resin composition A serving as a material for an oxygen-absorbing layer having a thickness of 30 μm was stacked on a sealant film (product name: "VMX XB15FT", manufactured by J-Film Corporation) having a thickness of 40 μm, in accordance with extrusion lamination, and thereafter, the

TABLE 3

| | | Transition metal catalyst | | Relative humidity 100% | | Relative humidity 30% | |
|---|---|---|---|---|---|---|---|
| | Constitution of container[1] | Type | Amount of transition metal[2] | Oxygen concentration (vol %)[3] | Odor | Oxygen concentration (vol %)[3] | Odor |
| Example 3-1 | LLDPE/Oxygen-absorbing layer A[4]/AD/EVOH//PET | Cobalt stearate | 0.05 | 0.1 or less | Satisfactory | 0.1 or less | Satisfactory |
| Example 3-2 | LLDPE/Oxygen-absorbing layer A[4]/AD/EVOH//PET | Cobalt stearate | 0.01 | 0.8 | Satisfactory | 0.4 | Satisfactory |
| Example 3-3 | LLDPE/Oxygen-absorbing layer A[4]/AD/EVOH//PET | Cobalt stearate | 0.1 | 0.1 or less | Satisfactory | 0.1 or less | Satisfactory |
| Example 3-4 | LLDPE/Oxygen-absorbing layer A[4]/AD/EVOH//PET | Cobalt acetate | 0.05 | 0.1 or less | Satisfactory | 0.3 | Satisfactory |
| Example 3-5 | LLDPE/Oxygen-absorbing layer A[4]/AD/EVOH//PET | Manganese stearate | 0.05 | 0.1 or less | Satisfactory | 0.1 or less | Satisfactory |
| Example 3-6 | LLDPE/Oxygen-absorbing layer A[4]/AD/EVOH//PET | Iron stearate | 0.05 | 0.7 | Satisfactory | 0.4 | Satisfactory |
| Example 3-7 | LLDPE/Oxygen-absorbing layer B[4]/AD/EVOH//PET | Cobalt stearate | 0.05 | 0.1 or less | Satisfactory | 0.1 or less | Satisfactory |
| Example 3-8 | LLDPE/Oxygen-absorbing layer B[4]/AD/EVOH//PET | Manganese stearate | 0.05 | 0.1 or less | Satisfactory | 0.1 or less | Satisfactory |
| Example 3-9 | LLDPE/Oxygen-absorbing layer B[4]/AD/EVOH//PET | Iron stearate | 0.05 | 0.1 or less | Satisfactory | 0.1 or less | Satisfactory |
| Example 3-10 | LLDPE/Oxygen-absorbing layer C[4]/AD/EVOH//PET | Cobalt stearate | 0.05 | 1.5 | Satisfactory | 1.2 | Satisfactory |
| Example 3-11 | LLDPE/Oxygen-absorbing layer D[4]/AD/EVOH//PET | Cobalt stearate | 0.05 | 1.1 | Satisfactory | 0.9 | Satisfactory |
| Comp. Example 3-1 | LLDPE/EMMA[5]/AD/EVOH//PET | Cobalt stearate | 0.05 | 5.4 | Satisfactory | 5.1 | Satisfactory |
| Comp. Example 3-2 | LLDPE/LLDPE + Iron based oxygen absorber/AD/EVOH//PET | — | — | 0.1 or less | Iron odor | 4.7 | Iron odor |
| Comp. Example 3-3 | LLDPE/AD/N-MXD6/AD/LLDPE//PET | Cobalt stearate | 0.05 | 2.6 | Satisfactory | 4.8 | Satisfactory |

[1]Symbol "//" of layer constitution represents dry lamination
[2]Parts by mass based on resin (100 parts by mass)
[3]Stored at 23° C.
[4]Alphabet attached to the end of "oxygen-absorbing layer" represents the type of tetraline ring containing copolymerized polyolefin compound contained in the oxygen-absorbing layer. For example, "oxygen-absorbing layer A" contains tetraline ring containing copolymerized polyolefin compound A.
[5]EMMA: ethylene-methyl methacrylate copolymer As is apparent from Examples 3-1 to 3-11, the oxygen-absorbing multilayer containers of the present invention delivered satisfactory oxygen-absorbing performance in a wide range of humidity conditions from low humidity to high humidity.

EXAMPLE 4-1

Using a multilayer-film manufacturing apparatus equipped with an extruder, a T die, a cooling roll, a corona discharge unit, a winder, etc., the above oxygen-absorbing resin composition A serving as a material for an oxygen-absorbing layer having a thickness of 30 μm was stacked on a sealant film (product name: "VMX XB15FT", manufactured by J-Film Corporation) having a thickness of 40 μm, in accordance with extrusion lamination, and thereafter, the surface of the oxygen-absorbing layer was treated with corona discharge at a rate of 60 m/minute to obtain a laminate film. Subsequently, onto a corona treated surface of the laminate film, a nylon 6 film (product name: "N1202", manufactured by Toyobo Co., Ltd.) and an alumina vapor deposition PET film (product name: "GL-ARH-F", manufactured by Toppan Printing Co., Ltd.) were stacked by dry lamination, using a urethane dry-lamination adhesive (product name: "AD-817/CAT-RT86L-60", manufactured by Toyo-Morton, Ltd.) to obtain an oxygen-absorbing multilayer film formed of an oxygen-absorbing multilayer body, which was constituted of alumina vapor deposition PET film (12 μm)/urethane dry-lamination adhesive (3 μm)/nylon 6 film (15 μm)/urethane dry-lamination adhesive (3 μm)/oxygen-absorbing layer (30 μm)/sealant film (40 μm).

Using a multilayer sheet molding apparatus (for forming a five-layer film formed of three types of materials) equipped with a first to third extruders, a feed block, a T die, a cooling roll and a sheet winder, an ethylene-propylene random copolymer (product name: "NOVATEC PP EG7F", hereinafter referred to as "PP" in Examples 4-1 to 4-11 and Comparative Examples 4-1 to 4-3, manufactured by Japan Polypropylene Corporation) was extruded from the first extruder, nylon MXD6 (product name: "MXnylon S7007", manufactured by Mitsubishi Gas Chemical Company, Inc.) was extruded from the second extruder; and a maleic anhydride modified polypropylene (product name: "ADMER QF500", manufactured by Mitsui Chemicals Inc.) was extruded from the third extruder, and passed through the feed block to obtain a gas barrier multilayer sheet, which was constituted of PP (80 μm)/maleic anhydride modified polypropylene (15 μm)/nylon MXD6 (40 μm)/maleic anhydride modified polypropylene (15 μm)/PP (350 μm) in the order from inside.

Subsequently, the obtained gas barrier multilayer sheet was thermoformed into a formed cup-form gas barrier molded container (inner volume: 70 cc, aperture: 62 mm×bottom diameter: 52 mm×depth 28 mm) by a vacuum molding machine such that the inner layer (PP having a thickness of 80 μm) faced inside. The obtained cup-form container was filled with a humidity conditioning agent (10 g) to adjust the relative humidity of the container to 100% or 30%. Next, the cup-form container was sealed using the oxygen-absorbing multilayer film as a cover material such that the initial oxygen concentration was adjusted to 2 vol % with nitrogen purge and bonded by means of heat sealing to obtain an oxygen-absorbing sealed container. Note that heat sealing was performed using a pack-sealing machine manufactured by Eshin Pack Industry Co. Ltd., at a heat-sealing temperature of 240° C. for a heat sealing time of 2 seconds, and at a heat sealing pressure of 0.3 MPa. Thereafter, the container was stored at 23° C. under conditions of a relative humidity of 50%. After storage for one month, the oxygen concentration in the container was measured and the sealing strength of the cover material and the gas barrier molded container after one month storage was measured. After the cover material was removed, odor of the container was checked. Note that in measuring sealing strength, a section having a width of 15 mm was cut out from the heat-sealing portion and the sealing strength of the section was measured by a tension tester (the same shall apply, hereinafter).

EXAMPLE 4-2

An oxygen-absorbing sealed container was manufactured in the same manner as in Example 4-1 except that cobalt (II) stearate (0.01 parts by mass in terms of cobalt) was dry-blended in place of cobalt (II) stearate (0.05 parts by mass in terms of cobalt). With respect to the sealed container, the oxygen concentration in the container and sealing strength were measured and odor of the container was checked in the same manner as in Example 4-1. These results are shown in Table 4.

EXAMPLE 4-3

An oxygen-absorbing sealed container was manufactured in the same manner as in Example 4-1 except that cobalt (II) stearate (0.1 parts by mass in terms of cobalt) was dry-blended in place of cobalt (II) stearate (0.05 parts by mass in terms of cobalt). With respect to the sealed container, the oxygen concentration in the container and sealing strength were measured and odor of the container was checked in the same manner as in Example 4-1. These results are shown in Table 4.

EXAMPLE 4-4

An oxygen-absorbing sealed container was manufactured in the same manner as in Example 4-1 except that cobalt (II) acetate was used in place of cobalt (II) stearate. With respect to the sealed container, the oxygen concentration in the container and sealing strength were measured and odor of the container was checked in the same manner as in Example 4-1. These results are shown in Table 4.

EXAMPLE 4-5

An oxygen-absorbing sealed container was manufactured in the same manner as in Example 4-1 except that manganese (II) stearate (0.05 parts by mass in terms of manganese) was dry-blended in place of cobalt (II) stearate (0.05 parts by mass in terms of cobalt). With respect to the sealed container, the oxygen concentration in the container and sealing strength were measured and odor of the container was checked in the same manner as in Example 4-1. These results are shown in Table 4.

EXAMPLE 4-6

An oxygen-absorbing sealed container was manufactured in the same manner as in Example 4-1 except that iron (III) stearate (0.05 parts by mass in terms of iron) was dry-blended in place of cobalt (II) stearate (0.05 parts by mass in terms of cobalt). With respect to the sealed container, the oxygen concentration in the container and sealing strength were measured and odor of the container was checked in the same manner as in Example 4-1. These results are shown in Table 4.

EXAMPLE 4-7

An oxygen-absorbing sealed container was manufactured in the same manner as in Example 4-1 except that tetralin ring-containing copolymerized polyolefin compound B was used in place of tetralin ring-containing copolymerized polyolefin compound A. With respect to the sealed container, the oxygen concentration in the container and sealing strength were measured and odor of the container was checked in the same manner as in Example 4-1. These results are shown in Table 4.

EXAMPLE 4-8

An oxygen-absorbing sealed container was manufactured in the same manner as in Example 4-7 except that manganese (II) stearate (0.05 parts by mass in terms of manganese) was dry-blended in place of cobalt (II) stearate (0.05 parts by mass in terms of cobalt). With respect to the sealed container, the oxygen concentration in the container and sealing strength were measured and odor of the container was checked in the same manner as in Example 4-1. These results are shown in Table 4.

EXAMPLE 4-9

An oxygen-absorbing sealed container was manufactured in the same manner as in Example 4-7 except that iron (III)

stearate (0.05 parts by mass in terms of iron) was dry-blended in place of cobalt (II) stearate (0.05 parts by mass in terms of cobalt). With respect to the sealed container, the oxygen concentration in the container and sealing strength were measured and odor of the container was checked in the same manner as in Example 4-1. These results are shown in Table 4.

EXAMPLE 4-10

An oxygen-absorbing sealed container was manufactured in the same manner as in Example 4-1 except that tetralin ring-containing copolymerized polyolefin compound C was used in place of tetralin ring-containing copolymerized polyolefin compound A. With respect to the sealed container, the oxygen concentration in the container and sealing strength were measured and odor of the container was checked in the same manner as in Example 4-1. These results are shown in Table 4.

EXAMPLE 4-11

An oxygen-absorbing sealed container was manufactured in the same manner as in Example 4-1 except that tetralin ring-containing copolymerized polyolefin compound D was used in place of tetralin ring-containing copolymerized polyolefin compound A. With respect to the sealed container, the oxygen concentration in the container and sealing strength were measured and odor of the container was checked in the same manner as in Example 4-1. These results are shown in Table 4.

COMPARATIVE EXAMPLE 4-1

A sealed container was manufactured in the same manner as in Example 4-1 except that an ethylene-methyl methacrylate copolymer (product name: "Acryft WK402", manufactured by Sumitomo Chemical Co., Ltd.) having a methyl methacrylate content of 25 mass % was used in place of tetralin ring-containing copolymerized polyolefin compound A. With respect to the sealed container, the oxygen concentration in the container and sealing strength were measured and odor of the container was checked in the same manner as in Example 4-1. These results are shown in Table 4.

COMPARATIVE EXAMPLE 4-2

A sealed container was manufactured in the same manner as in Example 4-1 except that cobalt (II) stearate was not used. With respect to the sealed container, the oxygen concentration in the container and sealing strength were measured and odor of the container was checked in the same manner as in Example 4-1. These results are shown in Table 4.

COMPARATIVE EXAMPLE 4-3

An iron powder having an average particle diameter of 30 μm and calcium chloride were mixed in a mass ratio of 100:1. The mixture and a linear and low-density polyethylene (product name: "NOVATEC LLUF641", hereinafter referred to as "LLDPE" in Comparative Example 4-3, manufactured by Japan Polyethylene Corporation) were kneaded in a mass ratio of 30:70 to obtain an iron based oxygen-absorbing resin composition. Next, a sealed container was manufactured in the same manner as in Example 4-1 except that the iron based oxygen-absorbing resin composition obtained above was used in place of oxygen-absorbing resin composition A. With respect to the sealed container, the oxygen concentration in the container and sealing strength were measured and odor of the container was checked in the same manner as in Example 4-1. These results are shown in Table 4.

TABLE 4

| | Resin used in resin composition | Transitional metal catalyst Type | Amount of transition metal[1] | Oxygen concentration (vol %)[2] Relative humidity 100% | Oxygen concentration (vol %)[2] Relative humidity 30% | Sealing strength (kg/15 mm) Before storage | Sealing strength (kg/15 mm) Relative humidity 100% | Sealing strength (kg/15 mm) Relative humidity 30% | Odor Before storage | Odor Relative humidity 100% | Odor Relative humidity 30% |
|---|---|---|---|---|---|---|---|---|---|---|---|
| Example 4-1 | Tetralin ring-containing copolymerized polyolefin compound A | Cobalt stearate | 0.05 | 0.1 or less | 0.1 or less | 2.4 | 2.3 | 2.5 | Satisfactory | Satisfactory | Satisfactory |
| Example 4-2 | Tetralin ring-containing copolymerized polyolefin compound A | Cobalt stearate | 0.01 | 0.3 | 0.4 | 2.5 | 2.4 | 2.4 | Satisfactory | Satisfactory | Satisfactory |
| Example 4-3 | Tetralin ring-containing copolymerized polyolefin compound A | Cobalt stearate | 0.1 | 0.1 or less | 0.1 or less | 2.3 | 2.4 | 2.3 | Satisfactory | Satisfactory | Satisfactory |
| Example 4-4 | Tetralin ring-containing copolymerized polyolefin compound A | Cobalt acetate | 0.05 | 0.1 or less | 0.2 | 2.5 | 2.3 | 2.4 | Satisfactory | Satisfactory | Satisfactory |
| Example 4-5 | Tetralin ring-containing copolymerized polyolefin compound A | Manganese stearate | 0.05 | 0.1 or less | 0.1 or less | 2.4 | 2.3 | 2.3 | Satisfactory | Satisfactory | Satisfactory |

TABLE 4-continued

| | Resin used in resin composition | Transitional metal catalyst | | Oxygen concentration (vol %)[2)] | | Sealing strength (kg/15 mm) | | | Odor | | |
|---|---|---|---|---|---|---|---|---|---|---|---|
| | | Type | Amount of transition metal[1)] | Relative humidity 100% | Relative humidity 30% | Before storage | Relative humidity 100% | Relative humidity 30% | Before storage | Relative humidity 100% | Relative humidity 30% |
| Example 4-6 | Tetralin ring-containing copolymerized polyolefin compound A | Iron stearate | 0.05 | 0.3 | 0.3 | 2.4 | 2.4 | 2.5 | Satisfactory | Satisfactory | Satisfactory |
| Example 4-7 | Tetralin ring-containing copolymerized polyolefin compound B | Cobalt stearate | 0.05 | 0.1 or less | 0.1 or less | 2.5 | 2.4 | 2.5 | Satisfactory | Satisfactory | Satisfactory |
| Example 4-8 | Tetralin ring-containing copolymerized polyolefin compound B | Manganese stearate | 0.05 | 0.1 or less | 0.1 or less | 2.3 | 2.5 | 2.4 | Satisfactory | Satisfactory | Satisfactory |
| Example 4-9 | Tetralin ring-containing copolymerized polyolefin compound B | Iron stearate | 0.05 | 0.1 or less | 0.1 or less | 2.5 | 2.4 | 2.4 | Satisfactory | Satisfactory | Satisfactory |
| Example 4-10 | Tetralin ring-containing copolymerized polyolefin compound C | Cobalt stearate | 0.05 | 0.8 | 1.0 | 2.4 | 2.3 | 2.3 | Satisfactory | Satisfactory | Satisfactory |
| Example 4-11 | Tetralin ring-containing copolymerized polyolefin compound D | Cobalt stearate | 0.05 | 0.7 | 0.6 | 2.4 | 2.4 | 2.3 | Satisfactory | Satisfactory | Satisfactory |
| Comp. Example 4-1 | EMMA[3)] | Cobalt stearate | 0.05 | 2.4 | 2.2 | 2.5 | 2.4 | 2.4 | Satisfactory | Satisfactory | Satisfactory |
| Comp. Example 4-2 | Tetralin ring-containing copolymerized polyolefin compound A | — | — | 2.3 | 2.4 | 2.4 | 2.5 | 2.5 | Satisfactory | Satisfactory | Satisfactory |
| Comp. Example 4-3 | Iron + LLDPE | — | — | 0.1 or less | 1.9 | 2.3 | 2.4 | 2.3 | Slight iron odor | Slight iron odor | Slight iron odor |

[1)]Parts by mass based on resin (100 parts by mass)
[2)]Oxygen concentration in container after storage at 23° C. for one month. Initial oxxygen concentration value: 2.0 vol %
[3)]EMMA: ethylene-methyl methacrylate copolymer As is apparent from Examples 4-1 to 4-11, the oxygen-absorbing sealed containers of the present invention delivered satisfactory oxygen-absorbing performance under both high humidity conditions and low humidity conditions, maintained sealing strength and generated no odor after absorption of oxygen.

EXAMPLE 5-1

With a tetralin ring-containing copolymerized polyolefin compound A (100 parts by mass), cobalt stearate (II) (0.05 parts by mass in terms of cobalt) was dry-blended. The obtained mixture was supplied to a double-screw extruder having two screws of 37 mm in diameter, at a rate of 15 kg/h and melt-kneading was performed at a cylinder temperature of 240° C. and a strand was extruded from an extruder head. After cooling, the strand was pelletized to obtain oxygen-absorbing resin composition C.

Next, using a coextrusion apparatus equipped with two extruders, a feed block, a T die, a cooling roll, and a winder, a low-density polyethylene (product name: "NOVATEC LD LC602A", hereinafter referred to as "LDPE" in Examples 5-1 to 5-11 and Comparative Examples 5-1 to 5-5, manufactured by Japan Polyethylene Corporation) was extruded from a first extruder and oxygen-absorbing resin composition C serving as a material for an oxygen-absorbing layer was extruded from a second extruder, and passed through the feed block to manufacture a three-layer film formed of two types of materials to manufacture an oxygen-absorbing multilayer film of 800 mm in width so as to obtain a structure of LDPE/oxygen-absorbing layer/LDPE laminated in this order. Thereafter, one of the surfaces of the oxygen-absorbing multilayer film C was treated with corona discharge at arte of 60 m/minute.

Next, on the corona treated surface of the obtained oxygen-absorbing multilayer film C, a multilayer paper base material was stacked by extrusion lamination of LDPE to obtain a film-form oxygen-absorbing paper base material multilayer body (oxygen-absorbing multilayer body), which was constituted of a bleached craft paper (basis weight: 330 g/m²)/urethane dry-lamination adhesive (product name: "TM-250HV/CAT-RT86L-60", manufactured by Toyo-Morton, Ltd., 3 µm)/alumina vapor deposition PET film (product name: "GL-AEH", manufactured by Toppan Printing Co., Ltd., 12 µm)/urethane anchor coating agent (product name: "EL-557A/B", manufactured by Toyo-Morton, Ltd., 0.5 µm)/LDPE (15 µm)/LDPE (20 µm)/oxygen-absorbing layer (30 µm)/LDPE (20 µm). The multilayer body was manufactured into a carton to obtain gable-top oxygen-absorbing paper container (1000 mL) having a bottom of 7 cm squares. The moldability and processability of the paper container were satisfactory, in other words, the carton was easily manufactured.

Oxygen-absorbing paper container was filled with 1000 mL of Japanese sake such that the amount of air in the head space was 20 cc, and then, the upper inner surfaces (LDPE) of the gable-top paper container were mutually sealed by heat sealing. The sealed paper container thus obtained was stored at 35° C. for one month. After storage for one month, the oxygen concentration (head-space oxygen concentration) in the paper container was measured and the taste and flavor of the Japanese wine was checked. Furthermore, the heat sealing strength of the upper portion of the gable-top paper container after one month storage was measured. These results are shown in Table 5.

EXAMPLE 5-2

An oxygen-absorbing paper container was manufactured in the same manner as in Example 5-1 except that cobalt (II) stearate (0.01 parts by mass in terms of cobalt) was dry-blended in place of cobalt (II) stearate (0.05 parts by mass in terms of cobalt). Thereafter, the head-space oxygen concentration was measured; the taste and flavor of Japanese sake was checked, and the heat sealing strength of the upper portion of the paper container was measured in the same manner as in Example 5-1. These results are shown in Table 5.

EXAMPLE 5-3

An oxygen-absorbing paper container was manufactured in the same manner as in Example 5-1 except that cobalt (II) stearate (0.1 parts by mass in terms of cobalt) was dry-blended in place of cobalt (II) stearate (0.05 parts by mass in terms of cobalt). Thereafter, the head-space oxygen concentration was measured; the taste and flavor of Japanese sake was checked, and the heat sealing strength of the upper portion of the paper container was measured in the same manner as in Example 5-1. These results are shown in Table 5.

EXAMPLE 5-4

An oxygen-absorbing paper container was manufactured in the same manner as in Example 5-1 except that cobalt (II) acetate was used in place of cobalt (II) stearate. Thereafter, the head-space oxygen concentration was measured; the taste and flavor of Japanese sake was checked; and the heat sealing strength of the upper portion of the paper container was measured in the same manner as in Example 5-1. These results are shown in Table 5.

EXAMPLE 5-5

An oxygen-absorbing paper container was manufactured in the same manner as in Example 5-1 except that manganese (II) stearate (0.05 parts by mass in terms of manganese) was dry-blended in place of cobalt (II) stearate (0.05 parts by mass in terms of cobalt). Thereafter, the head-space oxygen concentration was measured; the taste and flavor of Japanese sake was checked and the heat sealing strength of the upper portion of the paper container was measured in the same manner as in Example 5-1. These results are shown in Table 5.

EXAMPLE 5-6

An oxygen-absorbing paper container was manufactured in the same manner as in Example 5-1 except that iron (II) stearate (0.05 parts by mass in terms of iron) was dry-blended in place of cobalt (II) stearate (0.05 parts by mass in terms of cobalt). Thereafter, the head-space oxygen concentration was measured; the taste and flavor of Japanese sake was checked and the heat sealing strength of the upper portion of the paper container was measured in the same manner as in Example 5-1. These results are shown in Table 5.

EXAMPLE 5-7

An oxygen-absorbing paper container was manufactured in the same manner as in Example 5-1 except that tetralin ring-containing copolymerized polyolefin compound B was used in place of tetralin ring-containing copolymerized polyolefin compound A. Thereafter, the head-space oxygen concentration was measured; the taste and flavor of Japanese sake was checked; and the heat sealing strength of the upper portion of the paper container was measured in the same manner as in Example 5-1. These results are shown in Table 5.

EXAMPLE 5-8

An oxygen-absorbing paper container was manufactured in the same manner as in Example 5-7 except that manganese (II) stearate (0.05 parts by mass in terms of manganese) was dry-blended in place of cobalt (II) stearate (0.05 parts by mass in terms of cobalt). Thereafter, the head-space oxygen concentration was measured; the taste and flavor of Japanese sake was checked and the heat sealing strength of the upper portion of the paper container was measured in the same manner as in Example 5-1. These results are shown in Table 5.

EXAMPLE 5-9

An oxygen-absorbing paper container was manufactured in the same manner as in Example 5-7 except that iron (II) stearate (0.05 parts by mass in terms of iron) was dry-blended in place of cobalt (II) stearate (0.05 parts by mass in terms of cobalt). Thereafter, the head-space oxygen concentration was measured; the taste and flavor of Japanese sake was checked and the heat sealing strength of the upper portion of the paper container was measured in the same manner as in Example 5-1. These results are shown in Table 5.

EXAMPLE 5-10

An oxygen-absorbing paper container was manufactured in the same manner as in Example 5-1 except that tetralin ring-containing copolymerized polyolefin compound C was used in place of tetralin ring-containing copolymerized polyolefin compound A. Thereafter, the head-space oxygen concentration was measured; the taste and flavor of Japanese sake was checked; and the heat sealing strength of the upper portion of the paper container was measured in the same manner as in Example 5-1. These results are shown in Table 5.

EXAMPLE 5-11

An oxygen-absorbing paper container was manufactured in the same manner as in Example 5-1 except that tetralin ring-containing copolymerized polyolefin compound D was used in place of tetralin ring-containing copolymerized polyolefin compound A. Thereafter, the head-space oxygen concentration was measured; the taste and flavor of Japanese sake was checked; and the heat sealing strength of the upper portion of the paper container was measured in the same manner as in Example 5-1. These results are shown in Table 5.

COMPARATIVE EXAMPLE 5-1

A paper container was manufactured in the same manner as in Example 5-1 except that an ethylene-methyl methacrylate copolymer having a methyl methacrylate content of 25 mass % used in Synthesis Example 1 was used in place of tetralin ring-containing copolymerized polyolefin compound A. Thereafter, the head-space oxygen concentration was measured; the taste and flavor of Japanese sake was checked; and the heat sealing strength of the upper portion of the paper container was measured in the same manner as in Example 5-1. These results are shown in Table 5.

COMPARATIVE EXAMPLE 5-2

A paper container was manufactured in the same manner as in Example 5-1 except that cobalt (II) stearate was not used. Thereafter, the head-space oxygen concentration was measured; the taste and flavor of Japanese sake was checked and the heat sealing strength of the upper portion of the paper container was measured in the same manner as in Example 5-1. These results are shown in Table 5.

COMPARATIVE EXAMPLE 5-3

Oxygen-absorbing resin composition D was prepared in the same manner as in Example 5-1 except that N-MXD6 (product name: "MX nylon 56011", manufactured by Mitsubishi Gas Chemical Company, Inc.) was used in place of tetralin ring-containing copolymerized polyolefin compound A. Subsequently, using a multilayer film manufacturing apparatus equipped with a first to third extruders, a feed block, a T die, a cooling roll, a corona discharge unit, a winder, etc., LDPE was extruded from the first extruder; oxygen-absorbing resin composition D serving as a material for an oxygen-absorbing layer was extruded from the second extruder; and a polyethylene adhesive resin (product name: "MODIC M545", hereinafter referred to as "AD" in Comparative Example 5-3, manufactured by Mitsubishi Chemical Corporation) was extruded from the third extruder; and passed through the feed block to obtain oxygen-absorbing multilayer film D. The multilayer film was constituted of LDPE (20 μm)/polyethylene adhesive resin (10 μm)/oxygen-absorbing layer (30 μm)/polyethylene adhesive resin (10 μm)/LDPE (20 μm) from inside. Subsequently, an oxygen-absorbing paper container was manufactured in the same manner as in Example 5-1 except that the above oxygen-absorbing multilayer film D was used in place of oxygen-absorbing multilayer film C. Thereafter, the head-space oxygen concentration was measured; the taste and flavor of Japanese sake was checked; and the heat sealing strength of the upper portion of the paper container was measured in the same manner as in Example 5-1. These results are shown in Table 5.

COMPARATIVE EXAMPLE 5-4

Iron powder having an average particle diameter of 30 μm and calcium chloride were mixed in a mass ratio of 100:1. The mixture and LDPE were kneaded in a mass ratio of 30:70 to obtain an iron-based oxygen-absorbing resin composition. We tried to manufacture a three-layer film formed of two types of materials in the same manner as in Example 5-1 except that iron-based oxygen-absorbing resin composition was used in place of oxygen-absorbing resin composition C; however, a film having smooth surface that can be sufficiently subjected to further studies was not able to be obtained because of the presence of convexoconcave portions produced in the surface of the film due to iron powder.

COMPARATIVE EXAMPLE 5-5

On the LDPE film having a thickness 50 μm, a film (30 μm in thickness) of iron-based oxygen-absorbing resin composition obtained in Comparative Example 5-4 and serving as an oxygen-absorbing layer was stacked in accordance with extrusion lamination to manufacture a laminate film, which was constituted of iron-based oxygen-absorbing layer (30 μm)/LDPE (50 μm). Thereafter, the oxygen-absorbing layer surface was treated with corona discharge.

An oxygen-absorbing paper base material multilayer body, which was constituted of bleached craft paper (basis weight: 330 g/m$^2$)/urethane dry-lamination adhesive (3 μm)/alumina vapor deposition PET film (12 μm)/urethane anchor coating agent (0.5 μm)/LDPE (15 μm)/oxygen-absorbing layer (30 μm)/LDPE (50 μm), was manufactured by extrusion lamination of LDPE on a multilayer paper base material in the same manner as in Example 5-1 except that the laminate film obtained above was used in place of the oxygen-absorbing multilayer film C constituted of three layers of two types of materials. Thereafter, we tried to manufacture a gable-top paper container from the multilayer body; however it was difficult to form the corners of the paper container. Then, we tried to manufacture a paper container by lowering a speed of manufacturing a container. As a result, the paper container was finally obtained with a large number of defective products (that were eliminated). Thereafter, the head-space oxygen concentration of the obtained paper container was measured, the taste and flavor of Japanese sake was checked and the heat sealing strength of the upper portion of the paper container was measured in the same manner as in Example 5-1. These results are shown in Table 5.

TABLE 5

| | Layer constitution of paper container[1] | Transition metal catalyst Type | Amount[2] |
|---|---|---|---|
| Example 5-1 | LDPE/Oxygen-absorbing layer A[8]/LDPE/LDPE/*/Alumina vapor deposition PET/**/Paper base material | Cobalt stearate | 0.05 |
| Example 5-2 | LDPE/Oxygen-absorbing layer A[8]/LDPE/LDPE/*/Alumina vapor deposition PET/**/Paper base material | Cobalt stearate | 0.01 |
| Example 5-3 | LDPE/Oxygen-absorbing layer A[8]/LDPE/LDPE/*/Alumina vapor deposition PET/**/Paper base material | Cobalt stearate | 0.1 |
| Example 5-4 | LDPE/Oxygen-absorbing layer A[8]/LDPE/LDPE/*/Alumina vapor deposition PET/**/Paper base material | Cobalt acetate | 0.05 |
| Example 5-5 | LDPE/Oxygen-absorbing layer A[8]/LDPE/LDPE/*/Alumina vapor deposition PET/**/Paper base material | Manganese stearate | 0.05 |
| Example 5-6 | LDPE/Oxygen-absorbing layer A[8]/LDPE/LDPE/*/Alumina vapor deposition PET/**/Paper base material | Iron stearate | 0.05 |
| Example 5-7 | LDPE/Oxygen-absorbing layer B[8]/LDPE/LDPE/*/Alumina vapor deposition PET/**/Paper base material | Cobalt stearate | 0.05 |
| Example 5-8 | LDPE/Oxygen-absorbing layer B[8]/LDPE/LDPE/*/Alumina vapor deposition PET/**/Paper base material | Manganese stearate | 0.05 |
| Example 5-9 | LDPE/Oxygen-absorbing layer B[8]/LDPE/LDPE/*/Alumina vapor deposition PET/**/Paper base material | Iron stearate | 0.05 |
| Example 5-10 | LDPE/Oxygen-absorbing layer C[8]/LDPE/LDPE/*/Alumina vapor deposition PET/**/Paper base material | Cobalt stearate | 0.05 |
| Example 5-11 | LDPE/Oxygen-absorbing layer D[8]/LDPE/LDPE/*/Alumina vapor deposition PET/**/Paper base material | Cobalt stearate | 0.05 |
| Comparative Example 5-1 | LDPE/EMMA[4]/LDPE/LDPE/*/Alumina vapor deposition PET/**/Paper base material | Cobalt stearate | 0.05[5] |
| Comparative Example 5-2 | LDPE/Oxygen-absorbing layer A[8]/LDPE/LDPE/*/Alumina vapor deposition PET/**/Paper base material | — | — |
| Comparative Example 5-3 | LDPE/AD/N-MXD6/AD/LDPE/LDPE/*/Alumina vapor deposition PET/**/Paper base material | Cobalt stearate | 0.05[6] |
| Comparative Example 5-5 | LDPE/LDPE + Iron based oxygen absorber/LDPE/*/Alumina vapor deposition PET/**/Paper base material | — | — |

| | Oxygen concentration[3] (vol %) | Taste and flavor | Heat-sealing strength (kg) Before storage | After storage |
|---|---|---|---|---|
| Example 5-1 | 0.1 or less | Satisfactory | 3.8 | 3.9 |
| Example 5-2 | 2.7 | Almost satisfactory | 3.7 | 3.7 |
| Example 5-3 | 0.1 or less | Satisfactory | 3.8 | 3.7 |
| Example 5-4 | 0.1 or less | Satisfactory | 3.8 | 3.9 |
| Example 5-5 | 0.1 or less | Satisfactory | 3.9 | 3.9 |
| Example 5-6 | 0.1 or less | Satisfactory | 3.8 | 3.9 |
| Example 5-7 | 0.1 or less | Satisfactory | 3.8 | 3.7 |
| Example 5-8 | 0.1 or less | Satisfactory | 3.9 | 3.8 |
| Example 5-9 | 0.1 or less | Satisfactory | 3.9 | 3.7 |
| Example 5-10 | 3.3 | Almost satisfactory | 4.2 | 4.1 |
| Example 5-11 | 0.1 or less | Satisfactory | 4.0 | 4.0 |
| Comparative Example 5-1 | 15.2 | Reduced | 4.1 | 4.2 |
| Comparative Example 5-2 | 17.0 | Reduced | 3.8 | 3.7 |
| Comparative Example 5-3 | 5.5 | Almost satisfactory | 3.9 | 1.1 |
| Comparative Example 5-5 | 0.1 or less | Reduced[7] | 3.8 | 3.7 |

[1] In layer constitution, * represents anchor coat and ** represents dry lamination
[2] Content of transition metal (parts by mass) based on copolymerized polyolefin compound (100 parts by mass)
[3] After being stored at 35° C. for one month
[4] EMMA: ethylene-methyl methacrylate copolymer
[5] Content of transition metal (parts by mass) based on EMMA (100 parts by mass)
[6] Content of transition metal (parts by mass) based on N-MXD6100 (100 parts by mass)
[7] Aldehyde odor is sensed
[8] Alphabet attached to the end of "oxygen-absorbing layer" represents the type of tetraline ring containing copolymerized polyolefin compound contained in the oxygen-absorbing layer. For example, "oxygen-absorbing layer A" contains tetraline ring containing copolymerized polyolefin compound A.

As is apparent from Table 5, it was confirmed that the paper containers of Examples 5-1 to 5-11 deliver satisfactory oxygen-absorbing performance, and that the taste and flavor of the content and container strength even after storage are maintained.

EXAMPLE 6-1

Using a multilayer tube manufacturing apparatus (for forming a six-layer film formed of five types of materials) equipped with five extruders, a feed block, a T die, a cooling roll, etc., a high-density polyethylene (product name:

"NOVATEC HD HB420R", hereinafter referred to as "HDPE" in Examples 6-1 to 6-11 and Comparative Examples 6-1 to 6-3, manufactured by Japan Polyethylene Corporation) serving as an inner layer was extruded from a first extruder; oxygen-absorbing resin composition A serving as an oxygen-absorbing layer was extruded from a second extruder; an adhesive polyethylene (product name: "MODIC L502", hereinafter referred to as "adhesive PE" in Examples 6-1 to 6-11 and Comparative Examples 6-1 to 6-3, manufactured by Mitsubishi Chemical Corporation) serving as an adhesion layer was extruded from a third extruder; an ethylene-vinyl alcohol copolymer (product name: "EVAL F171B", hereinafter referred to as "EVOH" in Examples 6-1 to 6-11 and Comparative Examples 6-1 to 6-3 manufactured by Kuraray Co., Ltd.) serving as a gas barrier layer was extruded from a fourth extruder; and a low-density polyethylene (product name: "NOVATEC LD YF30", hereinafter referred to as "LDPE" in Examples 6-1 to 6-11 and Comparative Examples 6-1 to 6-3, manufactured by Japan Polyethylene Corporation) was extruded from a fifth extruder to obtain a multilayer tubular form constituted of six-layers formed of five types of materials (inner diameter 35 mm), which was constituted of HDPE (120 µm)/oxygen-absorbing layer (100 µm)/adhesive PE (30 µm)/gas barrier layer (50 µm)/adhesive PE (30 µm)/LDPE (120 µm), laminated in this order from the inner layer side toward the outer layer side.

The multilayer tubular form was cut into pieces having a length of 160 mm to obtain tubular molded articles. To one of the ends of each tubular molded article, a mouth part was bonded having a gas barrier property and primarily formed of a high-density polyethylene (product name: "NOVATEC HD HJ360", manufactured by Japan Polyethylene Corporation) and having an opening for ejecting the content. To an opening formed at the side of the mouth part opposite to the side close to the tubular molded article, a detachable cap was provided for sealing the opening. In this way, a tubular container was obtained. Note that the other end of the tubular molded article (the tubular container) was not closed in this stage and remained open in order to introduce a content in the following evaluation test.

Using the tubular container obtained in Example 6-1, the following tests were performed.
(1) Oxygen Concentration The open end of the tubular container was heat-sealed to seal the container, air (oxygen concentration: 20.8 vol %) was introduced through the opening provided to the mouth part of the tubular container into the tubular container and replaced for the atmosphere within the container. Thereafter, air (100 cc) was introduced and the opening of the mouth part was sealed with an aluminum foil laminate film and a cap was further provided on the film. The container was stored at 25° C. under 50% RH for 7 days. After the storage, the oxygen concentration in the container was measured. Furthermore, the container obtained in the same manner up to the step of providing a cap was stored at 25° C. under 50% RH for one month. Then, the oxygen concentration in the container after storage was measured. These results are shown in Table 6.
(2) Storage Stability of Content After the open end of the tubular container was sealed by heat sealing, an aqueous 10% vitamin C solution (100 mL) was introduced into the tubular container through the opening of the mouth part provided to the tubular container and the opening of the mouth part was sealed with an aluminum foil laminate film and a cap was further provided on the film. The container was stored under the environment of 25° C. and 50% RH for 2 months. Then, the aluminum foil laminate film was removed to check odor of the head space of the container and the color tone of the content.
(3) Strength Maintainability The content was removed from the tubular container in which aqueous vitamin C solution was stored for 2 months in the above test "(2) storage stability of content" and the multilayer body potion of the tubular container was squeezed 50 times by hand and the portion squeezed by hand was observed to check the presence or absence of interlayer peeling. Tubular containers in which interlayer peeling was not observed were evaluated as "good", whereas Tubular containers in which interlayer peeling was observed were evaluated as "poor".

EXAMPLE 6-2

A tubular container was manufactured in the same manner as in Example 6-1 except that cobalt (II) stearate (0.01 parts by mass in terms of cobalt) was dry-blended in place of cobalt (II) stearate (0.05 parts by mass in terms of cobalt). The individual tests were performed in the same manner as in Example 6-1. These results are shown in Table 6.

EXAMPLE 6-3

A tubular container was manufactured in the same manner as in Example 6-1 except that cobalt (II) stearate (0.1 parts by mass in terms of cobalt) was dry-blended in place of cobalt (II) stearate (0.05 parts by mass in terms of cobalt). The individual tests were performed in the same manner as in Example 6-1. These results are shown in Table 6.

EXAMPLE 6-4

A tubular container was manufactured in the same manner as in Example 6-1 except that cobalt (II) acetate was used in place of cobalt (II) stearate. The individual tests were performed in the same manner as in Example 6-1. These results are shown in Table 6.

EXAMPLE 6-5

A tubular container was manufactured in the same manner as in Example 6-1 except that manganese (II) stearate (0.05 parts by mass in terms of manganese) was dry-blended in place of cobalt (II) stearate (0.05 parts by mass in terms of cobalt). The individual tests were performed in the same manner as in Example 6-1. These results are shown in Table 6.

EXAMPLE 6-6

A tubular container was manufactured in the same manner as in Example 6-1 except that iron (III) stearate (0.05 parts by mass in terms of iron) was dry-blended in place of cobalt (II) stearate (0.05 parts by mass in terms of cobalt). The individual tests were performed in the same manner as in Example 6-1. These results are shown in Table 6.

EXAMPLE 6-7

A tubular container was manufactured in the same manner as in Example 6-1 except that tetralin ring-containing copolymerized polyolefin compound B was used in place of tetralin ring-containing copolymerized polyolefin compound A. The individual tests were performed in the same manner as in Example 6-1. These results are shown in Table 6.

EXAMPLE 6-8

A tubular container was manufactured in the same manner as in Example 6-7 except that manganese (II) stearate (0.05 parts by mass in terms of manganese) was dry-blended in place of cobalt (II) stearate (0.05 parts by mass in terms of cobalt). The individual tests were performed in the same manner as in Example 6-1. These results are shown in Table 6.

EXAMPLE 6-9

A tubular container was manufactured in the same manner as in Example 6-7 except that iron (III) stearate (0.05 parts by mass in terms of iron) was dry-blended in place of cobalt (II) stearate (0.05 parts by mass in terms of cobalt). The individual tests were performed in the same manner as in Example 6-1. These results are shown in Table 6.

EXAMPLE 6-10

A tubular container was manufactured in the same manner as in Example 6-1 except that tetralin ring-containing copolymerized polyolefin compound C was used in place of tetralin ring-containing copolymerized polyolefin compound A. The individual tests were performed in the same manner as in Example 6-1. These results are shown in Table 6.

EXAMPLE 6-11

A tubular container was manufactured in the same manner as in Example 6-1 except that tetralin ring-containing copolymerized polyolefin compound D was used in place of tetralin ring-containing copolymerized polyolefin compound A. The individual tests were performed in the same manner as in Example 6-1. These results are shown in Table 6.

COMPARATIVE EXAMPLE 6-1

A tubular container was manufactured in the same manner as in Example 6-1 except that an ethylene-methyl methacrylate copolymer having a methyl methacrylate content of 25 mass % (product name: "Acryft WK402", manufactured by Sumitomo Chemical Co., Ltd.) was used in place of tetralin ring-containing copolymerized polyolefin compound A. Individual tests were performed in the same manner as in Example 6-1. These results are shown in Table 6.

COMPARATIVE EXAMPLE 6-2

A tubular container was manufactured in the same manner as in Example 6-1 except that cobalt (II) stearate was not used. The individual tests were performed in the same manner as in Example 6-1. These results are shown in Table 6.

COMPARATIVE EXAMPLE 6-3

A granular oxygen absorbent obtained by coating reduced iron powder (100 parts by mass) having an average particle diameter of 20 μm with calcium chloride (3 parts by mass) and HDPE were kneaded in a mass ratio of 30:70 to obtain an iron based oxygen-absorbing resin composition. Subsequently, using a multilayer tube manufacturing apparatus (for forming a six-layer film formed of five types of materials) equipped with five extruders, a feed block, a T die, a cooling roll, etc., HDPE was extruded from a first extruder; the iron based oxygen-absorbing resin composition was extruded from a second extruder; adhesive PE was extruded from a third extruder; EVOH serving as a gas barrier layer was extruded from a fourth extruder; and LDPE was extruded from a fifth extruder to obtain a multilayer tubular form constituted of six-layer film formed of five types of materials (inner diameter: 35 mm), which was constituted of HDPE (60 μm)/iron based oxygen-absorbing resin composition (60 μm)/adhesive PE (30 μm)/gas barrier layer (50 μm)/adhesive PE (30 μm)/LDPE (120 μm) laminated in this order from the inner layer side toward the outer layer. The multilayer tubular form was cut into pieces having a length of 160 mm to obtain tubular molded articles. To one of the ends of each tubular molded articles, a mouth part was bonded having a gas barrier property and primarily formed of a high-density polyethylene (product name: "NOVATEC HD-HJ360", manufactured by Japan Polyethylene Corporation) and having an opening for ejecting the content. To an opening formed at the side of the mouth part opposite to the side close to the tubular molded article, a detachable cap was provided for sealing the opening. In this way, a tubular container was obtained. Using the tubular container, the individual tests were performed in the same manner as in Example 6-1. These results are shown in Table 6.

TABLE 6

|  | Resin used in resin composition | Transition metal catalyst Type | Amount of transition metal[1] | Oxygen concentration (vol %)[2] After 7 days | After one month | Storage stability of content[3] Odor | Color tone | Strength maintainability |
|---|---|---|---|---|---|---|---|---|
| Example 6-1 | Tetralin ring-containing copolymerized polyolefin compound A | Cobalt stearate | 0.05 | 1.8 | 0.1 or less | Satisfactory | Satisfactory | good |
| Example 6-2 | Tetralin ring-containing copolymerized polyolefin compound A | Cobalt stearate | 0.01 | 5.3 | 0.8 | Satisfactory | Almost satisfactory | good |
| Example 6-3 | Tetralin ring-containing copolymerized polyolefin compound A | Cobalt stearate | 0.1 | 2.0 | 0.1 or less | Satisfactory | Satisfactory | good |

TABLE 6-continued

| | Resin used in resin composition | Transition metal catalyst Type | Amount of transition metal[1] | Oxygen concentration (vol %)[2] After 7 days | After one month | Storage stability of content[3] Odor | Color tone | Strength maintainability |
|---|---|---|---|---|---|---|---|---|
| Example 6-4 | Tetralin ring-containing copolymerized polyolefin compound A | Cobalt acetate | 0.05 | 2.3 | 0.1 or less | Satisfactory | Satisfactory | good |
| Example 6-5 | Tetralin ring-containing copolymerized polyolefin compound A | Manganese stearate | 0.05 | 3.2 | 0.1 or less | Satisfactory | Satisfactory | good |
| Example 6-6 | Tetralin ring-containing copolymerized polyolefin compound A | Iron stearate | 0.05 | 3.1 | 0.1 or less | Satisfactory | Satisfactory | good |
| Example 6-7 | Tetralin ring-containing copolymerized polyolefin compound B | Cobalt stearate | 0.05 | 1.4 | 0.1 or less | Satisfactory | Satisfactory | good |
| Example 6-8 | Tetralin ring-containing copolymerized polyolefin compound B | Manganese stearate | 0.05 | 1.5 | 0.1 or less | Satisfactory | Satisfactory | good |
| Example 6-9 | Tetralin ring-containing copolymerized polyolefin compound B | Iron stearate | 0.05 | 1.8 | 0.1 or less | Satisfactory | Satisfactory | good |
| Example 6-10 | Tetralin ring-containing copolymerized polyolefin compound C | Cobalt stearate | 0.05 | 9.3 | 3.0 | Almost satisfactory | Almost satisfactory | good |
| Example 6-11 | Tetralin ring-containing copolymerized polyolefin compound D | Cobalt stearate | 0.05 | 6.9 | 1.8 | Almost satisfactory | Almost satisfactory | good |
| Comp. Example 6-1 | EMMA[4] | Cobalt stearate | 0.05 | 20.5 | 20.4 | Almost satisfactory | Reduced | good |
| Comp. Example 6-2 | Tetralin ring-containing copolymerized polyolefin compound A | — | — | 20.2 | 19.8 | Almost satisfactory | Reduced | good |
| Comp. Example 6-3 | Iron + HDPE | — | — | 10.3 | 6.0 | Iron odor | Slightly reduced | poor |

[1] Parts by mass based on resin (100 parts by mass)
[2] Stored at 25° C., 50% RH
[3] Results after 2 month storage at 25° C., 50% RH
[4] EMMA: ethylene-methyl methacrylate copolymer As is apparent from Examples 6-1 to 6-11, the tubular containers of the present invention delivered satisfactory oxygen-absorbing performance under low humidity conditions and improved storage stability of the content, and generated no odor after absorption of oxygen and maintained strength.

Note that vials are taken as an example and demonstrated in the following Examples 7-1 to 7-4. As is described in the specification of the present application, since characteristics demanded for ampules, prefilled syringes and vacuum blood collection tubes are the same as for vials, the present invention is not particularly limited by the following Examples 7-1 to 7-4.

EXAMPLE 7-1

With a tetralin ring-containing copolymerized polyolefin compound A (100 parts by mass), cobalt stearate (II) (0.05 parts by mass in terms of cobalt) was dry-blended. The obtained mixture was supplied to a double-screw extruder having two screws of 37 mm in diameter, at a rate of 30 kg/h. Melt-kneading was performed at a cylinder temperature of 220° C. and a strand was extruded from an extruder head. After cooling, the strand was pelletized to obtain an oxygen-absorbing resin composition E. Subsequently, as shown below, a multilayer injection molded container, i.e., vial, was manufactured by using the oxygen-absorbing resin composition E. Thereafter, performance of the obtained vial was evaluated as shown below. The evaluation results are shown in Table 7.

[Manufacturing of Vial]

Under the following conditions, the polyester for constituting a resin layer (layer B) was injected from an injection cylinder and then the oxygen-absorbing resin composition E for constituting an oxygen-absorbing layer (layer A) was injected from another injection cylinder simultaneously with the polyester for constituting layer B. Subsequently, the polyester for constituting layer B was injected in a necessary amount to fill the cavity of an injection mold to obtain an injection molded article of a three-layer constitution (B/A/B). Thereafter, the obtained injection-molded article was cooled to a predetermined temperature and transferred to a mold for blow molding. Blow molding was performed to manufacture a vial (bottle portion). The total mass of the vial herein was specified as 24 g and the mass of layer A was specified as 30 mass % of the total mass of the vial. Furthermore, as the polyester constituting layer B, a polyethylene terephthalate resin (product name: "RT-553C", hereinafter abbreviated as "PET" in Examples 7-1 to 7-4 and Comparative Examples 7-1 to 7-2, manufactured by Japan Unipet) was used.

(Shape of Vial)

The whole length of a vial was specified as 89 mm, the outer diameter as 40 mmϕ and the film thickness as 1.8 mm. Note that a vial was manufactured by use of an integrated injection blow molding machine (Type: IBS 85, proving 4 vials, manufactured by UNILOY).

(Molding Conditions for Vial)

Temperature of injection cylinder for layer A: 220° C.
Temperature of injection cylinder for layer B: 280° C.
Temperature of resin flow channel in injection mold: 280° C.
Blowing temperature: 150° C.
Temperature of cooling water for blow mold: 15° C.

[Evaluation of Vial Performance]

Measurement of oxygen concentration in the obtained vial, evaluation of visibility of a content, drop test and elution test were performed in accordance with the following methods and evaluation was made based on the following criteria.

(1) Oxygen Concentration in Vial

Vials were each filled with pure water (50 mL), sealed with a rubber tap and an aluminum cap and stored in an atmosphere of 23° C. and 60% RH. After 3 days and one month, the oxygen concentration of the head space was measured by an oxygen concentration measurement apparatus (LC-750F, manufactured by Toray Engineering Co. Ltd.).

(2) Visibility of Content

The visibility of the contents of vials was visually observed. If the content was visible without any problem, the vial was determined to come up to the standard.

(3) Drop Test

After a vial was stored in an atmosphere of 40° C. and 90% RH for one month, the vial was filled up with pure water (50 mL) and then sealed by a rubber tap and an aluminum cap. The sealed container thus obtained was allowed to drop from a height of 2 m. The appearance of the container at this time was checked.

(4) Elusion Test

After a vial was stored in an atmosphere of 40° C. and 90% RH for one month, the vial was filled up with pure water (50 mL) and then sealed by a rubber tap and an aluminum cap. The sealed container thus obtained was stored in an atmosphere of 40° C. and 60% RH for 4 months and then the total amount of carbon (hereinafter, TOC) in the pure water was measured.

(TOC Measurement)

Apparatus: TOC-V$_{CPH}$ manufactured by Shimadzu Corporation
Temperature of combustion furnace: 720° C.
Gas and flow rate: highly purified air, 150 mL/min in TOC meter
Injection amount: 150 μL
Detection limit: 1 μg/mL EXAMPLES 7-2 to 7-4

Oxygen-absorbing resin compositions and vials were manufactured in the same manner as in Example 7-1 except that each of the corresponding tetralin ring-containing copolymerized polyolefin compounds shown in Table 7 was used in place of the tetralin ring-containing copolymerized polyolefin compound A. The performance of the obtained vials was individually evaluated in the same manner as in Example 7-1. The evaluation results are shown in Table 7.

COMPARATIVE EXAMPLE 7-1

Single-layer vials having the same shape as that in Example 7-1 was manufactured in the same manner as in Example 7-1 except that PET (100 parts by mass) was used in place of oxygen-absorbing resin composition E and the injection cylinder temperature for layer A was changed from 220° C. to 280° C. The performance of the obtained vials was evaluated in the same manner as in Example 7-1. The evaluation results are shown in Table 7.

COMPARATIVE EXAMPLE 7-2

With nylon MXD6 (Product name: trade name "MX nylon S7007", manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 30 kg/h. Melt-kneading was performed at a cylinder temperature of 280° C. and a strand was extruded from an extruder head. After cooling, the strand was pelletized to obtain an oxygen-absorbing resin composition M. Vials were manufactured in the same manner as in Example 7-1 except that oxygen-absorbing resin composition M was used in place of oxygen-absorbing resin composition E and the injection cylinder temperature for layer A was changed from 220° C. to 280° C. The performance of the obtained vials was evaluated in the same manner as in Example 7-1. The evaluation results are shown in Table 7.

TABLE 7

| | Resin used in layer A | Resin used in layer B | Layer constitution | Oxygen concentration (vol %)[1] After 3 days | Oxygen concentration (vol %)[1] After one month | Visibility of content | Drop test | Elution test, TOC amount[2] (μg/mL) |
|---|---|---|---|---|---|---|---|---|
| Example 7-1 | Tetralin ring-containing copolymerized polyolefin compound A | PET | Three layers | 2.7 | 0.1 or less | Transparent (acceptable) | No breakage is observed in all containers | Detection limit or less |
| Example 7-2 | Tetralin ring-containing copolymerized polyolefin compound B | PET | Three layers | 1.3 | 0.1 or less | Transparent (acceptable) | No breakage is observed in all containers | Detection limit or less |
| Example 7-3 | Tetralin ring-containing copolymerized polyolefin compound C | PET | Three layers | 2.5 | 0.1 or less | Transparent (acceptable) | No breakage is observed in all containers | Detection limit or less |

TABLE 7-continued

| | Resin used in layer A | Resin used in layer B | Layer constitution | Oxygen concentration (vol %)[1] After 3 days | Oxygen concentration (vol %)[1] After one month | Visibility of content | Drop test | Elution test, TOC amount[2] (µg/mL) |
|---|---|---|---|---|---|---|---|---|
| Example 7-4 | Tetralin ring-containing copolymerized polyolefin compound D | PET | Three layers | 2.3 | 0.1 or less | Transparent (acceptable) | No breakage is observed in all containers | Detection limit or less |
| Comp. Example 7-1 | PET single layer | | Single layer | 20.5 | 20.5 | Transparent (acceptable) | No breakage is observed in all containers | Detection limit or less |
| Comp. Example 7-2 | Nylon MXD6 | PET | Three layers | 19.5 | 16.5 | Hazy (acceptable) | 7 out of 20 are broken | 38 |

[1]Stored at 23° C., 60% RH
[2]Detection lower limit is 0.1 (µg/mL)

As is apparent from Table 7, it was confirmed that the vials of Examples 7-1 to 7-4 have satisfactory oxygen-absorbing property and maintain satisfactory strength even after long-term storage, and that the amount of elution from the container to the content is small. Furthermore, it was confirmed that the vials of Examples 7-1 to 7-4 each have sufficient visibility of the content in a container, and are excellent in transparency.

EXAMPLE 8-1

As shown below, a syringe was manufactured by using the oxygen-absorbing resin composition E. Thereafter, performance of the obtained syringe was evaluated as shown below. The evaluation results are shown in Table 8.
[Manufacturing of Syringe]
Under the following conditions, the polyester for constituting a resin layer (layer B) was injected from an injection cylinder and then the oxygen-absorbing resin composition E for constituting an oxygen-absorbing layer (layer A) was injected from another injection cylinder simultaneously with the polyester for constituting layer B. Subsequently, the polyester for constituting layer B was injected in a necessary amount to fill the cavity of an injection mold to manufacture a syringe constituted of three layers (B/A/B). The total mass of the syringe herein was specified as 1.95 g and the mass of layer A was specified as 30 mass % of the total mass of the syringe. As the polyester constituting layer B, a polyethylene terephthalate (product name: "RT-553C", hereinafter abbreviated as "PET" in Examples 8-1 to 8-4 and Comparative Examples 8-1 to 8-2 manufactured by Japan Unipet) was used.
(Shape of Syringe)
The volume (1 cc) of the content was used as a standard in accordance with ISO11040-6. Note that a syringe was manufactured by use of an injection molding machine (type: ASB-12N/10, manufactured by Nissei ASB Machine Co., Ltd).
(Conditions for Molding Syringe)
Temperature of injection cylinder for layer A: 220° C.
Temperature of injection cylinder for layer B: 280° C.
Temperature of resin flow channel in injection mold: 280° C.
Mold temperature: 18° C.
[Performance Evaluation of Syringe]
Measurement of oxygen concentration in the obtained syringes, evaluation of visibility of content, drop test and elution test were performed in accordance with the following methods and evaluation was made based on the following criteria.
(1) Oxygen Concentration in Syringe
Vials were each filled with pure water (1 mL), provided with a top cap, sealed by a plunger equipped with a gasket, and stored in an atmosphere of 23° C. and 60% RH. After 3 days and one month, the oxygen concentration of the head space was measured by an oxygen concentration measurement apparatus (LC-750F manufactured by Toray Engineering Co. Ltd.).
(2) Visibility of Content in Syringe
The content in a syringe was visually observed. The visibility of a content in the syringe was evaluated. If the content was visible without any problem, the syringe was determined to come up to the standard.
(3) Impact Resistance Test
After a syringe was stored in an atmosphere of 40° C. and 90% RH for one month, a metal ball (50 g) was dropped on the body of the syringe from a height of 2 m. At this time, the presence or absence of breakage was checked with respect to 20 samples.
(4) Elution Test
After a syringe was stored in an atmosphere of 40° C. and 90% RH for one month, the syringe was filled with pure water (1 cc) and sealed with a plunger equipped with a top cap and a gasket. The syringe thus obtained was stored under the conditions of 40° C. and 60% RH for 4 months and thereafter, the total amount of carbon (hereinafter, TOC) in the pure water was measured.
(TOC Measurement)
Apparatus: TOC-V$_{CPH}$ manufactured by Shimadzu Corporation
Temperature of combustion furnace: 720° C.
Gas/flow rate: highly purified air, 150 mL/min measured by TOC meter
Injection amount: 150 µL
Detection limit: 1 µg/mL EXAMPLES 8-2 to 8-4

Oxygen-absorbing resin compositions and syringes were manufactured in the same manner as in Example 8-1 except that each of the corresponding tetralin ring-containing copolymerized polyolefin compounds shown in Table 8 was used in place of the tetralin ring-containing copolymerized polyolefin compound A. The performance of the obtained syringes was individually evaluated in the same manner as in Example 8-1. The evaluation results are shown in Table 8.

COMPARATIVE EXAMPLE 8-1

Single-layer syringes having the same shape as that in Example 8-1 were manufactured in the same manner as in Example 8-1 except that PET (100 parts by mass) was used in place of oxygen-absorbing resin composition E and the injection cylinder temperature for layer A was changed from 220° C. to 280° C. The performance of the obtained syringes was evaluated in the same manner as in Example 8-1. The evaluation results are shown in Table 8.

COMPARATIVE EXAMPLE 8-2

Syringes were manufactured in the same manner as in Example 8-1 except that oxygen-absorbing resin composition M was used in place of oxygen-absorbing resin composition E and the injection cylinder temperature for layer A was changed from 220° C. to 280° C. The performance of the obtained syringe was evaluated in the same manner as in Example 8-1. The evaluation results are shown in Table 8.

the performance of the obtained vials was evaluated as shown below. The evaluation results are shown in Table 9.

[Performance Evaluation of Vial]

Measurement of oxygen transmission rate, evaluation of appearance after molding, drop test and elution test of the obtained vials were performed in accordance with the following methods and evaluation was made based on the following criteria.

(1) Oxygen Transmission Rate of Vial (OTR)

At the 30th day from initiation of measurement, the oxygen transmission rate was measured at 23° C. and under an atmosphere having a relative humidity of 50%, which was measured outside the molded article and a relative humidity of 100%, which was measured within the molded article. Measurement was performed by use of an oxygen transmission rate measurement apparatus (trade name: OX-TRAN 2-21ML, manufactured by MOCON). The lower the measurement value, the more satisfactory the oxygen barrier property. Note that detection lower limit of oxygen transmission rate measured is $5 \times 10^{-5}$ mL/(0.21 atm·day·package).

(2) Appearance after Molding

Presence or absence of whitening of vial after molding was visually observed.

TABLE 8

| | | | | Oxygen concentration (vol %)[1] | | | | |
|---|---|---|---|---|---|---|---|---|
| | Resin used in layer A | Resin used in layer B | Layer constitution | After 3 days | After one month | Visibility of content | Drop test | Elution test, TOC amount[2] (μg/mL) |
| Example 8-1 | Tetralin ring-containing copolymerized polyolefin compound A | PET | Three layers | 4.2 | 0.1 or less | Transparent (acceptable) | No breakage is observed in all containers | Detection limit or less |
| Example 8-2 | Tetralin ring-containing copolymerized polyolefin compound B | PET | Three layers | 2.0 | 0.1 or less | Transparent (acceptable) | No breakage is observed in all containers | Detection limit or less |
| Example 8-3 | Tetralin ring-containing copolymerized polyolefin compound C | PET | Three layers | 4.0 | 0.1 or less | Transparent (acceptable) | No breakage is observed in all containers | Detection limit or less |
| Example 8-4 | Tetralin ring-containing copolymerized polyolefin compound D | PET | Three layers | 3.7 | 0.1 or less | Transparent (acceptable) | No breakage is observed in all containers | Detection limit or less |
| Comp. Example 8-1 | PET single layer | | Single layer | 20.5 | 20.5 | Transparent (acceptable) | No breakage is observed in all containers | Detection limit or less |
| Comp. Example 8-2 | Nylon MXD6 | PET | Three layers | 19.8 | 16.9 | Hazy (acceptable) | 7 out of 20 are broken | 38 |

[1]Stored at 23° C., 60% RH
[2]Detection lower limit is 0.1 (μg/mL)

As is apparent from Table 8, it was confirmed that the syringes of Examples 8-1 to 8-4 have satisfactory oxygen-absorbing property, maintain satisfactory strength after long-term storage and the amount of elution from the container to the content is low. It was also confirmed that the syringes of Examples 8-1 to 8-4 have sufficient visibility of the content in the container and have excellent transparency.

EXAMPLE 9-1

Vials were manufactured in the same manner as in Example 7-1 except that a polyethylene terephthalate resin (a product name: "BK-2180", hereinafter abbreviated as "PET" in Examples 9-1 to 9-4 and Comparative Examples 9-1 to 9-2, manufactured by Japan Unipet) was used in place of "RT-553C" (manufactured by Japan Unipet). Thereafter, (3) Drop Test After a vial was stored under the conditions of 40° C. and 90% RH for one month, the vial was filled up with pure water (50 mL) and then sealed by a rubber tap and an aluminum cap. The sealed container thus obtained was allowed to drop from a height of 2 m. The appearance of the container at this time was checked.

(4) Elusion Test

After a vial was stored under the conditions of 40° C. and 90% RH for one month, the vial was filled up with pure water (50 mL) and then sealed by a rubber tap and an aluminum cap. The sealed container thus obtained was stored under the conditions of 40° C. and 60% RH for 4 months and then the total amount of carbon (hereinafter, TOC) in the pure water was measured.

(TOC Measurement)
Apparatus: TOC-$V_{CPH}$ manufactured by Shimadzu Corporation
Temperature of combustion furnace: 720° C.
Gas/flow rate: highly purified air, 150 mL/min measured by TOC meter
Injection amount: 150 μL
Detection limit: 1 μg/mL
(5) Storage Test of Biopharmaceutical
(Binding-rate Measurement Method)

Using an isothermal titration calorimetry, a cell was filled with an antigen solution (5 μm) (FGF1-Mouse, manufactured by BIOLOGICAL Industries Ltd.). While adding an antibody solution (10 μL) dropwise to the cell, the binding rate was measured at 25° C.
(Storage Test)

A vial was filled with 1 cc of ANTI FGF1 monoclonal antibody (mAb1) (manufactured by Wako Pure Chemical Industries Ltd.), of which the concentration was adjusted to be 50 μm, and stored under the conditions of 8° C. and 50% RH for 180 days. As a solvent, a phosphate buffer (PBS pH 7.4) manufactured by Invitrogen was used. The binding rates in the antibody solution before and after the storage test (for 180 days) were measured by the method mentioned above and an antibody activity retention rate was obtained from the binding rates before and after the storage in accordance with the following expression:

Antibody activity retention rate (%)=(Binding rate in the antibody solution after storage of 180 days/Binding rate in the antibody solution before storage)×100

EXAMPLES 9-2 to 9-4

Oxygen-absorbing resin compositions and vials were manufactured in the same manner as in Example 9-1 except that each of the corresponding tetralin ring-containing copolymerized polyolefin compounds shown in Table 9 was used in place of the tetralin ring-containing copolymerized polyolefin compound A. The performance of the obtained vials was individually evaluated in the same manner as in Example 9-1. The evaluation results are shown in Table 9.

COMPARATIVE EXAMPLE 9-1

Single-layer vials having the same shape as that in Example 9-1 was manufactured in the same manner as in Example 9-1 except that PET (100 parts by mass) was used in place of oxygen-absorbing resin composition E and the injection cylinder temperature for layer A was changed from 220° C. to 280° C. The performance of the obtained vials was evaluated in the same manner as in Example 9-1. The evaluation results are shown in Table 9.

COMPARATIVE EXAMPLE 14-2

With nylon MXD6 (Product name: "MX nylon S7007", manufactured by Mitsubishi Gas Chemical Company, Inc.) (100 parts by mass), cobalt stearate (II) (0.04 parts by mass in terms of cobalt) was dry-blended. The obtained mixture was supplied to a double-screw extruder having two screws of 37 mm in diameter at a rate of 30 kg/h. Melt-kneading was performed at a cylinder temperature of 280° C. and a strand was extruded from an extruder head. After cooling, the strand was pelletized to obtain an oxygen-absorbing resin composition M. A vial was manufactured in the same manner as in Example 9-1 except that the oxygen-absorbing resin composition M was used in place of the oxygen-absorbing resin composition E and the injection cylinder temperature for layer A was changed from 220° C. to 280° C. The performance of the obtained vial was evaluated in the same manner as in Example 9-1. The evaluation results are shown in Table 9.

TABLE 9

|  | Resin used in Layer A | Resin used in Layer B | Layer constitution | Oxygen transmission rate (30th day)[1] |
|---|---|---|---|---|
| Example 9-1 | Tetralin ring-containing copolymerized polyolefin compound A | PET | Three layers | Detection limit or less |
| Example 9-2 | Tetralin ring-containing copolymerized polyolefin compound B | PET | Three layers | Detection limit or less |
| Example 9-3 | Tetralin ring-containing copolymerized polyolefin compound C | PET | Three layers | Detection limit or less |
| Example 9-4 | Tetralin ring-containing copolymerized polyolefin compound D | PET | Three layers | Detection limit or less |
| Comparative Example 9-1 | PET |  | Single layer | 0.0031 |
| Comparative Example 9-2 | Nylon MXD6 | PET | Three layers | Detection limit or less |

|  | Appearance after molding | Drop test | Elution test TOC amount[2] (μg/mL) | Antibody activity retention rate (%) |
|---|---|---|---|---|
| Example 9-1 | Transparent | No breakage is observed in all containers | Detection limit or less | 82 |
| Example 9-2 | Transparent | No breakage is observed in all containers | Detection limit or less | 74 |
| Example 9-3 | Transparent | No breakage is observed in all containers | Detection limit or less | 77 |
| Example 9-4 | Transparent | No breakage is observed in all containers | Detection limit or less | 75 |

TABLE 9-continued

| Comparative Example 9-1 | Transparent | No breakage is observed in all containers | Detection limit or less | 52 |
| Comparative Example 9-2 | Slightly whitened in whole | 14 out of 20 containers are broken | 15 | 72 |

[1]Unit: mL/(0.2 atm·day·package); Detection lower limit is $5 \times 10^{-5}$ mL/(0.21 atm·day·package)
[2]Detection lower limit is 0.1 (μg/mL)

As is apparent from Table 9, it was confirmed that when a biopharmaceutical is stored in the vials of Examples 9-1 to 9-5, satisfactory strength was maintained even after long-term storage and that the amount of elution from the container to the content is small and thus reduction of drug efficacy after storage was suppressed.

EXAMPLE 10-1

First, oxygen-absorbing resin composition A was obtained in the same manner as in Example 2-1. Then, using a multilayer-film manufacturing apparatus equipped with two extruders, a feed block, a T die, a cooling roll, a corona discharge unit, a winder, etc., a linear and low-density polyethylene (product name: "NOVATEC LL UF641", hereinafter referred also to as "LLDPE1" in Examples 10-1 to 10-4 and Comparative Example 10-1, manufactured by Japan Polyethylene Corporation, MFR at 190° C.: 2.1 g/10 minutes, MFR at 240° C.: 4.4 g/10 minutes, MFR at 250° C.: 5.2 g/10 minutes) serving as a material for a sealant layer, was extruded from a first extruder; and oxygen-absorbing resin composition A serving as a material for an oxygen-absorbing layer was extruded from a second extruder; and passed through a feed block to manufacture a two-layer film formed of two types of materials (thickness: oxygen-absorbing layer: 50 μm/sealant layer 50 μm) having a width of 900 mm. Thereafter, the surface of the oxygen-absorbing layer was treated with corona discharge at a rate of 60 m/minute to manufacture a film roll. When the obtained film roll was observed, thickness deviation such as bumps was not seen.

Subsequently, onto a corona treated surface, a nylon 6 film (product name: "N1202", manufactured by Toyobo Co., Ltd.), an alumina vapor deposition PET film (product name: "GL-ARH-F", manufactured by Toppan Printing Co., Ltd.) were stacked in accordance with dry lamination using urethane dry-lamination adhesive (product name: "TM-319/CAT-19B", manufactured by Toyo-Morton, Ltd.) to obtain an oxygen-absorbing multilayer film formed of an oxygen-absorbing multilayer body, which was constituted of an alumina vapor deposition PET film (12 μm)/urethane dry-lamination adhesive (3 μm)/nylon 6 film (15 μm)/urethane dry-lamination adhesive (3 μm)/oxygen-absorbing layer (50 μm)/LLDPE1 (50 μm).

Subsequently, a three-side sealed bag of 10 cm×20 cm was manufactured by use of the obtained oxygen-absorbing multilayer film such that the LLDPE1 layer side faced inside. Furthermore, a container formed of a block copolymerized polypropylene was filled with an eye drop (15 cc) containing taurine and sealed. After the container was placed in the three-side sealed bag and the bag was sealed. The sealed bag thus obtained was stored at 23° C. and 60% RH. After storage of 3 days and one month, the oxygen concentration in the bag was measured. After storage of 3 months, the retention rate of the taurine was determined. These results are shown in Table 10. Note that the taurine retention rate was determined based on the quantitative method described in Japanese Pharmacopoeia.

EXAMPLE 10-2

An oxygen-absorbing multilayer film was obtained in the same manner as in Example 10-1 except that tetralin ring-containing copolymerized polyolefin compound B was used in place of tetralin ring-containing copolymerized polyolefin compound A. Thereafter, a three-side sealed bag was manufactured in the same manner as in Example 10-1 except that the oxygen-absorbing multilayer film was used. Furthermore, a sealed bag was obtained in the same manner as in Example 10-1 except that the three-side sealed bag was used; and an infusion bag formed of a propylene-ethylene block copolymer and filled with a 50 mass % glucose solution (1000 cc) was used in place of the block copolymerized polypropylene container filled with an eye drop (15 cc) containing taurine, sealed and treated with heat at 121° C. for 20 minutes. The oxygen concentration in the sealed bag was measured in the same manner as in Example 10-1. Furthermore, the retention rate of the glucose solution was determined. Note that the glucose solution retention rate was determined based on the quantitative method described in Japanese Pharmacopoeia. These results are shown in Table 10.

EXAMPLE 10-3

An oxygen-absorbing multilayer film was obtained in the same manner as in Example 10-1 except that tetralin ring-containing copolymerized polyolefin compound C was used in place of tetralin ring-containing copolymerized polyolefin compound A. Thereafter, a three-side sealed bag was manufactured in the same manner as in Example 10-1 except that the oxygen-absorbing multilayer film was used. Furthermore, a sealed bag was obtained in the same manner as in Example 10-1 except that the three-side sealed bag was used; and an ampoule formed of a propylene-ethylene block copolymer and filled with a 10 mass % amino acid containing solution (5 cc) was used in place of the block copolymerized polypropylene container filled with an eye drop (15 cc) containing taurine and sealed. With respect to the sealed bag, the oxygen concentration in the bag was measured in the same manner as in Example 10-1. Furthermore, the retention rate of the amino acid was determined. Note that the amino acid retention rate was determined based on the quantitative method described in Japanese Pharmacopoeia. These results are shown in Table 10.

EXAMPLE 10-4

An oxygen-absorbing multilayer film was obtained in the same manner as in Example 10-1 except that tetralin ring-containing copolymerized polyolefin compound D was used in place of tetralin ring-containing copolymerized polyolefin compound A. Thereafter, a three-side sealed bag was manufactured in the same manner as in Example 10-1 except that the oxygen-absorbing multilayer film was used. Furthermore, a sealed bag was obtained in the same manner as in Example 10-1 except that the three-side sealed bag was used; and a prefilled syringe obtained by filling a prefilled syringe barrel formed of a propylene-ethylene block copolymer with a 0.1 mass % epinephrine containing solution (1 cc) was used in place of the block copolymerized polypropylene container filled with an eye drop (15 cc) containing taurine, and the tip and the plunger portion were sealed with a rubber tap formed of butyl rubber. With respect to the sealed bag, the oxygen concentration in the bag was measured in the same manner as in Example 10-1. Furthermore, the retention rate of the epinephrine was determined. Note that the epinephrine retention rate was determined based on the quantitative method described in Japanese Pharmacopoeia. These results are shown in Table 10.

COMPARATIVE EXAMPLE 10-1

An iron powder having an average particle diameter of 20 µm and calcium chloride were mixed in a mass ratio of 100:1. The mixture and LLDPE1 were kneaded in a mass ratio of 30:70 to obtain an iron based oxygen-absorbing resin composition. We tried to manufacture a two-layer film formed of two types of materials in the same manner as in Example 10-1 using the iron based oxygen-absorbing resin composition; however, a film having smooth surface that can be sufficiently subjected to further studies could not be obtained since convexoconcave portions were produced in the surface of the film due to iron powder. Because of this, on a linear and low-density polyethylene film of 50 µm in thickness (product name: "Tohcello T. U. X HC", hereinafter referred to as "LLDPE2" in Comparative Example 10-1, manufactured by Tohcello Inc.), a film of the iron based oxygen-absorbing resin composition of 50 µm in thickness serving as an oxygen-absorbing layer was stacked in accordance with extrusion lamination, and thereafter, the surface of the layer constituted of the iron based oxygen-absorbing resin composition was treated with corona discharge at a rate of 60 m/minute to obtain a laminate film.

Next, onto the corona treated surface of the laminate film, individual layers were stacked in accordance with dry lamination in the same manner as in Example 10-1 to manufacture an iron based oxygen-absorbing multilayer film, which was constituted of an alumina vapor deposition PET film (12 µm)/urethane dry-lamination adhesive (3 µm)/nylon 6 film (15 µm)/urethane dry-lamination adhesive (3 µm)/oxygen-absorbing layer (50 µm)/LLDPE2 (50 µm).

Subsequently, using the obtained iron based oxygen-absorbing multilayer film, a three-side sealed bag was manufactured in the same manner as in Example 10-1. A sealed bag was obtained in the same manner as in Example 10-2 except that the three-side sealed bag was used. With respect to the sealed bag, the oxygen concentration in the bag and the retention rate of the glucose solution were determined in the same manner as in Example 10-2. These results are shown in Table 10.

TABLE 10

| | Resin | Drug solution container | | Oxygen concentration (vol %)[1] | | Drug solution retention rate after 3 months (%) |
| | | Container | Drug solution | After 3 days | After one month | |
|---|---|---|---|---|---|---|
| Example 10-1 | Tetralin ring-containing copolymerized polyolefin compound A | Eye drop container | Taurine | 2.5 | 0.1 or less | 98.5 |
| Example 10-2 | Tetralin ring-containing copolymerized polyolefin compound B | Infusion container | Glucose solution | 1.2 | 0.1 or less | 99.5 |
| Example 10-3 | Tetralin ring-containing copolymerized polyolefin compound C | Ampoule | Amino acid | 2.4 | 0.1 or less | 97.2 |
| Example 10-4 | Tetralin ring-containing copolymerized polyolefin compound D | Prefilled syringe | Epinephrine | 2.1 | 0.1 or less | 99.1 |
| Comp. Example 10-1 | LLDPE + iron powder | Infusion container | Glucose solution | 18.8 | 15.7 | 63.5 |

[1] Stored at 23° C., 60% RH

As is apparent from the results of Examples 10-1 to 10-4, in the methods for storing a container filled with a drug solution according to the present invention, the container delivered satisfactory oxygen-absorbing performance and suppressed degradation of a drug-solution component stored in the sealed container.

EXAMPLE 11-1

First, oxygen-absorbing resin composition A was obtained in the same manner as in Example 2-1. Then, using a multilayer-film manufacturing apparatus equipped with two extruders, a feed block, a T die, a cooling roll, a corona discharge unit, a winder, etc., a linear and low-density polyethylene (product name: "NOVATEC LL UF641", hereinafter referred to as "LLDPE1" in Examples 11-1 to 11-4 and Comparative Example 11-1, manufactured by Japan Polyethylene Corporation, MFR at 190° C.: 2.1 g/10 minutes, MFR at 240° C.: 4.4 g/10 minutes, MFR at 250° C.: 5.2 g/10 minutes) serving as a material for a sealant layer was extruded from a first extruder; and oxygen-absorbing resin composition A serving as a material for an oxygen-absorbing layer was extruded from a second extruder; and passed through a feed block to manufacture a two-layer film formed of two types of materials and having a width of 900 mm (thickness: oxygen-absorbing layer 30 µm/sealant layer 30 µm). Thereafter, the surface of oxygen-absorbing layer was treated with corona discharge at a rate of 60 m/minute to manufacture a film roll. When the obtained film roll was observed, thickness deviation such as bumps was not seen.

Next, onto the corona treated surface of the obtained film, the following layers were stacked in accordance with extrusion lamination, using a low-density polyethylene (product name: "NOVATEC LD LC604", manufactured by Japan Polyethylene Corporation) to obtain an oxygen-absorbing multilayer paper base material, which was constituted of a bleached craft paper (basis weight: 50 g/m$^2$)/urethane dry-lamination adhesive (product name: "TM251/CAT-RT88", manufactured by Toyo-Morton, Ltd., 3 µm)/aluminum foil (7 µm)/urethane anchor coating agent ("EL-557A/B", manufactured by Toyo-Morton, Ltd., 0.5 µm)/low-density polyethylene (20 µm)/oxygen-absorbing layer (30 µm)/LLDPE1 (30 µm).

Subsequently, the obtained oxygen-absorbing multilayer paper base material was cut into pieces and two pieces of the oxygen-absorbing multilayer paper base materials of 12 cm×12 cm in size were prepared. The two pieces of the oxygen-absorbing multilayer paper base materials were heat-sealed at three sides with a sealing width of 5 mm such that LLDPE1 side faced inside to manufacture a bag of the oxygen-absorbing paper base material (three-side sealed bag). Furthermore, a composition containing a medicinal ingredient, indomethacin (0.5 mass %) and tocopherol acetate (0.3 mass %), talc (10 mass %) and a rubber adhesive (10 g) was spread to a support made of non-woven cloth of 10 cm×10 cm to manufacture a medicinal ingredient-containing layer. Furthermore, to the medicinal ingredient-containing layer, an embossed release film formed of a non-stretched polypropylene having a thickness of 25 µm was allowed to adhere to manufacture a patch containing a medicinal ingredient. The appearance of the patch at the release film side was white. The patch was placed in the three-side sealed bag and sealed. The sealed bag thus obtained was stored at 23° C. and 60% RH. After storage of 3 days and 7 days, the oxygen concentration in the bag was measured and the tocopherol acetate retention rate after storage of 3 months was determined. Furthermore, the sealed bag was stored at 40° C. and 20% RH for 3 months and the color tone of the release film of the patch was checked. These results are shown in Table 11. Note that the tocopherol acetate retention rate was determined based on the quantitative method described in Japanese Pharmacopoeia.

EXAMPLE 11-2

An oxygen-absorbing multilayer paper base material was obtained in the same manner as in Example 11-1 except that tetralin ring-containing copolymerized polyolefin compound B was used in place of tetralin ring-containing copolymerized polyolefin compound A. Thereafter, a three-side sealed bag and a sealed bag were manufactured in the same manner as in Example 11-1 except that the oxygen-absorbing multilayer paper base material was used. The oxygen concentration in the bag and tocopherol acetate retention rate were determined and the color tone of the release film of the patch was checked in the same manner as in Example 11-1. These results are shown in Table 11.

EXAMPLE 11-3

An oxygen-absorbing multilayer paper base material was obtained in the same manner as in Example 11-1 except that tetralin ring-containing copolymerized polyolefin compound C was used in place of tetralin ring-containing copolymerized polyolefin compound A. Thereafter, a three-side sealed bag and a sealed bag were manufactured in the same manner as in Example 11-1 except that the oxygen-absorbing multilayer paper base material was used. The oxygen concentration in the bag and tocopherol acetate retention rate were determined and the color tone of the release film of the patch was checked in the same manner as in Example 11-1. These results are shown in Table 11.

EXAMPLE 11-4

An oxygen-absorbing multilayer paper base material was obtained in the same manner as in Example 11-1 except that tetralin ring-containing copolymerized polyolefin compound D was used in place of tetralin ring-containing copolymerized polyolefin compound A. Thereafter, a three-side sealed bag and a sealed bag were manufactured in the same manner as in Example 11-1 except that the oxygen-absorbing multilayer paper base material was used. The oxygen concentration in the bag and tocopherol acetate retention rate were determined and the color tone of the release film of the patch was checked in the same manner as in Example 11-1. These results are shown in Table 11.

COMPARATIVE EXAMPLE 11-1

An iron powder having an average particle diameter of 20 µm and calcium chloride were mixed in a mass ratio of 100:1. The mixture and LLDPE1 were kneaded in a mass ratio of 30:70 to obtain an iron based oxygen-absorbing resin composition. We tried to manufacture a two-layer film formed of two types of materials in the same manner as in Example 11-1 using the iron based oxygen-absorbing resin composition; however, a film having smooth surface that can be sufficiently subjected to further studies could not be obtained since convexoconcave portions were produced in the surface of the film due to iron powder. Because of this, on a linear and low-density polyethylene film of 30 µm in thickness (product name: "Tohcello T. U. X HC", hereinafter referred to as "LLDPE2" in Comparative Example 11-1, manufactured by Tohcello Inc.), a film of the iron based oxygen-absorbing resin composition of 30 µm in thickness serving as an oxygen-absorbing layer was stacked in accordance with extrusion lamination, and thereafter, the surface of the layer constituted of the iron based oxygen-absorbing resin composition was treated with corona discharge at a rate of 60 m/minute to obtain a laminate film.

Next, onto the corona treated surface of the laminate film, individual layers were stacked in accordance with dry lamination in the same manner as in Example 11-1 to manufacture an iron based oxygen-absorbing multilayer paper base material, which was constituted of a bleached craft paper (basis weight: 50 g/m$^2$)/urethane dry-lamination adhesive (product name: "TM251/CAT-RT88", manufactured by Toyo-Morton, Ltd., 3 µm)/aluminum foil (7 µm)/urethane anchor coating agent ("EL-557A/B", manufactured by Toyo-Morton, Ltd., 0.5 µm)/low-density polyethylene (20 µm)/oxygen-absorbing layer (30 µm)/LLDPE2 (30 µm).

Subsequently, a three-side sealed bag and a sealed bag were manufactured in the same manner as in Example 11-1 except that the obtained iron based oxygen-absorbing multilayer paper base material was used. The oxygen concentration in the bag and tocopherol acetate retention rate were determined and the color tone of the release film of the patch was checked in the same manner as in Example 11-1. These results are shown in Table 11.

TABLE 11

|  | Resin | Oxygen concentration (vol %)[1] | | Retention rate after 3 months (%)[1] | Color tone after 3 months[2] |
|---|---|---|---|---|---|
|  |  | After 3 days | After 7 days |  |  |
| Example 11-1 | Tetralin ring-containing copolymerized polyolefin compound A | 1.2 | 0.1 or less | 94.4 | White |
| Example 11-2 | Tetralin ring-containing copolymerized polyolefin compound B | 0.3 | 0.1 or less | 99.1 | White |
| Example 11-3 | Tetralin ring-containing copolymerized polyolefin compound C | 0.9 | 0.1 or less | 96.3 | White |
| Example 11-4 | Tetralin ring-containing copolymerized polyolefin compound D | 0.7 | 0.1 or less | 98.5 | White |
| Comparative Example 11-1 | LLDPE + iron powder | 11.8 | 8.7 | 63.5 | Brown |

[1]Stored at 23° C., 60% RH
[2]Stored at 40° C., 20% RH

As is apparent from the results of Examples 11-1 to 11-4, in the methods for storing a patch containing a medicinal ingredient according to the present invention, the container delivered satisfactory oxygen-absorbing performance and suppressed degradation of the medicinal ingredients.

EXAMPLE 12-1

First, oxygen-absorbing resin composition A was obtained in the same manner as in Example 2-1. Then, using a multilayer-film manufacturing apparatus equipped with two extruders, a feed block, a T die, a cooling roll, a corona discharge unit, a winder, etc., a linear and low-density polyethylene (product name: "NOVATEC LL UF641", hereinafter referred to also as "LLDPE1" in Examples 12-1 to 12-4 and Comparative Example 12-1, manufactured by Japan Polyethylene Corporation, MFR at 190° C.: 2.1 g/10 minutes, MFR at 240° C.: 4.4 g/10 minutes, MFR at 250° C.: 5.2 g/10 minutes) serving as a material for a sealant layer, was extruded from a first extruder; and oxygen-absorbing resin composition A serving as a material for an oxygen-absorbing layer was extruded from a second extruder; and passed through a feed block to manufacture an oxygen-absorbing film, which is a two-layer film formed of two types of materials and having a width of 900 mm (oxygen-absorbing layer (30 µm)/sealant layer (30 µm). Thereafter, the surface of oxygen-absorbing layer was treated with corona discharge at a rate of 60 m/minute to manufacture a film roll. When the obtained film roll was observed, thickness deviation such as bumps was not seen.

Using a sheet manufacturing apparatus equipped with a single extruder, a feed block, a T die, a cooling roll, corona discharge unit, a winder, etc., a cycloolefin copolymer (product name: "TOPAS8007-F", hereinafter referred to as "COC" in Examples 12-1 to 12-4 and Comparative Example 12-1, manufactured by TOPAS ADVANCED POLYMERS) was extruded at a rate of 10 m/minute to manufacture a single layer sheet having a thickness 250 µm. One of the surfaces of the single layer sheet was treated with a corona discharge. Onto the corona treated surface, a water dispersion of a vinylidene chloride resin (product name: "SARAN latex L-509", hereinafter referred to as "PVDC" in Examples 12-1 to 12-4, and Comparative Example 12-1, manufactured by Asahi Kasei Corporation) was applied by gravure coating with a thickness of 15 µm to manufacture a gas barrier sheet constituted of two layers formed of two types of materials (thickness: gas barrier layer 15 µm/COC layer 250 µm).

Subsequently, using a urethane dry-lamination adhesive (product name: "TM251/CAT-RT88", manufactured by Toyo-Morton, Ltd.), the oxygen-absorbing layer of the oxygen-absorbing film was adhered to the gas barrier layer of the gas barrier sheet to manufacture an oxygen-absorbing multilayer body. The oxygen-absorbing multilayer body was constituted of LLDPE1 (30 µm)/oxygen-absorbing layer (30 µm)/adhesive layer (3 µm)/a gas barrier layer (15 µm)/COC layer (250 µm). The oxygen-absorbing multilayer body was subjected to plug assist air-pressure forming by using a blister pack manufacturing apparatus manufactured by CKD Corporation (trade name "FBP-M2") such that the inside of a pocket portion was formed of LLDPE1 to manufacture an oxygen-absorbing bottom material. The number of shots in molding was fixed to 50 shots/minute and the oxygen-absorbing bottom material had dimensions: bottom portion: 10 mmϕ, upper portion (opening portion) 9 mmϕ, and a depth of 4 mm.

The following individual layers were stacked in accordance with extrusion lamination to manufacture a gas barrier cover material, which was constituted of aluminum foil (20 µm)/urethane anchor coating agent ("EL-557A/B", manufactured by Toyo-Morton, Ltd., 0.5 µm)/LLDPE1 (20 µm).

In the oxygen-absorbing bottom material thus manufactured, tablets of 7 mmϕ and 3 mm in thickness, containing vitamin E (20 mg) were placed. LLDPE1 of the oxygen-absorbing bottom material and LLDPE1 of the gas barrier cover material were mutually sealed by heat-sealing to obtain an oxygen-absorbing PTP packaging body containing tablets. Tablets in the container could be visually seen through the oxygen-absorbing bottom material. This was stored in the environment of 40° C. and 60% RH. The oxygen concentration in a pocket portion after storage of one day and the vitamin E retention rate after storage of 3 months were determined. The vitamin E retention rate was determined by use of high performance liquid chromatography. These results are shown in Table 12.

EXAMPLE 12-2

An oxygen-absorbing bottom material was obtained in the same manner as in Example 12-1 except that tetralin ring-containing copolymerized polyolefin compound B was used in place of tetralin ring-containing copolymerized polyolefin compound A. Thereafter, an oxygen-absorbing PTP packaging body containing tablets was manufactured in the same manner as in Example 12-1. The oxygen concentration in a pocket portion and vitamin E retention rate were determined in the same manner as in Example 12-1. These results are shown in Table 12.

EXAMPLE 12-3

An oxygen-absorbing bottom material was obtained in the same manner as in Example 12-1 except that tetralin ring-containing copolymerized polyolefin compound C was used in place of tetralin ring-containing copolymerized polyolefin compound A. Thereafter, an oxygen-absorbing PTP packaging body containing tablets was manufactured in the same manner as in Example 12-1. The oxygen concentration in a pocket portion and vitamin E retention rate were determined in the same manner as in Example 12-1. These results are shown in Table 12.

EXAMPLE 12-4

An oxygen-absorbing bottom material was obtained in the same manner as in Example 12-1 except that tetralin ring-thickness (product name: "Tohcello T. U. X HC", hereinafter referred to as "LLDPE2" in Comparative Example 12-1, manufactured by Tohcello Inc.), a film of the iron based oxygen-absorbing resin composition of 30 µm in thickness serving as an oxygen-absorbing layer was stacked in accordance with extrusion lamination, and thereafter, the surface of the layer formed of the iron based oxygen-absorbing resin composition was treated with corona discharge at a rate of 60 m/minute to obtain a laminate film.

Next, onto the corona treated surface of the laminate film, the following individual layers were stacked in accordance with dry lamination in the same manner as in Example 12-1 to manufacture an iron based oxygen-absorbing bottom material, which was constituted of LLDPE2 (30 µm)/oxygen-absorbing layer (30 µm)/adhesive layer (3 µm)/gas barrier layer (15 µm)/COC layer (250 µm).

Subsequently, an oxygen-absorbing PTP packaging body containing tablets was manufactured in the same manner as in Example 12-1 using the obtained iron based oxygen-absorbing bottom material. The oxygen concentration in a pocket portion and vitamin E retention rate were determined in the same manner as in Example 12-1. These results are shown in Table 12.

TABLE 12

| | Resin | Oxygen concentration (vol %)[1] | Vitamin E retention rate[2] |
|---|---|---|---|
| Example 12-1 | Tetralin ring-containing copolymerized polyolefin compound A | 0.7 | 97.3 |
| Example 12-2 | Tetralin ring-containing copolymerized polyolefin compound B | 0.1 | 99.7 |
| Example 12-3 | Tetralin ring-containing copolymerized polyolefin compound C | 0.5 | 98.2 |
| Example 12-4 | Tetralin ring-containing copolymerized polyolefin compound D | 0.6 | 99.1 |
| Comparative Example 12-1 | LLDPE + iron powder | 9.8 | 61.5 |

[1]Value after storage of one day at 40° C., 60% RH
[2]Value after storage of 3 months at 40° C., 60% RH containing copolymerized polyolefin compound D was used in place of tetralin ring-containing copolymerized polyolefin compound A. Thereafter, an oxygen-absorbing PTP packaging body containing tablets was manufactured in the same manner as in Example 12-1. The oxygen concentration in a pocket portion and vitamin E retention rate were determined in the same manner as in Example 12-1. These results are shown in Table 12.

COMPARATIVE EXAMPLE 12-1

An iron powder having an average particle diameter of 20 µm and calcium chloride were mixed in a mass ratio of 100:1. The mixture and LLDPE1 were kneaded in a mass ratio of 30:70 to obtain an iron based oxygen-absorbing resin composition. We tried to manufacture a two-layer film formed of two types of materials in the same manner as in Example 12-1 using the iron based oxygen-absorbing resin composition; however, a film having smooth surface that can be sufficiently subjected to further studies could not be obtained since convexoconcave portions were produced in the surface of the film due to iron powder. Because of this, on a linear and low-density polyethylene film of 30 µm in As is apparent from the results of Examples 12-1 to 12-4, the oxygen-absorbing PTP packaging bodies of the present invention delivered satisfactory visibility of an article to be packaged and oxygen-absorbing performance and suppressed degradation of vitamin E stored in sealed containers.

EXAMPLE 13-1

First, oxygen-absorbing resin composition A was obtained in the same manner as in Example 2-1. Then, using a multilayer container manufacturing apparatus equipped with first to fourth extruders, a feed block, a cylindrical die, a blow mold, etc., a high-density polyethylene (product name: "NOVATEC HD HB420R", hereinafter referred to as "HDPE1" in Examples 13-1 to 13-4 and Comparative Example 13-1, manufactured by Japan Polyethylene Corporation) serving as an oxygen transmission layer as well as an outer layer was extruded from the first extruder; oxygen-absorbing resin composition A serving as an oxygen-absorbing layer was extruded from the second extruder; a polyethylene adhesive resin (product name: "MODIC M545", hereinafter referred to as "AD" in Examples 13-1 to 13-4 and Comparative Example 13-1, manufactured by Mitsubishi Chemical Corporation) serving as adhesive layer was extruded from the third extruder; an ethylene-vinyl alcohol copolymer (product name: "EVAL F101B", manufactured by Kuraray Co., Ltd.) serving as a gas barrier layer was extruded from the fourth extruder; and passed through a feed block and the mold to manufacture an oxygen-absorbing multilayer bottle (300 cc) constituted of six layers formed of four types of materials. The oxygen-absorbing multilayer bottle is constituted of an oxygen transmission layer (50 μm)/oxygen-absorbing layer (50 μm)/adhesive layer (10 μm)/gas barrier layer (30 μm)/adhesive layer (10 μm)/outer layer (750 μm).

Using a linear and low-density polyethylene (product name: "NOVATEC LL UF641", hereinafter referred to as "LLDPE1" in Examples 13-1 to 13-4 and Comparative Example 13-1, manufactured by Japan Polyethylene Corporation), the following individual layers were stacked in accordance with extrusion lamination to manufacture a gas barrier top film (cover material), which was constituted of an aluminum foil (20 μm)/urethane anchor coating agent ("EL-557A/B", manufactured by Toyo-Morton, Ltd., 0.5 μm)/LLDPE1 (20 μm).

To the oxygen-absorbing multilayer bottle manufactured, 200 tablets of 7 mmϕ and 3 mm in thickness containing vitamin C (2000 mg) were placed and then HDPE1 of the oxygen-absorbing multilayer bottle and LLDPE1 of the gas barrier top film (cover material) were sealed by heat-sealing to manufacture an oxygen-absorbing multilayer bottle containing tablets. The bottle was stored in the environment of 40° C., 60% RH. The oxygen concentration in the oxygen-absorbing multilayer bottle after storage of 7 days and the vitamin C retention rate after storage of 6 months were determined. The vitamin C retention rate was determined in accordance with test method described in Japanese Pharmacopoeia. These results are shown in Table 13.

EXAMPLE 13-2

An oxygen-absorbing multilayer bottle was obtained in the same manner as Example 13-1 except that the tetralin ring-containing copolymerized polyolefin compound B was used in place of tetralin ring-containing copolymerized polyolefin compound A. Thereafter, an oxygen-absorbing multilayer bottle containing tablets was manufactured in the same manner as in Example 13-1. The oxygen concentration in the oxygen-absorbing multilayer bottle and vitamin C retention rate were determined in the same manner as in Example 13-1. These results are shown in Table 13.

EXAMPLE 13-3

An oxygen-absorbing multilayer bottle was obtained in the same manner as Example 13-1 except that the tetralin ring-containing copolymerized polyolefin compound C was used in place of tetralin ring-containing copolymerized polyolefin compound A. Thereafter, an oxygen-absorbing multilayer bottle containing tablets was manufactured in the same manner as in Example 13-1. The oxygen concentration in the oxygen-absorbing multilayer bottle and vitamin C retention rate were determined in the same manner as in Example 13-1. These results are shown in Table 13.

EXAMPLE 13-4

An oxygen-absorbing multilayer bottle was obtained in the same manner as Example 13-1 except that tetralin ring-containing copolymerized polyolefin compound D was used in place of tetralin ring-containing copolymerized polyolefin compound A. Thereafter, an oxygen-absorbing multilayer bottle containing tablets was manufactured in the same manner as in Example 13-1. The oxygen concentration in the oxygen-absorbing multilayer bottle and vitamin C retention rate were determined in the same manner as in Example 13-1. These results are shown in Table 13.

COMPARATIVE EXAMPLE 13-1

An iron powder having an average particle diameter of 20 μm and calcium chloride were mixed in a mass ratio of 100:1. The mixture and LLDPE1 were kneaded in a mass ratio of 30:70 to obtain an iron based oxygen-absorbing resin composition. An oxygen-absorbing multilayer bottle constituted of six layers formed of four types of materials was manufactured in the same manner as in Example 13-1 except that the iron based oxygen-absorbing resin composition was used in place of oxygen-absorbing resin composition A. The oxygen-absorbing multilayer bottle was constituted of oxygen transmission layer (50 μm)/oxygen-absorbing layer (50 μm)/adhesive layer (10 μm)/oxygen barrier layer (30 μm)/adhesive layer (10 μm)/outer layer (750 μm). Thereafter, an oxygen-absorbing multilayer bottle containing tablets was manufactured in the same manner as in Example 13-1. The oxygen concentration in the oxygen-absorbing multilayer bottle and vitamin C retention rate were determined in the same manner as in Example 13-1. These results are shown in Table 13.

TABLE 13

|  | Resin | Oxygen concentration (vol %)[1] | Vitamin C retention rate[2] |
|---|---|---|---|
| Example 13-1 | Tetralin ring-containing copolymerized polyolefin compound A | 0.9 | 95.3 |
| Example 13-2 | Tetralin ring-containing copolymerized polyolefin compound B | 0.1 | 98.7 |
| Example 13-3 | Tetralin ring-containing copolymerized polyolefin compound C | 0.3 | 97.2 |
| Example 13-4 | Tetralin ring-containing copolymerized polyolefin compound D | 0.6 | 96.1 |
| Comparative Example 13-1 | LLDPE + iron powder | 12.8 | 68.5 |

[1] Value after storage of 7 days at 40° C., 60% RH
[2] Value after storage of 6 months at 40° C., 60% RH multilayer bottle containing tablets was manufactured in the same manner as in Example 13-1. The oxygen concentration in the oxygen-absorbing multilayer bottle and vitamin C retention rate were determined in the same manner as in Example 13-1. These results are shown in Table 13.

As is apparent from the results of Examples 13-1 to 13-4, the oxygen-absorbing multilayer bottles of the present invention delivered satisfactory visibility of an article to be packaged and oxygen-absorbing performance and suppressed degradation of vitamin C stored in the sealed bottle.

EXAMPLE 14-1

First, to a double-screw extruder having two screws of 37 mm in diameter, a mixture obtained by dry-blending tetralin ring-containing copolymerized polyolefin compound C (100 parts by mass), cobalt (II) stearate (0.05 parts by mass in terms of cobalt) was supplied and kneaded in the conditions: an extrusion temperature of 220° C. and a screw rotation number of 100 rpm, to obtain oxygen-absorbing resin composition F.

Then, using a multilayer-film manufacturing apparatus equipped with two extruders, a feed block, a T die, a cooling roll, a corona discharge unit, a winder, etc., a linear and low-density polyethylene (product name: "NOVATEC LL UF641", hereinafter referred to as "LLDPE1" in Examples 14-1 to 14-9 and Comparative Examples 14-1 to 14-3, manufactured by Japan Polyethylene Corporation, MFR at 190° C.: 2.1 g/10 minutes, MFR at 240° C.: 4.4 g/10 minutes, MFR at 250° C.: 5.2 g/10 minutes) serving as a material for a sealant layer was extruded from a first extruder; and oxygen-absorbing resin composition F serving as a material for an oxygen-absorbing layer was extruded from a second extruder; and passed through a feed block to manufacture a three-layer film formed of two types of materials and having a width of 900 mm (LLDPE1 (20 µm)/oxygen-absorbing layer (30 µm)/LLDPE1 (20 µm)). Thereafter, one of the surfaces of LLDPE1 was treated with corona discharge at a rate of 60 m/minute to manufacture a film roll. When the obtained film roll was observed, thickness deviation such as bumps was not seen.

Subsequently, using urethane dry-lamination adhesive (product name: "TM-319/CAT-19B", manufactured by Toyo-Morton, Ltd.), a nylon 6 film (product name: "N1202", manufactured by Toyobo Co., Ltd.) and an alumina vapor deposition PET film (product name: "GL-ARH-F", manufactured by Toppan Printing Co., Ltd.) were stacked in accordance with dry lamination on the corona treated surface to obtain an oxygen-absorbing multilayer film formed of an oxygen-absorbing multilayer body, which was constituted of alumina vapor deposition PET film (12 µm)/urethane dry-lamination adhesive (3 µm)/nylon 6 film (15 µm)/urethane dry-lamination adhesive (3 µm)/LLDPE1 (20 µm)/oxygen-absorbing layer (30 µm)/LLDPE1 (20 µm).

Using the obtained oxygen-absorbing multilayer film, more specifically using two side films and a single bottom surface film, a self-supporting bag (standing pouch of 120 mm in side×200 mm in length×40 mm in bottom gore) having an opening at the top was fabricated by heat sealing such that LLDPE1 side faced inside. As a result, the processability of the bag was satisfactory.

The oxygen-absorbing self-supporting bag was filled with a mixture of grapefruit (100 g) and syrup (100 g) and the top opening of the self-supporting bag was sealed by heat sealing while adjusting head-space air amount to be 5 cc. Subsequently, the sealed bag thus obtained was subjected to a boiling treatment at 90° C. for 40 minutes and thereafter, stored at 30° C. After storage of 7 days and one month, sealed bag was opened and the color tone and taste and flavor of grapefruit were separately evaluated. Note that the color tone and taste and flavor of grapefruit were evaluated based on an average value of 5 testers. Furthermore, the oxygen concentration in the sealed bag after one month storage was measured. These results are shown in Table 14.

EXAMPLE 14-2

An oxygen-absorbing multilayer film was obtained in the same manner as in Example 14-1 except that cobalt (II) stearate (0.01 parts by mass in terms of cobalt) was dry-blended in place of cobalt (II) stearate (0.05 parts by mass in terms of cobalt). Thereafter, a self-supporting bag and a sealed bag were manufactured in the same manner as in Example 14-1. The oxygen concentration in the bag was measured and taste and flavor and color tone of grapefruit were checked in the same manner as in Example 14-1. These results are shown in Table 14.

EXAMPLE 14-3

An oxygen-absorbing multilayer film was obtained in the same manner as in Example 14-1 except that cobalt (II) stearate (0.1 parts by mass in terms of cobalt) was dry-blended in place of cobalt (II) stearate (0.05 parts by mass in terms of cobalt). Thereafter, a self-supporting bag and a sealed bag were manufactured in the same manner as in Example 14-1. The oxygen concentration in the bag was measured and taste and flavor and color tone of grapefruit were checked in the same manner as in Example 14-1. These results are shown in Table 14.

EXAMPLE 14-4

An oxygen-absorbing multilayer film was obtained in the same manner as in Example 14-1 except that cobalt (II) acetate was used in place of cobalt (II) stearate. Thereafter, a self-supporting bag and a hermetic bag were manufactured in the same manner as in Example 14-1. The oxygen concentration in the bag was measured and taste and flavor and color tone of grapefruit were checked in the same manner as in Example 14-1. These results are shown in Table 14.

EXAMPLE 14-5

An oxygen-absorbing multilayer film was obtained in the same manner as in Example 14-1 except that manganese (II) stearate (0.05 parts by mass in terms of manganese) was dry-blended in place of cobalt (II) stearate (0.05 parts by mass in terms of cobalt). Thereafter, a self-supporting bag and a hermetic bag were manufactured in the same manner as in Example 14-1. The oxygen concentration in the bag was measured and taste and flavor and color tone of grapefruit were checked in the same manner as in Example 14-1. These results are shown in Table 14.

EXAMPLE 14-6

An oxygen-absorbing multilayer film was obtained in the same manner as in Example 14-1 except that iron (III) stearate (0.05 parts by mass in terms of iron) was dry-blended in place of cobalt (II) stearate (0.05 parts by mass in terms of cobalt). Thereafter, a self-supporting bag and a hermetic bag were manufactured in the same manner as in Example 14-1. The oxygen concentration in the bag was measured and taste and flavor and color tone of grapefruit were checked in the same manner as in Example 14-1. These results are shown in Table 14.

EXAMPLE 14-7

An oxygen-absorbing multilayer film was obtained in the same manner as in Example 14-1 except that tetralin ring-containing copolymerized polyolefin compound D was used in place of tetralin ring-containing copolymerized polyolefin compound C. Thereafter, a self-supporting bag and a hermetic bag were manufactured in the same manner as in Example 14-1. The oxygen concentration in the bag was measured and taste and flavor and color tone of grapefruit were checked in the same manner as in Example 14-1. These results are shown in Table 14.

EXAMPLE 14-8

An oxygen-absorbing multilayer film was obtained in the same manner as in Example 14-7 except that manganese (II) stearate (0.05 parts by mass in terms of manganese) was dry-blended in place of cobalt (II) stearate (0.05 parts by mass in terms of cobalt). Thereafter, a self-supporting bag and a hermetic bag were manufactured in the same manner as in Example 14-1. The oxygen concentration in the bag was measured and taste and flavor and color tone of grapefruit were checked in the same manner as in Example 14-1. These results are shown in Table 14.

EXAMPLE 14-9

An oxygen-absorbing multilayer film was obtained in the same manner as in Example 14-7 except that iron (III) stearate (0.05 parts by mass in terms of iron) was dry-blended in place of cobalt (II) stearate (0.05 parts by mass in terms of cobalt). Thereafter, a self-supporting bag and a hermetic bag were manufactured in the same manner as in Example 14-1. The oxygen concentration in the bag was measured and taste and flavor and color tone of grapefruit were checked in the same manner as in Example 14-1. These results are shown in Table 14.

COMPARATIVE EXAMPLE 14-1

An oxygen-absorbing multilayer film was obtained in the same manner as in Example 14-1 except that an ethylene-methyl methacrylate copolymer having a methyl methacrylate content of 5 mass % used in Synthesis Example 3 was used in place of tetralin ring-containing copolymerized polyolefin compound C. Thereafter, a self-supporting bag and a hermetic bag were manufactured in the same manner as in Example 14-1. The oxygen concentration in the bag was measured and taste and flavor and color tone of grapefruit were checked in the same manner as in Example 14-1. After one month storage, the oxygen concentration reduced to 5.4 vol % and the taste and flavor and color tone of grapefruit reduced. Since grapefruit itself was oxidized although the self-supporting bag does not absorb oxygen, the oxygen concentration conceivably reduced. These results are shown in Table 14.

COMPARATIVE EXAMPLE 14-2

An oxygen-absorbing multilayer film was obtained in the same manner as in Example 14-1 except that cobalt (II) stearate was not used. Thereafter, a self-supporting bag and a hermetic bag were manufactured in the same manner as in Example 14-1. The oxygen concentration in the bag was measured and taste and flavor and color tone of grapefruit were checked in the same manner as in Example 14-1. After one month storage, the oxygen concentration reduced to 6.1 vol % and the taste and flavor and color tone of grapefruit reduced. Since grapefruit itself was oxidized although the self-supporting bag does not absorb oxygen, the oxygen concentration conceivably reduced. These results are shown in Table 14.

COMPARATIVE EXAMPLE 14-3

Iron powder having an average particle diameter of 20 µm and calcium chloride were mixed in a mass ratio of 100:1. The mixture and LLDPE1 were kneaded in a mass ratio of 30:70 to obtain an iron-based oxygen-absorbing resin composition. We tried to manufacture a three-layer film formed of two types of materials in the same manner as in Example 14-1 except that the iron based oxygen-absorbing resin composition was used in place of oxygen-absorbing resin composition F; however, a film having smooth surface that can be sufficiently subjected to further studies could not be obtained since convexoconcave portions were produced in the surface of the film due to iron powder. Because of this, on the linear and low-density polyethylene film (product name: "Tohcello T. U. X HC", hereinafter referred to as "LLDPE2" in Comparative Example 14-3 manufactured by Tohcello Inc.) having a thickness of 50 µm, a layer of the iron based oxygen-absorbing resin composition of 30 µm in thickness serving as an oxygen-absorbing layer was stacked in accordance with extrusion lamination, and thereafter, the surface of the layer formed of the iron based oxygen-absorbing resin composition was treated with corona discharge at a rate of 60 m/minute to obtain a laminate film.

Next, on the corona treated surface of the laminate film, the following individual layers were stacked in accordance with dry lamination in the same manner as in Example 14-1 to manufacture an iron based oxygen-absorbing multilayer film, which was constituted of alumina vapor deposition PET film (12 µm)/urethane dry-lamination adhesive (3 µm)/nylon 6 film (15 µm)/urethane dry-lamination adhesive (3 µm)/oxygen-absorbing layer (30 µm)/LLDPE2 (50 µm).

Subsequently, a self-supporting bag and a hermetic bag were manufactured by use of the obtained iron based oxygen-absorbing multilayer film in the same manner as in Example 14-1. The oxygen concentration in the bag was measured and taste and flavor and color tone of grapefruit were checked in the same manner as in Example 14-1. These results are shown in Table 14.

TABLE 14

| | | Transition metal catalyst | | Oxygen concentration | Color tone[3] | | Taste and flavor[3] | |
|---|---|---|---|---|---|---|---|---|
| | Resin compound | Type | Amount of transition metal[1] | in a container[2] (vol %) | After 7 days | After one month | After 7 days | After one month |
| Example 14-1 | Tetralin ring-containing copolymerized polyolefin compound C | Cobalt stearate | 0.05 | 0.1 or less | S | S | S | S |

TABLE 14-continued

|  | Resin compound | Transition metal catalyst | | Oxygen concentration in a container[2] (vol %) | Color tone[3] | | Taste and flavor[3] | |
|---|---|---|---|---|---|---|---|---|
|  |  | Type | Amount of transition metal[1] |  | After 7 days | After one month | After 7 days | After one month |
| Example 14-2 | Tetralin ring-containing copolymerized polyolefin compound C | Cobalt stearate | 0.01 | 1.8 | S | SR | S | AS |
| Example 14-3 | Tetralin ring-containing copolymerized polyolefin compound C | Cobalt stearate | 0.1 | 0.1 or less | S | S | S | S |
| Example 14-4 | Tetralin ring-containing copolymerized polyolefin compound C | Cobalt acetate | 0.05 | 0.1 or less | S | S | S | S |
| Example 14-5 | Tetralin ring-containing copolymerized polyolefin compound C | Manganese stearate | 0.05 | 0.1 or less | S | S | S | S |
| Example 14-6 | Tetralin ring-containing copolymerized polyolefin compound C | Iron stearate | 0.05 | 0.1 or less | S | S | S | S |
| Example 14-7 | Tetralin ring-containing copolymerized polyolefin compound D | Cobalt stearate | 0.05 | 0.1 or less | S | S | S | S |
| Example 14-8 | Tetralin ring-containing copolymerized polyolefin compound D | Manganese stearate | 0.05 | 0.2 | S | AS | S | S |
| Example 14-9 | Tetralin ring-containing copolymerized polyolefin compound D | Iron stearate | 0.05 | 0.3 | S | AS | S | S |
| Comparative Example 14-1 | EMMA[4] | Cobalt stearate | 0.05 | 5.4 | AS | R | AS | R |
| Comparative Example 14-2 | Tetralin ring-containing copolymerized polyolefin compound C | — | — | 6.1 | SR | R | AS | R |
| Comparative Example 14-3 | Iron based oxygen absorber + LDPE | — | — | 0.1 or less | AS | SR | AS | R |

[1]Parts by mass based on resin compound (100 parts by mass)
[2]Initial head space air amount was set at 5 cc. After boiled, container was stored at 30° C. for one month
[3]S: Satisfactory, AS: Almost satisfactory, SR: Slightly reduced, R: Reduced
[4]EMMA: ethylene-methyl methacrylate copolymer As is apparent from the results of Examples 14-1 to 14-9, in the methods for storing fruit pulp of the present invention, the container delivered satisfactory oxygen-absorbing performance and suppressed reduction of the taste and flavor and color tone of the content.

EXAMPLE 15-1

First, oxygen-absorbing resin composition A was obtained in the same manner as in Example 2-1. Then, using a multilayer-film manufacturing apparatus equipped with two extruders, a feed block, a T die, a cooling roll, a corona discharge unit, a winder, etc., a linear and low-density polyethylene (product name: "NOVATEC LL UF641", manufactured by Japan Polyethylene Corporation, MFR at 190° C.: 2.1 g/10 minutes, MFR at 240° C.: 4.4 g/10 minutes, MFR at 250° C.: 5.2 g/10 minutes, hereinafter referred to as "LLDPE1" in Examples 15-1 to 15-11 and Comparative Examples 15-1 to 15-3) serving as a material for a sealant layer was extruded from a first extruder; oxygen-absorbing resin composition A serving as a material for an oxygen-absorbing layer was extruded from a second extruder; and passed through a feed block to manufacture an oxygen-absorbing multilayer film constituted of three layers formed of two types of materials, which constituted of (LLDPE1 (20 μm)/oxygen-absorbing layer (30 μm)/LLDPE1 (20 μm)) having a width of 900 mm. Thereafter, one of the surfaces of LLDPE1 was treated with corona discharge at a rate of 60 m/minute to manufacture a film roll. When the obtained film roll was observed, thickness deviation such as bumps was not seen.

Next, on a corona treated surface, a multilayer paper base material was stacked in accordance with the extrusion lamination by LLDPE1 to obtain an oxygen-absorbing paper base material multilayer body (oxygen-absorbing multilayer body), which was constituted of bleached craft paper (basis weight: 330 g/m$^2$)/urethane dry-lamination adhesive (product name: "TM-250HV/CAT-RT86L-60", manufactured by Toyo-Morton, Ltd., 3 μm)/alumina vapor deposition PET film (product name: "GL-AE", manufactured by Toppan Printing Co., Ltd., 12 μm)/urethane anchor coating agent (product name: "EL-557A/B", manufactured by Toyo-Morton, Ltd., 0.5 μm)/LLDPE1 (15 μm)/LLDPE1 (20 μm)/oxygen-absorbing layer (30 μm)/LLDPE1 (20 μm).

Subsequently, the obtained multilayer body was manufactured into a carton to obtain a 1000-mL gable-top oxygen-absorbing paper container having a bottom of 7 cm squares. The moldability and processability of the paper container herein were satisfactory and the carton could be easily manufactured.

The oxygen-absorbing paper container was filled with imo-shochu (1000 mL) such that the amount of air in the head space was 20 cc and inner surfaces (LLDPE1) of the top potion of the gable-top paper container were mutually sealed by heat sealing. The sealed paper container thus obtained was stored at 35° C. for one month. After storage of 7 days and one month, sealed paper containers were opened separately and taste and flavor of imo-shochu was evaluated. Note that the taste and flavor of imo-shochu was evaluated based on an average value of 5 testers. Furthermore, the oxygen concentration (head-space oxygen concentration) in the paper container after storage of one month and the heat sealing strength of the upper portion of the gable-top paper container were determined. These results are shown in Table 15. Note that heat sealing strength was measured in accordance with JIS Z0238 (the same shall apply hereinafter).

EXAMPLE 15-2

An oxygen-absorbing multilayer film was obtained in the same manner as in Example 15-1 except that cobalt (II) stearate (0.01 parts by mass in terms of cobalt) was dry-blended in place of cobalt (II) stearate (0.05 parts by mass in terms of cobalt). Thereafter, an oxygen-absorbing paper container and a sealed paper container were manufactured in the same manner as in Example 15-1. The head-space oxygen concentration was measured, taste and flavor of imo-shochu was checked, and the heat sealing strength of the upper portion of the paper container was measured in the same manner as in Example 15-1. These results are shown in Table 15.

EXAMPLE 15-3

An oxygen-absorbing multilayer film was obtained in the same manner as in Example 15-1 except that cobalt (II) stearate (0.1 parts by mass in terms of cobalt) was dry-blended in place of cobalt (II) stearate (0.05 parts by mass in terms of cobalt). Thereafter, an oxygen-absorbing paper container and a sealed paper container were manufactured in the same manner as in Example 15-1. The head-space oxygen concentration was measured, taste and flavor of imo-shochu was checked, and the heat sealing strength of the upper portion of the paper container was measured in the same manner as in Example 15-1. These results are shown in Table 15.

EXAMPLE 15-4

An oxygen-absorbing multilayer film was obtained in the same manner as in Example 15-1 except that cobalt (II) acetate was used in place of cobalt (II) stearate. Thereafter, an oxygen-absorbing paper container and sealed paper container were manufactured in the same manner as in Example 15-1. A head-space oxygen concentration was measured, taste and flavor of imo-shochu was checked and the heat sealing strength of the upper portion of the paper container was measured in the same manner as in Example 15-1. These results are shown in Table 15.

EXAMPLE 15-5

An oxygen-absorbing multilayer film was obtained in the same manner as in Example 15-1 except that manganese (II) stearate (0.05 parts by mass in terms of manganese) was dry-blended in place of cobalt (II) stearate (0.05 parts by mass in terms of cobalt). Thereafter, an oxygen-absorbing paper container and a sealed paper container were manufactured in the same manner as in Example 15-1. The head-space oxygen concentration was measured, taste and flavor of imo-shochu was checked, and the heat sealing strength of the upper portion of the paper container was measured in the same manner as in Example 15-1. These results are shown in Table 15.

EXAMPLE 15-6

An oxygen-absorbing multilayer film was obtained in the same manner as in Example 15-1 except that iron (III) stearate (0.05 parts by mass in terms of iron) was dry-blended in place of cobalt (II) stearate (0.05 parts by mass in terms of cobalt). Thereafter, an oxygen-absorbing paper container and a sealed paper container were manufactured in the same manner as in Example 15-1. The head-space oxygen concentration was measured, taste and flavor of imo-shochu was checked, and the heat sealing strength of the upper portion of the paper container was measured in the same manner as in Example 15-1. These results are shown in Table 15.

EXAMPLE 15-7

An oxygen-absorbing multilayer film was obtained in the same manner as in Example 15-1 except that tetralin ring-containing copolymerized polyolefin compound B was used in place of tetralin ring-containing copolymerized polyolefin compound A. Thereafter, an oxygen-absorbing paper container and sealed paper container were manufactured in the same manner as in Example 15-1. A head-space oxygen concentration was measured, taste and flavor of imo-shochu was checked and the heat sealing strength of the upper portion of the paper container was measured in the same manner as in Example 15-1. These results are shown in Table 15.

EXAMPLE 15-8

An oxygen-absorbing multilayer film was obtained in the same manner as in Example 15-7 except that manganese (H) stearate (0.05 parts by mass in terms of manganese) was dry-blended in place of cobalt (II) stearate (0.05 parts by mass in terms of cobalt). Thereafter, an oxygen-absorbing paper container and a sealed paper container were manufactured in the same manner as in Example 15-1. The head-space oxygen concentration was measured, taste and flavor of imo-shochu was checked, and the heat sealing strength of the upper portion of the paper container was measured in the same manner as in Example 15-1. These results are shown in Table 15.

EXAMPLE 15-9

An oxygen-absorbing multilayer film was obtained in the same manner as in Example 15-7 except that iron (III) stearate (0.05 parts by mass in terms of iron) was dry-blended in place of cobalt (II) stearate (0.05 parts by mass in terms of cobalt). Thereafter, an oxygen-absorbing paper container and a sealed paper container were manufactured in the same manner as in Example 15-1. The head-space oxygen concentration was measured, taste and flavor of imo-shochu was checked, and the heat sealing strength of the upper portion of the paper container was measured in the same manner as in Example 15-1. These results are shown in Table 15.

EXAMPLE 15-10

An oxygen-absorbing multilayer film was obtained in the same manner as in Example 15-1 except that tetralin ring-containing copolymerized polyolefin compound C was used in place of tetralin ring-containing copolymerized polyolefin compound A. Thereafter, an oxygen-absorbing paper container and sealed paper container were manufactured in the same manner as in Example 15-1. A head-space oxygen concentration was measured, taste and flavor of imo-shochu was checked and the heat sealing strength of the upper portion of the paper container was measured in the same manner as in Example 15-1. These results are shown in Table 15.

EXAMPLE 15-11

An oxygen-absorbing multilayer film was obtained in the same manner as in Example 15-1 except that tetralin ring-containing copolymerized polyolefin compound D was used in place of tetralin ring-containing copolymerized polyolefin compound A. Thereafter, an oxygen-absorbing paper container and sealed paper container were manufactured in the same manner as in Example 15-1. A head-space oxygen concentration was measured, taste and flavor of imo-shochu was checked and the heat sealing strength of the upper portion of the paper container was measured in the same manner as in Example 15-1. These results are shown in Table 15.

COMPARATIVE EXAMPLE 15-1

An oxygen-absorbing multilayer film was obtained in the same manner as in Example 15-1 except that an ethylene-methyl methacrylate copolymer having a methyl methacrylate content of 25 mass % used in Synthesis Example 1 was used in place of tetralin ring-containing copolymerized polyolefin compound A. Thereafter, an oxygen-absorbing paper container and a sealed paper container were manufactured in the same manner as in Example 15-1. The head-space oxygen concentration was measured, taste and flavor of imo-shochu was checked, and the heat sealing strength of the upper portion of the paper container was measured in the same manner as in Example 15-1. These results are shown in Table 15.

COMPARATIVE EXAMPLE 15-2

An oxygen-absorbing multilayer film was obtained in the same manner as in Example 15-1 except that cobalt (II) stearate was not used. Thereafter, an oxygen-absorbing paper container and a sealed paper container were manufactured in the same manner as in Example 15-1. The head-space oxygen concentration was measured, taste and flavor of imo-shochu was checked, and the heat sealing strength of the upper portion of the paper container was measured in the same manner as in Example 15-1. These results are shown in Table 15.

COMPARATIVE EXAMPLE 15-3

Iron powder having an average particle diameter of 20 μm and calcium chloride were mixed in a mass ratio of 100:1. The mixture and LLDPE 1 were kneaded in a mass ratio of 30:70 to obtain an iron-based oxygen-absorbing resin composition. We tried to manufacture a three-layer film formed of two types of materials in the same manner as in Example 15-1 except that the iron based oxygen-absorbing resin composition was used in place of oxygen-absorbing resin composition A; however, a film having smooth surface that can be sufficiently subjected to further studies could not be obtained since convexoconcave portions were produced in the surface of the film due to iron powder. Because of this, on the linear and low-density polyethylene film (product name: "Tohcello T. U. X HC", hereinafter referred to as "LLDPE2" in Comparative Example 15-3, manufactured by Tohcello Inc.) having a thickness of 50 μm, a film of the iron based oxygen-absorbing resin composition of 30 μm in thickness serving as an oxygen-absorbing layer was stacked in accordance with extrusion lamination, and thereafter, the surface of the layer formed of the iron based oxygen-absorbing resin composition was treated with corona discharge at a rate of 60 m/minute to obtain a laminate film.

Extrusion lamination was performed on a multilayer paper base material in the same manner as in Example 15-1, except that the laminate film obtained above was used in place of a three-layer film formed of two types of materials to manufacture an oxygen-absorbing paper base material multilayer body, which was constituted of a bleached craft paper (basis weight: 330 g/m$^2$)/urethane dry-lamination adhesive (3 μm)/alumina vapor deposition PET film (12 μm)/urethane anchor coating agent (0.5 μm)/LLDPE1 (20 μm)/oxygen-absorbing layer (30 μm)/LLDPE2 (50 μm). Thereafter, we tried to manufacture a gable-top paper container using the multilayer body; however, it was difficult to form the corners of the paper container. Then, we tried to manufacture a paper container by lowering the speed of manufacturing the container. As a result, the paper container was finally manufactured with a large number of defective products (that were eliminated). Thereafter, a sealed paper container was manufactured in the same manner as in Example 15-1. The head-space oxygen concentration was measured, taste and flavor of imo-shochu was checked and the heat sealing strength of the upper portion of the paper container was measured in the same manner as in Example 15-1. These results are shown in Table 15.

TABLE 15

|  | Resin compound | Transition metal catalyst | | Oxygen concentration[2] (vol %) | Taste and flavor[3] | | Heat-sealing strength (kg) | |
|  |  | Type | Amount of transition metal[1] |  | After 7 days | After one month | Before storage | After storage |
|---|---|---|---|---|---|---|---|---|
| Example 15-1 | Tetralin ring-containing copolymerized polyolefin compound A | Cobalt stearate | 0.05 | 0.1 or less | S | S | 3.7 | 3.8 |
| Example 15-2 | Tetralin ring-containing copolymerized polyolefin compound A | Cobalt stearate | 0.01 | 2.6 | S | A | 3.9 | 3.9 |

TABLE 15-continued

|   | Resin compound | Transition metal catalyst Type | Amount of transition metal[1] | Oxygen concentration[2] (vol %) | Taste and flavor[3] After 7 days | After one month | Heat-sealing strength (kg) Before storage | After storage |
|---|---|---|---|---|---|---|---|---|
| Example 15-3 | Tetralin ring-containing copolymerized polyolefin compound A | Cobalt stearate | 0.1 | 0.1 or less | S | S | 3.9 | 3.8 |
| Example 15-4 | Tetralin ring-containing copolymerized polyolefin compound A | Cobalt acetate | 0.05 | 0.1 or less | S | S | 3.9 | 4.0 |
| Example 15-5 | Tetralin ring-containing copolymerized polyolefin compound A | Manganese stearate | 0.05 | 0.1 or less | S | S | 3.8 | 3.8 |
| Example 15-6 | Tetralin ring-containing copolymerized polyolefin compound A | Iron stearate | 0.05 | 0.1 or less | S | S | 3.8 | 3.8 |
| Example 15-7 | Tetralin ring-containing copolymerized polyolefin compound B | Cobalt stearate | 0.05 | 0.1 or less | S | S | 3.9 | 3.8 |
| Example 15-8 | Tetralin ring-containing copolymerized polyolefin compound B | Manganese stearate | 0.05 | 0.1 or less | S | S | 3.8 | 3.8 |
| Example 15-9 | Tetralin ring-containing copolymerized polyolefin compound B | Iron stearate | 0.05 | 0.1 or less | S | S | 3.8 | 3.7 |
| Example 15-10 | Tetralin ring-containing copolymerized polyolefin compound C | Cobalt stearate | 0.05 | 3.4 | S | A | 4.1 | 4.0 |
| Example 15-11 | Tetralin ring-containing copolymerized polyolefin compound D | Cobalt stearate | 0.05 | 0.1 or less | S | S | 3.9 | 3.9 |
| Comp. Example 15-1 | EMMA[4] | Cobalt stearate | 0.05 | 15.4 | A | R | 4.2 | 4.2 |
| Comp. Example 15-2 | Tetralin ring-containing copolymerized polyolefin compound A | — | — | 16.9 | A | R | 3.9 | 3.8 |
| Comp. Example 15-3 | Iron based oxygen absorber + LDPE | — | — | 0.1 or less | A | R[5] | 3.8 | 3.8 |

[1] Parts by mass based on resin compound (100 parts by mass)
[2] Stored at 35° C. for one month
[3] S: Satisfactory, A: Almost satisfactory, R: Reduced
[4] EMMA: ethylene-methyl methacrylate copolymer
[5] Aldehyde odor was sensed As is apparent from the results of Examples 15-1 to 15-11, in the methods for storing an alcohol beverage of the present invention, the container delivered satisfactory oxygen-absorbing performance; suppressed reduction of the taste and flavor of the content; and maintained heat sealing strength before storage.

EXAMPLE 16-1

First, oxygen-absorbing resin composition A was obtained in the same manner as in Example 2-1. Then, using a multilayer-film manufacturing apparatus equipped with two extruders, a feed block, a T die, a cooling roll, a corona discharge unit, a winder, etc., a low-density polyethylene (product name: "NOVATEC LD LC602A" hereinafter abbreviated as "LDPE" in Examples 16-1 to 16-11 and Comparative Examples 16-1 to 16-3, manufactured by Japan Polyethylene Corporation) serving as a material for a sealant layer was extruded from a first extruder; oxygen-absorbing resin composition A serving as a material for an oxygen-absorbing layer was extruded from a second extruder; and passed through the feed block to manufacture a three-layer film formed of two types of materials and having a width of 800 mm (LDPE (20 μm)/oxygen-absorbing layer (30 μm)/LDPE (20 μm)). Thereafter, one of the surfaces of LDPE was treated with corona discharge at a rate of 60 m/minute to manufacture a film roll. When the obtained film roll was observed, thickness deviation such as bumps was not seen.

Next, on a corona treated surface of the obtained three-layer film formed of two types of materials, a multilayer paper base material was stacked in accordance with the extrusion lamination by LDPE to obtain an oxygen-absorbing paper base material multilayer body (oxygen-absorbing multilayer body), which was constituted of bleached craft paper (basis weight: 330 g/m$^2$)/urethane dry-lamination adhesive (product name: "TM-250HV/CAT-RT86L-60", manufactured by Toyo-Morton, Ltd., 3 μm)/alumina vapor deposition PET film (product name: "GL-AE", manufactured by Toppan Printing Co., Ltd., 12 μm)/urethane anchor coating agent (product name: "EL-557A/B", manufactured by Toyo-Morton, Ltd., 0.5 μm)/LDPE (15 μm)/LDPE (20 μm)/oxygen-absorbing layer (30 μm)/LDPE (20 μm). Subsequently, the obtained multilayer body was manufactured into a carton to obtain a 1000-mL gable-top oxygen-absorbing paper container having a bottom of 7 cm squares. The moldability and processability of the paper container herein were satisfactory and the carton could be easily manufactured.

The oxygen-absorbing paper container was filled with high-quality green tea (1000 mL) such that the amount of air in the head space was 20 cc and inner surfaces (LDPE) of the top potion of the gable-top paper container were mutually sealed by heat sealing. The sealed paper container thus obtained was stored at 35° C. for one month. After storage of 7 days and one month, taste and flavor of high-quality green tea was checked. Furthermore, the oxygen concentration (head-space oxygen concentration) in the paper container after storage of one month and the heat sealing strength of the upper portion of the gable-top paper container were determined. These results are shown in Table 16.

EXAMPLE 16-2

An oxygen-absorbing multilayer film was obtained in the same manner as in Example 16-1 except that cobalt (II) stearate (0.01 parts by mass in terms of cobalt) was dry-blended in place of cobalt (II) stearate (0.05 parts by mass in terms of cobalt). Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

EXAMPLE 16-3

An oxygen-absorbing multilayer film was obtained in the same manner as in Example 16-1 except that cobalt (II) stearate (0.1 parts by mass in terms of cobalt) was dry-blended in place of cobalt (II) stearate (0.05 parts by mass in terms of cobalt). Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

EXAMPLE 16-4

An oxygen-absorbing multilayer film was obtained in the same manner as in Example 16-1 except that cobalt (II) acetate was used in place of cobalt (II) stearate. Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

EXAMPLE 16-5

An oxygen-absorbing multilayer film was obtained in the same manner as in Example 16-1 except that manganese (II) stearate (0.05 parts by mass in terms of manganese) was dry-blended in place of cobalt (II) stearate (0.05 parts by mass in terms of cobalt). Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

EXAMPLE 16-6

An oxygen-absorbing multilayer film was obtained in the same manner as in Example 16-1 except that iron (III) stearate (0.05 parts by mass in terms of iron) was dry-blended in place of cobalt (II) stearate (0.05 parts by mass in terms of cobalt). Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

EXAMPLE 16-7

An oxygen-absorbing multilayer film was obtained in the same manner as in Example 16-1 except that tetralin ring-containing copolymerized polyolefin compound B was used in place of tetralin ring-containing copolymerized polyolefin compound A. Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

EXAMPLE 16-8

An oxygen-absorbing multilayer film was obtained in the same manner as in Example 16-7 except that manganese (II) stearate (0.05 parts by mass in terms of manganese) was dry-blended in place of cobalt (II) stearate (0.05 parts by mass in terms of cobalt). Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

EXAMPLE 16-9

An oxygen-absorbing multilayer film was obtained in the same manner as in Example 16-7 except that iron (III) stearate (0.05 parts by mass in terms of iron) was dry-blended in place of cobalt (H) stearate (0.05 parts by mass in terms of cobalt). Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

EXAMPLE 16-10

An oxygen-absorbing multilayer film was obtained in the same manner as in Example 16-1 except that tetralin ring-containing copolymerized polyolefin compound C was used in place of tetralin ring-containing copolymerized polyolefin compound A. Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

EXAMPLE 16-11

An oxygen-absorbing multilayer film was obtained in the same manner as in Example 16-1 except that tetralin ring-containing copolymerized polyolefin compound D was used in place of tetralin ring-containing copolymerized polyolefin compound A. Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

COMPARATIVE EXAMPLE 16-1

A multilayer film was obtained in the same manner as in Example 16-1 except that an ethylene-methyl methacrylate copolymer having a methyl methacrylate content of 25 mass % used in Synthesis Example 1 was used in place of tetralin ring-containing copolymerized polyolefin compound A. Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

COMPARATIVE EXAMPLE 16-2

A multilayer film was obtained in the same manner as in Example 16-1 except that cobalt (II) stearate was not used. Thereafter, an oxygen-absorbing paper container and a hermetic paper container were manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

COMPARATIVE EXAMPLE 16-3

An iron powder having an average particle diameter of 20 µm and calcium chloride were mixed in a mass ratio of 100:1. The mixture and LDPE were kneaded in a mass ratio of 30:70 to obtain an iron based oxygen-absorbing resin composition. We tried to manufacture a three-layer film formed of two types of materials in the same manner as in Example 16-1 except that the iron based oxygen-absorbing resin composition was used in place of oxygen-absorbing resin composition A; however, a film having smooth surface that can be sufficiently subjected to further studies could not be obtained since convexoconcave portions were produced in the surface of the film due to iron powder. Because of this, on the LDPE of 50 µm in thickness, a film of the iron based oxygen-absorbing resin composition of 30 µm in thickness serving as an oxygen-absorbing layer was stacked in accordance with extrusion lamination and thereafter the surface of the layer constituted of the iron based oxygen-absorbing resin composition was treated with corona discharge at a rate of 60 m/minute to obtain a laminate film. Extrusion lamination by LDPE was performed on a multilayer paper base material in the same manner as in Example 16-1 except that the laminate film was used in place of the oxygen-absorbing multilayer film having a three-layer structure formed of two types of materials to manufacture an oxygen-absorbing paper base material multilayer body, which was constituted of bleached craft paper (basis weight: 330 g/m$^2$)/urethane dry-lamination adhesive (3 µm)/alumina vapor deposition PET film (12 µm)/urethane anchor coating agent (0.5 µm)/LDPE (15 µm)/oxygen-absorbing layer (30 µm)/LDPE (50 µM). Thereafter, we tried to manufacture a gable-top paper container using the multilayer body; however, it was difficult to form the corners of the paper container. Then, we tried to manufacture the paper container by lowering the speed of manufacturing a container. As a result, the paper container was finally manufactured with a large number of defective products (that were eliminated). Thereafter, a sealed paper container was manufactured in the same manner as in Example 16-1. The head-space oxygen concentration was measured; taste and flavor of high-quality green tea was checked; and the heat sealing strength of the upper portion of the paper container was measured in the same manner as in Example 16-1. These results are shown in Table 16.

TABLE 16

|  | Resin compound | Transition metal catalyst | | Oxygen concentration in container[2] (vol %) | Taste and flavor[3] | | Heat-sealing strength (kg) | |
| --- | --- | --- | --- | --- | --- | --- | --- | --- |
|  |  | Type | Amount of transition metal[1] |  | After 7 days | After one month | Before storage | After storage |
| Example 16-1 | Tetralin ring-containing copolymerized polyolefin compound A | Cobalt stearate | 0.05 | 0.1 or less | S | S | 3.9 | 3.9 |
| Example 16-2 | Tetralin ring-containing copolymerized polyolefin compound A | Cobalt stearate | 0.01 | 2.9 | S | A | 3.9 | 4.0 |

TABLE 16-continued

| | Resin compound | Transition metal catalyst Type | Amount of transition metal[1] | Oxygen concentration in container[2] (vol %) | Taste and flavor[3] After 7 days | After one month | Heat-sealing strength (kg) Before storage | After storage |
|---|---|---|---|---|---|---|---|---|
| Example 16-3 | Tetralin ring-containing copolymerized polyolefin compound A | Cobalt stearate | 0.1 | 0.1 or less | S | S | 3.9 | 3.8 |
| Example 16-4 | Tetralin ring-containing copolymerized polyolefin compound A | Cobalt acetate | 0.05 | 0.1 or less | S | S | 3.9 | 3.8 |
| Example 16-5 | Tetralin ring-containing copolymerized polyolefin compound A | Manganese stearate | 0.05 | 0.1 or less | S | S | 3.8 | 3.8 |
| Example 16-6 | Tetralin ring-containing copolymerized polyolefin compound A | Iron stearate | 0.05 | 0.1 or less | S | S | 4.0 | 3.9 |
| Example 16-7 | Tetralin ring-containing copolymerized polyolefin compound B | Cobalt stearate | 0.05 | 0.1 or less | S | S | 3.9 | 3.9 |
| Example 16-8 | Tetralin ring-containing copolymerized polyolefin compound B | Manganese stearate | 0.05 | 0.1 or less | S | S | 3.8 | 3.8 |
| Example 16-9 | Tetralin ring-containing copolymerized polyolefin compound B | Iron stearate | 0.05 | 0.1 or less | S | S | 3.8 | 3.9 |
| Example 16-10 | Tetralin ring-containing copolymerized polyolefin compound C | Cobalt stearate | 0.05 | 3.3 | S | A | 3.9 | 4.0 |
| Example 16-11 | Tetralin ring-containing copolymerized polyolefin compound D | Cobalt stearate | 0.05 | 0.1 or less | S | S | 3.8 | 3.9 |
| Comp. Example 16-1 | EMMA[4] | Cobalt stearate | 0.05 | 16.7 | A | R | 4.1 | 4.0 |
| Comp. Example 16-2 | Tetralin ring-containing copolymerized polyolefin compound A | — | — | 17.3 | A | R | 3.9 | 3.8 |
| Comp. Example 16-3 | Iron based oxygen absorber + LDPE | — | — | 0.1 or less | A | R | 4.0 | 3.8 |

[1]Parts by mass based on resin compound (100 parts by mass)
[2]Stored at 35° C. for one month
[3]S: Satisfactory, A: Almost satisfactory, R: Reduced
[4]EMMA: ethylene-methyl methacrylate copolymer As is apparent from the results of Examples 16-1 to 16-11, in the methods for storing liquid-state tea or paste-state tea of the present invention, the container delivered satisfactory oxygen-absorbing performance; suppressed reduction of the taste and flavor of the content; and maintained heat sealing strength before storage.

EXAMPLE 17-1

First, oxygen-absorbing resin composition A was obtained in the same manner as in Example 2-1. Then, using a multilayer-film manufacturing apparatus equipped with two extruders, a feed block, a T die, a cooling roll, a corona discharge unit, a winder, etc., a low-density polyethylene (product name: "NOVATEC LD LC602A", hereinafter abbreviated as "LDPE" in Examples 17-1 to 17-11 and Comparative Examples 17-1 to 17-3, manufactured by Japan Polyethylene Corporation) serving as a material for a sealant layer was extruded from a first extruder; oxygen-absorbing resin composition A serving as a material for an oxygen-absorbing layer was extruded from a second extruder; and passed through the feed block to manufacture a three-layer film formed of two types of materials and having a width of 800 mm (LDPE (20 μm)/oxygen-absorbing layer (30 μm)/ LDPE (20 μm)). Thereafter, one of the surfaces of LDPE was treated with corona discharge at a rate of 60 m/minute to manufacture a film roll. When the obtained film roll was observed, thickness deviation such as bumps was not seen.

Next, on a corona treated surface of the obtained three-layer film formed of two types of materials, a multilayer paper base material was stacked in accordance with the extrusion lamination by LDPE to obtain an oxygen-absorbing paper base material multilayer body (oxygen-absorbing multilayer body), which was constituted of bleached craft paper (basis weight: 330 g/m$^2$)/urethane dry-lamination adhesive (product name: "TM-250HV/CAT-RT86L-60", manufactured by Toyo-Morton, Ltd., 3 μm)/alumina vapor deposition PET film (product name: "GL-AE", manufactured by Toppan Printing Co., Ltd., 12 μm)/urethane anchor coating agent (product name: "EL-557A/B", manufactured by Toyo-Morton, Ltd., 0.5 μm)/LDPE (15 μm)/LDPE (20 μm)/oxygen-absorbing layer (30 μm)/LDPE (20 μm). Subsequently, the obtained multilayer body was manufactured into a carton to obtain a 1000-mL gable-top oxygen-absorbing paper container having a bottom of 7 cm squares. The moldability and processability of the paper container herein were satisfactory and the carton could be easily manufactured.

The oxygen-absorbing paper container was filled with orange juice (1000 mL) such that the amount of air in the head space was 20 cc and the paper container was sealed by heat sealing inner surfaces (LDPE) of the top potion of the gable-top paper container mutually. The sealed paper container thus obtained was stored at 35° C. for one month. After storage of 7 days and one month, taste and flavor of orange juice was checked. Furthermore, the oxygen concentration (head-space oxygen concentration) in the paper container after storage of one month and the heat sealing strength of the upper portion of the gable-top paper container were determined. These results are shown in Table 17.

EXAMPLE 17-2

An oxygen-absorbing multilayer film was obtained in the same manner as in Example 17-1 except that cobalt (II) stearate (0.01 parts by mass in terms of cobalt) was dry-blended in place of cobalt (II) stearate (0.05 parts by mass in terms of cobalt). Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

EXAMPLE 17-3

An oxygen-absorbing multilayer film was obtained in the same manner as in Example 17-1 except that cobalt (II) stearate (0.1 parts by mass in terms of cobalt) was dry-blended in place of cobalt (II) stearate (0.05 parts by mass in terms of cobalt). Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

EXAMPLE 17-4

An oxygen-absorbing multilayer film was obtained in the same manner as in Example 17-1 except that cobalt (II) acetate was used in place of cobalt (II) stearate. Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

EXAMPLE 17-5

An oxygen-absorbing multilayer film was obtained in the same manner as in Example 17-1 except that manganese (II) stearate (0.05 parts by mass in terms of manganese) was dry-blended in place of cobalt (II) stearate (0.05 parts by mass in terms of cobalt). Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

EXAMPLE 17-6

An oxygen-absorbing multilayer film was obtained in the same manner as in Example 17-1 except that iron (III) stearate (0.05 parts by mass in terms of iron) was dry-blended in place of cobalt (II) stearate (0.05 parts by mass in terms of cobalt). Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

EXAMPLE 17-7

An oxygen-absorbing multilayer film was obtained in the same manner as in Example 17-1 except that tetralin ring-containing copolymerized polyolefin compound B was used in place of tetralin ring-containing copolymerized polyolefin compound A. Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

EXAMPLE 17-8

An oxygen-absorbing multilayer film was obtained in the same manner as in Example 17-7 except that manganese (II) stearate (0.05 parts by mass in terms of manganese) was dry-blended in place of cobalt (II) stearate (0.05 parts by mass in terms of cobalt). Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

EXAMPLE 17-9

An oxygen-absorbing multilayer film was obtained in the same manner as in Example 17-7 except that iron (III) stearate (0.05 parts by mass in terms of iron) was dry-blended in place of cobalt (II) stearate (0.05 parts by mass in terms of cobalt). Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

EXAMPLE 17-10

An oxygen-absorbing multilayer film was obtained in the same manner as in Example 17-1 except that tetralin ring-containing copolymerized polyolefin compound C was used in place of tetralin ring-containing copolymerized polyolefin compound A. Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

EXAMPLE 17-11

An oxygen-absorbing multilayer film was obtained in the same manner as in Example 17-1 except that tetralin ring-containing copolymerized polyolefin compound D was used in place of tetralin ring-containing copolymerized polyolefin compound A. Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

COMPARATIVE EXAMPLE 17-1

A multilayer film was obtained in the same manner as in Example 17-1 except that an ethylene-methyl methacrylate copolymer having a methyl methacrylate content of 25 mass % used in Synthesis Example 1 was used in place of tetralin ring-containing copolymerized polyolefin compound A. Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

COMPARATIVE EXAMPLE 17-2

A multilayer film was obtained in the same manner as in Example 17-1 except that cobalt (II) stearate was not used. Thereafter, an oxygen-absorbing paper container and a hermetic paper container were manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

COMPARATIVE EXAMPLE 17-3

An iron powder having an average particle diameter of 20 μm and calcium chloride were mixed in a mass ratio of 100:1. The mixture and LDPE were kneaded in a mass ratio of 30:70 to obtain an iron based oxygen-absorbing resin composition. We tried to manufacture a three-layer film formed of two types of materials in the same manner as in Example 17-1 except that the iron based oxygen-absorbing resin composition was used in place of oxygen-absorbing resin composition A; however, a film having smooth surface that can be sufficiently subjected to further studies could not be obtained since convexoconcave portions were produced in the surface of the film due to iron powder. Because of this, on the LDPE of 50 μm in thickness, a film of the iron based oxygen-absorbing resin composition of 30 μm in thickness serving as an oxygen-absorbing layer was stacked in accordance with extrusion lamination, and thereafter the surface of the layer formed of the iron based oxygen-absorbing resin composition was treated with corona discharge at a rate of 60 m/minute to obtain a laminate film. Extrusion lamination by LDPE was performed on a multilayer paper base material in the same manner as in Example 17-1 except that the laminate film was used in place of the oxygen-absorbing multilayer film having a three-layer structure formed of two types of materials to manufacture an oxygen-absorbing paper base material multilayer body, which was constituted of bleached craft paper (basis weight: 330 $g/m^2$)/urethane dry-lamination adhesive (3 μm)/alumina vapor deposition PET film (12 μm)/urethane anchor coating agent (0.5 μm)/LDPE (15 μm)/oxygen-absorbing layer (30 μm)/LDPE (50 μm). Thereafter, we tried to manufacture a gable-top paper container using the multilayer body; however, it was difficult to form the corners of the paper container. Then, we tried to manufacture a paper container by lowering the speed of manufacturing a container. As a result, the paper container was finally manufactured with a large number of defective products (that were eliminated). Thereafter, a hermetic paper container was manufactured in the same manner as in Example 17-1. The head-space oxygen concentration was measured; taste and flavor of orange juice was checked; and the heat sealing strength of the upper portion of the paper container was measured in the same manner as in Example 17-1. These results are shown in Table 17.

TABLE 17

| | Resin compound | Transition metal catalyst Type | Amount of transition metal[1] | Oxygen concentration in container[2] (vol %) | Taste and flavor[3] After 7 days | After one month | Heat-sealing strength (kg) Before storage | After storage |
|---|---|---|---|---|---|---|---|---|
| Example 17-1 | Tetralin ring-containing copolymerized polyolefin compound A | Cobalt stearate | 0.05 | 0.1 or less | S | S | 4.0 | 3.9 |
| Example 17-2 | Tetralin ring-containing copolymerized polyolefin compound A | Cobalt stearate | 0.01 | 2.7 | S | A | 3.8 | 3.9 |
| Example 17-3 | Tetralin ring-containing copolymerized polyolefin compound A | Cobalt stearate | 0.1 | 0.1 or less | S | S | 3.9 | 3.8 |
| Example 17-4 | Tetralin ring-containing copolymerized polyolefin compound A | Cobalt acetate | 0.05 | 0.1 or less | S | S | 3.8 | 3.9 |

TABLE 17-continued

| | Resin compound | Transition metal catalyst Type | Amount of transition metal[1] | Oxygen concentration in container[2] (vol %) | Taste and flavor[3] After 7 days | Taste and flavor[3] After one month | Heat-sealing strength (kg) Before storage | Heat-sealing strength (kg) After storage |
|---|---|---|---|---|---|---|---|---|
| Example 17-5 | Tetralin ring-containing copolymerized polyolefin compound A | Manganese stearate | 0.05 | 0.1 or less | S | S | 3.9 | 3.8 |
| Example 17-6 | Tetralin ring-containing copolymerized polyolefin compound A | Iron stearate | 0.05 | 0.1 or less | S | S | 4.0 | 3.9 |
| Example 17-7 | Tetralin ring-containing copolymerized polyolefin compound B | Cobalt stearate | 0.05 | 0.1 or less | S | S | 3.9 | 3.9 |
| Example 17-8 | Tetralin ring-containing copolymerized polyolefin compound B | Manganese stearate | 0.05 | 0.1 or less | S | S | 3.9 | 3.9 |
| Example 17-9 | Tetralin ring-containing copolymerized polyolefin compound B | Iron stearate | 0.05 | 0.1 or less | S | S | 3.8 | 3.9 |
| Example 17-10 | Tetralin ring-containing copolymerized polyolefin compound C | Cobalt stearate | 0.05 | 3.1 | S | A | 3.9 | 4.0 |
| Example 17-11 | Tetralin ring-containing copolymerized polyolefin compound D | Cobalt stearate | 0.05 | 0.1 or less | S | S | 3.8 | 3.9 |
| Comp. Example 17-1 | EMMA[4] | Cobalt stearate | 0.05 | 16.8 | R | R | 3.9 | 3.9 |
| Comp. Example 17-2 | Tetralin ring-containing copolymerized polyolefin compound A | — | — | 17.9 | R | R | 3.9 | 3.9 |
| Comp. Example 17-3 | Iron based oxygen absorber + LDPE | — | — | 0.1 or less | A | R | 4.0 | 3.8 |

[1] Parts by mass based on resin compound (100 parts by mass)
[2] Stored at 35° C. for one month
[3] S: Satisfactory, A: Almost satisfactory, R: Reduced
[4] EMMA: ethylene-methyl methacrylate copolymer As is apparent from the results of Examples 17-1 to 17-11, in the methods for storing fruit juice and/or vegetable juice of the present invention, the container delivered satisfactory oxygen-absorbing performance; suppressed reduction of the taste and flavor of the content; and maintained heat sealing strength before storage.

EXAMPLE 18-1

First, oxygen-absorbing resin composition A was obtained in the same manner as in Example 2-1. Then, using a multilayer-film manufacturing apparatus equipped with two extruders, a feed block, a T die, a cooling roll, a corona discharge unit, a winder, etc., a linear and low-density polyethylene (product name: "NOVATEC LL UF641", hereinafter referred to as "LLDPE1" in Examples 18-1 to 18-11 and Comparative Examples 18-1 to 18-3, manufactured by Japan Polyethylene Corporation, MFR at 190° C.: 2.1 g/10 minutes, MFR at 240° C.: 4.4 g/10 minutes, MFR at 250° C.: 5.2 g/10 minutes) serving as a material for a sealant layer was extruded from a first extruder; oxygen-absorbing resin composition A serving as a material for an oxygen-absorbing layer was extruded from a second extruder; and passed through the feed block to manufacture a three-layer film formed of two types of materials having a width of 900 mm (LLDPE1 (20 μm)/oxygen-absorbing layer (30 μm)/LLDPE1 (20 μm)). Thereafter, one of the surfaces of LLDPE1 was treated with corona discharge at a rate of 60 m/minute to manufacture a film roll. When the obtained film roll was observed, thickness deviation such as bumps was not seen.

Next, on a corona treated surface of the obtained three-layer film formed of two types of materials, nylon 6 film (product name: "N1202", manufactured by Toyobo Co., Ltd.) and an alumina vapor deposition PET film (product name: "GL-ARH-F", manufactured by Toppan Printing Co., Ltd.) were stacked in accordance with dry lamination using a urethane dry-lamination adhesive (product name: "TM-319/CAT-19B", manufactured by Toyo-Morton, Ltd.) to obtain an oxygen-absorbing multilayer film formed of an oxygen-absorbing multilayer body, which was constituted of alumina vapor deposition PET film (12 μm)/urethane dry-lamination adhesive (3 μm)/nylon 6 film (15 μm)/urethane dry-lamination adhesive (3 μm)/LLDPE1 (20 μm)/oxygen-absorbing layer (30 μm)/LLDPE1 (20 μm).

Next, a three-side sealed bag of 10 cm×20 cm was manufactured using the obtained oxygen-absorbing multilayer film such that the LLDPE1 side faced inside and filled with beef jerky (100 g). The atmosphere of the bag was substituted with nitrogen so as to obtain an oxygen concentration of 2 vol % and then sealed. The sealed bag thus obtained was stored at 23° C. After storage for 7 days and one month, the oxygen concentration in the bag was measured. The taste and flavor and color tone of the beef jerky after one month storage were checked. Furthermore, the sealing strength of the bag before and after storage for 6 months was measured. These results are shown in Table 18. Note that in measuring the sealing strength, the sealing strength of the short side portion of the three-side sealed bag was measured in accordance with JIS Z0238 (the same shall apply hereinafter).

EXAMPLE 18-2

An oxygen-absorbing multilayer film was obtained in the same manner as in Example 18-1 except that cobalt (II) stearate (0.01 parts by mass in terms of cobalt) was dry-blended in place of cobalt (II) stearate (0.05 parts by mass in terms of cobalt). Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

EXAMPLE 18-3

An oxygen-absorbing multilayer film was obtained in the same manner as in Example 18-1 except that cobalt (II) stearate (0.1 parts by mass in terms of cobalt) was dry-blended in place of cobalt (II) stearate (0.05 parts by mass in terms of cobalt). Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

EXAMPLE 18-4

An oxygen-absorbing multilayer film was obtained in the same manner as in Example 18-1 except that cobalt (II) acetate was used in place of cobalt (II) stearate. Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

EXAMPLE 18-5

An oxygen-absorbing multilayer film was obtained in the same manner as in Example 18-1 except that manganese (II) stearate (0.05 parts by mass in terms of manganese) was dry-blended in place of cobalt (II) stearate (0.05 parts by mass in terms of cobalt). Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

EXAMPLE 18-6

An oxygen-absorbing multilayer film was obtained in the same manner as in Example 18-1 except that iron (III) stearate (0.05 parts by mass in terms of iron) was dry-blended in place of cobalt (II) stearate (0.05 parts by mass in terms of cobalt). Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

EXAMPLE 18-7

An oxygen-absorbing multilayer film was obtained in the same manner as in Example 18-1 except that tetralin ring-containing copolymerized polyolefin compound B was used in place of tetralin ring-containing copolymerized polyolefin compound A. Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

EXAMPLE 18-8

An oxygen-absorbing multilayer film was obtained in the same manner as in Example 18-7 except that manganese (II) stearate (0.05 parts by mass in terms of manganese) was dry-blended in place of cobalt (II) stearate (0.05 parts by mass in terms of cobalt). Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

EXAMPLE 18-9

An oxygen-absorbing multilayer film was obtained in the same manner as in Example 18-7 except that iron (III) stearate (0.05 parts by mass in terms of iron) was dry-blended in place of cobalt (II) stearate (0.05 parts by mass in terms of cobalt). Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

EXAMPLE 18-10

An oxygen-absorbing multilayer film was obtained in the same manner as in Example 18-1 except that tetralin ring-containing copolymerized polyolefin compound C was used in place of tetralin ring-containing copolymerized polyolefin compound A. Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

EXAMPLE 18-11

An oxygen-absorbing multilayer film was obtained in the same manner as in Example 18-1 except that tetralin ring-containing copolymerized polyolefin compound D was used in place of tetralin ring-containing copolymerized polyolefin compound A. Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

COMPARATIVE EXAMPLE 18-1

A multilayer film was obtained in the same manner as in Example 18-1 except that an ethylene-methyl methacrylate copolymer having a methyl methacrylate content of 25 mass % used in Synthesis Example 1 was used in place of tetralin ring-containing copolymerized polyolefin compound A. Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

COMPARATIVE EXAMPLE 18-2

A multilayer film was obtained in the same manner as in Example 18-1 except that cobalt (II) stearate was not used. Thereafter, a three-side sealed bag and a sealed bag were manufactured in the same manner as in Example 18-1. The oxygen concentration in the bag was measured; taste and flavor and color tone of beef jerky were checked; and the sealing strength of the bag was measured in the same manner as in Example 18-1. These results are shown in Table 18.

COMPARATIVE EXAMPLE 18-3

An iron powder having an average particle diameter of 20 µm and calcium chloride were mixed in a mass ratio of 100:1. The mixture and LLDPE1 were kneaded in a mass ratio of 30:70 to obtain an iron based oxygen-absorbing resin composition. We tried to manufacture a three-layer film formed of two types of materials in the same manner as in Example 18-1 except that the iron based oxygen-absorbing resin composition was used in place of oxygen-absorbing resin composition A; however, a film having smooth surface that can be sufficiently subjected to further studies could not be obtained since convexoconcave portions were produced in the surface of the film due to iron powder. Because of this, on the linear and low-density polyethylene film (product name: "Tohcello T. U. X HC", hereinafter referred to as "LLDPE2" in Comparative Example 18-3, manufactured by Tohcello Inc.) of 50 µm in thickness, a film of the iron based oxygen-absorbing resin composition of 30 µm in thickness serving as an oxygen-absorbing layer was stacked in accordance with extrusion lamination, and thereafter the surface of the layer constituted of the iron based oxygen-absorbing resin composition was treated with corona discharge at a rate of 60 m/minute to obtain a laminate film.

Next, on a corona treated surface of the laminate film, layers were stacked in accordance with dry lamination in the same manner as in Example 18-1 to manufacture an iron based oxygen-absorbing multilayer film, which was constituted of alumina vapor deposition PET film (12 µm)/urethane dry-lamination adhesive (3 µm)/nylon 6 film (15 µm)/urethane dry-lamination adhesive (3 µm)/oxygen-absorbing layer (30 µm)/LLDPE2 (50 µm).

Subsequently, a three-side sealed bag and a sealed bag were manufactured in the same manner as in Example 18-1 except that the obtained iron based oxygen-absorbing multilayer film was used in place of the oxygen-absorbing multilayer film. The oxygen concentration in the bag was measured; taste and flavor and color tone of beef jerky was checked; and the sealing strength of the bag was measured in the same manner as in Example 18-1. These results are shown in Table 18.

TABLE 18

| | | Transition metal catalyst | | Oxygen concentration (vol %)[2] | | Beef jerky[3] | | Sealing strength (kg/15 mm) | |
|---|---|---|---|---|---|---|---|---|---|
| | Resin compound | Type | Amount of transition metal[1] | After 7 days | After one month | Taste and flavor | Color tone | Before storage | After storage[4] |
| Example 18-1 | Tetralin ring-containing copolymerized polyolefin compound A | Cobalt stearate | 0.05 | 0.5 | 0.1 or less | Satisfactory | Satisfactory | 7.8 | 7.5 |
| Example 18-2 | Tetralin ring-containing copolymerized polyolefin compound A | Cobalt stearate | 0.01 | 0.9 | 0.3 | Almost satisfactory | Satisfactory | 7.7 | 7.5 |
| Example 18-3 | Tetralin ring-containing copolymerized polyolefin compound A | Cobalt stearate | 0.1 | 0.4 | 0.1 or less | Satisfactory | Satisfactory | 7.3 | 7.4 |
| Example 18-4 | Tetralin ring-containing copolymerized polyolefin compound A | Cobalt acetate | 0.05 | 0.5 | 0.1 or less | Satisfactory | Satisfactory | 7.5 | 7.3 |
| Example 18-5 | Tetralin ring-containing copolymerized polyolefin compound A | Manganese stearate | 0.05 | 0.5 | 0.1 or less | Satisfactory | Satisfactory | 7.7 | 7.8 |
| Example 18-6 | Tetralin ring-containing copolymerized polyolefin compound A | Iron stearate | 0.05 | 0.6 | 0.1 or less | Satisfactory | Satisfactory | 7.6 | 7.4 |
| Example 18-7 | Tetralin ring-containing copolymerized polyolefin compound B | Cobalt stearate | 0.05 | 0.4 | 0.1 or less | Satisfactory | Satisfactory | 7.4 | 7.6 |
| Example 18-8 | Tetralin ring-containing copolymerized polyolefin compound B | Manganese stearate | 0.05 | 0.5 | 0.1 or less | Satisfactory | Satisfactory | 7.5 | 7.3 |

TABLE 18-continued

| | Resin compound | Transition metal catalyst Type | Amount of transition metal[1] | Oxygen concentration (vol %)[2] After 7 days | After one month | Beef jerky[3] Taste and flavor | Color tone | Sealing strength (kg/15 mm) Before storage | After storage[4] |
|---|---|---|---|---|---|---|---|---|---|
| Example 18-9 | Tetralin ring-containing copolymerized polyolefin compound B | Iron stearate | 0.05 | 0.4 | 0.1 or less | Satisfactory | Satisfactory | 7.8 | 7.5 |
| Example 18-10 | Tetralin ring-containing copolymerized polyolefin compound C | Cobalt stearate | 0.05 | 1.1 | 0.5 | Almost satisfactory | Almost satisfactory | 8.1 | 7.8 |
| Example 18-11 | Tetralin ring-containing copolymerized polyolefin compound D | Cobalt stearate | 0.05 | 1.0 | 0.3 | Almost satisfactory | Satisfactory | 7.9 | 7.7 |
| Comp. Example 18-1 | EMMA[5] | Cobalt stearate | 0.05 | 2.0 | 1.9 | Reduced | Reduced | 7.8 | 7.7 |
| Comp. Example 18-2 | Tetralin ring-containing copolymerized polyolefin compound A | — | — | 2.1 | 1.9 | Reduced | Reduced | 7.5 | 7.4 |
| Comp. Example 18-3 | Iron + LLDPE1 | — | — | 1.9 | 1.7 | Reduced | Reduced | 7.7 | 7.7 |

[1] Parts by mass based on resin compound (100 parts by mass)
[2] Stored at 23° C. and 50% RH
[3] Results after storage at 23° C. and 50% RH for one month
[4] Results after storage at 23° C. and 50% RH for 6 months
[5] EMMA: ethylene-methyl methacrylate copolymer As is apparent from the results of Examples 18-1 to 18-11, in the methods for storing dried products of the present invention, the container delivered satisfactory oxygen-absorbing performance; suppressed reduction of the taste and flavor and color tone of contents; and maintained the sealing strength before storage.

Note that the present application claims a priority right based on the following 20 Japanese Patent Applications, the contents of which are incorporated herein by reference.

Japanese Patent Application No. 2012-25177 filed with the Japanese Patent Office on Feb. 8, 2012.

Japanese Patent Application No. 2012-168304 filed with the Japanese Patent Office on Jul. 30, 2012.

Japanese Patent Application No. 2013-7769 filed with the Japanese Patent Office on Jan. 18, 2013.

Japanese Patent Application No. 2013-9176 filed with the Japanese Patent Office on Jan. 22, 2013.

Japanese Patent Application No. 2013-10498 filed with the Japanese Patent Office on Jan. 23, 2013.

Japanese Patent Application No. 2013-12444 filed with the Japanese Patent Office on Jan. 25, 2013.

Japanese Patent Application No. 2013-14493 filed with the Japanese Patent Office on Jan. 29, 2013.

Japanese Patent Application No. 2013-14562 filed with the Japanese Patent Office on Jan. 29, 2013.

Japanese Patent Application No. 2013-15002 filed with the Japanese Patent Office on Jan. 30, 2013.

Japanese Patent Application No. 2013-16602 filed with the Japanese Patent Office on Jan. 31, 2013.

Japanese Patent Application No. 2013-17248 filed with the Japanese Patent Office on Jan. 31, 2013.

Japanese Patent Application No. 2013-17330 filed with the Japanese Patent Office on Jan. 31, 2013.

Japanese Patent Application No. 2013-17424 filed with the Japanese Patent Office on Jan. 31, 2013.

Japanese Patent Application No. 2013-18142 filed with the Japanese Patent Office on Feb. 1, 2013.

Japanese Patent Application No. 2013-18203 filed with the Japanese Patent Office on Feb. 1, 2013.

Japanese Patent Application No. 2013-18216 filed with the Japanese Patent Office on Feb. 1, 2013.

Japanese Patent Application No. 2013-18243 filed with the Japanese Patent Office on Feb. 1, 2013.

Japanese Patent Application No. 2013-18696 filed with the Japanese Patent Office on Feb. 1, 2013.

Japanese Patent Application No. 2013-19543 filed with the Japanese Patent Office on Feb. 4, 2013.

Japanese Patent Application No. 2013-20299 filed with the Japanese Patent Office on Feb. 5, 2013.

INDUSTRIAL APPLICABILITY

The oxygen-absorbing resin composition etc. of the present invention, since they have excellent oxygen-absorbing performance in a wide range of humidity conditions from low humidity to high humidity, can be widely and effectively used in general technical fields requiring oxygen absorption. Furthermore, since the oxygen-absorbing resin composition etc. can absorb oxygen regardless of the presence or absence of the moisture content of an article to be packaged and produce no odor after absorption of oxygen, they can be particularly effectively used in e.g., foods, cooking foods, beverages, medicinal products and health foods. Moreover, since an oxygen-absorbing resin composition etc. not responsive to a metal detector can also be provided, they can be widely and effectively applied to uses requiring external inspection of metals, metal pieces, etc. by a metal detector, for example, packaging materials and containers.

The invention claimed is:

1. An oxygen-absorbing resin composition comprising a copolymerized compound and a transition metal catalyst, wherein the copolymerized compound comprises at least one constituent unit (a) selected from the group consisting of the constituent units represented by the following formulas (4) and (5):

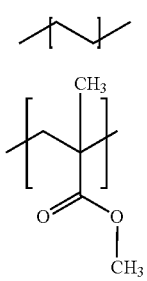

(4)

(5)

and, at least one constituent unit (b) having a tetralin ring, selected from the group consisting of the constituent units represented by the following formulas (2) and (3):

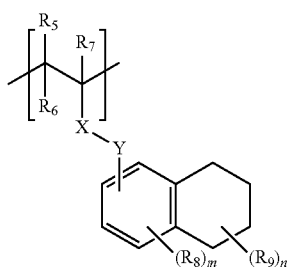

(2)

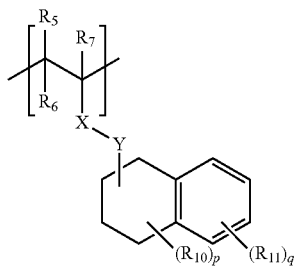

(3)

where $R_5$, $R_6$ and $R_7$ each independently represent a hydrogen atom or a second monovalent substituent, $R_8$, $R_9$, $R_{10}$ and $R_{11}$ each independently represent a third monovalent substituent, where the second monovalent substituent and the third monovalent substituent each independently represent at least one selected from the group consisting of a halogen atom, an alkyl group, an alkenyl group, an alkynyl group, an aryl group, a heterocyclic group, a cyano group, a hydroxy group, a carboxyl group, an ester group, an amido group, a nitro group, an alkoxy group, an aryloxy group, an acyl group, an amino group, a mercapto group, an alkylthio group, an arylthio group, a heterocyclic thio group and an imido group, these of which may further have a substituent; if a plurality of $R_8$, $R_9$, $R_{10}$ or $R_{11}$ are present, the plurality of $R_8$, $R_9$, $R_{10}$ and $R_{11}$ may be the same or different; m represents an integer of 0 to 3, n represents an integer of 0 to 7, p represents an integer of 0 to 6 and q represents an integer of 0 to 4; at least one hydrogen atom is bound to a benzyl position of the tetralin ring; X represents a bivalent group selected from the group consisting of —(C=O)O—, —(C=O)NH—, —O(C=O)—, —NH(C=O)— and —(CHR)s- where s represents an integer of 0 to 12; Y represents —(CHR)t- where t represents an integer of 0 to 12; and R represents a monovalent chemical species selected from the group consisting of a hydrogen atom, a methyl group and an ethyl group.

2. The oxygen-absorbing resin composition according to claim 1, wherein the transition metal catalyst comprises at least one transition metal selected from the group consisting of manganese, iron, cobalt, nickel and copper.

3. The oxygen-absorbing resin composition according to claim 1, wherein the transition metal catalyst is contained in an amount of 0.001 to 10 parts by mass in terms of a transition metal based on 100 parts by mass of the copolymerized compound.

4. The oxygen-absorbing resin composition according to claim 1, wherein a ratio of a content of the constituent unit (a) to a content of the constituent unit (b) contained in the copolymerized compound is 1/99 to 99/1 by molar ratio.

5. The oxygen-absorbing resin composition according to claim 1, wherein the constituent unit (b) is at least one constituent unit selected from the group consisting of the constituent units represented by the following formulas (6) and (7):

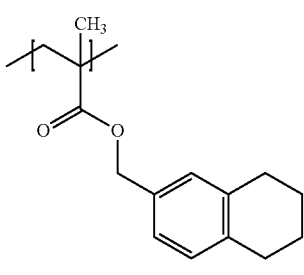

(6)

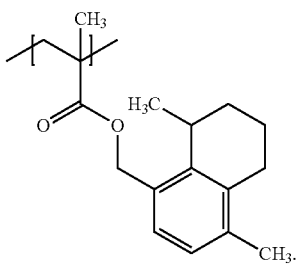

(7)

6. An oxygen-absorbing multilayer body comprising at least three layers comprising a sealant layer comprising a thermoplastic resin, an oxygen-absorbing layer comprising the oxygen-absorbing resin composition according to claim 1, and a gas barrier layer comprising a gas barrier substance, laminated in this order.

7. An oxygen-absorbing multilayer container comprising the oxygen-absorbing multilayer body according to claim 6.

8. An oxygen-absorbing multilayer container obtained by thermoforming of an oxygen-absorbing multilayer body comprising at least three layers comprising an oxygen transmission layer comprising a thermoplastic resin, an oxygen-absorbing layer comprising the oxygen-absorbing resin composition according to claim 1 and a gas barrier layer comprising a gas barrier substance, laminated in this order, such that the oxygen transmission layer faces inside.

9. An oxygen-absorbing sealed container comprising a cover material comprising the oxygen-absorbing multilayer body according to claim 6 and a gas barrier molded container comprising at least three layers comprising an inner layer comprising a thermoplastic resin, a gas barrier layer comprising a gas barrier substance and an outer layer comprising a thermoplastic resin, laminated in this order, wherein the sealant layer of the cover material and the inner layer of the gas barrier molded container are bonded.

10. An oxygen-absorbing paper container obtained by forming a carton from an oxygen-absorbing multilayer body comprising at least four layers comprising an isolation layer comprising a thermoplastic resin, an oxygen-absorbing layer comprising the oxygen-absorbing resin composition according to claim 1, a gas barrier layer comprising a gas barrier substance and a paper substrate layer, laminated in this order.

11. A tubular container comprising an oxygen-absorbing multilayer body comprising at least three layers comprising an inner layer comprising a thermoplastic resin, an oxygen-absorbing layer comprising the oxygen-absorbing resin composition according to claim 1 and a gas barrier layer comprising a gas barrier substance, laminated in this order.

12. An oxygen-absorbing medical multilayer molded container comprising at least three layers comprising a first resin layer at least comprising a polyester, an oxygen-absorbing layer comprising the oxygen-absorbing resin composition according to claim 1 and a second resin layer at least comprising a polyester, laminated in this order.

13. An oxygen-absorbing prefilled syringe made capable of storing a medicinal agent in advance in a sealed condition, and releasing the sealed condition to eject the medical agent at the time of use, wherein the prefilled syringe comprises a multilayered structure having at least three layers comprising a first resin layer comprising at least a polyester, an oxygen-absorbing layer comprising the oxygen-absorbing resin composition according to claim 1, and a second resin layer comprising at least a polyester, in this order.

14. A method for storing a biopharmaceutical, comprising storing the biopharmaceutical in the oxygen-absorbing medical multilayer molded container according to claim 12.

15. A method for storing a container filled with a drug solution, comprising storing the container filled with a drug solution in an oxygen-absorbing container using the oxygen-absorbing multilayer body according to claim 6 in whole or in part.

16. A method for storing a patch containing a medicinal ingredient, comprising storing the patch containing a medicinal ingredient in an oxygen-absorbing container using the oxygen-absorbing multilayer body according to claim 6 in whole or in part.

17. An oxygen-absorbing PTP packaging body, comprising an oxygen-absorbing bottom material formed of the oxygen-absorbing multilayer body according to claim 6 and a gas barrier cover material composing at least two layers comprising an inner layer comprising a thermoplastic resin and a gas barrier layer comprising a gas barrier substance, layered in this order, wherein the sealant layer of the oxygen-absorbing bottom material and the inner layer of the gas barrier cover material are bonded.

18. An oxygen-absorbing multilayer bottle having at least three layers comprising an oxygen transmission layer comprising a thermoplastic resin, an oxygen-absorbing layer comprising the oxygen-absorbing resin composition according to claim 1 and a gas barrier layer comprising a gas barrier substance, laminated in this order from inside.

19. A method for storing fruit pulps, comprising storing the fruit pulps in an oxygen-absorbing container using the oxygen-absorbing multilayer body according to claim 6 in whole or in part.

20. A method for storing an alcohol beverage, comprising storing the alcohol beverage in an oxygen-absorbing container using the oxygen-absorbing multilayer body according to claim 6 in whole or in part.

21. A method for storing liquid-state tea or paste-state tea, comprising storing the liquid-state tea or paste-state tea in an oxygen-absorbing container using the oxygen-absorbing multilayer body according to claim 6 in whole or in part.

22. A method for storing fruit juice and/or vegetable juice, comprising storing the fruit juice and/or vegetable juice in an oxygen-absorbing container using the oxygen-absorbing multilayer body according to claim 6 in whole or in part.

23. A method for storing a dry product, comprising storing the dry product in an oxygen-absorbing container using the oxygen-absorbing multilayer body according to claim 6 in whole or in part.

24. A method for storing a biopharmaceutical, comprising storing the biopharmaceutical in the oxygen asorbing prefilled syringe according to claim 13.

* * * * *

UNITED STATES PATENT AND TRADEMARK OFFICE
CERTIFICATE OF CORRECTION

PATENT NO. : 9,732,167 B2
APPLICATION NO. : 14/376563
DATED : August 15, 2017
INVENTOR(S) : S. Okada et al.

It is certified that error appears in the above-identified patent and that said Letters Patent is hereby corrected as shown below:

In the Claims

At Column 168, Line 40 (Claim 24, Line 2), please change "oxygen asorbing" to
-- oxygen-absorbing --.

Signed and Sealed this
Twenty-seventh Day of February, 2018

Andrei Iancu
*Director of the United States Patent and Trademark Office*